United States Patent
Claremon et al.

(10) Patent No.: US 9,624,217 B2
(45) Date of Patent: *Apr. 18, 2017

(54) DIHYDROPYRROLOPYRIDINE INHIBITORS OF ROR-GAMMA

(71) Applicant: Vitae Pharmaceuticals, Inc., Fort Washington, PA (US)

(72) Inventors: David A. Claremon, Maple Glen, PA (US); Lawrence Wayne Dillard, Yardley, PA (US); Chengguo Dong, Staten Island, NY (US); Yi Fan, Doylestown, PA (US); Lanqi Jia, Horsham, PA (US); Zhijie Liu, Harleysville, PA (US); Stephen D. Lotesta, Burlington, NJ (US); Andrew Marcus, Media, PA (US); Suresh B. Singh, Kendall Park, NJ (US); Colin M. Tice, Maple Glen, PA (US); Jing Yuan, Lansdale, PA (US); Wei Zhao, Germantown, MD (US); Yajun Zheng, Hockessin, DE (US); Linghang Zhuang, Chalfont, PA (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/990,430

(22) Filed: Jan. 7, 2016

(65) Prior Publication Data

US 2016/0200724 A1    Jul. 14, 2016

Related U.S. Application Data

(63) Continuation of application No. 14/609,798, filed on Jan. 30, 2015, now Pat. No. 9,266,886.

(60) Provisional application No. 61/970,637, filed on Mar. 26, 2014, provisional application No. 61/935,162, filed on Feb. 3, 2014.

(51) Int. Cl.

| | |
|---|---|
| *C07D 401/02* | (2006.01) |
| *C07D 401/10* | (2006.01) |
| *A61K 31/437* | (2006.01) |
| *A61K 31/4353* | (2006.01) |
| *C07D 471/04* | (2006.01) |
| *C07D 519/00* | (2006.01) |

(52) U.S. Cl.
CPC ......... *C07D 471/04* (2013.01); *C07D 519/00* (2013.01)

(58) Field of Classification Search
CPC .. C07D 401/02; C07D 401/10; A61K 31/437; A61K 31/4353
USPC ......................................... 546/113; 514/300
See application file for complete search history.

(56) References Cited

U.S. PATENT DOCUMENTS

| | | | |
|---|---|---|---|
| 5,238,950 | A | 8/1993 | Clader et al. |
| 5,272,158 | A | 12/1993 | Hartman et al. |
| 5,326,760 | A | 7/1994 | McElroy et al. |
| 5,364,869 | A | 11/1994 | De |
| 5,389,631 | A | 2/1995 | Claremon et al. |
| 5,571,774 | A | 11/1996 | Hamprecht et al. |
| 5,719,144 | A | 2/1998 | Hartman et al. |
| 5,770,590 | A | 6/1998 | Natsugari et al. |
| 5,786,352 | A | 7/1998 | Natsugari et al. |
| 6,103,659 | A | 8/2000 | Pasenok et al. |
| 6,177,443 | B1 | 1/2001 | Madsen et al. |
| 6,417,207 | B1 | 7/2002 | Garvey et al. |
| 6,444,617 | B1 | 9/2002 | Takaishi et al. |
| 6,489,315 | B1 | 12/2002 | Natsugari et al. |
| 6,512,117 | B1 | 1/2003 | Harclerode et al. |
| 6,770,666 | B2 | 8/2004 | Hashimoto et al. |
| 7,112,600 | B1 | 9/2006 | Hashimoto et al. |
| 7,115,752 | B2 | 10/2006 | Lesieur et al. |
| 7,183,318 | B2 | 2/2007 | Lesieur et al. |
| 7,244,730 | B2 | 7/2007 | Suzuki et al. |
| 7,732,616 | B2 | 6/2010 | Marlow et al. |
| 7,750,021 | B2 | 7/2010 | Mi et al. |
| 8,389,739 | B1 | 3/2013 | Thacher et al. |

(Continued)

FOREIGN PATENT DOCUMENTS

| | | |
|---|---|---|
| CA | 2031684 A1 | 6/1991 |
| CA | 2134192 A1 | 5/1995 |

(Continued)

OTHER PUBLICATIONS

Maddur et al., "Biology, Pathogenesis of Automimmune and Inflammatory Diseases, and Therapeutic Strategies", The American Journal of Pathology, 181(1):8-18 (2012).
Marcoux, et al., "Annulation of Ketones with Vinamidinium Hexafluorophosphate Salts: An Efficient Preparation of Trisubstituted Pyridines," Organic Letters, 2000, vol. 2, No. 15, 2339-2341.
Schlecker, et al., "Regioselective Metalation of Pyridinylcarbamates and Pyridinecarboxamides with (2,2,6,6-

(Continued)

*Primary Examiner* — Niloofar Rahmani
(74) *Attorney, Agent, or Firm* — McCarter & English, LLP; Steven G. Davis; Michael J. DeGrazia

(57) ABSTRACT

Provided are novel compounds of Formula (I):

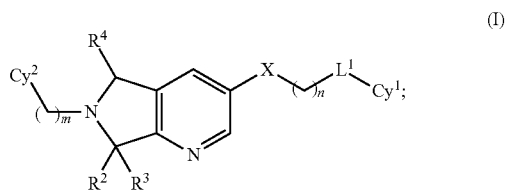

(I)

pharmaceutically acceptable salts thereof, and pharmaceutical compositions thereof, which are useful in the treatment of diseases and disorders mediated by RORγ. Also provided are pharmaceutical compositions comprising the novel compounds of Formula (I) and methods for their use in treating one or more inflammatory, metabolic, autoimmune and other diseases or disorders.

22 Claims, No Drawings

(56) References Cited

U.S. PATENT DOCUMENTS

| | | |
|---|---|---|
| 8,415,351 B2 | 4/2013 | Wagner et al. |
| 9,266,886 B2 | 2/2016 | Lotesta et al. |
| 2002/0132817 A1 | 9/2002 | Natsugari et al. |
| 2003/0050320 A1 | 3/2003 | Hashimoto et al. |
| 2004/0002424 A1 | 1/2004 | Minn et al. |
| 2004/0038973 A1 | 2/2004 | Nahra et al. |
| 2005/0004204 A1 | 1/2005 | Suzuki et al. |
| 2005/0020593 A1 | 1/2005 | Mailliet et al. |
| 2005/0234065 A1 | 10/2005 | Hulin et al. |
| 2006/0135557 A1 | 6/2006 | Nan et al. |
| 2007/0032497 A1 | 2/2007 | Hashimoto et al. |
| 2007/0112038 A1 | 5/2007 | Marlow et al. |
| 2007/0258887 A1 | 11/2007 | Tamagnan et al. |
| 2008/0277622 A1 | 11/2008 | Deshpande et al. |
| 2008/0287462 A1 | 11/2008 | Chessari et al. |
| 2009/0036423 A1 | 2/2009 | Pan et al. |
| 2009/0076275 A1 | 3/2009 | Bolin et al. |
| 2009/0233945 A9 | 9/2009 | Chessari et al. |
| 2009/0258871 A1 | 10/2009 | Jitsuoka et al. |
| 2009/0270405 A1 | 10/2009 | Cook, II et al. |
| 2010/0099684 A1 | 4/2010 | Cook, II et al. |
| 2011/0070193 A1 | 3/2011 | Wagner et al. |
| 2011/0189167 A1 | 8/2011 | Flynn et al. |
| 2011/0313003 A1 | 12/2011 | Shi et al. |
| 2012/0077840 A1 | 3/2012 | Turner et al. |
| 2012/0115903 A1 | 5/2012 | Frank et al. |
| 2012/0245163 A1 | 9/2012 | Gomtsyan et al. |
| 2012/0322837 A1 | 12/2012 | Maeba et al. |
| 2013/0143870 A1 | 6/2013 | Grauert et al. |
| 2013/0150347 A1 | 6/2013 | Rudolf et al. |
| 2014/0163001 A1 | 6/2014 | Yamamoto et al. |
| 2014/0228409 A1 | 8/2014 | Yamamoto et al. |

FOREIGN PATENT DOCUMENTS

| | | |
|---|---|---|
| CA | 2352612 A1 | 6/2000 |
| CA | 2524027 A1 | 12/2004 |
| CN | 1424770 A | 6/2003 |
| CN | 1869036 A | 11/2006 |
| CN | 101225070 A | 7/2008 |
| CN | 101455661 A | 6/2009 |
| CN | 102180780 A | 9/2011 |
| DE | 4343922 A1 | 6/1995 |
| DE | 4446396 A1 | 7/1995 |
| EP | 254951 A2 | 2/1988 |
| EP | 321368 A1 | 6/1989 |
| EP | 468187 A2 | 1/1992 |
| EP | 520277 A2 | 12/1992 |
| EP | 520573 A1 | 12/1992 |
| EP | 540334 A1 | 5/1993 |
| EP | 655439 A2 | 5/1995 |
| EP | 733632 A1 | 9/1996 |
| EP | 1178048 A1 | 2/2002 |
| FR | 2725946 A1 | 4/1996 |
| FR | 2926554 A1 | 7/2009 |
| GB | 2276384 A | 9/1994 |
| JP | H06236056 A | 8/1994 |
| JP | H1143489 A | 2/1999 |
| JP | 2000007661 A | 1/2000 |
| JP | 2003171380 A | 6/2003 |
| JP | 2003531894 A | 10/2003 |
| JP | 2004203791 A | 7/2004 |
| WO | 90/09787 A1 | 9/1990 |
| WO | 94/00119 A1 | 1/1994 |
| WO | 94/24712 A1 | 10/1994 |
| WO | 95/11680 A1 | 5/1995 |
| WO | 95/17397 A1 | 6/1995 |
| WO | 96/26187 A1 | 8/1996 |
| WO | 97/32832 A1 | 9/1997 |
| WO | 98/40385 A1 | 9/1998 |
| WO | 98/42666 A1 | 10/1998 |
| WO | 99/47132 A2 | 9/1999 |
| WO | 99/58495 A1 | 11/1999 |
| WO | 99/58496 A1 | 11/1999 |
| WO | 00/32192 A1 | 6/2000 |
| WO | 00/67754 A1 | 11/2000 |
| WO | 01/05790 A1 | 1/2001 |
| WO | 01/47883 A1 | 7/2001 |
| WO | 01/51128 A1 | 7/2001 |
| WO | 01/83445 A1 | 11/2001 |
| WO | 01/85722 A1 | 11/2001 |
| WO | 02/24650 A2 | 3/2002 |
| WO | 02/38107 A2 | 5/2002 |
| WO | 02/081443 A1 | 10/2002 |
| WO | 02/081447 A1 | 10/2002 |
| WO | 02/081463 A1 | 10/2002 |
| WO | 02/085855 A1 | 10/2002 |
| WO | 03/008421 A1 | 1/2003 |
| WO | 03/029252 A1 | 4/2003 |
| WO | 03/029254 A1 | 4/2003 |
| WO | 03/070710 A1 | 8/2003 |
| WO | 03/076440 A1 | 9/2003 |
| WO | 03/104216 A1 | 12/2003 |
| WO | 2004/014365 A1 | 2/2004 |
| WO | 2004/042029 A2 | 5/2004 |
| WO | 2004/065351 A1 | 8/2004 |
| WO | 2004/089897 A1 | 10/2004 |
| WO | 2004/103309 A2 | 12/2004 |
| WO | 2004/108133 A2 | 12/2004 |
| WO | 2004/111010 A1 | 12/2004 |
| WO | 2004/113330 A1 | 12/2004 |
| WO | 2005/005392 A1 | 1/2005 |
| WO | 2005/011601 A2 | 2/2005 |
| WO | 2005/023806 A2 | 3/2005 |
| WO | 2005/025504 A2 | 3/2005 |
| WO | 2005/028480 A2 | 3/2005 |
| WO | 2005/039564 A1 | 5/2005 |
| WO | 2005/051301 A2 | 6/2005 |
| WO | 2005/060958 A1 | 7/2005 |
| WO | 2005/063296 A2 | 7/2005 |
| WO | 2005/100334 A1 | 10/2005 |
| WO | 2006/032631 A1 | 3/2006 |
| WO | 2006/062981 A2 | 6/2006 |
| WO | 2006/065842 A2 | 6/2006 |
| WO | 2006/074428 A | 7/2006 |
| WO | 2006/082001 A1 | 8/2006 |
| WO | 2006/092731 A1 | 9/2006 |
| WO | 2006/109085 A1 | 10/2006 |
| WO | 2007/007054 A1 | 1/2007 |
| WO | 2007/036733 A1 | 4/2007 |
| WO | 2007/036734 A1 | 4/2007 |
| WO | 2007/050124 A1 | 5/2007 |
| WO | 2007/084451 A1 | 7/2007 |
| WO | 2007/084455 A1 | 7/2007 |
| WO | 2007/097931 A2 | 8/2007 |
| WO | 2007/101224 A2 | 9/2007 |
| WO | 2007/107545 A1 | 9/2007 |
| WO | 2007/109596 A2 | 9/2007 |
| WO | 2007/131982 A2 | 11/2007 |
| WO | 2008/013963 A2 | 1/2008 |
| WO | 2008/044029 A1 | 4/2008 |
| WO | 2008/044041 A1 | 4/2008 |
| WO | 2008/044045 A1 | 4/2008 |
| WO | 2008/044054 A2 | 4/2008 |
| WO | 2008/048991 A2 | 4/2008 |
| WO | 2008/0440027 A | 4/2008 |
| WO | 2008/073865 A1 | 6/2008 |
| WO | 2008/083070 A1 | 7/2008 |
| WO | 2008/086161 A1 | 7/2008 |
| WO | 2008/132155 A2 | 11/2008 |
| WO | 2008/135524 A2 | 11/2008 |
| WO | 2008/135526 A1 | 11/2008 |
| WO | 2008/149163 A2 | 12/2008 |
| WO | 2009/004496 A2 | 1/2009 |
| WO | 2009/013299 A2 | 1/2009 |
| WO | 2009/026248 A2 | 2/2009 |
| WO | 2009/050228 A1 | 4/2009 |
| WO | 2009/052319 A1 | 4/2009 |
| WO | 2009/052320 A1 | 4/2009 |
| WO | 2009/068463 A2 | 6/2009 |
| WO | 2009/073788 A1 | 6/2009 |
| WO | 2009/097972 A1 | 8/2009 |
| WO | 2009/112445 A1 | 9/2009 |
| WO | 2009/112678 A2 | 9/2009 |

(56) References Cited

FOREIGN PATENT DOCUMENTS

| | | |
|---|---|---|
| WO | 2009/112826 A1 | 9/2009 |
| WO | 2009/112839 A1 | 9/2009 |
| WO | 2009/124755 A1 | 10/2009 |
| WO | 2009/131926 A1 | 10/2009 |
| WO | 2009/144450 A1 | 12/2009 |
| WO | 2010/003022 A1 | 1/2010 |
| WO | 2010/021878 A1 | 2/2010 |
| WO | 2010/033350 A1 | 3/2010 |
| WO | 2010/056194 A1 | 5/2010 |
| WO | 2010/056195 A1 | 5/2010 |
| WO | 2010/077680 A2 | 7/2010 |
| WO | 2010/086311 A1 | 8/2010 |
| WO | 2011/078143 A1 | 6/2011 |
| WO | 2011/090473 A1 | 7/2011 |
| WO | 2011/094545 A2 | 8/2011 |
| WO | 2011/107248 A1 | 9/2011 |
| WO | 2011/140936 A1 | 11/2011 |
| WO | 2011/146358 A1 | 11/2011 |
| WO | 2011/159297 A1 | 12/2011 |
| WO | 2012/019015 A2 | 2/2012 |
| WO | 2012/027965 A1 | 3/2012 |
| WO | 2012/028100 A1 | 3/2012 |
| WO | 2012/031197 A1 | 3/2012 |
| WO | 2012/043505 A1 | 4/2012 |
| WO | 2012/062462 A1 | 5/2012 |
| WO | 2012/064744 A2 | 5/2012 |
| WO | 2012/100732 A1 | 8/2012 |
| WO | 2012/100734 A1 | 8/2012 |
| WO | 2012/106995 A1 | 8/2012 |
| WO | 2012/125521 A1 | 9/2012 |
| WO | 2012/136296 A1 | 10/2012 |
| WO | 2012/139775 A1 | 10/2012 |
| WO | 2013/000994 A1 | 1/2013 |
| WO | 2013/019621 A1 | 2/2013 |
| WO | 2013/019626 A1 | 2/2013 |
| WO | 2013/019635 A1 | 2/2013 |
| WO | 2013/019653 A1 | 2/2013 |
| WO | 2013/019682 A1 | 2/2013 |
| WO | 2013/029338 A1 | 3/2013 |
| WO | 2013/045431 A1 | 4/2013 |
| WO | 2013/064231 A1 | 5/2013 |
| WO | 2013/067036 A1 | 5/2013 |
| WO | 2013/079223 A1 | 6/2013 |
| WO | 2013/083741 A1 | 6/2013 |
| WO | 2013/087739 A1 | 6/2013 |
| WO | 2013/092460 A1 | 6/2013 |
| WO | 2013/092939 A1 | 6/2013 |
| WO | 2013/092941 A1 | 6/2013 |
| WO | 2013/096496 A2 | 6/2013 |
| WO | 2013/100027 A1 | 7/2013 |
| WO | 2013/159095 A1 | 10/2013 |
| WO | 2013/160418 A1 | 10/2013 |
| WO | 2013/160419 A1 | 10/2013 |
| WO | 2013/166013 A1 | 11/2013 |
| WO | 2013/169588 A1 | 11/2013 |
| WO | 2013/169704 A2 | 11/2013 |
| WO | 2013/169864 A2 | 11/2013 |
| WO | 2013/171729 A2 | 11/2013 |
| WO | 2013/178362 A1 | 12/2013 |
| WO | 2014/008214 A1 | 1/2014 |
| WO | 2014/009447 A1 | 1/2014 |
| WO | 2014/026327 A1 | 2/2014 |
| WO | 2014/026328 A1 | 2/2014 |
| WO | 2014/026329 A1 | 2/2014 |
| WO | 2014/026330 A1 | 2/2014 |
| WO | 2014/028589 A2 | 2/2014 |
| WO | 2014/028591 A2 | 2/2014 |
| WO | 2014/028597 A2 | 2/2014 |
| WO | 2014/028600 A2 | 2/2014 |
| WO | 2014/028669 A1 | 2/2014 |
| WO | 2014/062938 A1 | 4/2014 |
| WO | 2014/086894 A1 | 6/2014 |
| WO | 2015/116904 A1 | 8/2015 |

OTHER PUBLICATIONS

Tetramethylpiperidino)magnesium Chloride," J. Org. Chem., 1995, 60, 8414-8416.
Schlecker, et al., "Regioselective Monometalation of 2,5-Pyridinedicarboxamides with (2,2,6,6-Tetramethylpiperidino) magnesium Chloride (TMPMgCl)," Liebigs Annalen, 1995, vol. 8, pp. 1441-1446.
Co-pending U.S. Appl. No. 14/933,468, filed Nov. 5, 2015.
Co-pending U.S. Appl. No. 14/990,430, filed Jan. 7, 2016.

DIHYDROPYRROLOPYRIDINE INHIBITORS OF ROR-GAMMA

RELATED APPLICATIONS

This application is a Continuation of U.S. patent application Ser. No. 14/609,798 filed Jan. 30, 2015, now U.S. Pat. No. 9,266,886, which claims the benefit of U.S. Provisional Application No. 61/935,162 filed Feb. 3, 2014 and U.S. Provisional Application No. 61/970,637 filed Mar. 26, 2014. The entire contents of the aforementioned applications are incorporated by reference herein.

TECHNICAL FIELD OF THE INVENTION

The present invention is directed to novel retinoic acid receptor-related orphan receptor gamma ("RORγ" or "ROR-gamma") inhibitors, processes for their preparation, pharmaceutical compositions containing these inhibitors, and their use in the treatment of inflammatory, metabolic, autoimmune and other diseases mediated by RORγ.

BACKGROUND OF THE INVENTION

Retinoic acid receptor-related orphan receptors (RORs) are a subfamily of transcription factors in the steroid hormone nuclear receptor superfamily (Jetten & Joo (2006) Adv. Dev. Biol. 2006, 16, 313-355). The ROR family consists of ROR alpha (RORα), ROR beta (RORβ) and ROR gamma (RORγ), each encoded by a separate gene (in human: RORA, RORB and RORC, respectively; in mouse: rora, rorb and rorc, respectively). RORs contain four principal domains shared by the majority of nuclear receptors: an N-terminal domain, a highly conserved DNA-binding domain (DBD) consisting of two zinc finger motifs, a hinge domain, and a ligand binding domain (LBD). Each ROR gene generates several isoforms, differing only in their N-terminal domains. RORγ has two isoforms: RORγ1 and RORγ2 (also known as RORγt). RORγ refers to RORγ1 and/or RORγt. RORγ1 is expressed in a variety of tissues including thymus, muscle, kidney and liver, but RORγt is exclusively expressed in the cells of the immune system, has a critical role in thymopoiesis and the development of several secondary lymphoid tissues, and is a key regulator of Th17 cell differentiation (Jetten, 2009, Nucl. Recept. Signal., 7:e003, doi:10.1621/nrs.07003, Epub 2009 Apr. 3).

Th17 cells are a subset of T helper cells which preferentially produce the pro-inflammatory cytokines IL-17A, IL-17F, IL-21 and IL-22. Th17 cells and their effector molecules, such as IL-17, IL-21, IL-22, GM-CSF and CCL20, are associated with the pathogenesis of several autoimmune and inflammatory diseases, such as rheumatoid arthritis, systemic lupus erythematosus, multiple sclerosis, psoriasis, inflammatory bowel disease, allergy and asthma (Maddur et al., 2012, Am. J. Pathol., 181:8-18). Recent findings support a role for IL17 and Th17 cells in the pathogenesis of acne (Thiboutot et al., 2014, J. Invest. Dermatol., 134(2):307-10, doi: 10.1038/jid.2013.400; Agak et al., 2014, J. Invest. Dermatol., 134(2):366-73, doi: 10.1038/jid.2013.334, Epub 2013 Aug. 7). Th17 cells are also potent inducers of inflammation associated with endometriosis, a chronic inflammatory disease (Hirata et al., 2010, Endocrinol., 151:5468-5476; Hirata et al., 2011, Fertil Steril., July; 96(1):113-7, doi: 10.1016/j.fertnstert.2011.04.060, Epub 2011 May 20). Additionally, Th17 cells have a key role in the mouse autoimmune models of experimental autoimmune encephalomyelitis (EAE), collagen-induced arthritis (CIA) and adjuvant-induced arthritis (AIA) (Bedoya et al., 2013, Clin. Dev. Immunol., 2013: 986789. Epub 2013 Dec. 26. Th17 cells are activated during inflammatory and autoimmune disease processes and are responsible for recruiting other inflammatory cell types, particularly neutrophils, to mediate pathology in target tissues (Miossec & Kolls, 2012, Nature Rev., 11:763-776; Korn et al., 2009, Annu. Rev. Immunol., 27:485-517). Aberrant Th17 cell function has been implicated in a variety of autoimmune diseases, including multiple sclerosis and rheumatoid arthritis. Autoimmune disease is believed to arise from the disruption of the equilibrium between effector and regulatory T cells (Solt et al., 2012, ACS Chem. Biol., 7:1515-1519, Epub 2012 Jul. 9). The importance of RORγt to Th17 cell differentiation and the pathogenic role of Th17 cells is evidenced by the fact that RORγt-deficient mice have very few Th17 cells and have a reduction in severity of EAE (Ivanov et al., 2006, Cell, 126:1121-1133).

Circadian rhythms are daily cycles of behavioral and physiological changes that are regulated by endogenous circadian clocks. A number of studies have established links between nuclear receptor (including RORγ) function and expression, the circadian regulatory circuitry, and the regulation of various physiological processes (Jetten (2009) op. cit.).

Obstructive sleep apnea syndrome (OSAS) is a chronic inflammatory disease regulated by T lymphocytes. OSAS patients have a significant increase in peripheral Th17 cell frequency, IL-17 and RORγt levels (Ye et al., 2012, Mediators Inflamm., 815308, doi: 10.1155/2012/815308, Epub 2012 Dec. 31).

A number of studies have provided evidence of a role of RORs in cancer. Mice deficient in the expression of RORγ exhibit a high incidence of thymic lymphomas that metastasize frequently to liver and spleen. High expression of Th17-associated genes (including RORγ) and high levels of Th17 cells in the tumor microenvironment has been shown to correlate with a poor prognosis in various cancers, including lung, gastric, breast and colon cancer (Tosolini et al., 2011, Cancer Res., 71:1263-1271, doi: 10.1158/0008-5472.CAN-10-2907, Epub 2011 Feb. 8; Su et al., 2014, Immunol. Res., 58:118-124, doi: 10.1007/s12026-013-8483-y, Epub 2014 Jan. 9; Carmi et al., 2011, J. Immunol., 186:3462-3471, doi: 10.4049/jimmunol.1002901, Epub 2011 Feb. 7; Chen et al., 2013, Histopathology, 63:225-233, doi: 10.1111/his.12156, Epub 2013 Jun. 6).

RORγ has also been identified to have a regulatory role in lipid/glucose homeostasis, and has been implicated in metabolic syndrome, obesity (Meissburger et al., 2011, EMBO Mol. Med., 3:637-651), hepatosteatosis, insulin resistance and diabetes.

Further support for the role of RORγ in the pathogenesis of inflammatory, metabolic, circadian effect, cancer, and autoimmune diseases and disorders can be found in the following references: Chang et al., 2012, J. Exp. Pharmacol., 4:141-148; Jetten et al., 2013, Frontiers Endocrinol., 4:1-8; Huh & Littman, 2012, Eur. J. Immunol., 42:2232-2237; Martinez et al., 2008, Ann. N.Y. Acad. Sci., 1143:188-211; Pantelyushin et al., 2012, J. Clin. Invest., 122:2252-2256; Jetten & Ueda, 2002, Cell Death Differen., 9:1167-1171; Solt et al., 2010, Curr. Opin. Lipidol., 21:204-211.

In light of the role that RORγ plays in disease pathogenesis, inhibition of RORγ activity and Th17 cell differentiation and activity, including IL17 production, will be of significant therapeutic benefit. It is therefore desirable to prepare compounds that inhibit RORγ activity and hence have utility in the treatment of inflammatory, autoimmune, metabolic, circadian effect, cancer, and other diseases mediated by RORγ, such as e.g., asthma, atopic dermatitis, acne, Crohn's disease, regional enteritis, ulcerative colitis, Sjögren's syndrome, uveitis, Behçet's disease, dermatomyositis, multiple sclerosis, ankylosing spondylitis, systemic lupus erythematosus, scleroderma, psoriasis, psoriatic arthritis, steroid resistant asthma and rheumatoid arthritis.

SUMMARY OF THE INVENTION

It has now been found that compounds described herein, and pharmaceutically acceptable compositions thereof, are effective inhibitors of RORγ (see e.g., Table 2). Such compounds include those of Formula (I):

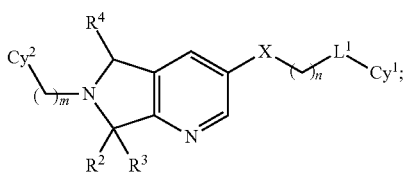

(I)

or a pharmaceutically acceptable salt thereof, wherein each of $R^2$, $R^3$, $R^4$, $X$, $L^1$, n, m, $Cy^1$, and $Cy^2$ are as defined and described herein.

The provided compounds, and pharmaceutically acceptable compositions thereof, are inverse agonists or antagonists of RORγ and are useful for treating a variety of diseases, disorders or conditions. Such diseases, disorders, or conditions include those described herein.

The provided compounds can be used alone (i.e., as a monotherapy) or in combination with one or more other therapeutic agent effective for treating any of the indications described herein.

DETAILED DESCRIPTION OF CERTAIN EMBODIMENTS

1. General Description of Compounds of the Invention

In certain embodiments, the present invention provides a compound of Formula (I):

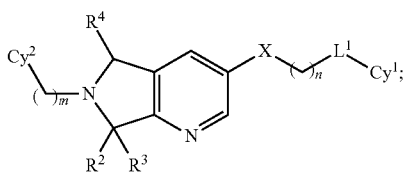

(I)

or a pharmaceutically acceptable salt thereof, wherein:
$R^2$ and $R^3$ are each independently hydrogen, hydroxy, monocyclic cycloalkyl, monocyclic heterocyclyl, or $(C_1-C_6)$alkyl, wherein the $(C_1-C_6)$alkyl is optionally substituted with 1 to 2 groups independently selected from hydroxy, halo, and cyano;
$R^4$ is hydrogen, $(C_1-C_3)$alkyl, or =O;
X is —C(O)NH— or —NHC(O)—;
m is 0, 1, or 2;
n is 0, 1, 2, or 3;
$L^1$ is absent or is $SO_2$ or $CR^7R^8$;

$Cy^1$ is absent or is selected from $(C_1-C_3)$alkyl, halo$(C_1-C_3)$alkyl, aryl, heteroaryl, heterocyclyl, and cycloalkyl, wherein the aryl, heteroaryl, heterocyclyl, and cycloalkyl are each optionally substituted with 1 to 3 groups independently selected from $R^5$;
$Cy^2$ is absent or is selected from $(C_1-C_6)$alkoxycarbonyl, phenyl$(C_1-C_3)$alkoxycarbonyl, halophenyl$(C_1-C_3)$alkoxycarbonyl, aryl, heteroaryl, monocyclic cycloalkyl, and monocyclic heterocyclyl, wherein the aryl, heteroaryl, monocyclic cycloalkyl, and moncyclic heterocyclyl are each optionally substituted with 1 to 3 groups independently selected from $R^6$;
$R^5$ and $R^6$ are each independently selected from halo, cyano, nitro, amino, hydroxy, carboxy, $(C_1-C_6)$alkyl, heterocyclyl, hydroxy$(C_1-C_6)$alkyl, $CO_2H$, $(CH_2)_{1-3}COOH$, $(C_1-C_3)$alkylcarbonyloxy, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkylsulfinyl, $(C_3-C_6)$cycloalkylsulfinyl, $(C_4-C_7)$cycloalkylsulfinyl, halo$(C_1-C_6)$alkylsulfonyl, halo$(C_3-C_6)$cycloalkylsulfinyl, halo$(C_4-C_7)$cycloalkylalkylsulfinyl, $(C_1-C_6)$alkylsulfonyl, $(C_3-C_6)$cycloalkylsulfonyl, $(C_4-C_7)$cycloalkylalkylsulfonyl, halo$(C_1-C_6)$alkylsulfonyl, halo$(C_3-C_6)$cycloalkylsulfonyl, halo$(C_4-C_7)$cycloalkylalkylsulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkyl-carbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, aryl, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, hydroxy$(C_1-C_6)$alkylcarbonyl, $(C_1-C_6)$alkylhydroxycarbonyl, $(C_1-C_6)$alkylhydroxy$(C_1-C_6)$alkyl, $(C_3-C_6)$cycloalkylcarbonyl, $(C_3-C_6)$cycloalkylaminocarbonyl, { $(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl, [$(C_1-C_6)$alkyl$(C_4-C_6)$heterocyclyl]$(C_1-C_6)$alkyl, and di$(C_3-C_6)$cycloalkylaminocarbonyl$(C_1-C_6)$alkyl; and
$R^7$ and $R^8$ are each independently hydrogen, hydroxy, $(C_1-C_3)$alkyl, hydroxy$(C_1-C_3)$alkyl, mono$(C_1-C_3)$alkylamino, di$(C_1-C_3)$alkylamino, $CO_2H$, $(CH_2)_{1-3}COOH$, monocyclic heterocyclyl, $(C_1-C_3)$alkoxycarbonyl, $(C_1-C_3)$alkyl$(C_1-C_3)$alkoxycarbonyl, halophenyl, halophenyl$(C_1-C_3)$alkyl, or quinolin-2(1H)one-4yl-methyl; or $R^7$ and $R^8$, together with the carbon atom to which they are attached, form a 3- to 6-membered cycloalkyl or heterocyclyl.

2. Compounds and Definitions

The terms "halo" and "halogen" as used herein refer to an atom selected from fluorine (fluoro, —F), chlorine (chloro, —Cl), bromine (bromo, —Br), and iodine (iodo, —I).

The term "alkyl", used alone or as a part of a larger moiety such as e.g., "haloalkyl", means a saturated monovalent straight or branched hydrocarbon radical having, unless otherwise specified, 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like. "Monovalent" means attached to the rest of the molecule at one point.

The term "haloalkyl" or "halocycloalkyl" include mono, poly, and perhaloalkyl groups where the halogens are independently selected from fluorine, chlorine, and bromine.

The terms "cycloalkyl" and "cycloaliphatic", used alone or as part of a larger moiety, refer to a saturated cyclic aliphatic monocyclic or bicyclic ring system, as described herein, having from, unless otherwise specified, 3 to 10 carbon ring atoms. Monocyclic cycloalkyl groups include, without limitation, cyclopropyl, cyclobutyl, cyclopentyl, cyclopentenyl, cyclohexyl, cyclohexenyl, cycloheptyl, cycloheptenyl, and cyclooctyl. It will be understood that when specified, optional substituents on a cycloalkyl or cycloaliphatic group may be present on any substitutable position and, include, e.g., the position at which the cycloalkyl or cycloaliphatic group is attached.

The term "carbocycle", "carbocyclyl", "carbocyclo", or "carbocyclic" used alone or as part of a larger moiety refer to saturated, partially saturated, or aromatic ring systems comprising all carbon atoms having, unless otherwise specified, a total of 3 to 10 ring members. It will be understood that when specified, optional substituents on a carbocycle, carbocyclyl, carbocyclo, or carbocyclic may be present on any substitutable position and, include, e.g., the position at which the cycloalkyl is attached.

The term "aryl" used alone or as part of a larger moiety as in "aralkyl", "aralkoxy", or "aryloxyalkyl", refers to an aromatic carbocyclic ring system having, unless otherwise specified, a total of 6 to 10 ring members. The term "aryl" may be used interchangeably with the term "aryl ring", "aryl group", "aryl moiety", or "aryl radical". In certain embodiments of the present disclosure, "aryl" refers to an aromatic ring system which includes, but is not limited to, phenyl (abbreviated as "Ph"), naphthyl and the like. It will be understood that when specified, optional substituents on an aryl group may be present on any substitutable position and, include, e.g., the position at which the aryl is attached.

The term "heteroaryl" used alone or as part of a larger moiety as in "heteroarylalkyl", "heteroarylalkoxy", or "heteroarylaminoalkyl", refers to a 5-10-membered aromatic radical containing 1-4 heteroatoms selected from N, O, and S and includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The term "heteroaryl" may be used interchangeably with the terms "heteroaryl ring", "heteroaryl group", or "heteroaromatic". The terms "heteroaryl" and "heteroar-", as used herein, also include groups in which a heteroaromatic ring is fused to one or more aryl rings, where the radical or point of attachment is on the heteroaromatic ring. Nonlimiting examples include indolyl, indazolyl, benzimidazolyl, benzthiazolyl, quinolyl, quinazolinyl, and quinoxalinyl. A heteroaryl group may be mono- or bicyclic. It will be understood that when specified, optional substituents on a heteroaryl group may be present on any substitutable position and, include, e.g., the position at which the heteroaryl is attached.

The term "heterocyclyl" means a 4-, 5-, 6- and 7-membered saturated or partially unsaturated heterocyclic ring containing 1 to 4 heteroatoms independently selected from N, O, and S. The terms "heterocycle", "heterocyclyl", "heterocyclyl ring", "heterocyclic group", "heterocyclic moiety", and "heterocyclic radical", are used interchangeably herein. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, terahydropyranyl, pyrrolidinyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, and tetrahydropyrimidinyl. A heterocyclyl group may be mono- or bicyclic. Unless otherwise specified, bicyclic heterocyclyl groups include, e.g., unsaturated heterocyclic radicals fused to another unsaturated heterocyclic radical or aromatic or heteroaryl ring, such as for example, tetrahydronaphthyridine, indolinone, dihydropyrrolotriazole, imidazopyrimidine, quinolinone, dioxaspirodecane. It will also be understood that when specified, optional substituents on a heterocyclyl group may be present on any substitutable position and, include, e.g., the position at which the heterocyclyl is attached.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity, i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule.

The compounds of the invention may be prepared as individual enantiomers by either enantio-specific synthesis or resolved from an enantiomerically enriched mixture. Conventional resolution techniques include forming the salt of a free base of each isomer of an enantiomeric pair using an optically active acid (followed by fractional crystallization and regeneration of the free base), forming the salt of the acid form of each enantiomer of an enantiomeric pair using an optically active amine (followed by fractional crystallization and regeneration of the free acid), forming an ester or amide of each of the enantiomers of an enantiomeric pair using an optically pure acid, amine or alcohol (followed by chromatographic separation and removal of the chiral auxiliary), or resolving an enantiomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, e.g., the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

3. Description of Exemplary Compounds

In a first embodiment, the present invention provides a compound of Formula (I),

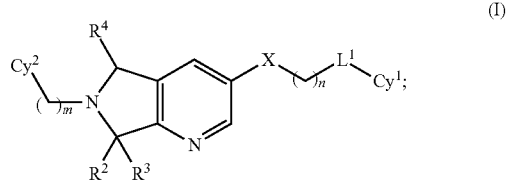

(I)

or a pharmaceutically acceptable salt thereof, wherein the variables are as described above.

In a second embodiment, the compound of Formula (I) is of Formula (II):

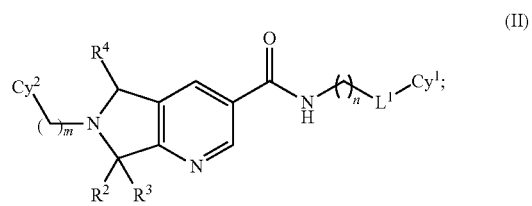

(II)

or a pharmaceutically acceptable salt thereof, wherein the variables in structural Formula (II) are as described for Formula (I).

In a third embodiment, the compound of Formula (I) is of Formula (III):

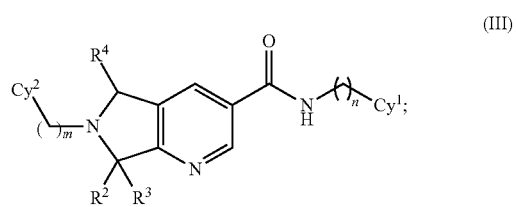

(III)

or a pharmaceutically acceptable salt thereof, wherein the variables in structural Formula (III) are as described for Formula (I).

In a fourth embodiment, the compound of Formula (I) is of Formula (IV):

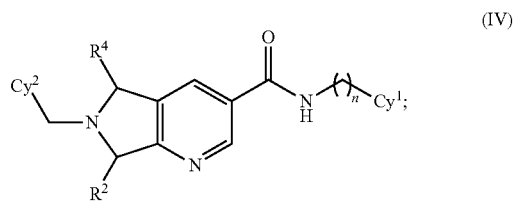

(IV)

or a pharmaceutically acceptable salt thereof, wherein the variables in structural Formula (IV) are as described for Formula (I).

In a fifth embodiment, the compound of Formula (I) is of Formula (V):

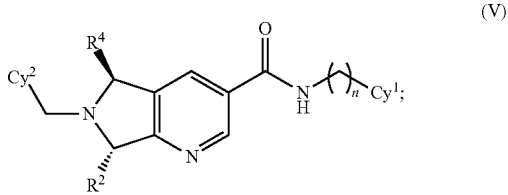

(V)

or a pharmaceutically acceptable salt thereof, wherein the variables in structural Formula (V) are as described for Formula (I).

In a sixth embodiment, the compound of Formula (I) is of Formula (VI):

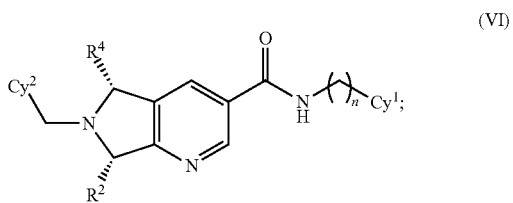

(VI)

or a pharmaceutically acceptable salt thereof, wherein the variables in structural Formula (VI) are as described for Formula (I).

In a seventh embodiment, the compound of Formula (I) is of Formula (VII):

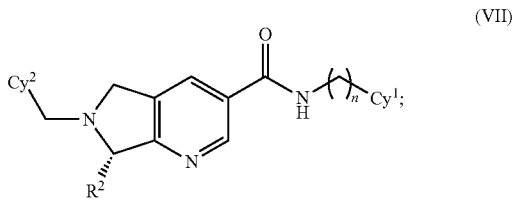

(VII)

or a pharmaceutically acceptable salt thereof, wherein the variables in structural Formula (VII) are as described for Formula (I).

In an eighth embodiment, $R^2$ and $R^3$ in Formulas (I) to (VII) are each independently hydrogen, hydroxy, or $(C_1-C_3)$ alkyl, wherein the remainder of the variables are as described in Formula (I).

In a ninth embodiment, $Cy^2$ in Formulas (I) to (VII) is present and is selected from aryl, heteroaryl, monocyclic cycloalkyl, and monocyclic heterocyclyl, each of which is optionally substituted with 1 to 2 groups independently selected from $R^6$, wherein the remainder of the variables are as described in Formula (I) or the eighth embodiment.

In a tenth embodiment, $Cy^2$ in Formulas (I) to (VII) is phenyl, pyrimidinyl, cyclohexyl, or pyridinyl, each of which are optionally substituted with 1 to 2 groups independently selected from $R^6$, wherein the remainder of the variables are as described in Formula (I) and the eighth or ninth embodiment.

In an eleventh embodiment, $Cy^1$ in Formulas (I) to (VII) is phenyl, piperidinyl, tetrahydro-2H-thiopyranyl 1,1-dioxide, pyridinyl, piperazinyl, azetidinyl, imidazolyl, tetrahydropyranyl, 1,4-dioxanyl, pyridazinyl, pyrazolyl, pyrrolidinyl, cyclohexyl, morpholinyl, 6,7-dihydro-5H-pyrrolo[2,1-c][1,2,4]triazolyl, 1,2,3,4-tetrahydro-1,8-naphthyridinyl, 2,3-dihydro-1H-indenyl, or imidazo[1,2-a]pyrimidinyl, each of which is optionally substituted with 1 to 2 groups independently selected from $R^5$, wherein the remainder of the variables are as described in Formula (I) and the eighth, ninth, or tenth embodiment.

In a twelfth embodiment, $Cy^1$ in Formulas (I) to (VII) is phenyl, piperidinyl, tetrahydro-2H-thiopyranyl 1,1-dioxide, pyridinyl, piperazinyl, azetidinyl, imidazolyl, tetrahydropyranyl, 1,4-dioxanyl, pyridazinyl, pyrazolyl, pyrrolidinyl, cyclohexyl, morpholinyl, 6,7-dihydro-5H-pyrrolo[2,1-c][1,2,4]triazolyl, 1,2,3,4-tetrahydro-1,8-naphthyridinyl, 2,3-dihydro-1H-indenyl, or imidazo[1,2-a]pyrimidinyl, each of which is optionally substituted with 1 to 2 groups independently selected from $R^5$, wherein at least one $R^5$ is $(C_1-C_3)$ alkylsulfonyl or $(C_1-C_3)$alkylaminosulfonyl, and wherein the remainder of the variables are as described in Formula (I) and the eighth, ninth, tenth, or eleventh embodiment.

In a thirteenth embodiment, $R^2$ in Formulas (I) to (VII) is $(C_1-C_3)$alkyl; n is 1 or 2; and $Cy^1$ is phenyl, pyridinyl, or piperidinyl, each of which is optionally substituted with 1 to 2 groups independently selected from $R^5$, wherein at least one $R^5$ is $(C_1-C_3)$alkylsulfonyl or $(C_1-C_3)$alkylaminosulfonyl, and wherein the remainder of the variables are as described in Formula (I) and the eighth, ninth, tenth, eleventh, or twelfth embodiment.

In a fourteenth embodiment, $Cy^2$ in Formulas (I) to (VII) is cyclohexyl optionally substituted with 1 to 2 groups independently selected from $R^6$, wherein the remainder of the variables are as described in Formula (I) and the eighth, ninth, tenth, eleventh, twelfth, or thirteenth embodiment.

In a fifteenth embodiment, $R^5$ is selected from halo, $(C_1-C_3)$alkyl, halo$(C_1-C_3)$alkyl, cyano, hydroxy$(C_1-C_3)$alkyl, $(C_1-C_3)$alkoxycarbonyl, $(C_1-C_3)$alkylsulfonyl, $(C_1-C_3)$alkoxy, halo$(C_1-C_3)$alkoxy, oxo, hydroxy, $(C_1-C_3)$alkylcarbonyl, hydroxy$(C_1-C_3)$alkylcarbonyl, $(C_1-C_3)$alkylhydroxycarbonyl, $(C_1-C_3)$alkylaminosulfonyl, $(C_1-C_3)$alkylaminocarbonyl, di$(C_1-C_3)$alkylamino$(C_2-C_6)$alkoxy, $(C_1-C_6)$alkoxycarbonyl, [$(C_1-C_3)$alkyl$(C_4-C_6)$heterocyclyl]$(C_1-C_3)$alkyl, and $(C_1-C_3)$alkylhydroxy$(C_1-C_3)$alkyl; and $R^6$ is selected from halo, $(C_1-C_3)$alkyl, halo$(C_1-C_3)$alkyl, cyano, hydroxy$(C_1-C_3)$alkyl, $(C_1-C_3)$alkoxycarbonyl, $(C_1-C_3)$alkylsulfonyl, $(C_1-C_3)$alkoxy, halo$(C_1-C_3)$alkoxy, oxo, hydroxy, aryl$(C_1-C_3)$alkoxycarbonyl, $(C_1-C_3)$alkylhydroxy$(C_1-C_3)$alkyl, heteroaryl, and $(C_1-C_3)$alkoxycarbonyl, wherein the remainder of the variables are as described in Formula (I) and the eighth, ninth, tenth, eleventh, twelfth, thirteenth, or fourteenth embodiment.

Alternatively, $R^5$ is selected from halo, $(C_1-C_3)$alkoxy, hydroxy, $(C_1-C_3)$alkyl, hydroxy$(C_1-C_3)$alkyl, halo$(C_1-C_3)$alkyl, $(C_1-C_6)$alkoxycarbonyl, di$(C_1-C_3)$alkylamino$(C_2-C_6)$alkoxy, [$(C_1-C_3)$alkyl$(C_4-C_6)$heterocyclyl]$(C_1-C_3)$alkyl, oxo, $(C_1-C_3)$alkylcarbonyl, $(C_1-C_3)$alkylaminosulfonyl, $(C_1-C_3)$alkylsulfonyl, and cyano; and $R^6$ is selected from halo$(C_1-C_3)$alkyl, $(C_1-C_3)$alkoxy, halo, cyano, $(C_1-C_3)$alkoxycarbonyl, $(C_1-C_3)$alkylhydroxy$(C_1-C_3)$alkyl, 2-methyl-2H-tetrazolyl, hydroxy$(C_1-C_3)$alkyl, and halo$(C_1-C_3)$alkoxy, wherein the remainder of the variables are as described in Formula (I) and the eighth, ninth, tenth, eleventh, twelfth, thirteenth, or fourteenth embodiment. In another alternative, $R^5$ is selected from halo, cyano, $(C_1-C_3)$alkyl, $(C_1-C_3)$alkylaminosulfonyl, and $(C_1-C_3)$alkylsulfonyl; and $R^6$ is selected from halo$(C_1-C_3)$alkyl, $(C_1-C_3)$alkoxy, halo, cyano, $(C_1-C_3)$alkoxycarbonyl, 2-methyl-2H-tetrazolyl, and halo$(C_1-C_3)$alkoxy, wherein the remainder of the variables are as described in Formula (I) and the eighth, ninth, tenth, eleventh, twelfth, thirteenth, or fourteenth embodiment.

In a sixteenth embodiment, $Cy^1$ in Formulas (I) to (VII) is

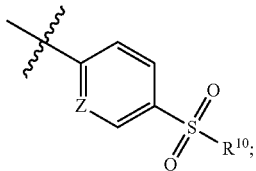

$R^{10}$ is $(C_1-C_3)$alkyl or $(C_1-C_3)$alkylamino; and Z is CH or N, wherein the remainder of the variables are as described in Formula (I) and the eighth, ninth, tenth, eleventh, twelfth, thirteenth, fourteenth, or fifteenth embodiment.

In an seventeenth embodiment, $Cy^2$ in Formulas (I) to (VII) is

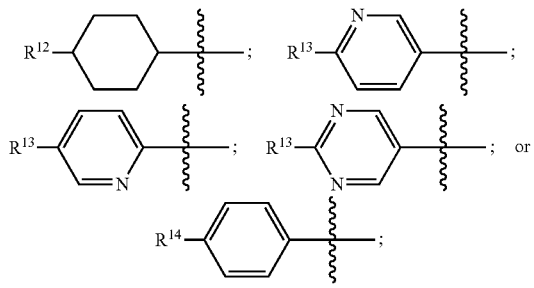

$R^{12}$ is $(C_1-C_3)$alkoxycarbonyl, halo, dihalo, $(C_1-C_3)$alkoxy, or halo$(C_1-C_3)$alkyl; $R^{13}$ is halo or halo$(C_1-C_3)$alkyl; and $R^{14}$ is halo, cyano, halo$(C_1-C_3)$alkyl, halo$(C_1-C_3)$alkoxy, or 2-methyl-2H-tetrazolyl, wherein the remainder of the variables are as described in Formula (I) and the eighth, ninth, tenth, eleventh, twelfth, thirteenth, fifteenth, or sixteenth embodiment.

In an eighteenth embodiment, $R^{12}$ to $R^{14}$ are each $CF_3$, wherein the remainder of the variables are as described in Formula (I) and the eighth, ninth, tenth, eleventh, twelfth, thirteenth, fifteenth, sixteenth, or seventeenth embodiment.

In a nineteenth embodiment, $R^2$ in Formulas (I) to (VII) is isopropyl and the remainder of the variables are as described in Formula (I) and the eighth, ninth, tenth, eleventh, twelfth, thirteenth, fourteenth, fifteenth, sixteenth, seventeenth, or eighteenth embodiment.

In a twentieth embodiment, the compound of Formula (I) is of Formula (X):

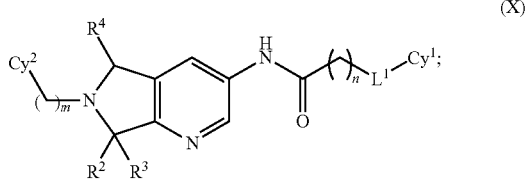

(X)

or a pharmaceutically acceptable salt thereof, wherein $L^1$ is absent; $Cy^1$ is phenyl optionally substituted with $SO_2(C_1-C_3)$alkyl or $SO_2(C_1-C_3)$alkylamino; n is 0 or 1; $R^4$ is hydrogen or $(C_1-C_3)$alkyl; $R^2$ and $R^3$ are each independently hydrogen or $(C_1-C_6)$alkyl; m is 0 or 1; and $Cy^2$ is phenyl or cyclohexyl, each optionally substituted with halo$(C_1-C_3)$alkyl, $(C_1-C_3)$alkyl, halo, or CN.

Specific examples of compounds of the invention are provided in the EXEMPLIFICATION. Pharmaceutically acceptable salts as well as the neutral forms of these compounds are included in the invention.

In certain embodiments, the present invention provides a method of treating a patient (e.g., a human) with a disorder mediated by RORγ comprising the step of administering to the patient an effective amount of the compound with any compound described herein, or a pharmaceutically acceptable salt or composition thereof.

4. Uses, Formulation and Administration

Pharmaceutically Acceptable Compositions

According to another embodiment, the present invention provides a method of treating a subject (e.g., a human) with a disorder mediated by RORγ using a composition comprising a compound of Formula (I) and a pharmaceutically acceptable carrier, adjuvant, or vehicle. In certain embodiments, the amount of compound of Formula (I) in a provided composition is such that it is effective as an inverse agonist or antagonist to RORγ in a biological sample or in a subject. In certain embodiments, a provided composition is formulated for administration to a subject in need of such composition. In some embodiments, a provided composition is formulated for oral administration to a subject.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Uses of Compounds and Pharmaceutically Acceptable Compositions

Compounds and compositions described herein are generally useful for the inhibition of RORγ. Thus, in some embodiments, the present invention provides a method of treating inflammatory, metabolic and autoimmune diseases or disorders mediated by RORγ, comprising administering a provided compound or composition. More particularly, the compounds and compositions described herein act as inverse agonists or antagonists of RORγ.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

Diseases and conditions treatable according to the methods of the invention include, but are not limited to, inflammatory, metabolic and autoimmune diseases or disorders mediated by RORγ. These diseases and conditions include, for example, asthma, chronic obstructive pulmonary disease (COPD), bronchitis, allergic rhinitis, atopic dermatitis, contact dermatitis, acne, cystic fibrosis, allograft rejection, multiple sclerosis, scleroderma, arthritis, rheumatoid arthritis, juvenile rheumatoid arthritis, osteoarthritis, ankylosing spondylitis, systemic lupus erythematosus (SLE), psoriasis, Hashimoto's disease, pancreatitis, autoimmune diabetes, type I diabetes, autoimmune ocular disease, ulcerative colitis, Crohn's disease, regional enteritis, inflammatory bowel disease (IBD), inflammatory bowel syndrome (IBS), Sjögren's syndrome, optic neuritis, obesity, hepatosteatosis, adipose tissue-associated inflammation, insulin resistance, type II diabetes, neuromyelitis optica, myasthenia gravis, age related macular degeneration, dry eye, uveitis, Guillain-Barré syndrome, psoriasis, psoriatic arthritis (PsA), steroid resistant asthma, Graves' disease, scleritis, endometriosis, obstructive sleep apnea syndrome (OSAS), Behçet's disease, dermatomyositis, polymyocitis, graft versus host disease, primary biliary cirrhosis, liver fibrosis, non-alcoholic fatty liver disease (NAFLD), sarcoidosis, primary sclerosing cholangitis, autoimmune thyroid disease, autoimmune polyendocrine syndrome type I, autoimmune polyendocrine syndrome type II, celiac disease, neuromyelitis, juvenile idiopathic arthritis, systemic sclerosis, myocardial infarction, pulmonary hypertension, osteoarthritis, cutaneous leishmaniasis, sinonasal polyposis, and cancer, including but not limited to lung cancer, gastric cancer, breast cancer and colon cancer.

Also included are diseases or disorders which are implicated by the regulation of the circadian rhythm of individuals and include, e.g., major depression, seasonal affective disorder, post-traumatic stress disorder (PTSD), bipolar disorder, autism, epilepsy, Alzheimer's disease and other central nervous system (CNS) disorders associated with altered sleep and/or circadian rhythms.

In one embodiment, a human patient is treated with a compound of Formula (I) and a pharmaceutically acceptable carrier, adjuvant, or vehicle, wherein said compound is present in an amount to treat or ameliorate one or more of the diseases and conditions recited above. In an alternative embodiment, the diseases and conditions treated or ameliorated by a compound of Formula (I) include, e.g., asthma, atopic dermatitis, acne, Crohn's disease, regional enteritis, ulcerative colitis, Sjögren's syndrome, uveitis, Behçet's disease, dermatomyositis, multiple sclerosis, ankylosing spondylitis, systemic lupus erythematosus (SLE), scleroderma, psoriasis, psoriatic arthritis (PsA), steroid resistant asthma and rheumatoid arthritis in the patient.

The invention further relates to a combination therapy for treating or ameliorating a disease or a disorder described herein. In some embodiments, the combination therapy comprises administering at least one compound represented by Structural Formula I in combination with one or more agents for treating or ameliorating inflammatory, metabolic and autoimmune diseases or disorders mediated by RORγ. In some embodiments, the combination therapy comprises administering at least one compound represented by Structural Formula I in combination with one or more agents for the treatment of diseases including asthma, chronic obstructive pulmonary disease (COPD), bronchitis, allergic rhinitis, atopic dermatitis, contact dermatitis, acne, cystic fibrosis, allograft rejection, multiple sclerosis, scleroderma, arthritis, rheumatoid arthritis, juvenile rheumatoid arthritis, osteoarthritis, ankylosing spondylitis, systemic lupus erythematosus (SLE), psoriasis, Hashimoto's disease, pancreatitis, autoimmune diabetes, type I diabetes, autoimmune ocular disease, ulcerative colitis, Crohn's disease, regional enteritis, inflammatory bowel disease (IBD), inflammatory bowel syndrome (IBS), Sjögren's syndrome, optic neuritis, obesity, hepatosteatosis, adipose tissue-associated inflammation, insulin resistance, type II diabetes, neuromyelitis optica, myasthenia gravis, age related macular degeneration, dry eye, uveitis, Guillain-Barré syndrome, psoriasis, psoriatic arthritis (PsA), steroid resistant asthma, Graves' disease, scleritis, major depression, seasonal affective disorder, PTSD, bipolar disorder, autism, epilepsy, Alzheimer's, CNS disorders associated with altered sleep and/or circadian rhythms, endometriosis, obstructive sleep apnea syndrome (OSAS), Behçet's disease, dermatomyositis, polymyocitis, graft versus host disease, primary biliary cirrhosis, liver fibrosis, non-alcoholic fatty liver disease (NAFLD), sarcoidosis, primary sclerosing cholangitis, autoimmune thyroid disease, autoimmune polyendocrine syndrome type I, autoimmune polyendocrine syndrome type II, celiac disease, neuromyelitis, juvenile idiopathic arthritis, systemic sclerosis, myocardial infarction, pulmonary hypertension, osteoarthritis, cutaneous leishmaniasis, sinonasal polyposis, and cancer, including but not limited to, lung cancer, gastric cancer, breast cancer and colon cancer.

The compounds according to the invention may also be used in combination with immunotherapies for the treatment of a disease or disorder disclosed herein.

Combination therapy includes, e.g., co-administration of a compound of the invention and one or more other agents, sequential administration of a compound of the invention and one or more other agents, administration of a composition containing a compound of the invention and one or more other agents, or simultaneous administration of separate compositions containing a compound of the invention and one or more other agents.

The invention further provides a method of treating a subject, such as a human, suffering from one of the above-mentioned disorders or diseases.

The invention further relates to the use of provided compounds for the production of pharmaceutical compositions which are employed for the treatment and/or prophylaxis and/or amelioration of the diseases and disorders mentioned herein.

Compounds or compositions described herein may be administered using any amount and any route of administration effective for treating or lessening the severity of one or more of the diseases and conditions described herein. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

The term "biological sample", as used herein, includes, without limitation, cell cultures or extracts thereof; biopsied material obtained from a mammal or extracts thereof, and blood, saliva, urine, feces, semen, tears, or other body fluids or extracts thereof.

The amount of both, a provided compound and additional therapeutic agent (in those compositions which comprise an additional therapeutic agent as described above) that may be combined with the carrier materials to produce a single dosage form will vary depending upon the host treated and the particular mode of administration.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent.

The amount of additional therapeutic agent present in the compositions of this disclosure will be no more than the amount that would normally be administered in a composition comprising that therapeutic agent as the only active agent.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Description of Synthesis

The compounds of the present invention can be readily prepared according to the following reaction schemes and examples, or modifications thereof, using readily available starting materials, reagents and conventional synthesis procedures. Many of the reactions can also be carried out under microwave (MW) conditions or using conventional heating or utilizing other technologies such as solid phase reagents/scavengers or flow chemistry. In these reactions, it is also possible to make use of variants which are themselves known to those of ordinary skill in the art, but are not mentioned in greater detail. Furthermore, other methods for preparing compounds of the invention will be readily apparent to a person of ordinary skill in the art in light of the following reaction schemes and examples. In cases where synthetic intermediates and final products contain potentially reactive functional groups, for example amino, hydroxy, thiol and carboxylic acid groups, that may interfere with the desired reaction, it may be advantageous to employ protected forms of the intermediate. Methods for the selection, introduction and subsequent removal of protecting groups are well known to those skilled in the art. In the discussion below variables have the meanings indicated above unless otherwise indicated. The abbreviations used in these experimental details are listed below and additional ones should be known to a person skilled in the art of synthesis. In addition, one can refer to the following references for suitable methods of synthesis as described in March, Advanced Organic Chemistry, 3rd edition, John Wiley & Sons, 1985, Greene and Wuts, Protective Groups in Organic Synthesis, $2^{nd}$ edition, John Wiley & Sons, 1991, and Richard Larock, Comprehensive Organic Transformations, $4^{th}$ edition, VCH publishers Inc., 1989.

Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

Where NMR data are presented, spectra were obtained on a Varian 400 (400 MHz) or 300 (300 MHz) and are reported as ppm downfield from tetramethylsilane with number of proton, multiplicities and coupling constants indicated parenthetically along with reference to deuterated solvent.

The invention is illustrated by way of the following examples, in which the following abbreviations may be employed.

| Abbreviation | Meaning |
|---|---|
| ACN, MeCN, $CH_3CN$ | acetonitrile |
| AIBN | azobisisobutyronitrile |
| aq | aqueous |
| Boc | tert-butoxycarbonyl or t-butoxycarbonyl |
| brine | saturated aqueous NaCl |
| Cbz | benzyloxy carbonyl |

| Abbreviation | Meaning |
| --- | --- |
| $CeCl_3$ | ceric chloride |
| $Cs_2CO_3$ | cesium carbonate |
| CuI | cuprous iodide |
| DCM or $CH_2Cl_2$ | methylene chloride |
| DIEA | diisopropyl ethyl amine |
| DMF | dimethyl formamide |
| $DMS/Me_2S$ | dimethyl sulfide |
| DMSO | dimethyl sulfoxide |
| EDCI | 1-(3-dimethylaminopropyl)-3-ethylcarbodiimide hydrochloride |
| EtI | ethyl iodide |
| Et | ethyl |
| $Et_2O$ | ethyl ether |
| $Et_3SiH$ | triethylsilane |
| $Et_3N$ | triethylamine |
| EtOAc, EA, AcOEt | ethyl acetate |
| EtOH | ethanol |
| $FeCl_3$ | ferric chloride |
| h, hr | hour(s) |
| HATU | O-(7-azabenzotriazol-1-yl)-N,N,N',N'-tetramethyluronium-hexafluorophosphate |
| HBTU | O-benzotriazole-1-yl-N,N,N',N'-tetramethyluronium-hexafluorophosphate |
| HCl | hydrochloric acid |
| $H_2O$ | water |
| $H_2O_2$ | hydrogen peroxide |
| HPLC | high performance liquid chromatography |
| i-BuOCOCl | iso-butoxycarbonyl chloride |
| ICl | iodochloride |
| $K_2CO_3$ | potassium carbonate |
| $K_3PO_4$ | tripotassium phosphate |
| LC-MS | liquid chromatography-mass spectrometry |
| LDA | lithium diiisopropylamide |
| LiCl | lithium chloride |
| LiOH | lithium hydroxide |
| MCPBA, m-CPBA | meta-chloroperoxybenzoic acid |
| MeOH | methanol |
| MeI | methyl iodide |
| Me | methyl |
| mg | milligram |
| $MgSO_4$ | magnesium sulfate (anhydrous) |
| min | minute(s) |
| mL | milliliters |
| mmol | millimoles |
| mp, m.p. | melting point |
| MS | mass spectrometry |
| MW, uwave | microwave |
| $NaBH_4$ | sodium borohydride |
| $NaBH_3CN$ | sodium cyanoborohydride |
| NaH | sodium hydride |
| $NaHCO_3$ | sodium bicarbonate |
| NaOH | sodium hydroxide |
| NaOMe | sodium methoxide |
| $Na_2S_2O_3$ | sodium thiosulfate |
| $Na_2S_2O_5$ | sodium dithionate |
| $Na_2SO_4$ | sodium sulfate |
| $NH_4OH$ | ammonium hydroxide |
| $(NH_4)_2CO_3$ | ammonium carbonate |
| $NH_4Cl$ | ammonium chloride |
| $Na_2CO_3$ | sodium carbonate |
| $NaHCO_3$ | sodium bicarbonate |
| NaH | sodium hydride |
| NBS | N-bromosuccinimide |
| n-BuLi | n-butyllithium |
| NMM | N-methyl-morpholine |
| NMP | N-methyl-pyrrolidin-2-one |
| OTf | trifluoromethanesulfonate |
| OTs | tosylate |
| $PdCl_2dppf$ | [1,1-bis(diphenylphosphino)ferrocene]dichloropalladium(ii) |
| $Pd_2(dba)_3$ | tris(dibenzylideneacetone)dipalladium(0) |
| PE | petroleum ether |
| rt | room temperature |
| sat. | saturated |
| SFC | supercritical fluid chromatography |
| t-BuOK | potassium tert butoxide |
| t-BuLi | tert butyl lithium |
| t-BuOOH | tert butyl peroxide |
| TBAF | tetrabutylammonium fluoride |
| TFA | trifluoroacetic acid |
| THF | tetrahydrofuran |
| TLC | thin layer chromatography |
| $Ti(OEt)_4$ | titanium tetra ethoxide |
| Zn | zinc |
| $Zn(CN)_2$ | zinc cyanide |

Compounds according to Formula (I), can be prepared by reacting an intermediate compound of Formula (500) with an alkyl or aryl halide, according to reaction Scheme 1, a reaction that is performed in a polar aprotic solvent, such as, for example, acetonitrile, in the presence of a suitable base, such as, for example, N,N-diisopropylethylamine or potassium carbonate. Alternatively, the final compounds according to Formula (I), can be prepared by reacting an intermediate compound of Formula (500) with an aldehyde or ketone, according to reaction Scheme 1, following art-known reductive amination procedure, in the typical solvent, such as, for example, dichloroethane, dichloromethane, or methanol; in the presence of suitable reducing reagent, such as sodium cyanoborohydride or sodium triacetoxyborohydride. In reaction Scheme 1, all variables are defined as in Formula (I) and $G^1$ is a leaving group, such as for example, bromide, chloride, mesylate (methanesulfonate), tosylate (p-toluenesulfonate), or iodide.

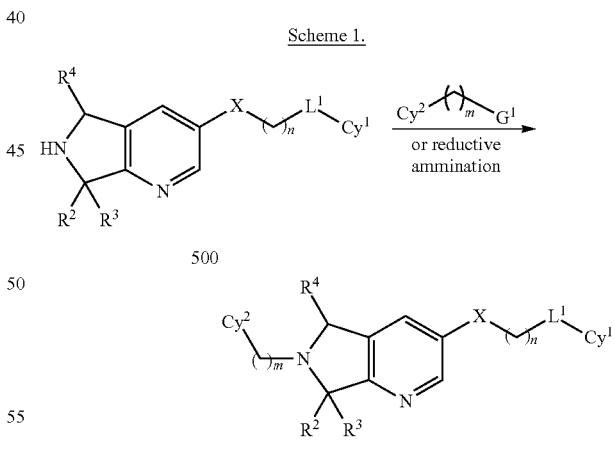

Scheme 1.

Intermediate compound of Formula (500) can be can be prepared by deprotecting an intermediate compound of Formula (501), wherein Pg is a suitable nitrogen protecting group (Greene and Wuts, Protective Groups in Organic Synthesis, $2^{nd}$ edition, John Wiley & Sons, 1991), e.g., Pg=tert-butoxycarbonyl, removed with trifluoroacetic acid according to Scheme 2. In reaction Scheme 2, all variables are defined as in Formula (I).

Scheme 2.

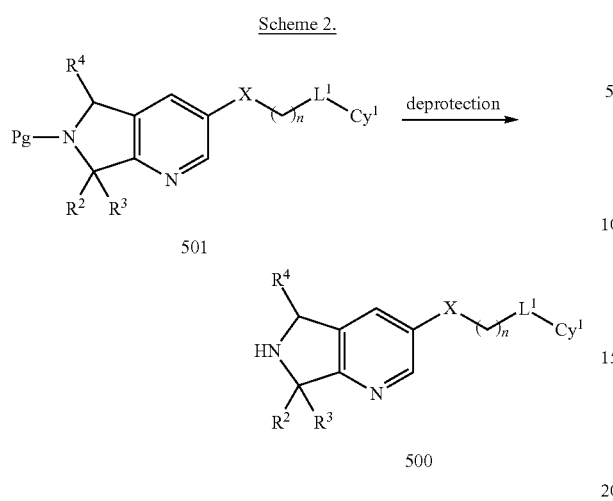

Scheme 4.

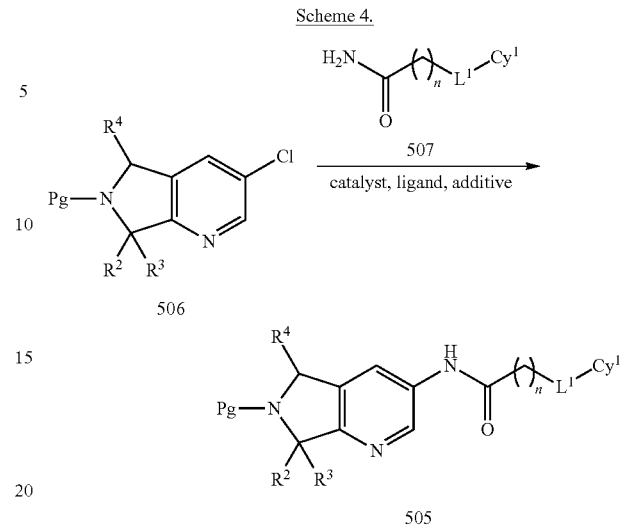

Intermediate compound of Formula (502), wherein X is C(=O)NH, can be prepared from a carboxylic acid (504) and an amine (503), according to Scheme 3. The reaction is conveniently carried out in the presence of an activating reagent, for example, N-(3-dimethylaminopropyl)-N'-ethylcarbodiimide hydrochloride (EDCI) or O-(7-azabenzotriazol-1-yl)-N,N,N',N'-tetramethyluronium hexafluorophosphate (HATU), in an organic solvent, for example, N,N-dimethylformamide or dichloromethane, optionally in the presence of a base, e.g., N,N-diisopropylethylamine or triethylamine, at a temperature, for example in the range from 0 to 60° C.

Preparation of Intermediates

As a representative example, intermediate compound of Formula (504) wherein $R^4$ is H, $R^2$ is isopropyl, $R^3$ is H and Pg is tert-butoxycarbonyl, can be prepared by following the reaction steps shown in Scheme 5. An intermediate compound of Formula (504) with variables $R^4$, $R^2$ and $R^3$ can be prepared readily according to Scheme 5, or modifications thereof, using readily available starting materials and reagents.

Scheme 3.

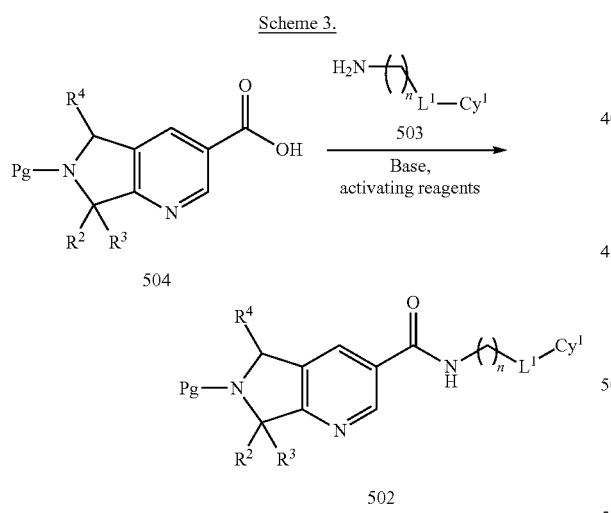

Scheme 5.

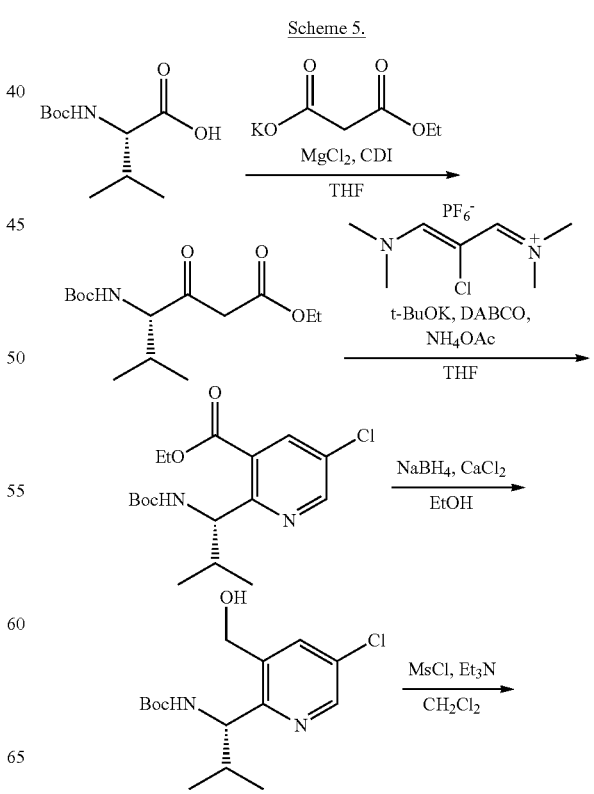

Intermediate compound of Formula (505), wherein X is NHC=O, can be prepared from an intermediate compound of Formula (506) and an amide (507), according to Scheme 4. The reaction is carried out in the presence of a catalyst, for example, tris(dibenzylideneacetone)dipalladium (0) (Pd$_2$(dba)$_3$), in an organic solvent, for example, dioxane or tert-butanol, in the presence of an additive, e.g., potassium phosphate, at a temperature, for example, in the range from 80 to 150° C.

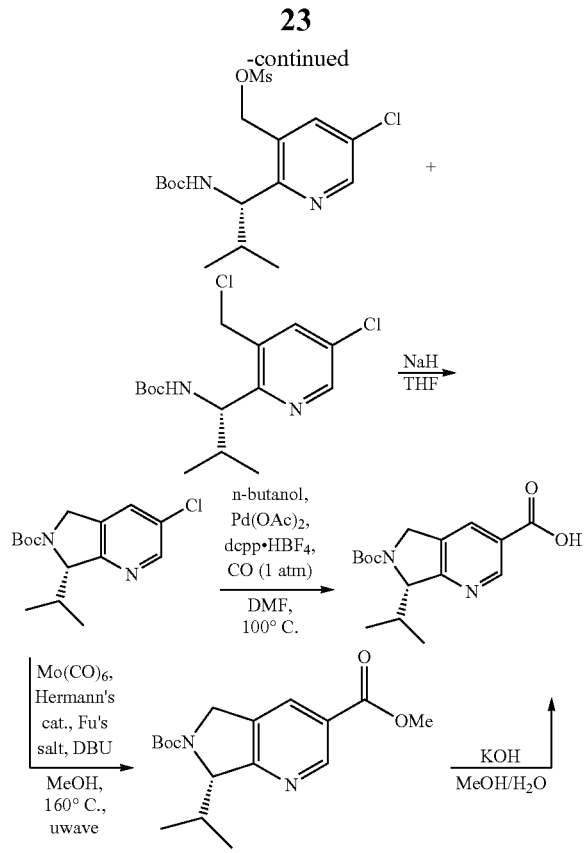

To a stirred solution of compound Boc-Val-OH (3.11 g, 14.3 mmol) in THF (40 mL) at rt was added 1,1'-carbonyldiimidazole (3.48 g, 21.5 mmol). The mixture was stirred at rt for 1 h, then magnesium chloride (1.36 g, 14.3 mmol) and ethyl potassium malonate (2.44 g, 14.3 mmol) were added successively. The mixture was then heated to 50° C. and stirred for 15 h. The mixture was cooled to rt and quenched with 1 N HCl (100 mL). The aqueous phase was extracted with EtOAc (3×100 mL), then the combined organic layer was washed with brine (50 mL). The organic layer was dried over anhydrous MgSO$_4$, filtered and concentrated under reduced pressure. The residue was purified by silica gel chromatography (eluting with 5% EtOAc in hexanes) to afford ethyl (S)-4-((tert-butoxycarbonyl)amino)-5-methyl-3-oxohexanoate (3.53 g, 86% yield) as a yellow oil. LC-MS $t_R$=0.91 min in 1 min chromatography, MS (ESI) m/z 288.3 [M+H]$^+$. $^1$H NMR (CDCl$_3$, 400 MHz): δ 5.08 (d, J=8.4 Hz, 1H), 4.33 (dd, J=4.4 Hz, 8.8 Hz, 1H), 4.20 (q, J=7.2 Hz, 2H), 3.54 (s, 2H), 2.27-2.17 (m, 1H), 1.44 (s, 9H), 1.27 (t, J=7.2 Hz, 3H), 1.01 (d, J=6.8 Hz, 3H), 0.82 (d, J=6.8 Hz, 3H).

To a mixture of ethyl (S)-4-((tert-butoxycarbonyl)amino)-5-methyl-3-oxohexanoate (9.68 g, 33.7 mmol) from above in THF (100 mL) at 0° C. was added potassium tert-butoxide (3.78 g, 35.4 mmol). The mixture was warmed to rt and stirred for 45 min, at which point 1,4-diazabicyclo[2.2.2]octane (3.78 g, 33.7 mmol) and 2-chloro-1,3-bis(dimethylamino)trimethinium hexaflurophosphate (15.5 g, 50.5 mmol) were added successively. The mixture was heated to 45° C. and stirred for 3 h, at which point ammonium acetate (5.19 g, 67.4 mmol) was added. The mixture was then heated to reflux and stirred for 15 h. It was then cooled to rt and concentrated under reduced pressure. The residue was dry-loaded onto a silica gel column and purified (eluting with 5% EtOAc in hexanes, gradient to 15%) to yield 6.09 g of ethyl (S)-2-(1-((tert-butoxycarbonyl)amino)-2-methylpropyl)-5-chloronicotinate (51%). LC-MS $t_R$=1.14 min in 1 min chromatography, MS (ESI) m/z 357.3 [M+H]$^+$. $^1$H NMR (CDCl$_3$, 400 MHz): δ 8.61 (d, J=2.4 Hz, 1H), 8.18 (d, J=2.8 Hz, 1H), 5.71 (d, J=9.6 Hz, 1H), 5.62 (dd, J=5.2 Hz, 9.6 Hz, 1H), 4.42 (q, J=7.2 Hz, 2H), 2.08-2.00 (m, 1H), 1.42 (s, 9H), 1.42 (t, J=7.2 Hz, 3H), 0.93 (d, J=6.4 Hz, 3H), 0.83 (d, J=6.4 Hz, 3H).

To a stirred solution of ethyl (S)-2-(1-((tert-butoxycarbonyl)amino)-2-methylpropyl)-5-chloronicotinate (6.09 g, 17.1 mmol) at 0° C. in EtOH (70 mL) was added sodium borohydride (1.30 g, 34.1 mmol). Calcium chloride (1.89 g, 17.1 mmol) was added portionwise while maintaining the temperature between 0° C. and 5° C. The resulting mixture was stirred at 0° C. for 90 min, then quenched slowly at 0° C. with saturated aqueous ammonium chloride solution (100 mL). The aqueous phase was extracted with EtOAc (3×100 mL), then the combined organic layer was washed with brine (50 mL), dried over anhydrous MgSO$_4$, filtered and concentrated under reduced pressure. Crude tert-butyl (S)-(1-(5-chloro-3-(hydroxymethyl)pyridin-2-yl)-2-methylpropyl)carbamate was carried forward without any purification. LC-MS $t_R$=0.94 min in 1 min chromatography, MS (ESI) m/z 315.3 [M+H]$^+$. $^1$H NMR (CDCl$_3$, 400 MHz): δ 8.46 (d, J=2.4 Hz, 1H), 7.67 (d, J=2.8 Hz, 1H), 5.34 (d, J=9.2 Hz, 1H), 4.99 (dd, J=2.0 Hz, 8.4 Hz, 1H), 4.54 (t, J=9.2 Hz, 1H), 4.41 (dd, J=10.0 Hz, 12.4 Hz, 1H), 4.33 (d, J=10.0 Hz, 1H), 2.18-2.12 (m, 1H), 1.36 (s, 9H), 1.10 (d, J=6.4 Hz, 3H), 0.69 (d, J=6.8 Hz, 3H).

To a solution of tert-butyl (S)-(1-(5-chloro-3-(hydroxymethyl)pyridin-2-yl)-2-methylpropyl)carbamate (5.33 g, 16.9 mmol) in CH$_2$Cl$_2$ (70 mL) at 0° C. was added triethylamine (3.54 mL, 25.4 mmol) and methanesulfonyl chloride (1.44 mL, 18.6 mmol). The mixture was warmed to rt and stirred for 3 h, at which point it was quenched with saturated aqueous sodium bicarbonate solution (100 mL). The aqueous phase was extracted with ethyl acetate (3×100 mL). The combined organic layer was washed with brine (50 mL), dried over anhydrous MgSO$_4$, filtered and concentrated under reduced pressure. The crude residue (a 3:1 mixture of (S)-(2-(1-((tert-butoxycarbonyl)amino)-2-methylpropyl)-5-chloropyridin-3-yl)methyl methanesulfonate and tert-butyl (S)-(1-(5-chloro-3-(chloromethyl)pyridin-2-yl)-2-methylpropyl)carbamate) was carried forward without any purification. LC-MS $t_R$=1.01 min in 1 min chromatography, MS (ESI) m/z 393.3 [M+H]$^+$. $^1$H NMR (CDCl$_3$, 400 MHz): δ 8.53 (d, J=2.4 Hz, 1H), 7.74 (d, J=2.8 Hz, 1H), 5.44 (d, J=12.4 Hz, 1H), 5.37 (d, J=12.8 Hz, 1H), 5.31 (d, J=8.4 Hz, 1H), 4.59 (t, J=9.2 Hz, 1H), 3.13 (s, 3H), 2.13-2.04 (m, 1H), 1.36 (s, 9H), 1.03 (d, J=6.8 Hz, 3H), 0.77 (d, J=6.8 Hz, 3H). Characterization data from a purified sample of (S)-(2-(1-((tert-butoxycarbonyl)amino)-2-methylpropyl)-5-chloropyridin-3-yl)methyl methanesulfonate.

To a solution of (S)-(2-(1-((tert-butoxycarbonyl)amino)-2-methylpropyl)-5-chloropyridin-3-yl)methyl methanesulfonate and tert-butyl (S)-(1-(5-chloro-3-(chloromethyl)pyridin-2-yl)-2-methylpropyl)carbamate (3:1 mixture, 6.39 g, 16.9 mmol) in THF (75 mL) at 0° C. was added sodium hydride (60% dispersion in mineral oil, 811 mg, 20.3 mmol). The mixture was warmed to rt and stirred for 15 h, at which point it was quenched with saturated aqueous ammonium chloride solution (100 mL). The aqueous phase was extracted with ethyl acetate (3×100 mL). The combined organic layer was washed with brine (50 mL), dried over anhydrous MgSO$_4$, filtered and concentrated under reduced pressure. The residue was purified by silica gel chromatography (eluting with 5% EtOAc in hexanes, gradient to 10%)

to give tert-butyl (S)-3-chloro-7-isopropyl-5,7-dihydro-6H-pyrrolo[3,4-b]pyridine-6-carboxylate (4.31 g, 85% yield over 3 steps) as a yellow oil. LC-MS $t_R$=1.12 min in 1 min chromatography, MS (ESI) m/z 297.3 [M+H]$^+$. $^1$H NMR (CDCl$_3$, 400 MHz, mixture of rotamers): δ 8.43 (s, 1H), 7.56 (s, 0.6H), 7.50 (s, 0.4H), 4.96 (s, 0.4H), 4.87 (s, 0.6H), 4.86 (d, J=16.0 Hz, 0.6H), 4.74 (d, J=15.6 Hz, 0.4H), 4.52 (d, J=12.0 Hz, 0.4H), 4.49 (d, J=15.2 Hz, 0.6H), 2.60-2.51 (m, 0.4H), 2.40-2.36 (m, 0.6H), 1.49 (s, 9H), 1.08 (d, J=7.2 Hz, 1.2H), 0.99 (d, J=7.2 Hz, 1.8H), 0.78 (d, J=6.8 Hz, 1.8H), 0.72 (d, J=6.8 Hz, 1.2H).

Potassium carbonate (758 mg, 5.49 mmol) and 4 Å molecular sieves (250 mg) were placed in a 50 mL round-bottom flask which was then flame dried. Palladium (II) acetate (32.8 mg, 146 μmol) and 1,3-bis(dicyclohexylphosphonium)propane bis (tetrafluoroborate) (179 mg, 292 μmol) were added to the flask, which was then sealed with a septum. Tert-butyl (S)-3-chloro-7-isopropyl-5,7-dihydro-6H-pyrrolo[3,4-b]pyridine-6-carboxylate (1.09 g, 3.66 mmol) was dissolved in DMF (12 mL) and added to the flask, followed by 1-butanol (3.34 mL, 36.6 mmol). The flask was then evacuated and backfilled with CO three times, with the final time under a balloon of 1 atm of CO. The flask was heated to 100° C. and stirred for 6 h. The mixture was then cooled to rt and quenched with 1 N NaOH (25 mL). The mixture was stirred for 30 min, at which point isopropyl acetate (50 mL) was added. The phases were separated, then the organic phase was extracted with 1 N NaOH (2×50 mL), then the combined aqueous layer was acidified to pH=2 with concentrated HCl. The aqueous layer was then extracted with EtOAc (3×25 mL), then the combined organic layer was dried over anhydrous MgSO$_4$, filtered and concentrated under reduced pressure. The crude residue (S)-6-(tert-butoxycarbonyl)-7-isopropyl-6,7-dihydro-5H-pyrrolo[3,4-b]pyridine-3-carboxylic acid was carried forward without any purification.

Alternative two-step procedure for (S)-6-(tert-butoxycarbonyl)-7-isopropyl-6,7-dihydro-5H-pyrrolo[3,4-b]pyridine-3-carboxylic acid: To a solution of tert-butyl (S)-3-chloro-7-isopropyl-5,7-dihydro-6H-pyrrolo[3,4-b]pyridine-6-carboxylate (158 mg, 532 μmol) in MeOH (2.5 mL) in a MW vial was added molybdenum hexacarbonyl (155 mg, 587 μmol) and 1,8-diazabicyclo[5.4.0]undec-7-ene (279 μL, 1.86 mmol). The mixture was degassed with N$_2$ for 15 min, at which point trans-bis(acetate)bis[o-(di-o-tolylphosphino)benzyl]dipalladium (II) (25.0 mg, 26.6 μmol) and tri-tert-butylphosphonium tetrafluoroborate (30.9 mg, 107 μmol) were added. The vial was sealed and heated in the MW at 160° C. for 20 min. After cooling to rt, the mixture was filtered through Celite with MeOH and concentrated under reduced pressure. The residue was purified by silica gel chromatography (eluting with 10% EtOAc in hexanes, gradient to 25%) to afford 70.7 mg of 6-(tert-butyl) 3-methyl (S)-7-isopropyl-5,7-dihydro-6H-pyrrolo[3,4-b]pyridine-3,6-dicarboxylate (41% yield). LC-MS $t_R$=1.04 min in 1 min chromatography, MS (ESI) m/z 321.4 [M+H]$^+$. $^1$H NMR (CDCl$_3$, 400 MHz, mixture of rotamers): δ 9.10 (s, 1H), 8.17 (s, 0.6H), 8.13 (s, 0.4H), 5.05 (s, 0.4H), 4.95 (s, 0.6H), 4.90 (d, J=15.6 Hz, 0.6H), 4.79 (d, J=15.6 Hz, 0.4H), 4.58 (d, J=11.2 Hz, 0.4H), 4.54 (d, J=15.6 Hz, 0.6H), 3.96 (s, 3H), 2.62-2.53 (m, 0.4H), 2.45-2.38 (m, 0.6H), 1.52 (s, 9H), 1.09 (d, J=6.8 Hz, 1.2H), 0.99 (d, J=7.2 Hz, 1.8H), 0.79 (d, J=6.8 Hz, 1.8H), 0.72 (d, J=6.8 Hz, 1.2H).

To a solution of 6-(tert-butyl) 3-methyl (S)-7-isopropyl-5,7-dihydro-6H-pyrrolo[3,4-b]pyridine-3,6-dicarboxylate (70.7 mg, 221 μmol) in MeOH was added potassium hydroxide (5.9 M solution in H$_2$O, 187 μL, 1.10 mmoL). The mixture was stirred at 40° C. for 1 h, at which point it was cooled to rt and partitioned between diethyl ether (25 mL) and 1 N NaOH (25 mL). The organic phase was extracted with 1 N NaOH (2×25 mL), then the combined aqueous layer was acidified to pH=2 with concentrated HCl. The aqueous layer was then extracted with EtOAc (3×25 mL), then the combined organic layer was dried over anhydrous MgSO$_4$, filtered and concentrated under reduced pressure. The crude residue (S)-6-(tert-butoxycarbonyl)-7-isopropyl-6,7-dihydro-5H-pyrrolo[3,4-b]pyridine-3-carboxylic acid was carried forward without any purification. LC-MS $t_R$=0.93 min in 1 min chromatography, MS (ESI) m/z 307.4 [M+H]$^+$. $^1$H NMR (CDCl$_3$, 400 MHz, mixture of rotamers): δ 9.19 (s, 1H), 8.23 (s, 0.6H), 8.19 (s, 0.4H), 5.09 (s, 0.4H), 4.99 (s, 0.6H), 4.94 (d, J=15.6 Hz, 0.6H), 4.82 (d, J=14.4 Hz, 0.4H), 4.60 (d, J=8.8 Hz, 0.4H), 4.57 (d, J=16.0 Hz, 0.6H), 2.65-2.57 (m, 0.4H), 2.49-2.41 (m, 0.6H), 1.53 (s, 9H), 1.10 (d, J=6.4 Hz, 1.2H), 1.00 (d, J=6.8 Hz, 1.8H), 0.82 (d, J=6.8 Hz, 1.8H), 0.75 (d, J=6.8 Hz, 1.2H).

(4-(ethylsulfonyl)phenyl)methanamine was prepared following the synthetic route shown in Scheme 6.

Scheme 6.

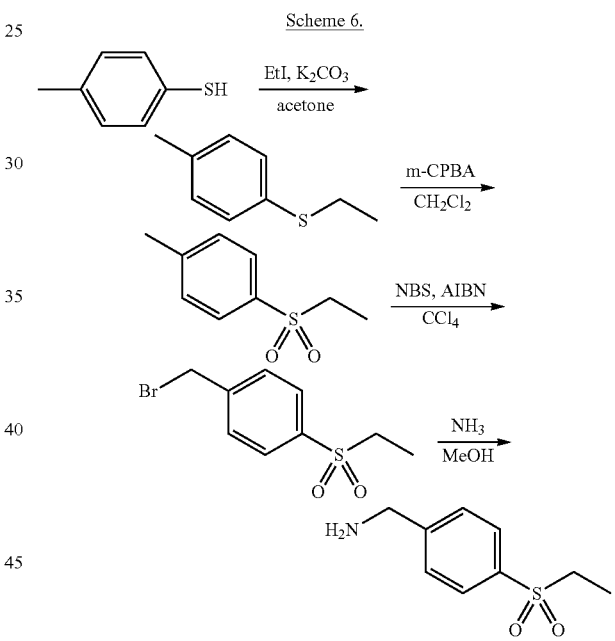

A mixture of 4-methylbenzenethiol (100 g, 0.8 mol) in acetone (1 L) was added iodoethane (190 g, 1.2 mol) and potassium carbonate (220 g, 1.6 mol). The mixture was stirred at 60° C. overnight. The mixture was filtered and the filtrate was concentrated under reduced pressure to afford crude ethyl(p-tolyl)sulfane (120 g, 99%) as a yellow solid, which was used for the next step without further purification.

To a solution of crude ethyl(p-tolyl)sulfane (35 g, 0.23 mol) in CH$_2$Cl$_2$ (1.5 L) was added m-chloroperoxybenzoic acid (101 g, 0.59 mol) at 0° C. The mixture was stirred at rt overnight. The mixture was filtered. The filtrate was added to saturated aqueous Na$_2$SO$_3$ (500 mL) slowly and then stirred for 0.5 h. After partitioning, the organic layer was washed with saturated aqueous NaHCO$_3$ (500 mL), dried over anhydrous Na$_2$SO$_4$, filtered and concentrated under reduced pressure to afford crude 1-(ethylsulfonyl)-4-methylbenzene (42.3 g, 100%) as a pale yellow solid, which was used for the next step without further purification.

To a solution of 1-(ethylsulfonyl)-4-methylbenzene (5 g, 25.7 mmol) in CCl₄ (30 mL) was added N-bromosuccinimide (5.54 g, 30.8 mmol) and azobisisobutyronitrile (0.46 g, 2.57 mmol). The mixture was stirred at 80° C. overnight. The mixture was filtered and the filtrate was concentrated under reduced pressure. The residue was added to water (50 mL) and extracted with EtOAc (3×30 mL). The combined organic layers were washed with water (2×40 mL) and brine (50 mL), dried over anhydrous Na₂SO₄, filtered and concentrated under reduced pressure to afford crude 1-(bromomethyl)-4-(ethylsulfonyl)benzene (6.62 g, 98%) as a yellow solid, which was used for the next step without further purification.

To a solution of 1-(bromomethyl)-4-(ethylsulfonyl)benzene (6.62 g, 25.2 mmol) in MeOH (30 mL) was added 28% aqueous ammonium hydroxide solution (30 mL). The mixture was stirred at rt overnight. The mixture was then concentrated under reduced pressure. The residue was purified by basic preparative HPLC separation to afford (4-(ethylsulfonyl)phenyl)methanamine (1.5 g, 30%) as a yellow solid. LC-MS $t_R$=1.747 min in 0-30CD_3 min chromatography (Durashell C18, 2.1*30 mm, 3 um), MS (ESI) m/z 200.0 [M+H]⁺ and 399.0 [2M+H]⁺. ¹H NMR (CDCl₃, 400 MHz): δ 7.85 (d, J=8.0 Hz, 2H), 7.53 (d, J=8.0 Hz, 2H), 3.98 (s, 2H), 3.10 (q, J=7.6 Hz, 2H), 1.26 (t, J=7.6 Hz, 3H). Preparative Basic HPLC Method mobile phase A: water with 0.05% NH₃H₂O solution; mobile phase B: MeCN; flow rate: 30 mL/min; detection: UV 220 nm/254 nm; column: Synergi 200 mm×25 mm×5 μm; column temperature: 30° C.

| Time in min | % A | % B |
| --- | --- | --- |
| 0.0 | 63 | 37 |
| 8.0 | 33 | 67 |
| 8.10 | 0 | 100 |
| 10.0 | 0 | 100 |
| 10.1 | 70 | 30 |
| 12 | 70 | 30 |

(S)—N-(4-(ethylsulfonyl)benzyl)-7-isopropyl-6,7-dihydro-5H-pyrrolo[3,4-b]pyridine-3-carboxamide was prepared following the synthetic route shown in Scheme 7.

Scheme 7.

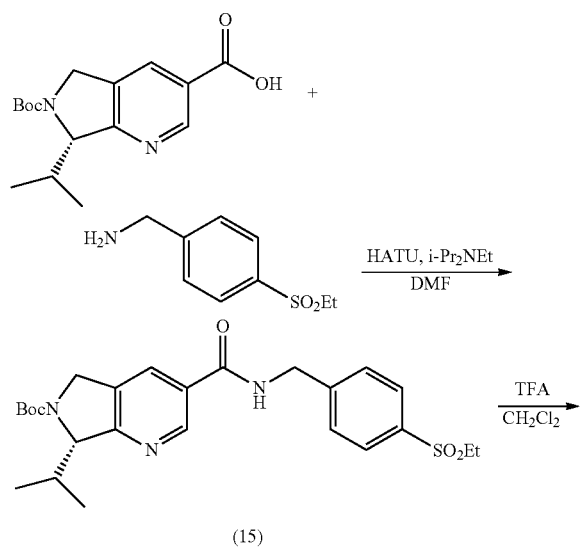

(15)

-continued

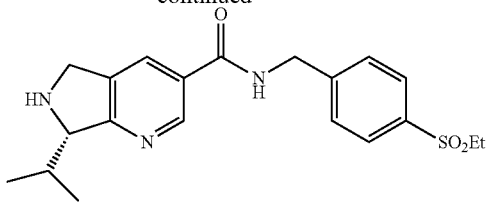

To a solution of (S)-6-(tert-butoxycarbonyl)-7-isopropyl-6,7-dihydro-5H-pyrrolo[3,4-b]pyridine-3-carboxylic acid (83.3 mg, 281 μmol) and (4-(ethylsulfonyl)phenyl)methanamine (67.1 mg, 337 μmol) in DMF (2 mL) at rt was added HATU (160 mg, 421 μmol) and diisopropylethylamine (97.8 μL, 561 μmol). The mixture was stirred at rt for 15 h, at which point it was quenched with saturated aqueous ammonium chloride solution (15 mL). EtOAc (25 mL) was added, then the phases were separated. The organic layer was washed with brine (15 mL), dried over anhydrous MgSO₄, filtered and concentrated under reduced pressure. The residue was purified by silica gel chromatography (eluting with 50% EtOAc in hexanes, gradient to 100%) to afford 98.0 mg tert-butyl (S)-3-((4-(ethylsulfonyl)benzyl)carbamoyl)-7-isopropyl-5,7-dihydro-6H-pyrrolo[3,4-b]pyridine-6-carboxylate, (15), (77%). LC-MS $t_R$=0.92 min in 1 min chromatography, MS (ESI) m/z 488.5 [M+H]⁺. ¹H NMR (CD₃OD, 400 MHz, mixture of rotamers): δ 8.94 (d, J=2.0 Hz, 1H), 8.16 (d, J=12.0 Hz, 1H), 7.89 (dd, J=2.0 Hz, 8.4 Hz, 2H), 7.64 (d, J=8.8 Hz, 2H), 4.96 (m, 1H), 4.83 (m, 1H), 4.70 (s, 2H), 4.59 (m, 1H), 3.20 (q, J=7.2 Hz, 2H), 2.56-2.42 (m, 1H), 1.48 (s, 9H), 1.20 (t, J=7.2 Hz, 3H), 1.06 (d, J=7.2 Hz, 1.5H), 1.02 (d, J=6.8 Hz, 1.5H), 0.80 (d, J=6.8 Hz, 1.5H), 0.74 (d, J=6.8 Hz, 1.5H).

To a solution of tert-butyl (S)-3-((4-(ethylsulfonyl)benzyl)carbamoyl)-7-isopropyl-5,7-dihydro-6H-pyrrolo[3,4-b]pyridine-6-carboxylate (98.0 mg, 201 μmol) in CH₂Cl₂ (4 mL) at rt was added trifluoroacetic acid (1.5 mL). The solution was stirred for 30 min, then it was cooled to 0° C. and quenched carefully with saturated sodium bicarbonate solution (20 mL). The mixture was warmed to rt, then 1 N NaOH (10 mL) and brine (10 mL) were added. The aqueous phase was extracted with CH₂Cl₂ (5×25 mL), then the combined organic layer was dried over anhydrous MgSO₄, filtered and concentrated under reduced pressure. The crude (S)—N-(4-(ethylsulfonyl)benzyl)-7-isopropyl-6,7-dihydro-5H-pyrrolo[3,4-b]pyridine-3-carboxamide was carried forward without any purification. LC-MS $t_R$=0.49 min in 1 min chromatography, MS (ESI) m/z 388.4 [M+H]⁺. ¹H NMR (CDCl₃, 400 MHz): δ 9.06 (t, J=0.8 Hz, 1H), 8.23 (t, J=0.8 Hz, 1H), 7.89 (dd, J=1.6 Hz, 8.4 Hz, 2H), 7.65 (d, J=8.8 Hz, 2H), 4.85 (d, J=4.0 Hz, 1H), 4.73 (s, 2H), 4.71 (s, 2H), 3.20 (q, J=7.6 Hz, 2H), 2.59-2.54 (m, 1H), 1.21 (t, J=7.6 Hz, 3H), 1.21 (d, J=6.8 Hz, 3H), 1.07 (d, J=7.2 Hz, 3H).

(5-(ethylsulfonyl)pyridin-2-yl)methanamine was prepared following the synthetic route shown in Scheme 8.

Scheme 8.

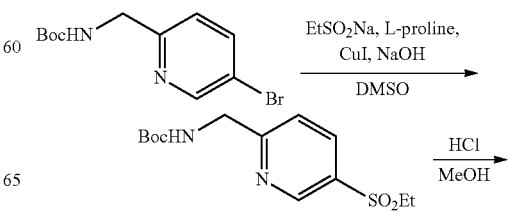

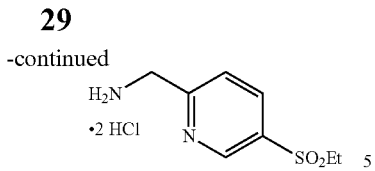

To a flame dried flask equipped with a stir bar was added tert-butyl ((5-bromopyridin-2-yl)methyl)carbamate (2.92 g, 10.2 mmol), ethane sulfinic acid sodium salt (2.36 g, 20.3 mmol), L-proline (234 mg, 2.03 mmol), copper (I) iodide (194 mg, 1.02 mmol) and sodium hydroxide (81.3 mg, 2.03 mmol). The flask was purged with $N_2$, then DMSO (35 mL) was added. The reaction mixture was heated to 110° C. and stirred for 15 h. The flask was then cooled to rt and the mixture was partitioned between EtOAc (150 mL) and saturated aqueous ammonium chloride (150 mL). The organic phase was separated, washed with brine (50 mL), dried over anhydrous $MgSO_4$, filtered and concentrated under reduced pressure. The residue was purified by silica gel chromatography (eluting with 35% EtOAc in hexanes, gradient to 60%) to afford 1.81 g tert-butyl ((5-bromopyridin-2-yl)methyl)carbamate (59%). LC-MS $t_R$=0.74 min in 1 min chromatography, MS (ESI) m/z 301.4 [M+H]$^+$. $^1$H NMR (CDCl$_3$, 400 MHz): δ 9.02 (dd, J=0.8 Hz, 2.0 Hz, 1H), 8.15 (dd, J=2.4 Hz, 8.4 Hz, 1H), 7.49 (dd, J=0.8 Hz, 8.4 Hz, 1H), 5.49 (broad s, 1H), 4.55 (d, J=7.0 Hz, 2H), 3.15 (q, J=7.2 Hz, 2H), 1.47 (s, 9H), 1.31 (t, J=7.2 Hz, 3H).

To a solution of tert-butyl ((5-bromopyridin-2-yl)methyl)carbamate (1.81 g, 6.03 mmol) in MeOH (40 mL) at 0° C. was added acetyl chloride (4.30 mL, 60.3 mmol) dropwise over 5 min. The solution was allowed to warm to rt and was stirred for 3 h. The mixture was concentrated under reduced pressure to yield 1.64 g (5-(ethylsulfonyl)pyridin-2-yl)methanamine bishydrochloride (~100%). LC-MS $t_R$=0.25 min in 1 min chromatography, MS (ESI) m/z 201.2 [M+H]$^+$. $^1$H NMR (CD$_3$OD, 400 MHz): δ 9.09 (d, J=1.2 Hz, 1H), 8.35 (dd, J=2.4 Hz, 8.4 Hz, 1H), 7.49 (d, J=8.4 Hz, 1H), 4.45 (s, 2H), 3.31 (q, J=7.2 Hz, 2H), 1.26 (t, J=7.2 Hz, 3H).

46

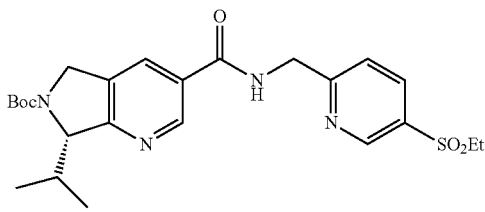

Tert-butyl (S)-3-(((5-(ethylsulfonyl)pyridin-2-yl)methyl)carbamoyl)-7-isopropyl-5,7-dihydro-6H-pyrrolo[3,4-b]pyridine-6-carboxylate (46): Procedure same as that for tert-butyl (S)-3-((4-(ethylsulfonyl)benzyl)carbamoyl)-7-isopropyl-5,7-dihydro-6H-pyrrolo[3,4-b]pyridine-6-carboxylate, using (5-(ethylsulfonyl)pyridin-2-yl)methanamine as a starting material. LC-MS $t_R$=0.86 min in 1 min chromatography, MS (ESI) m/z 489.4 [M+H]$^+$. $^1$H NMR (CDCl$_3$, 400 MHz, mixture of rotamers): δ 9.06 (s, 1H), 8.96 (s, 1H), 8.20 (dd, J=2.0 Hz, 8.4 Hz, 1H), 8.05 (d, J=7.0 Hz, 1H), 7.56 (d, J=8.0 Hz, 1H), 7.52 (s, 1H), 4.99 (m, 2H), 4.90 (m, 2H), 4.80 (d, J=15.2 Hz, 1H), 4.51 (m, 1H), 3.17 (q, J=7.6 Hz, 2H), 2.63-2.54 (m, 0.5H), 2.48-2.39 (m, 0.5H), 1.52 (s, 9H), 1.33 (t, J=7.6 Hz, 3H), 1.10 (d, J=7.2 Hz, 1.5H), 1.01 (d, J=6.8 Hz, 1.5H), 0.78 (d, J=6.8 Hz, 1.5H), 0.73 (d, J=7.2 Hz, 1.5H).

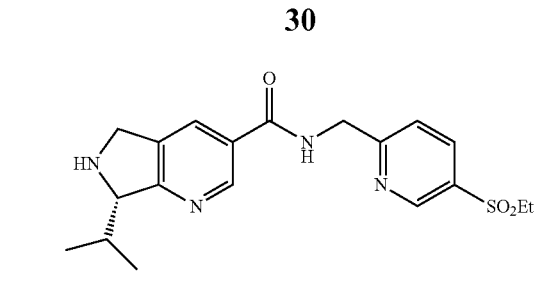

(S)—N-((5-(ethylsulfonyl)pyridin-2-yl)methyl)-7-isopropyl-6,7-dihydro-5H-pyrrolo[3,4-b]pyridine-3-carboxamide: Procedure same as that for (S)—N-(4-(ethylsulfonyl)benzyl)-7-isopropyl-6,7-dihydro-5H-pyrrolo[3,4-b]pyridine-3-carboxamide, using tert-butyl (S)-3-(((5-(ethylsulfonyl)pyridin-2-yl)methyl)carbamoyl)-7-isopropyl-5,7-dihydro-6H-pyrrolo[3,4-b]pyridine-6-carboxylate as a starting material. LC-MS $t_R$=0.48 min in 1 min chromatography, MS (ESI) m/z 389.3 [M+H]$^+$. $^1$H NMR (CDCl$_3$, 400 MHz): δ 9.06 (dd, J=0.8 Hz, 2.0 Hz, 1H), 8.93 (t, J=0.8 Hz, 1H), 8.19 (dd, J=2.0 Hz, 8.4 Hz, 1H), 8.01 (t, J=0.8 Hz, 1H), 7.56 (dd, J=0.8 Hz, 8.0 Hz, 1H), 7.52 (s, 1H), 4.89 (d, J=5.2 Hz, 2H), 4.35 (dd, J=1.2 Hz, 4.0 Hz, 1H), 4.32 (d, J=0.8 Hz, 2H), 3.17 (q, J=7.6 Hz, 2H), 2.34-2.26 (m, 1H), 1.33 (t, J=7.6 Hz, 3H), 1.09 (d, J=7.2 Hz, 3H), 0.79 (d, J=6.8 Hz, 3H).

2-(4-(ethylsulfonyl)phenyl)acetamide was prepared following the synthetic route shown in Scheme 9.

Scheme 9.

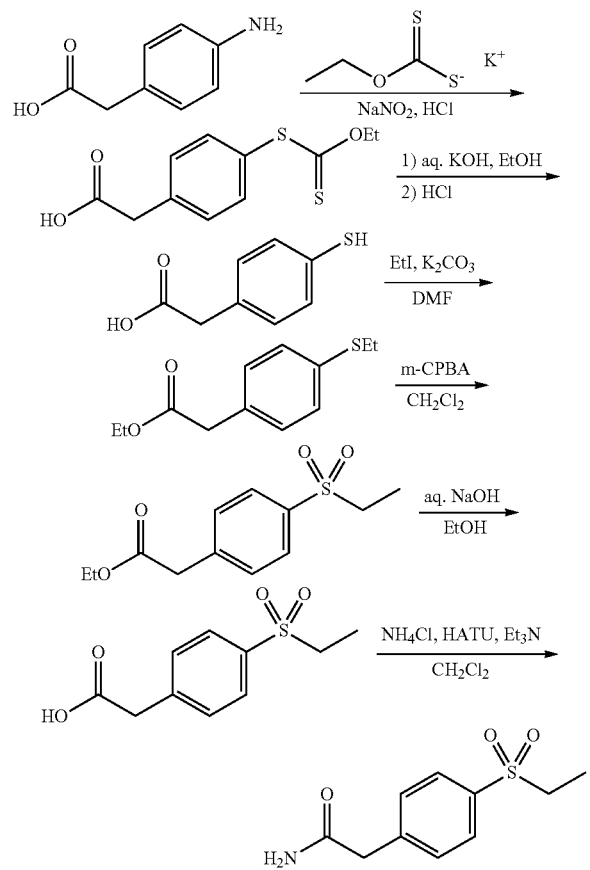

A solution of sodium nitrite (18.4 g, 0.267 mol) in water (133 mL) was added dropwise to a suspension of 2-(4- aminophenyl)acetic acid (40.3 g, 0.267 mol) in water (133 mL) and conc. HCl (54 mL, 0.65 mol) at 0° C. After addition, the reaction mixture was stirred at the same temperature for 45 min. The solution of the cold diazonium salt was then added dropwise to a mixture of potassium ethyl xanthate (49.3 g, 0.31 mol), water (80 mL) and aqueous sodium carbonate solution (200 mL, 2 M) at rt. After addition, the mixture was allowed to warm to 45° C. and stirred at this temperature until gas evolution ceased (about 3 h to overnight). The mixture was cooled to rt and adjusted to pH=1 with conc. HCl. The aqueous layer was extracted with ethyl acetate (3×300 mL). The combined organic layers were dried over anhydrous $Na_2SO_4$, filtered and concentrated under reduced pressure to afford crude 2-(4-((ethoxycarbonothioyl)thio)phenyl)acetic acid (50 g, 73%) as a dark red liquid, which was used for next step directly without further purification. $^1$H NMR (purified by pre-TLC, $CDCl_3$ 300 MHz): δ 7.40 (d, J=7.5 Hz, 2H), 7.28 (d, J=7.8 Hz, 2H), 4.54 (q, J=6.9 Hz, 2H), 3.63 (s, 2H), 1.26 (t, J=6.9 Hz, 3H).

To a solution of 2-(4-((ethoxycarbonothioyl)thio)phenyl) acetic acid (50.0 g, crude, 0.195 mol) in EtOH (180 mL) was added a solution of KOH (40.5 g, 0.724 mol) in water (180 mL). The mixture was stirred at reflux overnight. The mixture was concentrated under reduced pressure to remove EtOH. The aqueous phase was adjusted to pH=1~2 with conc. HCl. The aqueous phase was then extracted with ethyl acetate (3×200 mL). The combined organic layers were dried over anhydrous $Na_2SO_4$, filtered and concentrated under reduced pressure to afford crude 2-(4-mercaptophenyl)acetic acid (32.0 g, 98%) as a gray solid, which was used for next step directly without further purification. $^1$H NMR (purified by pre-TLC, $CD_3OD$, 400 MHz): δ 7.23 (d, J=8.4 Hz, 2H), 7.15 (d, J=8.0 Hz, 2H), 3.54 (s, 2H).

To a solution of 2-(4-mercaptophenyl)acetic acid (32 g, crude, 0.19 mol) in dry DMF (300 mL) was added potassium carbonate (105 g, 0.76 mol) and iodoethane (118 g, 0.76 mol). The reaction mixture was stirred at rt overnight. Ethyl acetate (800 mL) and water (600 mL) were added to the mixture. After partitioning, the aqueous layer was extracted with ethyl acetate (3×500 mL). The combined organic layers were washed with brine (2×800 mL), dried over anhydrous $Na_2SO_4$, filtered and concentrated under reduced pressure. The residue was purified by column chromatography on silica gel (eluting with 30:1 petroleum ether:ethyl acetate) to give ethyl 2-(4-(ethylthio)phenyl)acetate (15.3 g, 36%) as a yellow oil. LC-MS $t_R$=0.881 min in 5-95AB_1.5 min chromatography (Welch Xtimate C18, 2.1*30 mm, 3 um), MS (ESI) m/z 224.8 [M+H]$^+$. $^1$H NMR ($CDCl_3$ 300 MHz): δ 7.02 (d, J=8.1 Hz, 2H), 6.94 (d, J=8.1 Hz, 2H), 3.89 (q, J=7.2 Hz, 2H), 3.31 (s, 2H), 2.67 (q, J=7.5 Hz, 2H), 1.07-0.97 (m, 6H).

To a solution of ethyl 2-(4-(ethylthio)phenyl)acetate (7.8 g, 35 mmol) in $CH_2Cl_2$ (100 mL) was added m-chloroperoxybenzoic acid (21 g, 123 mmol) in portions at 0° C. The reaction mixture was stirred for 16 h at rt. The reaction mixture was filtered. $CH_2Cl_2$ (200 mL) was added to the filtrate and then the mixture was quenched with saturated aqueous $Na_2SO_3$ solution (200 mL). After partitioning, the organic layer was washed with saturated aqueous $Na_2SO_3$ solution (200 mL) and then saturated aqueous $Na_2CO_3$ solution (300 mL). The combined aqueous layers were extracted with $CH_2Cl_2$ (3×400 mL). The combined organic layers were washed with brine (500 mL), dried over anhydrous $Na_2SO_4$, filtered and concentrated under reduced pressure. The residue was purified by column on silica gel (eluting with 15% EtOAc in petroleum ether, gradient to 25%) to afford ethyl 2-(4-(ethylsulfonyl)phenyl)acetate (7.0 g, 78%) as a white solid. LC-MS $t_R$=0.807 min in 5-95AB_2 min chromatography (Welch Xtimate C18, 2.1*30 mm, 3 um), MS (ESI) m/z 256.8 [M+H]$^+$. $^1$H NMR ($CDCl_3$ 400 MHz): δ 7.87 (d, J=8.4 Hz, 2H), 7.50 (d, J=8.0 Hz, 2H), 4.18 (q, J=6.8 Hz, 2H), 3.72 (s, 2H), 3.11 (q, J=7.6 Hz, 2H), 1.30-1.25 (m, 6H).

To a solution of ethyl 2-(4-(ethylsulfonyl)phenyl)acetate (10.0 g, 39 mmol) in EtOH (100 mL) was added a solution of NaOH (5.7 g, 142.5 mmol) in water (100 mL). The reaction mixture was stirred at rt for 16 h. EtOH was removed under reduced pressure. The aqueous layer was adjusted to pH=1 with 6 N aq. HCl and extracted with ethyl acetate (3×100 mL). The combined organic layers were washed with brine (2×100 mL), dried over anhydrous $Na_2SO_4$, filtered and concentrated under reduced pressure to give the desired product 2-(4-(ethylsulfonyl)phenyl)acetic acid (7.3 g, 82%) as a white solid. LC-MS $t_R$=0.573 min in 5-95AB_1.5 min chromatography (Welch Xtimate C18, 2.1*30 mm, 3 um), MS (ESI) m/z 228.8 [M+H]$^+$. $^1$H NMR ($CDCl_3$ 400 MHz): δ 7.88 (d, J=8.0 Hz, 2H), 7.50 (d, J=8.4 Hz, 2H), 3.77 (s, 2H), 3.12 (q, J=7.6 Hz, 2H), 1.28 (t, J=7.6 Hz, 3H).

To a mixture of 2-(4-(ethylsulfonyl)phenyl)acetic acid (3 g, 13.2 mmol), $Et_3N$ (4.0 g, 39.6 mmol) and HATU (5.93 g, 15.6 mmol) in anhydrous $CH_2Cl_2$ (100 mL) was added $NH_4Cl$ (1.54 g, 26.4 mmol). The resulting mixture was stirred at rt overnight. The mixture was diluted with $CH_2Cl_2$ (100 mL) and washed with water (3×80 mL). The organic layer was dried over anhydrous $Na_2SO_4$, filtered and concentrated under reduced pressure. The residue was purified by column chromatography on silica gel (eluting with 50% EtOAc in petroleum ether, gradient to 100%) to afford crude 2-(4-(ethylsulfonyl)phenyl)acetamide. The crude product was added to petroleum ether/ethyl acetate (20 mL, 1/1), then the mixture was stirred for 0.5 h. The mixture was filtered and the filter cake was dried under vacuum to give 2-(4-(ethylsulfonyl)phenyl)acetamide (1.5 g, 50%) as a white solid. LC-MS $t_R$=0.900 min in 0-30AB_2 min chromatography (Welch Xtimate C18, 2.1*30 mm, 3 um), MS (ESI) m/z 269.0 [M+H+$CH_3CN$]$^+$. $^1$H NMR (DMSO-$d_6$, 400 MHz): δ 7.80 (d, J=8.0 Hz, 2H), 7.58 (broad s, 1H), 7.51 (d, J=8.0 Hz, 2H), 7.00 (broad s, 1H), 3.50 (s, 2H), 3.25 (q, J=7.2 Hz, 2H), 1.08 (t, J=7.2 Hz, 3H).

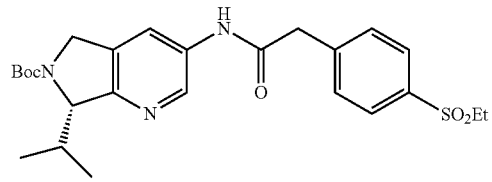

Tert-butyl (S)-3-(2-(4-(ethylsulfonyl)phenyl)acetamido)-7-isopropyl-5,7-dihydro-6H-pyrrolo[3,4-b]pyridine-6-carboxylate: To a flame-dried vial equipped with a stir bar was added tert-butyl (S)-3-chloro-7-isopropyl-5,7-dihydro-6H-pyrrolo[3,4-b]pyridine-6-carboxylate (74.7 mg, 252 μmol), 2-(4-(ethylsulfonyl)phenyl)acetamide (68.6 mg, 302 μmol), and potassium phosphate (64.1 mg, 302 μmol). Tert-butanol (1.5 mL) was added, then the mixture was degassed with $N_2$ for 15 min. Tris(dibenzylideneacetone)dipalladium (O) (2.3 mg, 252 nmol) and 2-(di-t-butylphosphino)-3,6-dimethoxy-2',4',6'-tri-i-propyl-1,1'-biphenyl (4.9 mg, 10.1 μmol) were added to the mixture, then the vial was sealed and heated at 110° C. for 15 h. The mixture was cooled to rt, then partitioned between EtOAc (15 mL) and brine (15 mL). The organic phase was separated, dried over anhydrous MgSO$_4$, filtered and concentrated under reduced pressure. The residue was purified by silica gel chromatography (eluting with 10% EtOAc in hexanes, gradient to 100%) to afford 70.2 mg of Tert-butyl (S)-3-(2-(4-(ethylsulfonyl)phenyl)acetamido)-7-isopropyl-5,7-dihydro-6H-pyrrolo[3,4-b]pyridine-6-carboxylate (57%). LC-MS $t_R$=0.90 min in 1 min chromatography, MS (ESI) m/z 488.5 [M+H]$^+$. $^1$H NMR (CD$_3$OD, 400 MHz, mixture of rotamers): δ 8.58 (s, 0.5H), 8.54 (s, 0.5H), 8.10 (s, 1H), 7.89 (dd, J=8.0 Hz, 2H), 7.64 (d, J=8.4 Hz, 2H), 4.77 (d, J=15.6 Hz, 1H), 4.51 (m, 2H), 3.87 (s, 2H), 3.21 (q, J=7.2 Hz, 2H), 2.46-2.37 (m, 1H), 1.52 (s, 9H), 1.22 (t, J=7.6 Hz, 3H), 1.02 (d, J=6.8 Hz, 1.5H), 0.99 (d, J=6.4 Hz, 1.5H), 0.77 (d, J=7.2 Hz, 1.5H), 0.73 (d, J=6.8 Hz, 1.5H).

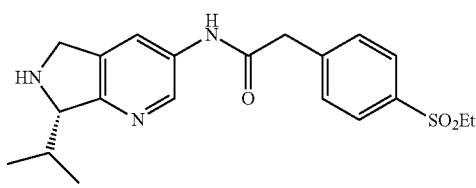

(S)-2-(4-(ethylsulfonyl)phenyl)-N-(7-isopropyl-6,7-dihydro-5H-pyrrolo[3,4-b]pyridin-3-yl)acetamide: Procedure same as that for (S)—N-(4-(ethylsulfonyl)benzyl)-7-isopropyl-6,7-dihydro-5H-pyrrolo[3,4-b]pyridine-3-carboxamide, using tert-butyl (S)-3-(2-(4-(ethylsulfonyl)phenyl)acetamido)-7-isopropyl-5,7-dihydro-6H-pyrrolo[3,4-b]pyridine-6-carboxylate as a starting material. LC-MS $t_R$=0.50 min in 1 min chromatography, MS (ESI) m/z 388.3 [M+H]$^+$. $^1$H NMR (CD$_3$OD, 400 MHz): δ 9.02 (s, 1H), 8.48 (s, 1H), 8.26 (d, J=2.0 Hz, 1H), 7.84 (m, 2H), 7.66 (d, J=8.0 Hz, 1H), 7.56 (d, J=8.4 Hz, 1H), 4.78 (m, 2H), 3.98 (s, 1H), 3.81 (s, 1H), 3.70 (s, 1H), 3.20 (q, J=7.6 Hz, 2H), 2.65-2.57 (m, 1H), 1.21 (t, J=7.6 Hz, 3H), 1.21 (d, J=6.8 Hz, 3H), 1.03 (d, J=6.8 Hz, 3H).

Preparation of Compounds of Formula I

Compounds of Formula (I) were prepared according to the general procedures outlined below.

General Procedure A (S)—N-(4-(ethylsulfonyl)benzyl)-7-isopropyl-6-(4-(trifluoromethyl)benzyl)-6,7-dihydro-5H-pyrrolo[3,4-b]pyridine-3-carboxamide (1)

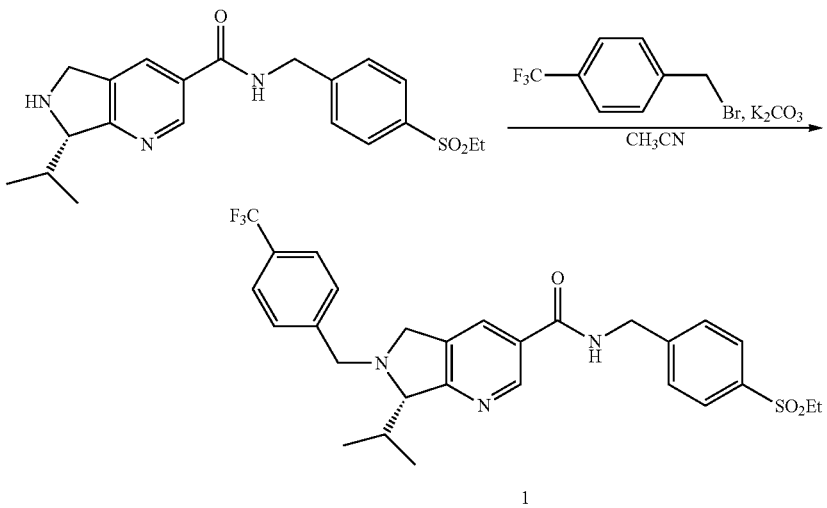

(S)—N-(4-(ethylsulfonyl)benzyl)-7-isopropyl-6,7-dihydro-5H-pyrrolo[3,4-b]pyridine-3-carboxamide (11.3 mg, 29.2 µmol), 4-(trifluoromethyl)benzyl bromide (10.5 mg, 43.9 µmol), and potassium carbonate (8.1 mg, 58.6 µmol) were stirred together in CH$_3$CN (1 mL) at rt for 2 h. The reaction mixture was quenched with saturated aqueous ammonium chloride solution (5 mL) and extracted with EtOAc (10 mL). The organic phase was separated, washed with brine (5 mL), dried over anhydrous MgSO$_4$, filtered and concentrated under reduced pressure. The residue was purified by silica gel chromatography (eluting with 50% EtOAc in hexanes, gradient to 100%), then further purified by reverse-phase HPLC to yield 5.2 mg of the HCl salt of (S)—N-(4-(ethylsulfonyl)benzyl)-7-isopropyl-6-(4-(trifluoromethyl)benzyl)-6,7-dihydro-5H-pyrrolo[3,4-b]pyridine- 3-carboxamide (1, 31%). LC-MS m/z 546.5 [M+H]⁺. ¹H NMR (CD₃OD, 400 MHz): δ 9.08 (d, J=1.6 Hz, 1H), 8.28 (s, 1H), 7.89 (d, J=8.8 Hz, 2H), 7.84 (d, J=8.0 Hz, 2H), 7.64 (d, J=8.4 Hz, 2H), 5.03 (d, J=16.0 Hz, 1H), 4.91 (m, 2H), 4.82 (m, 2H), 4.71 (s, 2H), 3.20 (q, J=7.2 Hz, 2H), 2.42-2.29 (m, 1H), 1.21 (t, J=7.6 Hz, 3H), 1.17 (d, J=8.0 Hz, 3H), 0.89 (d, J=6.8 Hz, 3H).

Trans-4-(trifluoromethyl)cyclohexane-1-carbaldehyde (was prepared following the synthetic route shown in Scheme 10.

Scheme 10.

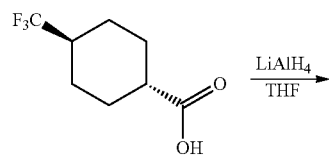

(12.5 mL, 0.17 mol) at −78° C. under N₂. After the mixture was stirred at −78° C. for 30 min., a solution of (trans-4-(trifluoromethyl)cyclohexyl)methanol (5.3 g, 29.1 mmol) in CH₂Cl₂ (40 mL) was added dropwise while keeping the internal temperature below −65° C. After being stirred for 30 min., a solution of Et₃N (40.5 mL, 0.29 mol) in CH₂Cl₂ (60 mL) was added dropwise slowly, keeping the internal temperature below −65° C. The reaction mixture was stirred at −78° C. for 1 h, and warmed to rt overnight. The mixture was washed with water (3×300 mL) and brine (300 mL), dried over anhydrous Na₂SO₄, filtered and concentrated under reduced pressure. The residue was purified by column chromatography on silica (eluting with 15% EtOAc in petroleum ether) to give trans-4-(trifluoromethyl)cyclohexane-1-carbaldehyde (4.6 g, 87%) as a yellow oil.

General Procedure B (S)—N-((5-(ethylsulfonyl)pyridin-2-yl)methyl)-7-isopropyl-6-((trans-4-(trifluoromethyl)cyclohexyl)methyl)-6,7-dihydro-5H-pyrrolo[3,4-b]pyridine-3-carboxamide (2)

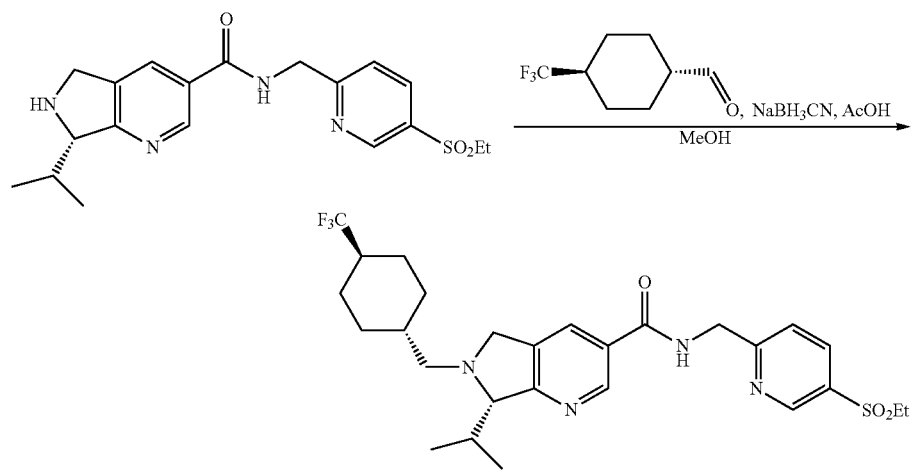

-continued

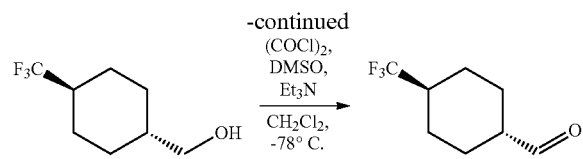

To a solution of trans-4-(trifluoromethyl)cyclohexane carboxylic acid (789 mg, 4.02 mmol) in THF (12 mL) at rt was added lithium aluminum hydride (1.0 M in THF, 4.02 mL). The mixture was heated to reflux and stirred for 3 h. It was then cooled to 0° C. and quenched successively with water (152 μL), 15% aqueous sodium hydroxide (152 μL), and water (456 μL). The mixture was then filtered through Celite and concentrated under reduced pressure. The crude liquid (trans-4-(trifluoromethyl)cyclohexyl)methanol was carried forward without any purification and without placing under high vacuum due to its volatility.

To a solution of oxalyl chloride (6.2 mL, 87.4 mmol) in anhydrous CH₂Cl₂ (300 mL) was added dropwise DMSO To a solution of (S)—N-((5-(ethylsulfonyl)pyridin-2-yl)methyl)-7-isopropyl-6,7-dihydro-5H-pyrrolo[3,4-b]pyridine-3-carboxamide (3.6 g, 9.25 mmol), trans-4-(trifluoromethyl)cyclohexane-1-carbaldehyde (3.3 g, 18.5 mmol) in anhydrous MeOH (100 mL) was added acetic acid dropwise until the pH was between 6 and 7. Sodium cyanoborohydride (1.7 g, 27.75 mmol) was added portionwise at rt. The mixture was heated to 70° C. for 1 h. Upon completion, the reaction mixture was cooled to rt and concentrated under reduced pressure. The residue was dissolved in ethyl acetate (100 mL), then the organic phase was washed with water (3×100 mL) and brine (100 mL). The organic layer was dried over anhydrous Na₂SO₄, filtered and concentrated under reduced pressure. The residue was purified by silica gel chromatography (eluting with 50% EtOAc in hexanes, gradient to 100%), then further purified by a chiral column using the following conditions: instrument: Berger Multi-Gram™ SFC, Mettler Toledo Co, Ltd; column: AD 300 mm×50 mm, 10 μm; mobile phase: A: supercritical CO₂, B: iPrOH (0.05% diethylamine), A:B=60:40 at 200 mL/min;

column temp: 38° C.; nozzle pressure: 100 bar; nozzle temp: 60° C.; evaporator temp: 20° C.; trimmer temp: 25° C.; wavelength: 220 nm. Isomer SFC $t_R$=2.28 min in 12 min chromatography was isolated as the major isomer, which was then further purified by reverse-phase HPLC to give (S)—N-((5-(ethylsulfonyl)pyridin-2-yl)methyl)-7-isopropyl-6-((trans-4-(trifluoromethyl)cyclohexyl)methyl)-6,7-dihydro-5H-pyrrolo[3,4-b]pyridine-3-carboxamide (2, HCl salt) as a light yellow solid. LC-MS $t_R$=0.69 min in 1 min chromatography, MS (ESI) m/z 553.1 [M+H]$^+$. $^1$H NMR (CD$_3$OD, 400 MHz): δ 9.12 (s, 1H), 9.01 (d, J=2.0 Hz, 1H), 8.36-8.32 (m, 2H), 7.75 (d, J=8.0 Hz, 1H), 5.16 (d, J=15.6 Hz, 1H), 4.89-4.87 (m, 2H), 4.73 (d, J=15.2 Hz, 1H), 3.42-3.34 (m, 3H), 3.31-3.28 (m, 2H), 2.58-2.51 (m, 1H), 2.20-1.90 (m, 6H), 1.50-1.39 (m, 2H), 1.33 (d, J=7.2 Hz, 3H), 1.26 (t, J=7.2 Hz, 3H), 1.24-1.20 (m, 2H), 1.10 (d, J=6.8 Hz, 3H). HCl preparative HPLC method mobile phase A: water with 0.05% HCl; mobile phase B: CH$_3$CN; flow rate: 80 mL/min; detection: UV 220 nm/254 nm; column: Phenomenex Gemini C18 (250 mm×50 mm×5 μm); column temperature: 30° C.

| Time in min | % A | % B |
| --- | --- | --- |
| 0.00 | 75 | 25 |
| 25.00 | 50 | 50 |
| 30.00 | 0 | 100 |

A sample of 2 was converted to the HBr salt by the following procedure: The HCl salt of 2 (57.5 mg, 97.7 μmol) was dissolved in EtOAc (25 mL) and washed with saturated aqueous sodium bicarbonate (20 mL) and brine (10 mL). The organic phase was dried over anhydrous MgSO$_4$, filtered and concentrated under reduced pressure. It was then redissolved in acetonitrile (200 μL), to which was added hydrobromic acid (48 wt % in water, 69 μL) to give a light yellow clear solution. The solvent was removed under reduced pressure, then more acetonitrile (300 μL) was added. This procedure was performed iteratively until most of the water and excess HBr was removed, leaving behind a yellow solid. This solid was redissolved in acetonitrile (6 mL), seeded with an HBr salt crystal (<1 mg), and stirred at rt for 30 min to give a white solid. The solid was filtered and dried under high vacuum for 3 h to give the HBr salt (40.2 mg, 86%). Melting point=171-173° C. $^1$H NMR (CD$_3$OD, 400 MHz): δ 9.12 (s, 1H), 9.07 (s, 1H), 8.46 (d, J=8.4 Hz, 1H), 8.34 (s, 1H), 7.85 (d, J=8.4 Hz, 1H), 5.18 (d, J=14.2 Hz, 1H), 4.94 (m, 1H), 4.87 (s, 2H), 4.75 (d, J=14.2 Hz. 1H), 3.41 (m, 2H), 3.38 (q, J=7.6 Hz, 2H), 2.54 (m, 1H), 2.17 (m, 1H), 2.04 (m, 5H), 1.45 (m, 2H), 1.32 (d, J=7.2 Hz, 3H), 1.27 (t, J=7.6 Hz, 3H), 1.23 (m, 2H), 1.10 (d, J=6.4 Hz, 3H).

HBr seed crystals were formed as follows: 2 (5.6 mg) was converted to the free base, then to the HBr salt, as described above. The resultant yellow solid was dissolved in acetonitrile (200 μL), then left to stand overnight at rt in a capped vial. Colorless crystals formed, which were identified as plate-shaped under a microscope.

General Procedure C (S)—N-(4-(ethylsulfonyl)benzyl)-7-isopropyl-6-(4-(trifluoromethyl)pyrimidin-2-yl)-6,7-dihydro-5H-pyrrolo[3,4-b]pyridine-3-carboxamide (6)

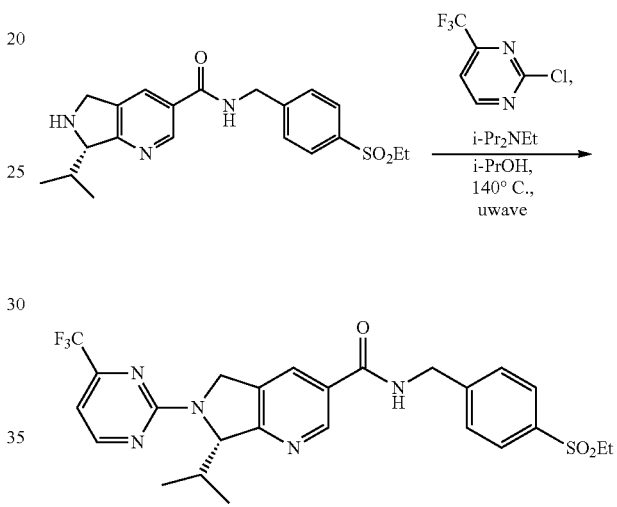

To a solution of (S)—N-(4-(ethylsulfonyl)benzyl)-7-isopropyl-6,7-dihydro-5H-pyrrolo[3,4-b]pyridine-3-carboxamide (27.3 mg, 70.4 μmol) in isopropanol (1.5 mL) in a MW vial was added 2-chloro-5-(trifluoromethyl)pyrimidine (19.3 mg, 106 μmol) and diisopropylethylamine (24.5 μL, 140.7 μmol). The vial was sealed and heated in the MW at 140° C. for 2 h. The solvent was then evaporated and the residue was purified by silica gel chromatography (eluting with 60% EtOAc in hexanes, gradient to 100%), then further purified by reverse-phase HPLC to yield 7.2 mg of (S)—N-(4-(ethylsulfonyl)benzyl)-7-isopropyl-6-(4-(trifluoromethyl)pyrimidin-2-yl)-6,7-dihydro-5H-pyrrolo[3,4-b]pyridine-3-carboxamide (6, 19%). LC-MS $t_R$=0.97 min in 1 min chromatography, MS (ESI) m/z 534.5 [M+H]$^+$. $^1$H NMR (CD$_3$OD, 400 MHz): δ 9.34 (t, J=1.2 Hz, 1H), 8.97 (s, 1H), 8.69 (d, J=4.8 Hz, 1H), 8.25 (s, 1H), 7.90 (d, J=8.4 Hz, 2H), 7.65 (d, J=8.0 Hz, 2H), 7.02 (d, J=4.8 Hz, 1H), 5.39 (s, 1H), 5.14 (d, J=15.6 Hz, 1H), 4.87 (m, 1H), 4.72 (d, J=6.0 Hz, 2H), 3.20 (q, J=7.6 Hz, 2H), 2.79-2.68 (m, 1H), 1.22 (broad s, 3H), 1.21 (t, J=7.6 Hz, 3H), 0.69 (broad s, 3H).

General Procedure D (S)-6-((4-cyanophenyl)sulfonyl)-N-(4-(ethylsulfonyl)benzyl)-7-isopropyl-6,7-dihydro-5H-pyrrolo[3,4-b]pyridine-3-carboxamide (13)

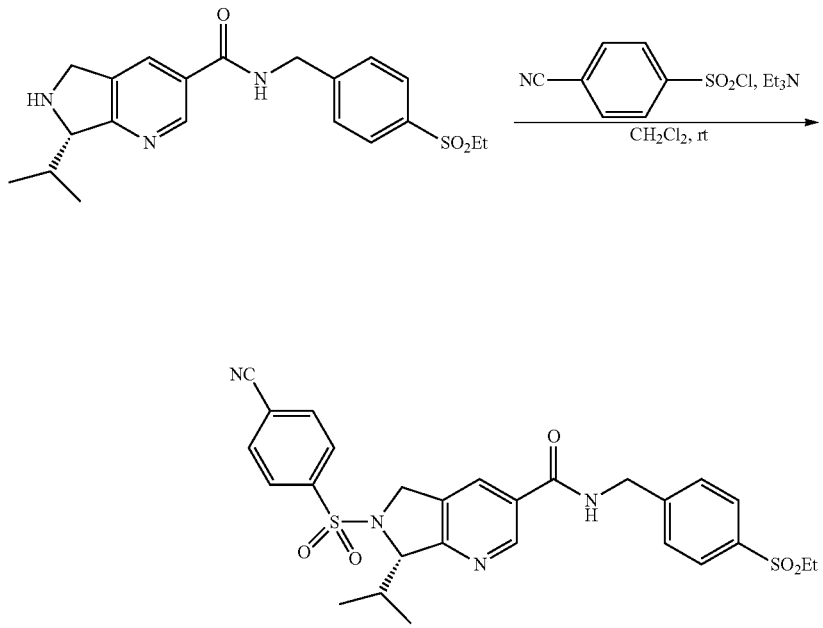

13

To a solution of (S)—N-(4-(ethylsulfonyl)benzyl)-7-isopropyl-6,7-dihydro-5H-pyrrolo[3,4-b]pyridine-3-carboxamide (6.9 mg, 17.8 μmol) in CH$_2$Cl$_2$ (600 μL) was added triethylamine (5.0 μL, 36.6 μmol) and 4-cyanobenzenesulfonyl chloride (5.4 mg, 26.8 μmol). The mixture was stirred at rt for 15 h, at which point it was quenched with saturated aqueous sodium bicarbonate (10 mL). The mixture was extracted with EtOAc (10 mL), then the organic phase was washed with brine (10 mL), dried over anhydrous MgSO$_4$, filtered and concentrated under reduced pressure. The residue was purified by reverse-phase HPLC to yield 4.9 mg of (S)-6-((4-cyanophenyl)sulfonyl)-N-(4-(ethylsulfonyl)benzyl)-7-isopropyl-6,7-dihydro-5H-pyrrolo[3,4-b]pyridine-3-carboxamide as an HCl salt (13, 46%). LC-MS t$_R$=0.84 min in 1 min chromatography, MS (ESI) m/z 553.5 [M+H]$^+$. $^1$H NMR (CD$_3$OD, 400 MHz): δ 8.85 (d, J=2.0 Hz, 1H), 8.09 (d, J=1.6 Hz, 1H), 8.03 (dd, J=2.0 Hz, 8.8 Hz, 2H), 7.86 (m, 4H), 7.60 (d, J=8.4 Hz, 2H), 4.93 (m, 2H), 4.73 (dt, J=1.2 Hz, 16.4 Hz, 1H), 4.66 (s, 2H), 3.19 (q, J=7.6 Hz, 2H), 2.41-2.32 (m, 1H), 1.20 (t, J=7.6 Hz, 3H), 1.00 (d, J=7.2 Hz, 3H), 0.96 (d, J=6.8 Hz, 3H).

General Procedure E benzyl (S)-3-((4-(ethylsulfonyl)benzyl)carbamoyl)-7-isopropyl-5,7-dihydro-6H-pyrrolo[3,4-b]pyridine-6-carboxylate (16)

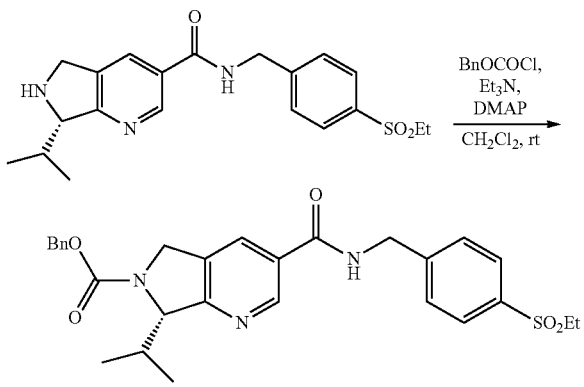

16

To a solution of (S)—N-(4-(ethylsulfonyl)benzyl)-7-isopropyl-6,7-dihydro-5H-pyrrolo[3,4-b]pyridine-3-carboxamide (11.3 mg, 29.2 μmol) in CH$_2$Cl$_2$ (1 mL) was added benzyl chloroformate (11.7 μL, 3.0 M in toluene), triethylamine (6.1 μL, 43.8 μmol) and 4-dimethylaminopyridine (50 μg, 4.09 μmol). The mixture was stirred at rt for 15 h, at which point it was quenched with saturated aqueous sodium bicarbonate (10 mL). The mixture was extracted with EtOAc (10 mL), then the organic phase was washed with brine (10 mL), dried over anhydrous MgSO$_4$, filtered and concentrated under reduced pressure. The residue was purified by silica gel chromatography (eluting with 30% EtOAc in hexanes, gradient to 100%), then further purified by reverse-phase HPLC to yield 14.9 mg of benzyl (S)-3-((4-(ethylsulfonyl)benzyl)carbamoyl)-7-isopropyl-5,7-dihydro-6H-pyrrolo[3,4-b]pyridine-6-carboxylate as an HCl salt (16, 91%). LC-MS $t_R$=0.91 min in 1 min chromatography, MS (ESI) m/z 522.5 [M+H]$^+$. $^1$H NMR (CD$_3$OD, 400 MHz): δ 9.00 (s, 1H), 8.34 (s, 1H), 7.87 (dd, J=1.6 Hz, 6.8 Hz, 2H), 7.63 (d, J=8.8 Hz, 2H), 7.42 (dd, J=1.6 Hz, 8.4 Hz, 2H), 7.33 (m, 3H), 5.20 (m, 3H), 4.96 (m, 1H), 4.71 (m, 3H), 3.20 (q, J=7.6 Hz, 2H), 2.57-2.36 (m, 1H), 1.19 (t, J=7.6 Hz, 3H), 1.00 (dd, J=6.8 Hz, 16.0 Hz, 3H), 0.78 (dd, J=6.8 Hz, 25.6 Hz, 3H).

(7S)—N-(4-(ethylsulfonyl)benzyl)-7-isopropyl-5-methyl-6,7-dihydro-5H-pyrrolo[3,4-b]pyridine-3-carboxamide was prepared following the synthetic route shown in Scheme 11.

Scheme 11.

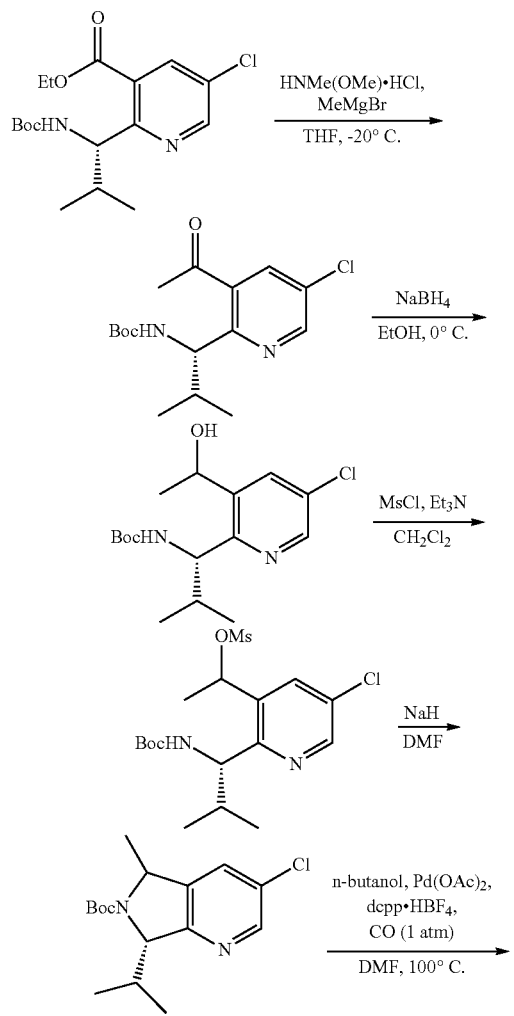

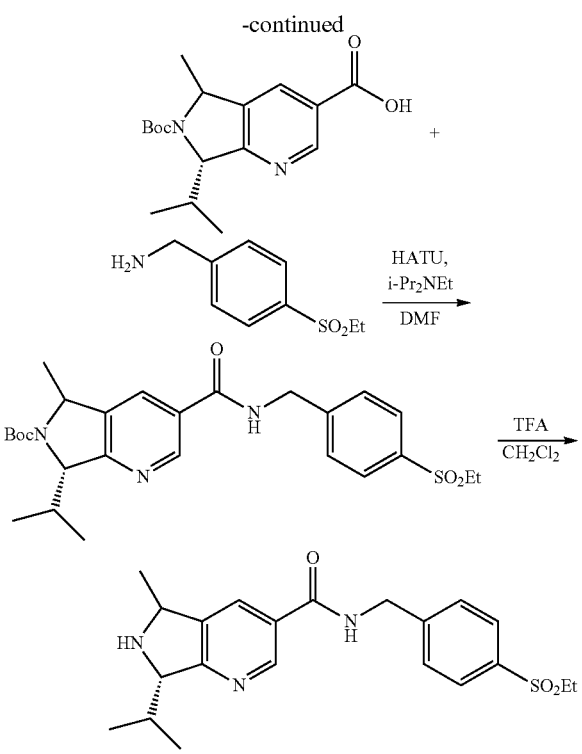

To a solution of ethyl (S)-2-(1-((tert-butoxycarbonyl)amino)-2-methylpropyl)-5-chloronicotinate (104 mg, 291 μmol) and N,O-dimethylhydroxylamine hydrochloride (45.5 mg, 466 μmol) in THF (1 mL) was added dropwise methylmagnesium bromide (1.4 M in 3:1 toluene:THF, 1.04 mL) at –20° C. The mixture was stirred at –20° C. for 45 min, at which point it was quenched carefully with cold saturated aqueous ammonium chloride (10 mL). The mixture was extracted with EtOAc (20 mL), then the organic phase was washed with brine (10 mL), dried over anhydrous MgSO$_4$, filtered and concentrated under reduced pressure. The residue was purified by silica gel chromatography (eluting with 10% EtOAc in hexanes, gradient to 60%) to afford 62.3 mg of tert-butyl (S)-(1-(3-acetyl-5-chloropyridin-2-yl)-2-methylpropyl)carbamate (56% yield). LC-MS $t_R$=1.08 min in 1 min chromatography, MS (ESI) m/z 327.4 [M+H]$^+$.

To a solution of tert-butyl (S)-(1-(3-acetyl-5-chloropyridin-2-yl)-2-methylpropyl)carbamate (62.3 mg, 191 μmol) in EtOH (1 mL) at 0° C. was added sodium borohydride (7.2 mg, 191 μmol) as a solid. The mixture was stirred at 0° C. for 90 min, then it was quenched with saturated aqueous ammonium chloride (10 mL). The mixture was extracted with EtOAc (20 mL), then the organic phase was washed with brine (10 mL), dried over anhydrous MgSO$_4$, filtered and concentrated under reduced pressure. The residue was purified by silica gel chromatography (eluting with 10% EtOAc in hexanes, gradient to 100%) to afford 53.4 mg of tert-butyl((1S)-1-(5-chloro-3-(1-hydroxyethyl)pyridin-2-yl)-2-methylpropyl)carbamate (85% yield). LC-MS $t_R$=1.01 min in 1 min chromatography, MS (ESI) m/z 329.4 [M+H]$^+$. $^1$H NMR (CDCl$_3$, 400 MHz, mixture of diastereomers): δ 8.44 (d, J=2.4 Hz, 0.3H), 8.41 (d, J=2.4 Hz, 0.7H), 7.86 (d, J=2.4 Hz, 0.3H), 7.77 (d, J=2.4 Hz, 0.7H), 5.44 (d, J=9.6 Hz, 0.7H), 5.31 (m, 0.7H), 5.23 (m, 0.7H), 4.73 (t, J=8.8 Hz, 0.3H), 4.63 (t, J=9.6 Hz, 0.3H), 4.56 (s, 0.3H), 2.18-2.12 (m, 0.3H), 2.08-2.00 (m, 0.7H), 1.56 (d, J=6.8 Hz, 0.9H), 1.52

(d, J=6.8 Hz, 2.1H), 1.40 (s, 9H), 1.11 (d, J=6.8 Hz, 0.9H), 1.00 (d, J=6.8 Hz, 2.1H), 0.80 (d, J=6.8 Hz, 2.1H), 0.69 (d, J=6.8 Hz, 0.9H).

1-(2-((S)-1-((tert-butoxycarbonyl)amino)-2-methylpropyl)-5-chloropyridin-3-yl)ethyl methanesulfonate. Procedure same as that for (S)-(2-(1-((tert-butoxycarbonyl)amino)-2-methylpropyl)-5-chloropyridin-3-yl)methyl methanesulfonate, using tert-butyl ((1S)-1-(5-chloro-3-(1-hydroxyethyl)pyridin-2-yl)-2-methylpropyl)carbamate as a starting material. LC-MS $t_R$=1.03 min in 1 min chromatography, MS (ESI) m/z 407.4 [M+H]$^+$.

Tert-butyl (7S)-3-chloro-7-isopropyl-5-methyl-5,7-dihydro-6H-pyrrolo[3,4-b]pyridine-6-carboxylate. Procedure same as that for tert-butyl (S)-3-chloro-7-isopropyl-5,7-dihydro-6H-pyrrolo[3,4-b]pyridine-6-carboxylate, using 1-(2-((S)-1-((tert-butoxycarbonyl)amino)-2-methylpropyl)-5-chloropyridin-3-yl)ethyl methanesulfonate as a starting material. LC-MS $t_R$=1.12 min in 1 min chromatography, MS (ESI) m/z 311.4 [M+H]$^+$. $^1$H NMR (CDCl$_3$, 400 MHz, mixture of diastereomers): δ 8.43 (d, J=1.6 Hz, 1H), 7.52 (s, 0.7H), 7.46 (s, 0.3H), 5.05-5.00 (m, 1H), 4.94 (s, 0.3H), 4.81 (s, 0.7H), 2.88-2.39 (m, 0.3H), 2.32-2.08 (m, 0.7H), 1.55 (m, 3H), 1.44 (s, 9H), 1.26 (d, J=7.2 Hz, 0.9H), 1.09 (broad s, 2.1H), 0.81 (broad s, 2.1H), 0.48 (d, J=7.2 Hz, 0.9H).

(7S)-6-(tert-butoxycarbonyl)-7-isopropyl-5-methyl-6,7-dihydro-5H-pyrrolo[3,4-b]pyridine-3-carboxylic acid. Procedure same as that for (S)-6-(tert-butoxycarbonyl)-7-isopropyl-6,7-dihydro-5H-pyrrolo[3,4-b]pyridine-3-carboxylic acid, using tert-butyl (7S)-3-chloro-7-isopropyl-5-methyl-5,7-dihydro-6H-pyrrolo[3,4-b]pyridine-6-carboxylate as a starting material. LC-MS $t_R$=0.99 min in 1 min chromatography, MS (ESI) m/z 321.5 [M+H]$^+$.

Tert-butyl (7S)-3-((4-(ethylsulfonyl)benzyl)carbamoyl)-7-isopropyl-5-methyl-5,7-dihydro-6H-pyrrolo[3,4-b]pyridine-6-carboxylate. Procedure same as that for tert-butyl (S)-3-((4-(ethylsulfonyl)benzyl)carbamoyl)-7-isopropyl-5,7-dihydro-6H-pyrrolo[3,4-b]pyridine-6-carboxylate, using (7S)-6-(tert-butoxycarbonyl)-7-isopropyl-5-methyl-6,7-dihydro-5H-pyrrolo[3,4-b]pyridine-3-carboxylic acid as a starting material. LC-MS $t_R$=0.95 min in 1 min chromatography, MS (ESI) m/z 502.6 [M+H]$^+$. $^1$H NMR (CD$_3$OD, 400 MHz, mixture of diastereomers): δ 8.93 (s, 1H), 7.79 (d, J=8.4 Hz, 2H), 7.50 (d, J=8.4 Hz, 2H), 7.24 (s, 1H), 5.06-4.88 (m, 2H), 4.82-4.70 (m, 2H), 3.06 (q, J=7.2 Hz, 2H), 2.48-2.26 (m, 1H), 1.59 (d, J=7.2 Hz, 0.9H), 1.56 (d, J=7.2 Hz, 2.1H), 1.53 (s, 9H), 1.25 (t, J=7.2 Hz, 3H), 1.09 (d, J=7.2 Hz, 0.9H), 0.97 (broad s, 2.1H), 0.83 (broad s, 2.1H), 0.48 (d, J=7.2 Hz, 0.9H).

(7S)—N-(4-(ethylsulfonyl)benzyl)-7-isopropyl-5-methyl-6,7-dihydro-5H-pyrrolo[3,4-b]pyridine-3-carboxamide. Procedure same as that for (S)—N-(4-(ethylsulfonyl)benzyl)-7-isopropyl-6,7-dihydro-5H-pyrrolo[3,4-b]pyridine-3-carboxamide, using tert-butyl (7S)-3-((4-(ethylsulfonyl)benzyl)carbamoyl)-7-isopropyl-5-methyl-5,7-dihydro-6H-pyrrolo[3,4-b]pyridine-6-carboxylate as a starting material. LC-MS $t_R$=0.49 min in 1 min chromatography, MS (ESI) m/z 402.3 [M+H]$^+$. $^1$H NMR (CD$_3$OD, 400 MHz, mixture of diastereomers): δ 8.91 (dd, J=1.2 Hz, 2.0 Hz, 1H), 8.11 (dd, J=0.8 Hz, 2.0 Hz, 0.4H), 8.07 (dd, J=1.2 Hz, 1.6 Hz, 0.6H), 7.89 (d, J=8.4 Hz, 2H), 7.63 (d, J=8.4 Hz, 2H), 4.70 (s, 2H), 4.57 (m, 0.4H), 4.48 (m, 0.6H), 4.30 (m, 1H), 3.20 (q, J=7.2 Hz, 2H), 2.40-2.33 (m, 0.6H), 2.27-2.21 (m, 0.4H), 1.50 (d, J=6.8 Hz, 1.8H), 1.47 (d, J=7.2 Hz, 1.2H), 1.20 (t, J=7.6 Hz, 3H), 1.14 (d, J=7.2 Hz, 1.8H), 1.08 (d, J=6.8 Hz, 1.2H), 0.81 (d, J=6.8 Hz, 1.2H), 0.80 (d, J=6.8 Hz, 1.8H).

N-(4-(ethylsulfonyl)benzyl)-7-(tetrahydrofuran-3-yl)-6,7-dihydro-5H-pyrrolo[3,4-b]pyridine-3-carboxamide was prepared following the synthetic route shown in Scheme 12.

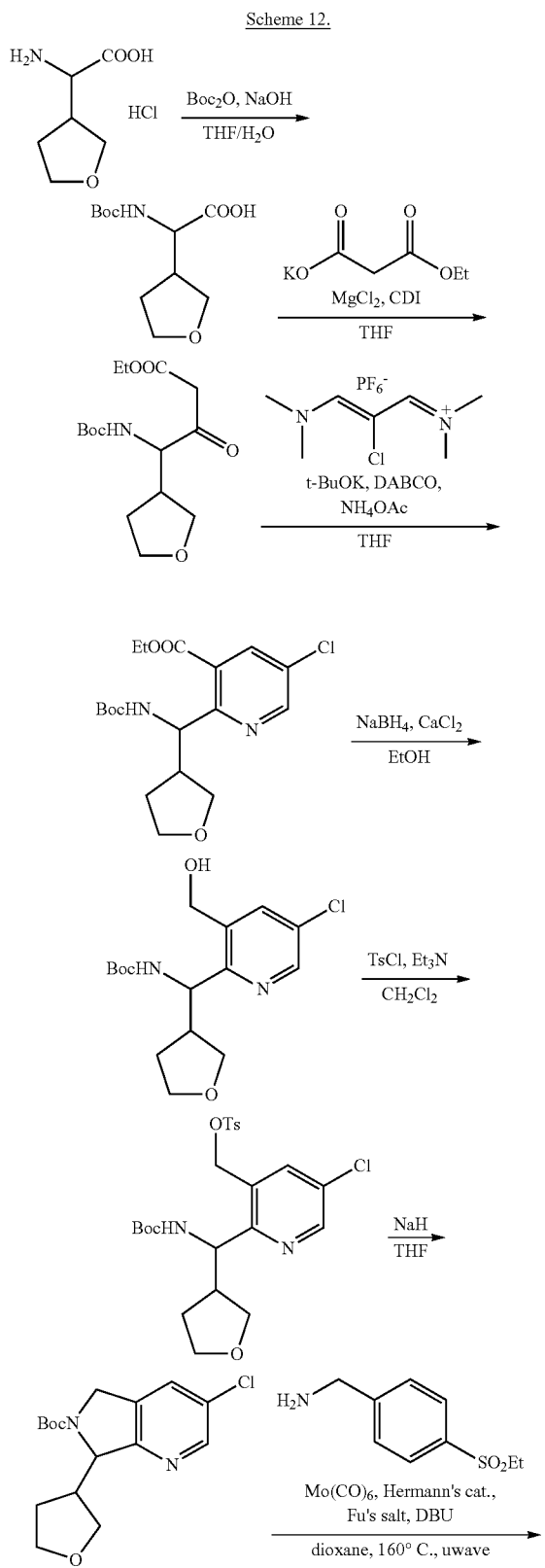

Scheme 12.

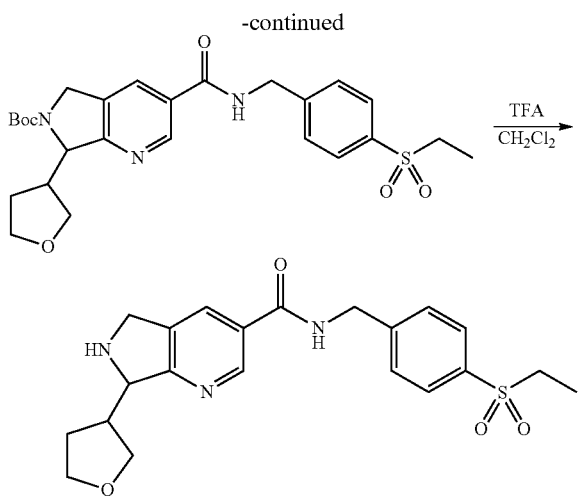

To a solution of 2-amino-2-(tetrahydrofuran-3-yl)acetic acid hydrochloride (1 g, 5.52 mmol) in a mixture of THF (15 mL) and water (1.5 mL) was added di-tert-butyl dicarbonate (1.2 g, 5.52 mmol) and sodium hydroxide (0.9 g, 22.1 mmol). The mixture was stirred at rt overnight. Water (50 mL) was added to the mixture, followed by acidification with 2N aq. HCl solution to pH=2. The mixture was extracted with ethyl acetate (3×20 mL). The combined organic layers were dried over anhydrous sodium sulfate, filtered, concentrated under reduce pressure to afford 2-((tert-butoxycarbonyl)amino)-2-(tetrahydrofuran-3-yl) acetic acid (1.11 g, 80%) as a colorless oil, which was used for the next step without further purification. MS: MS (ESI) m/z 268.1180 [M+Na]$^+$.

Ethyl 4-((tert-butoxycarbonyl)amino)-3-oxo-4-(tetrahydrofuran-3-yl)butanoate. Procedure same as that for ethyl (S)-4-((tert-butoxycarbonyl)amino)-5-methyl-3-oxohexanoate, using 2-((tert-butoxycarbonyl)amino)-2-(tetrahydrofuran-3-yl)acetic acid as a starting material. $^1$H NMR (CD$_3$OD, 400 MHz): δ 4.25-4.13 (m, 3H), 4.00-3.45 (m, 4H), 2.75-2.65 (m, 1H), 2.12-1.98 (m, 1H), 1.77-1.62 (m, 1H), 1.49 (s 9H), 1.30 (t, J=7.2 Hz, 3H).

Ethyl 2-(((tert-butoxycarbonyl)amino)(tetrahydrofuran-3-yl)methyl)-5-chloronicotinate. Procedure same as that for ethyl (S)-2-(1-((tert-butoxycarbonyl)amino)-2-methylpropyl)-5-chloronicotinate, using ethyl 4-((tert-butoxycarbonyl)amino)-3-oxo-4-(tetrahydrofuran-3-yl)butanoate as a starting material. $^1$H NMR (CD$_3$OD, 400 MHz): δ 8.73 (s, 1H), 8.24 (s, 1H), 5.66 (d, J=8.0 Hz, 1H), 4.61 (s, 1H), 4.45 (q, J=6.8 Hz, 2H), 3.92-3.86 (m, 1H), 3.82-3.56 (m, 3H), 2.82-2.86 (m, 1H), 1.95 (q, J=7.2 Hz, 1H), 1.74 (q, J=6.8 Hz, 1H), 1.44 (t, J=7.2 Hz, 3H), 1.40 (d, J=6.8 Hz, 9H).

Tert-butyl ((5-chloro-3-(hydroxymethyl)pyridin-2-yl)(tetrahydrofuran-3-yl)methyl)carbamate. Procedure same as that for tert-butyl (S)-1-(5-chloro-3-(hydroxymethyl)pyridin-2-yl)-2-methylpropyl)carbamate, using ethyl 2-(((tert-butoxycarbonyl)amino)(tetrahydrofuran-3-yl)methyl)-5-chloronicotinate as a starting material. LCMS: t$_R$=0.753 min in 5-95AB_1.5 min chromatography (MK RP18e 25-2 mm), MS (ESI) m/z 342.9 [M+H]$^+$.

To a solution of tert-butyl ((5-chloro-3-(hydroxymethyl)pyridin-2-yl)(tetrahydrofuran-3-yl)methyl)carbamate (600 mg, 1.74 mmol) in anhydrous CH$_2$Cl$_2$ (25 mL) was added Et$_3$N (0.5 mL, 2.62 mmol) and p-toluenesulfonyl chloride (400 mg, 2.1 mmol) at 0° C. The mixture was stirred at rt for 2 h. The mixture was then washed with water (3×20 mL).

The organic layer was dried over anhydrous sodium sulfate, filtered, concentrated under reduced pressure and purified by chromatography column on silica gel (eluting with 10% EtOAc in petroleum ether, gradient to 20%) to afford (2-(((tert-butoxycarbonyl)amino)(tetrahydrofuran-3-yl) methyl)-5-chloropyridin-3-yl)methyl 4-methylbenzenesulfonate (470 mg, 54%) as a colorless oil and tert-butyl ((5-chloro-3-(chloromethyl)pyridin-2-yl)(tetrahydrofuran-3-yl)methyl)carbamate (200 mg, 32%) as a white solid. LCMS: t$_R$=0.947 min in 5-95AB_1.5 min chromatography (MK RP18e 25-2 mm), MS (ESI) m/z 519.1 [M+Na]$^+$.

To a solution of tert-butyl ((5-chloro-3-(chloromethyl) pyridin-2-yl)(tetrahydrofuran-3-yl)methyl)carbamate (470 mg, 0.95 mmol) in anhydrous DMF (5 mL) was added with sodium hydride (115 mg, 2.84 mmol, 60% in mineral oil) in portions at 0° C. The mixture was stirred at rt for 2 h. The mixture was quenched with water (40 mL) and extracted with ethyl acetate (3×20 mL). The combined organic layers were dried over anhydrous sodium sulfate, filtered, concentrated under reduced pressure and purified by chromatography column on silica gel (eluting with 10% EtOAc in petroleum ether) to afford tert-butyl 3-chloro-7-(tetrahydrofuran-3-yl)-5,7-dihydro-6H-pyrrolo[3,4-b]pyridine-6-carboxylate (285 mg, 91%) as a colorless oil. LCMS: t$_R$=0.862 min in 5-95AB_1.5 min chromatography (MK RP-18e 25-2 mm), MS (ESI) m/z 324.9 [M+H]$^+$. $^1$H NMR (CD$_3$OD, 400 MHz): δ 8.47 (s, 1H), 7.83 (d, J=13.6 Hz, 1H), 5.10 (s, 1H), 4.65-4.50 (m, 1.5H), 3.95 (t, J=8.0 Hz, 0.5H), 3.85-3.67 (m, 4H), 3.03-2.87 (m, 1H), 2.15-1.65 (m, 2H), 1.54 (s, 9H).

To a solution of tert-butyl 3-chloro-7-(tetrahydrofuran-3-yl)-5,7-dihydro-6H-pyrrolo[3,4-b]pyridine-6-carboxylate (60 mg, 0.19 mmol) in a MW vial in anhydrous dioxane (0.5 mL) was added molybdenum hexacarbonyl (6 mg, 0.02 mmol), (4-(ethylsulfonyl)phenyl)methanamine (56 mg, 0.28 mmol) and 1,8-diazabicyclo[5.4.0]undec-7-ene (90 mg, 0.57 mmol). The mixture was degassed with N$_2$ for 15 min, at which point tri-tert-butylphosphonium tetrafluoroborate (58 mg, 0.19 mmol) and trans-bis(acetate)bis[o-(di-o-tolylphosphino)benzyl]dipalladium (II) (10 mg, 0.01 mmol) were added. The vial was sealed and heated in the MW at 160° C. for 20 min. The reaction mixture was filtered, then the filtrate was concentrated under reduced pressure and purified by preparative TLC (eluting with 12% EtOAc in petroleum ether) to afford tert-butyl 3-((4-(ethylsulfonyl)benzyl)carbamoyl)-7-(tetrahydrofuran-3-yl)-5,7-dihydro-6H-pyrrolo[3,4-b]pyridine-6-carboxylate (25 mg, 26%) as a colorless oil. LCMS: t$_R$=0.761 min in 5-95AB_1.5 min chromatography (MK RP18e 25-2 mm), MS (ESI) m/z 516.2 [M+H]$^+$. $^1$H NMR (CD$_3$OD, 400 MHz): δ 8.96 (s, 1H), 8.20 (d, J=10.0 Hz, 1H), 8.15-8.00 (m, 1H), 7.91 (d, J=8.4 Hz, 2H), 7.65 (d, J=8.0 Hz, 2H), 5.19 (s, 1H), 5.00-4.90 (m, 2H), 4.75-4.60 (m, 3H), 4.00-3.65 (m, 5H), 3.25 (q, J=7.2 Hz, 2H), 3.05-2.95 (m, 1H), 2.15-1.75 (m, 2H), 1.56 (s, 9H), 1.23 (t, J=7.2 Hz, 3H).

N-(4-(ethylsulfonyl)benzyl)-7-(tetrahydrofuran-3-yl)-6, 7-dihydro-5H-pyrrolo[3,4-b]pyridine-3-carboxamide. Procedure same as that for (S)—N-(4-(ethylsulfonyl)benzyl)-7-isopropyl-6,7-dihydro-5H-pyrrolo[3,4-b]pyridine-3-carboxamide, using tert-butyl 3-((4-(ethylsulfonyl)benzyl) carbamoyl)-7-(tetrahydrofuran-3-yl)-5,7-dihydro-6H-pyrrolo[3,4-b]pyridine-6-carboxylate as a starting material.

(S)-6-(4-chlorobenzyl)-N-(4-(ethylsulfonyl)benzyl)-7-isopropyl-6,7-dihydro-5H-pyrrolo[3,4-b]pyridine-3-carboxamide (9) was prepared following the synthetic route shown in Scheme 13.

Scheme 13.

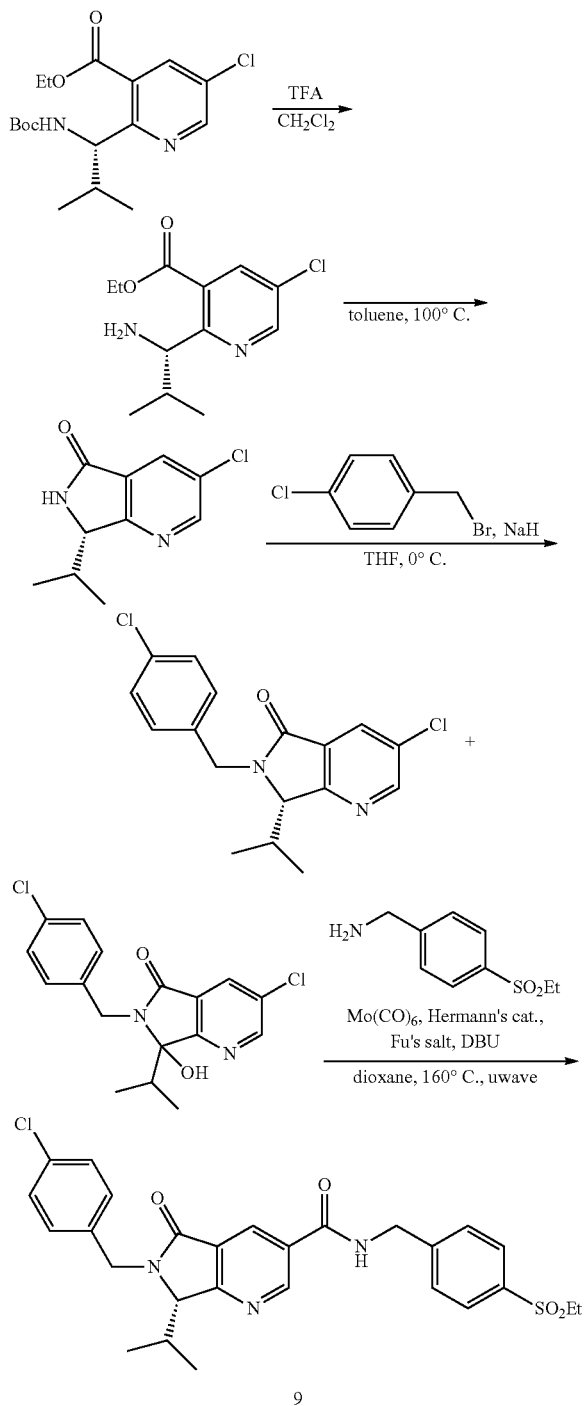

Ethyl (S)-2-(1-amino-2-methylpropyl)-5-chloronicotinate. Procedure same as that for (S)—N-(4-(ethylsulfonyl)benzyl)-7-isopropyl-6,7-dihydro-5H-pyrrolo[3,4-b]pyridine-3-carboxamide, using ethyl (S)-2-(1-((tert-butoxycarbonyl)amino)-2-methylpropyl)-5-chloronicotinate as a starting material. LCMS: $t_R$=0.59 min in 1 min chromatography, MS (ESI) m/z 257.3 [M+H]⁺.

A solution of ethyl (S)-2-(1-amino-2-methylpropyl)-5-chloronicotinate (282 mg, 1.10 mmol) was heated in toluene (5 mL) at 100° C. for 15 h. The solvent was removed in vacuo to yield crude (S)-3-chloro-7-isopropyl-6,7-dihydro-5H-pyrrolo[3,4-b]pyridin-5-one, which was carried forward without further purification. LCMS: $t_R$=0.73 min in 1 min chromatography, MS (ESI) m/z 211.2 [M+H]⁺. ¹H NMR (CD₃OD, 400 MHz): δ 8.70 (d, J=2.8 Hz, 1H), 8.07 (d, J=2.0 Hz, 1H), 6.75 (broad s, 1H), 4.55 (dd, J=1.2 Hz, 3.6 Hz, 1H), 2.49-2.41 (m, 1H), 1.23 (d, J=7.2 Hz, 3H), 0.74 (d, J=6.8 Hz, 3H).

To a degassed solution of (S)-3-chloro-7-isopropyl-6,7-dihydro-5H-pyrrolo[3,4-b]pyridin-5-one (42.2 mg, 200 μmol) in THF (2 mL) at 0° C. was added sodium hydride (60% dispersion in mineral oil, 9.6 mg, 240 mol). The mixture was stirred at 0° C. for 30 min, at which point 4-chlorobenzyl bromide (49.3 mg, 240 μmol) was added. The mixture was allowed to warm to rt and was stirred for 15 h. The mixture was quenched with saturated aqueous ammonium chloride (10 mL) and extracted with EtOAc (10 mL). The organic phase was washed with brine (10 mL), dried over anhydrous MgSO₄, filtered and concentrated under reduced pressure. The residue was purified by silica gel chromatography (eluting with 5% EtOAc in hexanes, gradient to 50%) to afford (S)-3-chloro-6-(4-chlorobenzyl)-7-isopropyl-6,7-dihydro-5H-pyrrolo[3,4-b]pyridin-5-one (19.6 mg, 29%) and 3-chloro-6-(4-chlorobenzyl)-7-hydroxy-7-isopropyl-6,7-dihydro-5H-pyrrolo[3,4-b]pyridin-5-one (20.1 mg, 29%). LCMS: $t_R$=1.09 min in in 1 min chromatography, MS (ESI) m/z 335.3 [M+H]⁺. ¹H NMR (CD₃OD, 400 MHz): δ 8.74 (d, J=2.0 Hz, 1H), 8.17 (d, J=2.4 Hz, 1H), 7.37-7.32 (m, 4H), 5.16 (d, J=15.6 Hz, 1H), 4.47 (d, J=15.2 Hz, 1H), 4.40 (d, J=3.2 Hz, 1H), 2.56-2.48 (m, 1H), 1.27 (d, J=7.2 Hz, 3H), 0.48 (d, J=7.2 Hz, 3H).

General Procedure F (S)-6-(4-chlorobenzyl)-N-(4-(ethylsulfonyl)benzyl)-7-isopropyl-6,7-dihydro-5H-pyrrolo[3,4-b]pyridine-3-carboxamide (9)

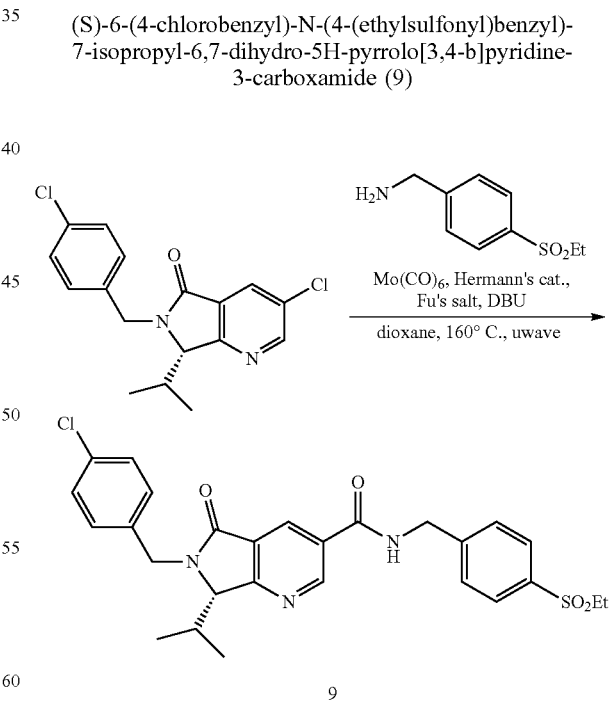

Procedure same as that for tert-butyl 3-((4-(ethylsulfonyl)benzyl)carbamoyl)-7-(tetrahydrofuran-3-yl)-5,7-dihydro-6H-pyrrolo[3,4-b]pyridine-6-carboxylate (Scheme 12), using (S)-3-chloro-6-(4-chlorobenzyl)-7-isopropyl-6,7-dihydro-5H-pyrrolo[3,4-b]pyridin-5-one as a starting material. LCMS: $t_R$=0.92 min in 1 min chromatography, MS (ESI) m/z 526.4 [M+H]$^+$. $^1$H NMR (CD$_3$OD, 400 MHz): δ 9.22 (d, J=2.0 Hz, 1H), 8.57 (d, J=2.0 Hz, 1H), 7.90 (dd, J=2.0 Hz, 6.8 Hz, 2H), 7.66 (d, J=8.8 Hz, 2H), 7.36 (m, 4H), 5.19 (d, J=15.6 Hz, 1H), 4.73 (s, 2H), 4.48 (m, 2H), 3.20 (q, J=7.2 Hz, 2H), 2.60-2.52 (m, 1H), 1.29 (d, J=7.2 Hz, 3H), 1.21 (t, J=7.2 Hz, 3H), 0.49 (d, J=6.8 Hz, 3H).

(S)-7-isopropyl-6-(4-(trifluoromethyl)benzyl)-6,7-dihydro-5H-pyrrolo[3,4-b]pyridine-3-carboxylic acid was prepared following the synthetic route shown in Scheme 14.

Scheme 14.

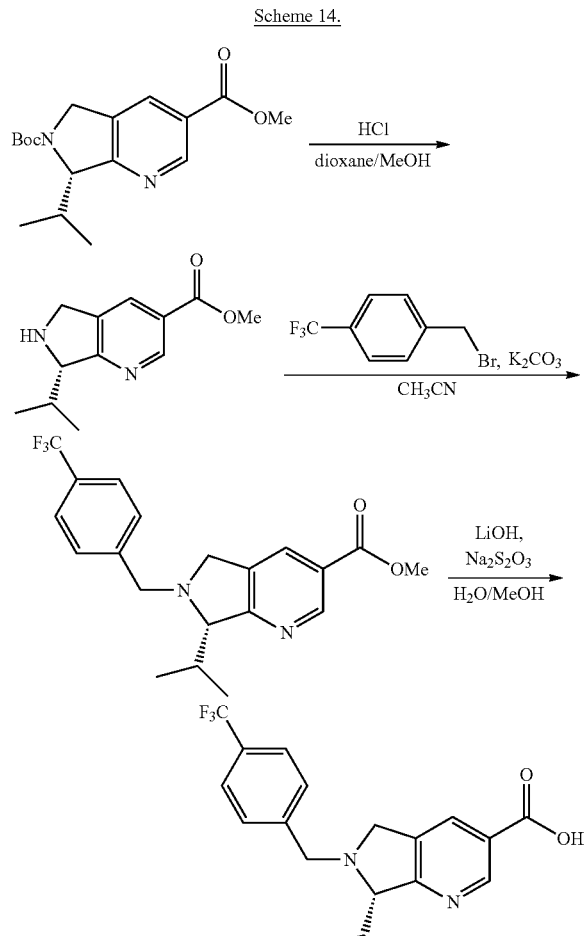

To a solution of 6-(tert-butyl) 3-methyl (S)-7-isopropyl-5,7-dihydro-6H-pyrrolo[3,4-b]pyridine-3,6-dicarboxylate (296 mg, 0.92 mmol) in MeOH (3 mL) was added HCl (4 mL, 4.0 M in dioxane). The mixture was stirred for 30 min at rt for 30 min. The reaction mixture was concentrated to dryness to give methyl (S)-7-isopropyl-6,7-dihydro-5H-pyrrolo[3,4-b]pyridine-3-carboxylate as the HCl salt. LC-MS $t_R$=0.56 min in 2 min chromatography, MS (ESI) m/z 221 [M+H]$^+$.

6-(tert-butyl) 3-methyl(S)-7-isopropyl-5,7-dihydro-6H-pyrrolo[3,4-b]pyridine-3,6-dicarboxylate. Procedure same as that for (S)—N-(4-(ethylsulfonyl)benzyl)-7-isopropyl-6-(4-(trifluoromethyl)benzyl)-6,7-dihydro-5H-pyrrolo[3,4-b]pyridine-3-carboxamide, using methyl (S)-7-isopropyl-6,7-dihydro-5H-pyrrolo[3,4-b]pyridine-3-carboxylate as a starting material. LC-MS $t_R$=1.45 min in 2 min chromatography, MS (ESI) m/z 379 [M+H]$^+$.

To a solution of 6-(tert-butyl) 3-methyl (S)-7-isopropyl-5,7-dihydro-6H-pyrrolo[3,4-b]pyridine-3,6-dicarboxylate (216 mg, 674 μmol) in MeOH (4 mL) was added 10% aqueous Na$_2$S$_2$O$_3$ (3 drops) and aqueous lithium hydroxide (1.2 mL, 2.0 M). The mixture was stirred for 3 h at rt. The reaction mixture was then concentrated, and the residue was purified by preparative HPLC to give 230 mg of (S)-7-isopropyl-6-(4-(trifluoromethyl)benzyl)-6,7-dihydro-5H-pyrrolo[3,4-b]pyridine-3-carboxylic acid as the TFA salt. LC-MS $t_R$=1.22 min in 2 min chromatography, MS (ESI) m/z 365 [M+H]$^+$. $^1$H NMR (CD$_3$OD, 400 MHz): δ 9.14, (s, 1H), 8.35 (s 1H), 7.84-7.81 (m, 4H), 4.81-4.58 (m, 5H), 2.38 (m, 1H), 1.13 (d, J=6.8 Hz, 3H), 0.91 (d, J=6.8 Hz, 3H).

General Procedure G tert-butyl (S)-7-isopropyl-3-((4-(methoxycarbonyl)benzyl)carbamoyl)-5,7-dihydro-6H-pyrrolo[3,4-b]pyridine-6-carboxylate

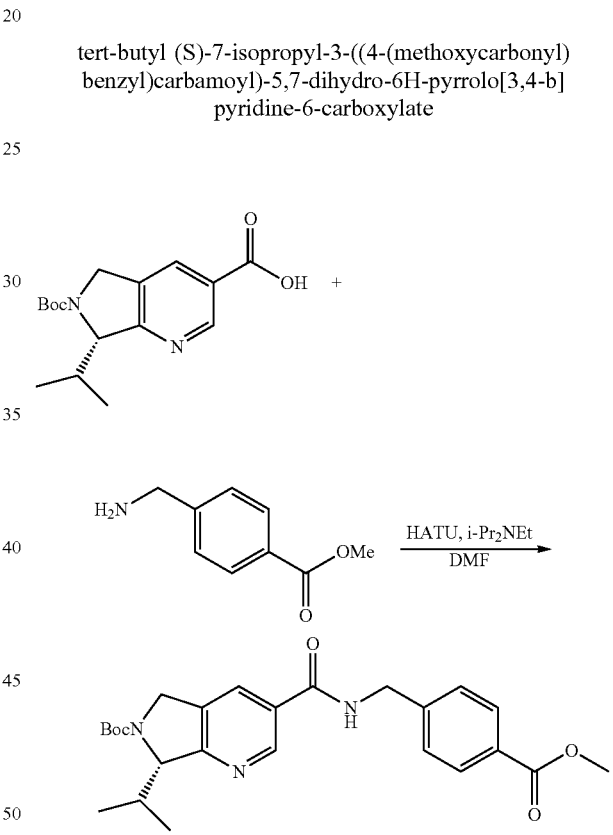

Tert-butyl (S)-7-isopropyl-3-((4-(methoxycarbonyl)benzyl)carbamoyl)-5,7-dihydro-6H-pyrrolo[3,4-b]pyridine-6-carboxylate. Procedure same as that for tert-butyl (S)-3-((4-(ethylsulfonyl)benzyl)carbamoyl)-7-isopropyl-5,7-dihydro-6H-pyrrolo[3,4-b]pyridine-6-carboxylate, using methyl 4-(aminomethyl)benzoate as a starting material. LC-MS $t_R$=1.61 min in 2 min chromatography, MS (ESI) m/z 454.

(S)-4-((7-isopropyl-6-(4-(trifluoromethyl)benzyl)-6,7-dihydro-5H-pyrrolo[3,4-b]pyridine-3-carboxamido)methyl)benzoic acid was prepared following the synthetic route shown in Scheme 15.

Scheme 15.

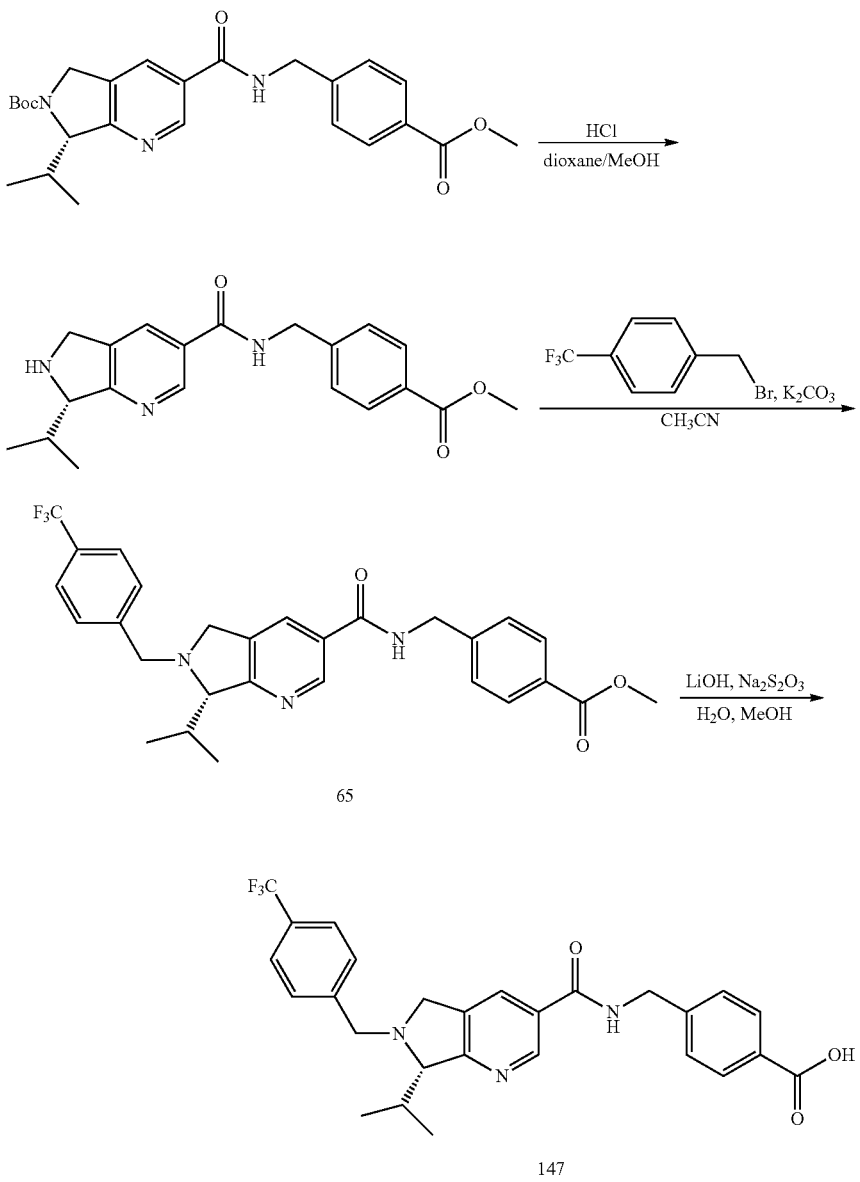

Methyl (S)-4-((7-isopropyl-6,7-dihydro-5H-pyrrolo[3,4-b]pyridine-3-carboxamido)methyl)benzoate. Procedure same as that for methyl (S)-7-isopropyl-6,7-dihydro-5H-pyrrolo[3,4-b]pyridine-3-carboxylate, using tert-butyl (S)-7-isopropyl-3-((4-(methoxycarbonyl)benzyl)carbamoyl)-5,7-dihydro-6H-pyrrolo[3,4-b]pyridine-6-carboxylate as a starting material. LC-MS $t_R$=0.73 min in 2 min chromatography, MS (ESI) m/z 354.

Methyl (S)-4-((7-isopropyl-6-(4-(trifluoromethyl)benzyl)-6,7-dihydro-5H-pyrrolo[3,4-b]pyridine-3-carboxamido)methyl)benzoate (65). Procedure same as that for (S)—N-(4-(ethylsulfonyl)benzyl)-7-isopropyl-6-(4-(trifluoromethyl)benzyl)-6,7-dihydro-5H-pyrrolo[3,4-b]pyridine-3-carboxamide, using methyl (S)-4-((7-isopropyl-6,7-dihydro-5H-pyrrolo[3,4-b]pyridine-3-carboxamido)methyl)benzoate as a starting material. LC-MS $t_R$=1.34 min in 2 min chromatography, MS (ESI) m/z 512 [M+H]$^+$.

General Procedure H (S)-4-((7-isopropyl-6-(4-(trifluoromethyl)benzyl)-6,7-dihydro-5H-pyrrolo[3,4-b]pyridine-3-carboxamido)methyl)benzoic acid (147). Procedure same as that for (S)-7-isopropyl-6-(4-(trifluoromethyl)benzyl)-6,7-dihydro-5H-pyrrolo[3,4-b]pyridine-3-carboxylic acid, using methyl (S)-4-((7-isopropyl-6-(4-(trifluoromethyl)benzyl)-6,7-dihydro-5H-pyrrolo[3,4-b]pyridine-3-carboxamido)methyl)benzoate as a starting material. LC-MS $t_R$=1.20 min in 2 min chromatography, MS (ESI) m/z 498 [M+H]$^+$.

The following compounds in Table 1 were prepared according to the methods described herein.

TABLE 1

| Cmpd No. | Structure | LCMS | ¹H-NMR | Starting Material | General Method |
|---|---|---|---|---|---|
| 3 | (4-chlorobenzyl pyrrolopyridine isopropyl carboxamide ethylsulfonyl benzyl structure) | 512.4 (M + H)+ | (CD$_3$OD) δ 9.36 (t, J = 1.2 Hz, 1H), 9.05 (s, 1H), 8.23 (s, 1H), 7.89 (d, J = 8.4 Hz, 2H), 7.63 (d, J = 8.4 Hz, 2H), 7.59 (d, J = 8.4 Hz, 2H), 7.52 (d, J = 8.4 Hz, 2H), 4.90 (m, 1H), 4.74 (m, 4H), 4.57 (s, 2H), 3.20 (q, J = 7.6 Hz, 2H), 2.42-2.29 (m, 1H), 1.21 (t, J = 7.6 Hz, 3H), 1.13 (d, 6.8 Hz, 3H), 0.90 (d, J = 6.8 Hz, 3H). | (4-chlorobenzyl bromide) | A |
| 4 | (4-cyanobenzyl pyrrolopyridine isopropyl carboxamide ethylsulfonyl benzyl structure) | 503.5 (M + H)+ | (CD$_3$OD) δ 9.36 (t, J = 1.2 Hz, 1H), 9.03 (s, 1H), 8.21 (s, 1H), 7.88 (d, J = 8.8 Hz, 2H), 7.86 (d, J = 8.4 Hz, 2H), 7.78 (d, J = 8.8 Hz, 2H), 7.63 (d, J = 8.4 Hz, 2H), 4.84 (d, J = 15.6 Hz, 1H), 4.71 (m, 3H), 4.59 (m, 3H), 3.20 (q, J = 7.6 Hz, 2H), 2.43-2.32 (m, 1H), 1.21 (t, J = 7.2 Hz, 3H), 1.12 (d, 6.8 Hz, 3H), 0.92 (d, J = 6.8 Hz, 3H). | (4-cyanobenzyl bromide) | A |

TABLE 1-continued

| Cmpd No. | Structure | LCMS | ¹H-NMR | Starting Material | General Method |
|---|---|---|---|---|---|
| 5 | 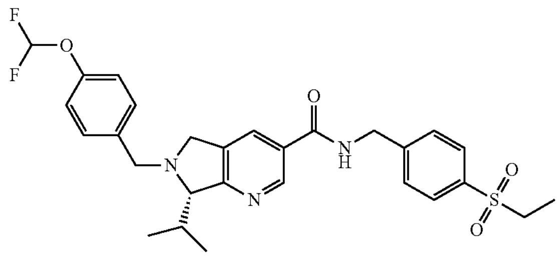 [SMILES: CCS(=O)(=O)c1ccc(CNC(=O)c2cnc3c(c2)CN(Cc2ccc(OC(F)F)cc2)[C@H]3C(C)C)cc1] | 544.4 (M + H)+ | (CD$_3$OD) δ 9.36 (t, J = 1.2 Hz, 1H), 9.04 (s, 1H), 8.23 (s, 1H), 7.89 (d, J = 8.8 Hz, 2H), 7.64 (d, J = 8.4 Hz, 4H), 7.27 (d, J = 8.4 Hz, 2H), 6.92 (t, J = 73.6 Hz, 1H), 4.90 (m, 2H), 4.72 (m, 3H), 4.56 (m, 2H), 3.20 (q, J = 7.6 Hz, 2H), 2.40-2.29 (m, 1H), 1.21 (t, J = 7.6 Hz, 3H), 1.12 (d, 6.8 Hz, 3H), 0.90 (d, J = 6.8 Hz, 3H). | | A |
| 7 | 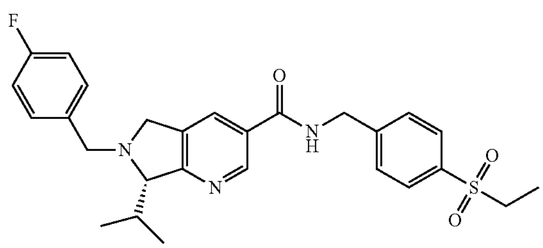 [SMILES: CCS(=O)(=O)c1ccc(CNC(=O)c2cnc3c(c2)CN(Cc2ccc(F)cc2)[C@H]3C(C)C)cc1] | 496.5 (M + H)+ | (CD$_3$OD) δ 9.06 (s, 1H), 8.26 (s, 1H), 7.89 (d, J = 8.4 Hz, 2H), 7.66 (m, 4H), 7.26 (d, J = 8.4 Hz, 2H), 4.96 (d, J = 15.6 Hz, 1H), 4.82 (m, 2H), 4.73 (d, J = 6.0 Hz, 2H), 4.64 (d, J = 13.2 Hz, 1H), 4.59 (d, J = 13.2 Hz, 1H), 3.20 (q, J = 7.6 Hz, 2H), 2.42-2.33 (m, 1H), 1.21 (t, J = 7.2 Hz, 3H), 1.12 (d, 6.8 Hz, 3H), 0.87 (d, J = 6.8 Hz, 3H). | | A |

TABLE 1-continued

| Cmpd No. | Structure | LCMS | ¹H-NMR | Starting Material | General Method |
|---|---|---|---|---|---|
| 8 | 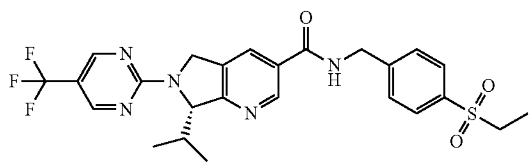 [SMILES: CCS(=O)(=O)c1ccc(CNC(=O)c2cnc3c(c2)CN(c2ncc(C(F)(F)F)cn2)[C@H]3C(C)C)cc1] | 534.4 (M + H)+ | (CD$_3$OD) δ 8.97 (d, J = 2.0 Hz, 1H), 8.68 (s, 2H), 8.25 (t, J = 0.8 Hz, 1H), 7.89 (dd, J = 1.6 Hz, 8.4 Hz, 2H), 7.65 (d, J = 8.4 Hz, 2H), 5.39 (dd, J = 2.0 Hz, 3.2 Hz, 1H), 5.15 (d, J = 16.4 Hz, 1H), 4.88 (d, J = 16.4 Hz, 1H), 4.72 (s, 2H), 3.20 (q, J = 7.2 Hz, 2H), 2.80-2.71 (m, 1H), 1.22 (d, J = 6.8 Hz, 3H), 1.21 (t, J = 7.2 Hz, 3H), 0.64 (d, J = 6.8 Hz, 3H). | | C |
| 10 | 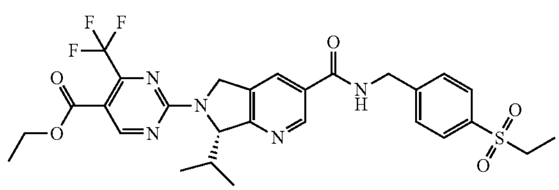 [SMILES: CCOC(=O)c1cnc(N2Cc3cc(C(=O)NCc4ccc(S(=O)(=O)CC)cc4)cnc3[C@@H]2C(C)C)nc1C(F)(F)F] | 606.6 (M + H)+ | (CD$_3$OD) δ 9.02 (d, J = 7.6 Hz, 1H), 8.99 (s, 1H), 8.26 (s, 1H), 7.90 (dd, J = 2.0 Hz, 6.8 Hz, 2H), 7.65 (d, J = 8.8 Hz, 2H), 5.44 (d, J = 9.2 Hz, 1H), 5.22 (dd, J = 10.0 Hz, 16.8 Hz, 1H), 4.93 (d, J = 16.4 Hz, 1H), 4.72 (s, 2H), 4.36 (q, J = 7.2 Hz, 2H), 3.20 (q, J = 7.6 Hz, 2H), 2.81-2.70 (m, 1H), 1.37 (t, J = 7.2 Hz, 3H), 1.21 (t, J = 7.6 Hz, 3H), 0.88 (dd, J = 7.2 Hz, 13.2 Hz, 3H), 0.69 (dd, J = 7.2 Hz, 17.6 Hz, 3H). | | C |

TABLE 1-continued
| Cmpd No. | Structure | LCMS | ¹H-NMR | Starting Material | General Method |
|---|---|---|---|---|---|
| 11 | 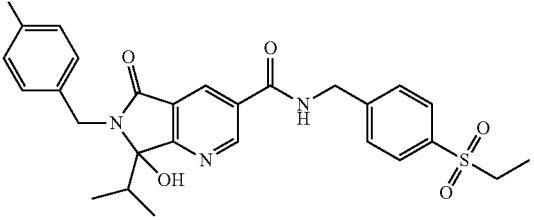 | 542.5 (M + H)+ | (CD$_3$OD) δ 9.23 (d, J = 2.4 Hz, 1H), 8.53 (d, J = 2.4 Hz, 1H), 7.90 (dd, J = 2.0 Hz, 6.8 Hz, 2H), 7.65 (d, J = 8.4 Hz, 2H), 7.49 (d, J = 8.4 Hz, 2H), 7.32 (dd, J = 2.0 Hz, 6.8 Hz, 2H), 4.80 (d, J = 14.0 Hz, 1H), 4.73 (m, 2H), 4.61 (d, J = 15.2 Hz, 1H), 3.20 (q, J = 7.2 Hz, 2H), 2.48-2.41 (m, 1H), 1.27 (d, 6.8 Hz, 3H), 1.20 (t, J = 7.2 Hz, 3H), 0.39 (d, J = 7.2 Hz, 3H). | 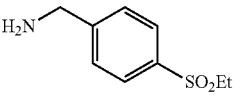 | F |
| 12 | 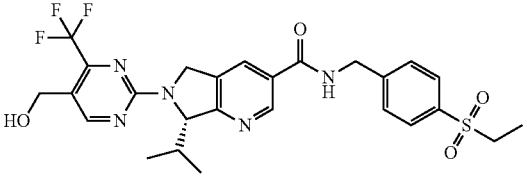 [SMILES: CCS(=O)(=O)c1ccc(CNC(=O)c2cnc3c(c2)CN(c2ncc(CO)c(C(F)(F)F)n2)[C@H]3C(C)C)cc1] | 564.5 (M + H)+ | (CD$_3$OD) δ 9.02 (s, 1H), 8.75 (s, 1H), 8.40 (s, 1H), 7.90 (dd, J = 1.6 Hz, 6.8 Hz, 2H), 7.66 (d, J = 8.4 Hz, 2H), 5.51 (t, J = 2.8 Hz, 1H), 5.21 (d, J = 16.4 Hz, 1H), 4.93 (m, 1H), 4.73 (s, 2H), 4.67 (s, 2H), 3.20 (q, J = 7.2 Hz, 2H), 2.78-2.66 (m, 1H), 1.21 (t, J = 7.2 Hz, 3H), 1.17 (d, J = 5.6 Hz, 3H), 0.78 (d, J = 5.6 Hz, 3H). | Reduction of 10 | |

TABLE 1-continued

| Cmpd No. | Structure | LCMS | ¹H-NMR | Starting Material | General Method |
|---|---|---|---|---|---|
| 14 | 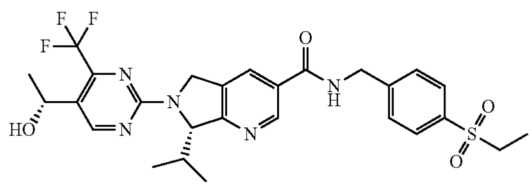 [SMILES: CCS(=O)(=O)c1ccc(CNC(=O)c2cnc3c(c2)CN(c2ncc([C@@H](C)O)c(C(F)(F)F)n2)[C@H]3C(C)C)cc1] | 578.5 (M + H)+ | (CD₃OD) δ 9.09 (d, J = 2.0 Hz, 1H), 8.93 (s, 1H), 8.59 (s, 1H), 7.90 (dd, J = 1.6 Hz, 6.8 Hz, 2H), 7.67 (d, J = 8.4 Hz, 2H), 5.64 (dd, J = 3.2 Hz, 7.0 Hz, 1H), 5.28 (d, J = 16.4 Hz, 1H), 5.13 (q, J = 6.4 Hz, 1H), 4.95 (d, J = 15.6 Hz, 1H), 4.74 (s, 2H), 3.20 (q, J = 7.6 Hz, 2H), 2.76-2.66 (m, 1H), 1.47 (d, J = 6.4 Hz, 3H), 1.21 (t, J = 7.2 Hz, 3H), 1.13 (d, 6.8 Hz, 3H), 0.81 (dd, J = 6.8 Hz, 3H). | Oxidation of 12 followed by methyl Grignard addition | |
| 17 | 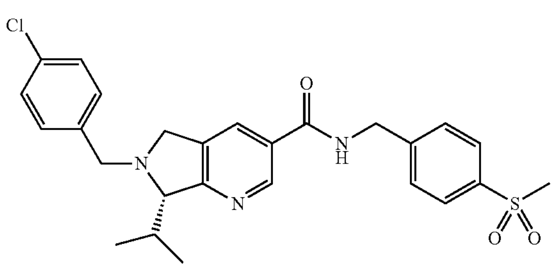 | 498.0 (M + H)+ | (CD₃OD) δ 9.39 (brs, 1H), 9.09 (s, 1H), 8.28 (s, 1H), 7.96 (d, J = 8.4 Hz, 2H), 7.70-7.60 (m, 4H), 7.56 (d, J = 8.0 Hz, 2H), 5.05-4.95 (m, 2H), 4.75-4.60 (m, 5H), 3.13 (s, 3H), 2.39-2.35 (m, 1H), 1.16 (d, J = 6.8 Hz, 3H), 0.90 (d, J = 6.8 Hz, 3H). | 4-Cl-C₆H₄-CH₂Br | A |

TABLE 1-continued

| Cmpd No. | Structure | LCMS | ¹H-NMR | Starting Material | General Method |
|---|---|---|---|---|---|
| 18 | 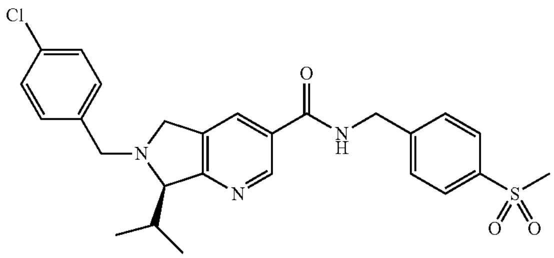 [SMILES: CC(C)[C@@H]1c2ncc(C(=O)NCc3ccc(S(C)(=O)=O)cc3)cc2CN1Cc1ccc(Cl)cc1] | 498.0 (M + H)+ | (CD₃OD) δ 9.08 (d, J = 1.6 Hz, 1H), 8.27 (s, 1H), 7.96 (dd, J = 1.6, 6.8 Hz, 2H), 7.67-7.63 (m, 4H), 7.55 (d, J = 8.4 Hz, 2H), 5.10-4.95 (m, 2H), 4.75-4.60 (m, 5H), 3.13 (s, 3H), 2.38-2.34 (m, 1H), 1.14 (d, J = 6.8 Hz, 3H), 0.90 (d, J = 7.2 Hz, 3H). | 4-chlorobenzyl bromide | A |
| 19 | 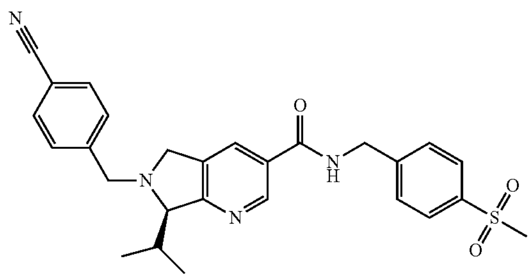 [SMILES: CC(C)[C@@H]1c2ncc(C(=O)NCc3ccc(S(C)(=O)=O)cc3)cc2CN1Cc1ccc(C#N)cc1] | 489.1 (M + H)+ | (CD₃OD) δ 9.07 (d, J = 1.6 Hz, 1H), 8.27 (s, 1H), 7.96 (dd, J = 2.0, 6.8 Hz, 2H), 7.88 (dd, J = 8.8, 22.4 Hz, 4H), 7.65 (d, J = 8.4 Hz, 2H), 4.85-4.65 (m, 7H), 3.13 (s, 3H), 2.42-2.37 (m, 1H), 1.16 (d, J = 6.8 Hz, 3H), 0.91 (d, J = 6.8 Hz, 3H). | 4-cyanobenzyl bromide | A |
| 20 | 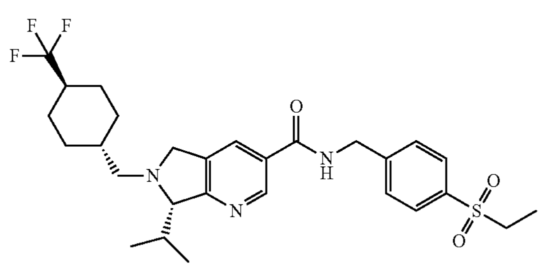 | 489.0 (M + H)+ | (CD₃OD) δ 9.08 (s, 1H), 8.30 (s, 1H), 7.95 (d, J = 8.4 Hz, 2H), 7.91 (s, 4H), 7.66 (d, J = 8.4 Hz, 2H), 5.07 (d, J = 15.6 Hz, 1H), 4.90-4.70 (m, 3H), 4.72 (s, 3H), 3.13 (s, 3H), 2.42-2.37 (m, 1H), 1.16 (d, J = 6.8 Hz, 3H), 0.90 (d, J = 6.8 Hz, 3H). | trans-4-(trifluoromethyl)cyclohexanecarbaldehyde | B |

TABLE 1-continued
| Cmpd No. | Structure | LCMS | ¹H-NMR | Starting Material | General Method |
|---|---|---|---|---|---|
| 21 | 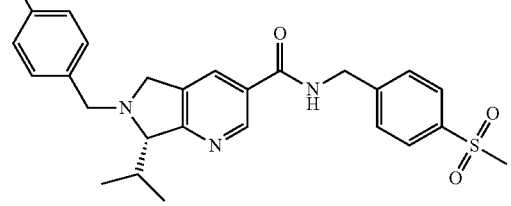 | 489.0 (M + H)+ | (CD₃OD) δ 9.08 (s, 1H), 8.30 (s, 1H), 7.95 (d, J = 8.4 Hz, 2H), 7.91 (s, 4H), 7.66 (d, J = 8.4 Hz, 2H), 5.07 (d, J = 15.6 Hz, 1H), 4.90-4.70 (m, 3H), 4.72 (s, 3H), 3.13 (s, 3H), 2.42-2.37 (m, 1H), 1.16 (d, J = 6.8 Hz, 3H), 0.90 (d, J = 6.8 Hz, 3H). | 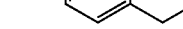 | A |
| 22 | 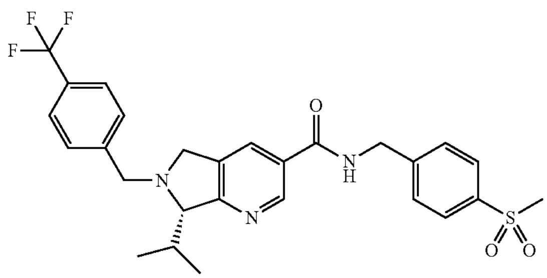 [SMILES: CC(C)[C@H]1c2ncc(C(=O)NCc3ccc(S(C)(=O)=O)cc3)cc2CN1Cc1ccc(C(F)(F)F)cc1] | 532.1 (M + H)+ | (CD₃OD) δ 9.09 (d, J = 2.0 Hz, 1H), 8.30 (s, 1H), 7.95 (d, J = 8.0 Hz, 2H), 8.88 (q, J = 8.4 Hz, 4H), 7.66 (d, J = 8.4 Hz, 2H), 5.04 (d, J = 15.2 Hz, 2H), 4.85-4.70 (m, 5H), 3.13 (s, 3H), 2.41-2.37 (m, 1H), 1.17 (d, J = 6.8 Hz, 3H), 0.90 (d, J = 6.8 Hz, 3H). |  | A |
| 23 | 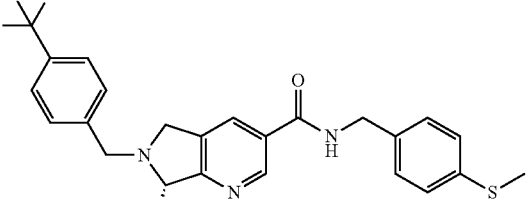 | 499.1 (M + H)+ | (CD₃OD) δ 9.08 (s, 1H), 8.71 (d, J = 2.4 Hz, 1H), 8.32 (s, 1H), 8.00 (dd, J = 2.4, 8.4 Hz, 1H), 7.95 (d, J = 8.4 Hz, 2H), 7.66 (d, J = 8.4 Hz, 2H), 7.62 (d, J = 8.8 Hz, 1H), 5.15 (d, J = 16.0 Hz, 2H), 4.85-4.75 (m, 3H), 4.73 (s, 2H), 3.13 (s, 3H), 2.62-2.54 (m, 1H), 1.22 (d, J = 7.2 Hz, 3H), 0.96 (d, J = 6.8 Hz, 3H). |  | A |

TABLE 1-continued

| Cmpd No. | Structure | LCMS | ¹H-NMR | Starting Material | General Method |
|---|---|---|---|---|---|
| 24 | 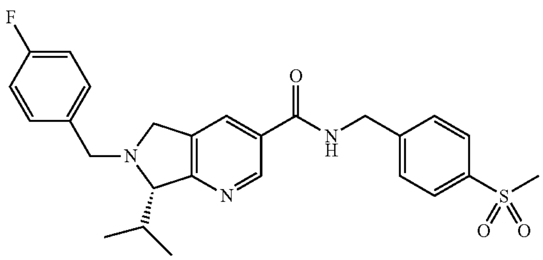 [SMILES: CC(C)[C@H]1c2ncc(C(=O)NCc3ccc(S(C)(=O)=O)cc3)cc2CN1Cc1ccc(F)cc1] | 482.1 (M + H)+ | (CD₃OD) δ 9.08 (d, J = 1.6 Hz, 1H), 8.31 (s, 1H), 7.95 (d, J = 8.4 Hz, 2H), 7.75 (dd, J = 4.8, 8.4 Hz, 2H), 7.66 (d, J = 8.4 Hz, 2H), 7.28 (t, J = 8.4 Hz, 2H), 5.10-5.03 (m, 2H), 4.90-4.70 (m, 4H), 4.59 (d, J = 12.8 Hz, 1H), 3.13 (s, 3H), 2.37-2.30 (m, 1H), 1.11 (d, J = 6.4 Hz, 3H), 0.87 (d, J = 6.8 Hz, 3H). | | A |
| 25 | 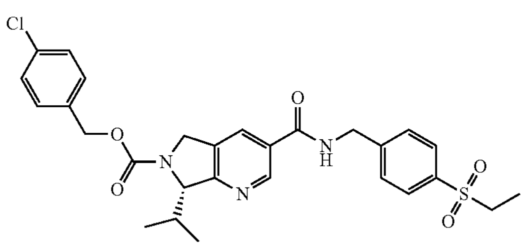 [SMILES: CCS(=O)(=O)c1ccc(CNC(=O)c2cnc3c(c2)CN(C(=O)OCc2ccc(Cl)cc2)[C@H]3C(C)C)cc1] | 556.6 (M + H)+ | (CD₃OD) δ 8.96 (s, 1H), 8.22 (d, J = 11.6 Hz, 1H), 7.89 (d, J = 8.8 Hz, 2H), 7.64 (d, J = 8.8 Hz, 2H), 7.42 (d, J = 8.8 Hz, 2H), 7.38 (d, J = 8.8 Hz, 2H), 5.20 (s, 2H), 5.07 (m, 1H), 4.85 (m, 2H), 4.71 (s, 2H), 3.20 (q, J = 7.2 Hz, 2H), 2.58-2.39 (m, 1H), 1.21 (t, J = 7.2 Hz, 3H), 1.03 (dd, 6.8 Hz, 16.8 Hz, 3H), 0.75 (dd, J = 6.8 Hz, 18.8 Hz, 3H). | | E |

TABLE 1-continued

| Cmpd No. | Structure | LCMS | ¹H-NMR | Starting Material | General Method |
|---|---|---|---|---|---|
| 26 | 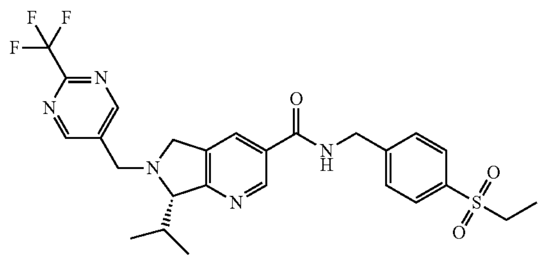 [SMILES: CCS(=O)(=O)c1ccc(CNC(=O)c2cnc3c(c2)CN(Cc2cnc(C(F)(F)F)nc2)[C@H]3C(C)C)cc1] | 548.5 (M + H)+ | (CD$_3$OD) δ 9.30 (s, 2H), 9.09 (s, 1H), 8.30 (s, 2H), 7.89 (dd, J = 2.0 Hz, 8.4 Hz, 2H), 7.65 (d, J = 8.4 Hz, 2H), 4.95 (m, 3H), 4.82 (m, 2H), 4.71 (s, 2H), 3.20 (q, J = 7.2 Hz, 2H), 2.62-2.53 (m, 1H), 1.25 (d, J = 6.8 Hz, 3H), 1.21 (t, J = 7.6 Hz, 3H), 0.98 (d, J = 6.8 Hz, 3H). | | A |
| 27 | 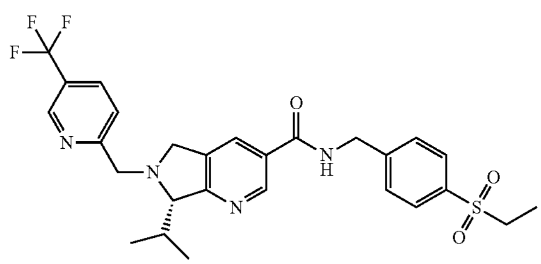 [SMILES: CCS(=O)(=O)c1ccc(CNC(=O)c2cnc3c(c2)CN(Cc2ccc(C(F)(F)F)cn2)[C@H]3C(C)C)cc1] | 547.5 (M + H)+ | (CD$_3$OD) δ 9.08 (d, J = 1.6 Hz, 1H), 9.03 (s, 1H), 8.32 (d, J = 1.6 Hz, 1H), 8.26 (dd, J = 2.0 Hz, 8.0 Hz, 1H), 7.89 (d, J = 8.4 Hz, 2H), 7.77 (d, J = 8.0 Hz, 1H), 7.65 (d, J = 8.4 Hz, 2H), 5.18 (d, J = 15.6 Hz, 1H), 4.97 (s, 2H), 4.92 (m, 2H), 4.72 (s, 2H), 3.20 (q, J = 7.6 Hz, 2H), 2.68-2.59 (m, 1H), 1.24 (d, J = 7.2 Hz, 3H), 1.21 (t, J = 7.6 Hz, 3H), 0.96 (d, J = 6.8 Hz, 3H). | | B |

TABLE 1-continued

| Cmpd No. | Structure | LCMS | ¹H-NMR | Starting Material | General Method |
|---|---|---|---|---|---|
| 28 | 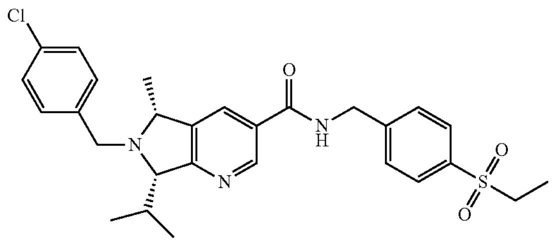 [SMILES: CCS(=O)(=O)c1ccc(CNC(=O)c2cnc3c(c2)[C@@H](C)N(Cc2ccc(Cl)cc2)[C@H]3C(C)C)cc1] | 526.3 (M + H)+ | (CD₃OD) δ 9.11 (s, 1H), 8.32 (s, 1H), 7.90 (d, J = 8.8 Hz, 2H), 7.65 (d, J = 8.4 Hz, 2H), 7.59 (m, 4H), 5.25-4.83 (m, 2H), 4.73 (s, 2H), 4.62 (m, 1H), 4.15 (m, 1H), 3.20 (q, J = 7.2 Hz, 2H), 2.21-2.10 (m, 1H), 1.47 (d, J = 6.4 Hz, 3H), 1.21 (t, J = 7.2 Hz, 3H), 0.95 (m, 3H), 0.79 (d, J = 6.8 Hz, 3H). | | A |
| 29 | 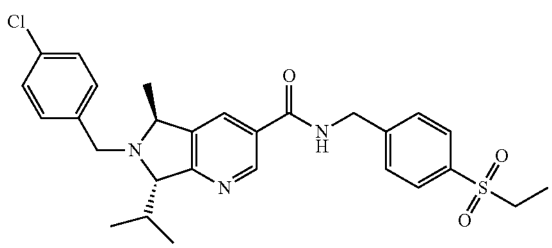 [SMILES: CCS(=O)(=O)c1ccc(CNC(=O)c2cnc3c(c2)[C@H](C)N(Cc2ccc(Cl)cc2)[C@H]3C(C)C)cc1] | 526.3 (M + H)+ | (CD₃OD) δ 9.07 (d, J = 2.0 Hz, 1H), 8.22 (s, 1H), 7.89 (dd, J = 2.0 Hz, 6.8 Hz, 2H), 7.71 (d, J = 6.8 Hz, 2H), 7.64 (d, J = 8.0 Hz, 2H), 7.57 (m, 2H), 5.21 (q, J = 6.8 Hz, 1H), 4.99 (d, J = 3.2 Hz, 1H), 4.82 (d, J = 3.6 Hz, 1H), 4.72 (m, 3H), 3.20 (q, J = 7.2 Hz, 2H), 2.16-2.09 (m, 1H), 1.75 (d, J = 6.8 Hz, 3H), 1.29 (d, J = 6.8 Hz, 3H), 1.21 (t, J = 7.2 Hz, 3H), 0.86 (d, J = 6.8 Hz, 3H). | | A |

TABLE 1-continued

| Cmpd No. | Structure | LCMS | ¹H-NMR | Starting Material | General Method |
|---|---|---|---|---|---|
| 30 | 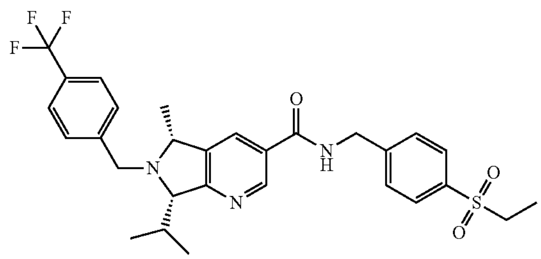 [SMILES: CCS(=O)(=O)c1ccc(CNC(=O)c2cnc3c(c2)[C@@H](C)N(Cc2ccc(C(F)(F)F)cc2)[C@H]3C(C)C)cc1] | 560.6 (M + H)+ | (CD₃OD) δ 9.11 (s, 1H), 8.32 (s, 1H), 7.87 (m, 6H), 7.66 (d, J = 8.0 Hz, 2H), 5.35 (m, 1H), 4.83 (m, 1H), 4.73 (s, 2H), 4.63 (m, 1H), 4.28 (m, 1H), 3.21 (q, J = 7.2 Hz, 2H), 2.23-2.11 (m, 1H), 1.97 (d, J = 6.8 Hz, 3H), 1.21 (t, J = 7.2 Hz, 3H), 0.97 (m, 3H), 0.80 (d, J = 6.8 Hz, 3H). | | A |
| 31 | 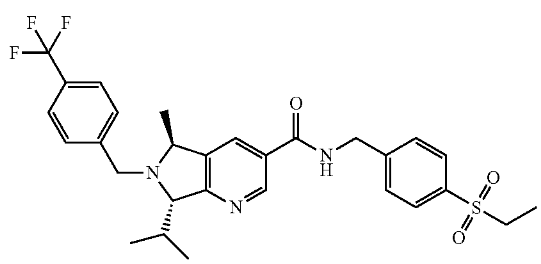 [SMILES: CCS(=O)(=O)c1ccc(CNC(=O)c2cnc3c(c2)[C@H](C)N(Cc2ccc(C(F)(F)F)cc2)[C@H]3C(C)C)cc1] | 560.6 (M + H)+ | (CD₃OD) δ 9.08 (d, J = 1.2 Hz, 1H), 8.24 (s, 1H), 7.95 (d, J = 8.4 Hz, 2H), 7.89 (m, 4H), 7.64 (d, J = 8.8 Hz, 2H), 5.24 (m, 1H), 5.01 (d, J = 2.8 Hz, 1H), 4.88 (m, 2H), 4.71 (s, 2H), 3.20 (q, J = 7.6 Hz, 2H), 2.18-2.10 (m, 1H), 1.75 (d, J = 6.8 Hz, 3H), 1.28 (d, J = 6.8 Hz, 3H), 1.21 (t, J = 7.6 Hz, 3H), 0.87 (d, J = 6.8 Hz, 3H). | | A |

TABLE 1-continued

| Cmpd No. | Structure | LCMS | ¹H-NMR | Starting Material | General Method |
|---|---|---|---|---|---|
| 32 | 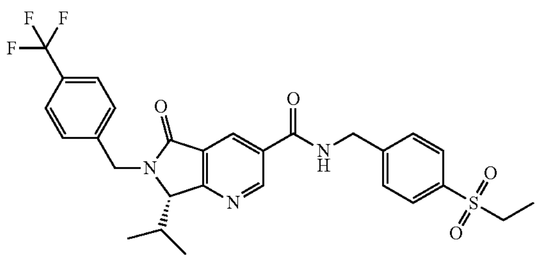 [SMILES: CCS(=O)(=O)c1ccc(CNC(=O)c2cnc3c(c2)C(=O)N(Cc2ccc(C(F)(F)F)cc2)[C@H]3C(C)C)cc1] | 560.5 (M + H)+ | (CD$_3$OD) δ 9.23 (d, J = 2.0 Hz, 1H), 8.59 (d, J = 2.4 Hz, 1H), 7.90 (d, J = 8.8 Hz, 2H), 7.65 (m, 4H), 7.55 (d, J = 8.8 Hz, 2H), 5.26 (d, J = 15.6 Hz, 1H), 4.74 (s, 2H), 4.63 (d, J = 16.4 Hz, 1H), 4.53 (d, J = 3.2 Hz, 1H), 3.20 (q, J = 7.2 Hz, 2H), 2.60-2.52 (m, 1H), 1.30 (d, J = 6.8 Hz, 3H), 1.21 (t, J = 7.6 Hz, 3H), 0.50 (d, J = 6.8 Hz, 3H). | H$_2$N–C$_6$H$_4$–SO$_2$Et | F |
| 33 | 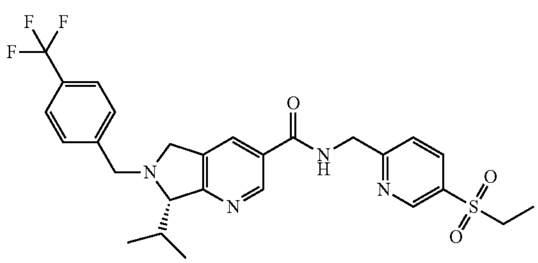 | 547.5 (M + H)+ | (CD$_3$OD) δ 9.12 (s, 1H), 9.10 (d, J = 1.2 Hz, 1H), 8.53 (dd, J = 2.0 Hz, 8.4 Hz, 1H), 8.34 (s, 1H), 7.93 (d, J = 8.0 Hz, 2H), 7.91 (d, J = 6.4 Hz, 1H), 7.84 (d, J = 8.0 Hz, 2H), 5.07 (d, J = 15.6 Hz, 1H), 4.84 (m, 3H), 4.73 (d, J = 12.8 Hz, 1H), 3.35 (q, J = 7.2 Hz, 2H), 2.42-2.29 (m, 1H), 1.28 (t, J = 7.2 Hz, 3H), 1.15 (d, J = 6.8 Hz, 3H), 0.89 (d, J = 6.8 Hz, 3H). | F$_3$C–C$_6$H$_4$–CH$_2$Br | A |

TABLE 1-continued

| Cmpd No. | Structure | LCMS | ¹H-NMR | Starting Material | General Method |
|---|---|---|---|---|---|
| 34 | 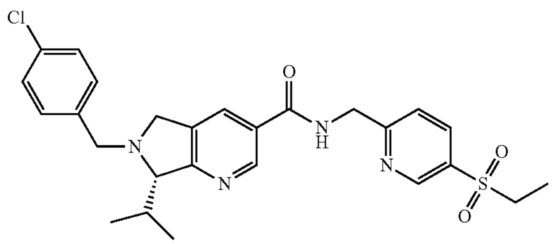 [SMILES: CCS(=O)(=O)c1ccc(CNC(=O)c2cnc3c(c2)CN(Cc2ccc(Cl)cc2)[C@H]3C(C)C)nc1] | 513.5 (M + H)+ | (CD$_3$OD) δ 9.13 (dd, J = 1.6 Hz, 3.6 Hz, 2H), 8.59 (dd, J = 2.0 Hz, 8.4 Hz, 1H), 8.35 (s, 1H), 7.98 (d, J = 8.0 Hz, 1H), 7.70 (d, J = 8.8 Hz, 2H), 7.54 (d, J = 8.8 Hz, 2H), 5.07 (d, J = 15.2 Hz, 1H), 4.87 (m, 2H), 4.73 (d, J = 13.2 Hz, 1H), 4.60 (d, J = 12.8 Hz, 1H), 3.37 (q, J = 7.6 Hz, 2H), 2.41-2.25 (m, 1H), 1.29 (t, J = 7.6 Hz, 3H), 1.12 (d, J = 6.4 Hz, 3H), 0.88 (d, J = 6.8 Hz, 3H). | | A |
| 35 | 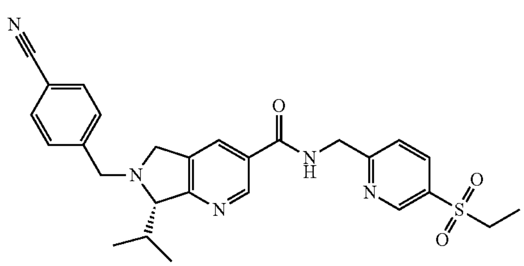 | 504.5 (M + H)+ | (CD$_3$OD) δ 9.11 (d, J = 2.0 Hz, 2H), 8.56, (dd, J = 2.0 Hz, 8.4 Hz, 1H), 8.33 (s, 1H), 8.01-7.79 (m, 5H), 5.07 (d, J = 15.2 Hz, 1H), 4.91-4.80 (m, 3H), 4.72 (d, J = 14.4 Hz, 1H), 3.36 (q, J = 7.2 Hz, 2H), 2.64-2.53 (m, 1H), 1.28 (t, J = 7.2 Hz, 3H), 1.15 (d, J = 6.8 Hz, 3H), 0.89 (d, J = 7.2 Hz, 3H). | | A |

TABLE 1-continued

| Cmpd No. | Structure | LCMS | ¹H-NMR | Starting Material | General Method |
|---|---|---|---|---|---|
| 36 | 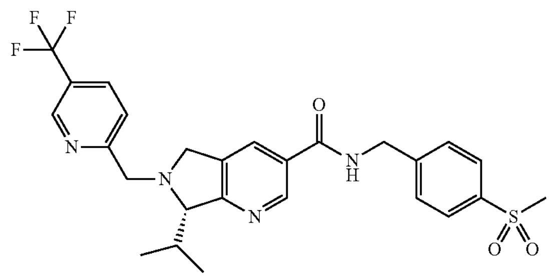 [SMILES: CC(C)[C@H]1c2ncc(C(=O)NCc3ccc(S(C)(=O)=O)cc3)cc2CN1Cc1ccc(C(F)(F)F)cn1] | 533.1 (M + H)+ | (CD$_3$OD) δ 9.09 (s, 1H), 9.04 (s, 1H), 8.33 (s, 1H), 8.28 (d, J = 8.0 Hz, 2H), 7.95 (d, J = 8.4 Hz, 2H), 7.80 (d, J = 8.0 Hz, 2H), 7.66 (d, J = 8.4 Hz, 2H), 5.20 (d, J = 15.6 Hz, 1H), 5.25-4.93 (m, 4H), 4.73 (s, 2H), 3.13 (s, 3H), 2.68-2.63 (m, 1H), 1.25 (d, J = 6.8 Hz, 3H), 0.98 (d, J = 6.8 Hz, 3H). | | A |
| 37 | 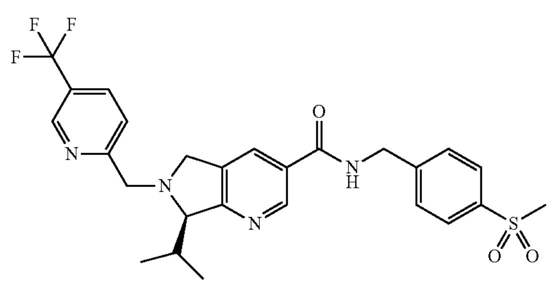 [SMILES: CC(C)[C@@H]1c2ncc(C(=O)NCc3ccc(S(C)(=O)=O)cc3)cc2CN1Cc1ccc(C(F)(F)F)cn1] | 533.0 (M + H)+ | (CD$_3$OD) δ 9.43 (t, J = 6.0 Hz, 1H), 9.07 (d, J = 18.8 Hz, 2H), 8.33-8.25 (m, 2H), 7.96 (d, J = 8.4 Hz, 2H), 7.76 (d, J = 8.0 Hz, 1H), 7.66 (d, J = 8.4 Hz, 2H) 5.20-4.92 (m, 5H), 4.73 (d, J = 6.0 Hz, 2H), 3.13 (s, 3H), 2.68-2.61 (m, 1H), 1.25 (d, J = 7.2 Hz, 3H), 0.98 (d, J = 6.8 Hz, 3H). | | A |

TABLE 1-continued

| Cmpd No. | Structure | LCMS | ¹H-NMR | Starting Material | General Method |
|---|---|---|---|---|---|
| 38 | 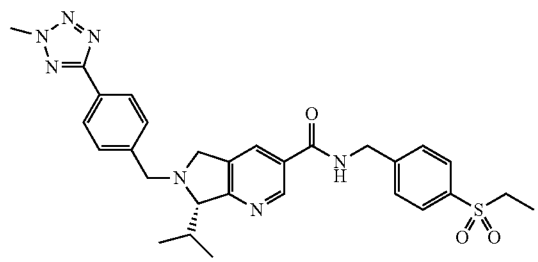 [SMILES: CCS(=O)(=O)c1ccc(CNC(=O)c2cnc3c(c2)CN(Cc2ccc(-c4nnn(C)n4)cc2)[C@H]3C(C)C)cc1] | 560.1 (M + H)+ | (CD$_3$OD) δ 9.08 (s, 1H), 8.31 (s, 1H), 8.26 (d, J = 8.0 Hz, 2H), 7.90 (d, J = 8.0 Hz, 2H), 7.86 (d, J = 8.0 Hz, 2H), 7.65 (d, J = 8.0 Hz, 2H), 5.10 (d, J = 15.2 Hz, 1H), 4.99-4.96 (m, 1H), 4.85-4.77 (m, 2H), 4.73-4.67 (m, 3H), 4.46 (s, 3H), 3.22 (q, J = 7.6 Hz, 2H), 2.38-2.32 (m, 1H), 1.22 (t, J = 7.6 Hz, 3H), 1.14 (d, J = 6.4 Hz, 3H), 0.90 (d, J = 6.8 Hz, 3H). | | B |
| 39 | 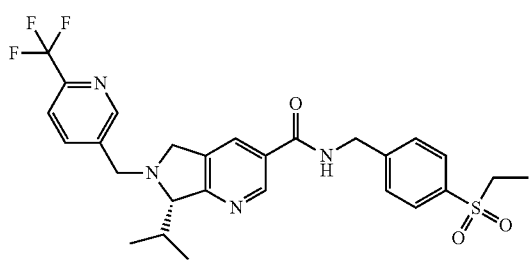 [SMILES: CCS(=O)(=O)c1ccc(CNC(=O)c2cnc3c(c2)CN(Cc2ccc(C(F)(F)F)nc2)[C@H]3C(C)C)cc1] | 547.1 (M + H)+ | (CD$_3$OD) δ 9.10 (d, J = 2.0 Hz, 1H), 9.05 (s, 1H), 8.46 (dd, J = 2.0, 8.0 Hz, 1H), 8.31 (s, 1H), 7.99 (d, J = 8.0 Hz, 1H), 7.91 (d, J = 8.4 Hz, 2H), 7.66 (d, J = 8.0 Hz, 2H), 5.06-4.98 (m, 2H), 4.86-4.81 (m, 3H), 4.73 (s, 2H), 3.22 (q, J = 7.6 Hz, 2H), 2.52-2.48 (m, 1H), 1.23-1.19 (m, 6H), 0.94 (d, J = 6.8 Hz, 3H). | | A |

TABLE 1-continued

| Cmpd No. | Structure | LCMS | ¹H-NMR | Starting Material | General Method |
|---|---|---|---|---|---|
| 40 | 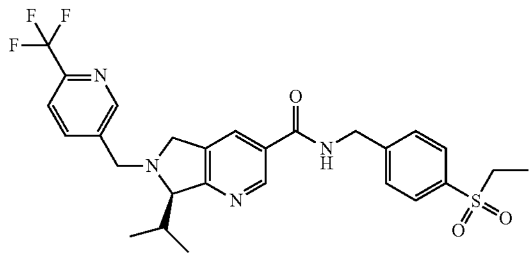 [SMILES: CCS(=O)(=O)c1ccc(CNC(=O)c2cnc3c(c2)CN(Cc2ccc(C(F)(F)F)nc2)[C@@H]3C(C)C)cc1] | 547.1 (M + H)+ | (CD₃OD) δ 9.08 (s, 1H), 8.99 (s, 1H), 8.36 (d, J = 7.6 Hz, 1H), 8.26 (s, 1H), 7.98 (d, J = 8.0 Hz, 1H), 7.91 (d, J = 8.0 Hz, 2H), 7.66 (d, J = 8.4 Hz, 2H), 5.01-4.96 (m, 1H), 4.82-4.68 (m, 6H), 3.22 (q, J = 7.2 Hz, 2H), 2.52-2.48 (m, 1H), 1.23-1.19 (m, 6H), 0.47 (d, J = 6.8 Hz, 3H). | | A |
| 41 | 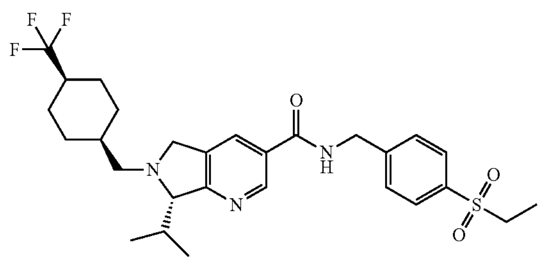 [SMILES: CCS(=O)(=O)c1ccc(CNC(=O)c2cnc3c(c2)CN(C[C@H]2CC[C@@H](C(F)(F)F)CC2)[C@H]3C(C)C)cc1] | 552.1 (M + H)+ | (CD₃OD) δ 9.09 (d, J = 1.6 Hz, 1H), 8.30 (d, J = 1.2 Hz,, 1H), 7.91 (d, J = 8.4 Hz, 2H), 7.67 (d, J = 8.4 Hz, 2H), 5.14 (d, J = 14.4 Hz, 1H), 4.74 (s, 3H), 3.52 (d, J = 5.6 Hz, 2H), 3.22 (q, J = 7.6 Hz, 2H), 2.54-2.52 (m, 1H), 2.22-2.19 (m, 2H), 1.83-1.60 (m, 8H), 1.33 (d, J = 6.8 Hz, 4H), 1.22 (d, J = 7.2 Hz, 3H), 1.11 (d, J = 6.4 Hz, 3H). | | B |
| 42 | 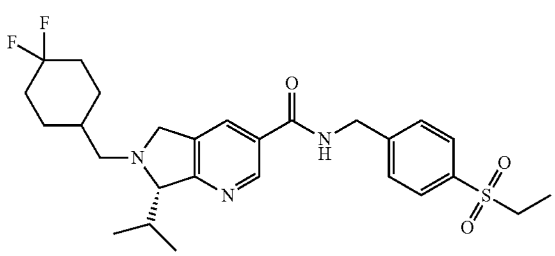 [SMILES: CCS(=O)(=O)c1ccc(CNC(=O)c2cnc3c(c2)CN(CC2CCC(F)(F)CC2)[C@H]3C(C)C)cc1] | 520.6 (M + H)+ | (CD₃OD) δ 9.08 (s, 1H), 8.29, (s, 1H), 7.90 (d, J = 7.6 Hz, 2H), 7.65 (d, J = 7.6 Hz, 2H), 5.16 (d, J = 14.4 Hz, 1H), 4.73 (d, J = 14.4 Hz, 1H), 4.72 (s, 2H), 3.41 (m, 1H), 3.20 (q, J = 7.2 Hz, 2H), 2.58-2.47 | | B |

TABLE 1-continued

| Cmpd No. | Structure | LCMS | ¹H-NMR | Starting Material | General Method |
|---|---|---|---|---|---|
| | | | (m, 1H), 2.20-2.06 (m, 3H), 2.05-1.95 (m, 4H), 1.92-1.82 (m, 2H), 1.58-1.41 (m, 2H), 1.32 (d, J = 7.2 Hz, 3H), 1.21 (t, J = 7.2 Hz, 3H), 1.09 (d, J = 6.0 Hz, 3H). | | |
| 43 | 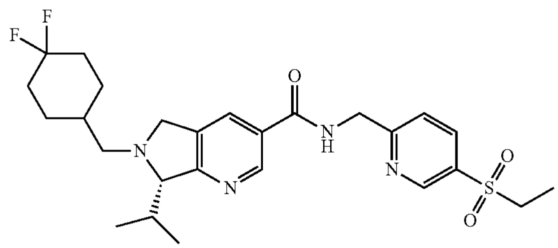 [SMILES: CCS(=O)(=O)c1ccc(CNC(=O)c2cnc3c(c2)CN(CC2CCC(F)(F)CC2)[C@H]3C(C)C)nc1] | 521.5 (M + H)+ | (CD₃OD) δ 9.12 (s, 1H), 9.00, (d, J = 2.0 Hz, 1H), 8.32 (s, 1H), 8.30 (d, J = 2.0 Hz, 1H), 7.72 (d, J = 8.4 Hz, 1H), 5.17 (d, J = 15.6 Hz, 1H), 4.83 (s, 2H), 4.74 (d, J = 14.8 Hz, 1H), 3.46 (m, 1H), 3.30 (q, J = 7.6 Hz, 2H), 2.60-2.49 (m, 1H), 2.20-2.06 (m, 3H), 2.05-1.95 (m, 4H), 1.92-1.82 (m, 2H), 1.58-1.41 (m, 2H), 1.33 (d, J = 6.8 Hz, 3H), 1.27 (t, J = 7.6 Hz, 3H), 1.10 (d, J = 6.8 Hz, 3H). | | B |
| 44 | 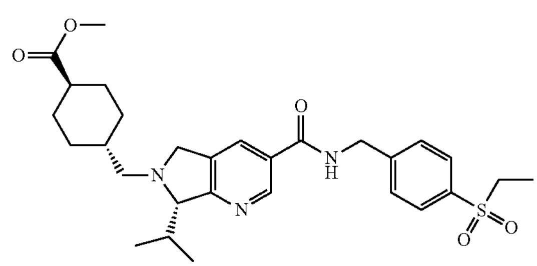 [SMILES: CCS(=O)(=O)c1ccc(CNC(=O)c2cnc3c(c2)CN(C[C@H]2CC[C@H](C(=O)OC)CC2)[C@H]3C(C)C)cc1] | 542.1 (M + H)+ | (CD₃OD) δ 9.08 (s, 1H), 8.28 (s, 1H), 7.90 (d, J = 8.4 Hz, 2H), 7.65 (d, J = 8.4 Hz, 2H), 5.16-5.05 (m, 1H), 4.72 (s, 3H), 3.68 (s, 3H), 3.44-3.29 (m, 2H), 3.21 (q, J = 7.6 Hz, 2H), 2.52-2.33 (m, 2H), 2.13-1.83 (m, 6H), 1.57-1.44 (m, 2H), 1.31 (d, J = 6.4 Hz, 4H), 1.21 (t, J = | | B |

TABLE 1-continued

| Cmpd No. | Structure | LCMS | ¹H-NMR | Starting Material | General Method |
|---|---|---|---|---|---|
| | | | 7.6 Hz, 4H), 1.09 (d, J = 6.4 Hz, 3H). | | |
| 45 | 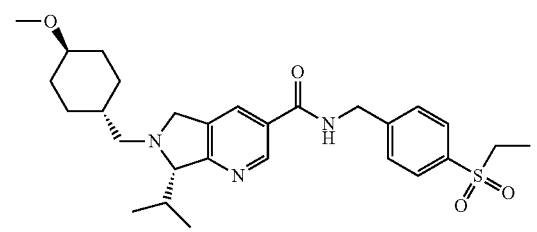 [SMILES: CCS(=O)(=O)c1ccc(CNC(=O)c2cnc3c(c2)CN(C[C@H]2CC[C@H](OC)CC2)[C@H]3C(C)C)cc1] | 514.2 (M + H)+ | (CD₃OD) δ 9.42 (t, J = 6.0 Hz, 1H), 9.10 (s, 1H), 8.30 (s, 1H), 7.91 (d, J = 8.4 Hz, 2H), 7.66 (d, J = 8.4 Hz, 2H), 5.13-5.08 (m, 2H), 4.77-4.62 (m, 4H), 3.41-3.37 (m, 5H), 3.26-3.17 (m, 3H), 2.56-2.48 (m, 2H), 2.21-2.13 (m, 2H), 2.03-1.92 (m, 3H), 1.32 (d, J = 7.2 Hz, 3H), 1.28-1.19 (m, 6H), 1.10 (d, J = 6.8 Hz, 3H). | | B |
| 47 | 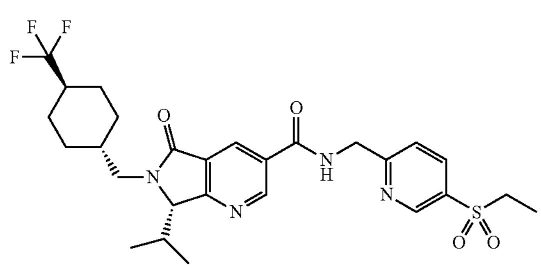 [SMILES: CCS(=O)(=O)c1ccc(CNC(=O)c2cnc3c(c2)C(=O)N(C[C@H]2CC[C@H](C(F)(F)F)CC2)[C@H]3C(C)C)nc1] | 567.53 (M + H)+ | (CD₃OD) δ 9.24 (d, J = 2.0 Hz, 1H), 8.99 (d, J = 1.6 Hz, 1H), 8.55 (d, J = 2.0 Hz, 1H), 8.27 (dd, J = 2.4, 8.4 Hz, 1H), 7.69 (d, J = 8.4 Hz, 1H), 4.83 (s, 2H), 4.71 (d, J = 3.2 Hz, 1H), 3.88 (dd, J = 9.2, 13.8 Hz, 1H), 3.30 (q, J = 7.6 Hz, 2H), 3.16 (dd, J = 5.2, 13.8 Hz, 1H), 2.62-2.58 (m, 1H), 2.33-1.71 (m, 6H), 1.38 (d, J = 6.8 Hz, 3H), 1.35-1.04 (m, 4H), 1.25 (t, J = 7.6 Hz, 3H), 0.53 (d, J = 6.8 Hz, 3H). | | F |

TABLE 1-continued

| Cmpd No. | Structure | LCMS | ¹H-NMR | Starting Material | General Method |
|---|---|---|---|---|---|
| 48 | 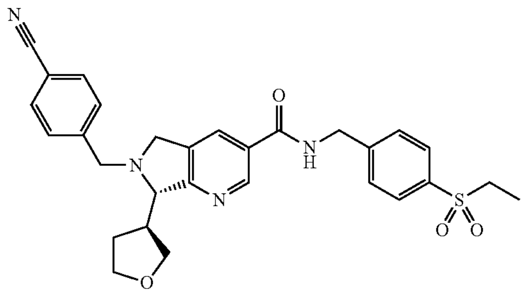 [SMILES: CCS(=O)(=O)c1ccc(CNC(=O)c2cnc3c(c2)CN(Cc2ccc(C#N)cc2)[C@H]3[C@@H]2CCOC2)cc1] | 531.1 (M + H)+ | (CD$_3$OD) δ 9.01 (s, 1H), 8.21 (s, 1H), 7.86 (dd, J = 8.4, 10.4 Hz, 4H), 7.76 (d, J = 8.0 Hz, 2H), 7.62 (d, J = 8.4 Hz, 2H), 4.75-4.50 (m, 6H), 4.00-3.68 (m, 5H), 3.18 (q, J = 7.6 Hz, 2H), 3.00-2.90 (m, 1H), 2.10-2.04 (m, 1H), 1.98-1.85 (m, 1H), 1.19 (t, J = 7.6 Hz, 3H). | | A |
| 49 | 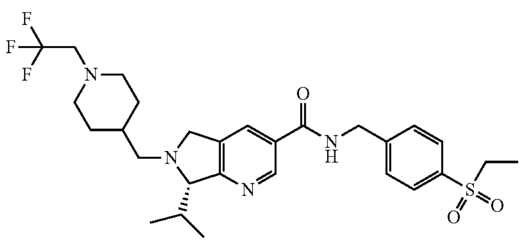 [SMILES: CCS(=O)(=O)c1ccc(CNC(=O)c2cnc3c(c2)CN(CC2CCN(CC(F)(F)F)CC2)[C@H]3C(C)C)cc1] | 567.1 (M + H)+ | (CD$_3$OD) δ 9.08 (s, 1H), 8.30 (s, 1H), 7.89 (d, J = 8.4 Hz, 2H), 7.65 (d, J = 8.4 Hz, 2H), 4.72 (s, 2H), 4.12-4.05 (m, 2H), 3.65-3.60 (m, 2H), 3.50-3.40 (m, 2H), 3.30-3.25 (m, 5H), 3.20 (q, J = 7.2 Hz, 2H), 2.60-2.50 (m, 1H), 2.34-2.20 (m, 3H), 1.82-1.73 (m, 2H), 1.32 (d, J = 7.2 Hz, 3H), 1.21 (t, J = 7.6 Hz, 3H), 1.15-1.00 (m, 3H). | | B |
| 50 | 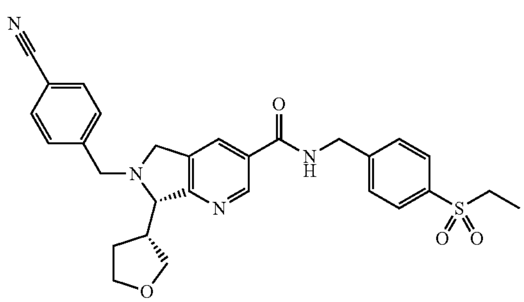 [SMILES: CCS(=O)(=O)c1ccc(CNC(=O)c2cnc3c(c2)CN(Cc2ccc(C#N)cc2)[C@H]3[C@H]2CCOC2)cc1] | 531.1 (M + H)+ | (CD$_3$OD) δ 8.98 (s, 1H), 8.17 (s, 1H), 7.85 (dd, J = 8.4, 14.4 Hz, 4H), 7.76 (d, J = 8.0 Hz, 2H), 7.62 (d, J = 8.4 Hz, 2H), 4.80-4.40 (m, 6H), 4.00-3.65 (m, 5H), 3.18 (q, J = 7.6 Hz, 2H), 3.00-2.88 (m, 1H), 2.25- | | A |

TABLE 1-continued

| Cmpd No. | Structure | LCMS | ¹H-NMR | Starting Material | General Method |
|---|---|---|---|---|---|
| | | | 2.13 (m, 1H), 2.13-2.00 (m, 1H), 1.19 (t, J = 7.6 Hz, 3H). | | |
| 51 | 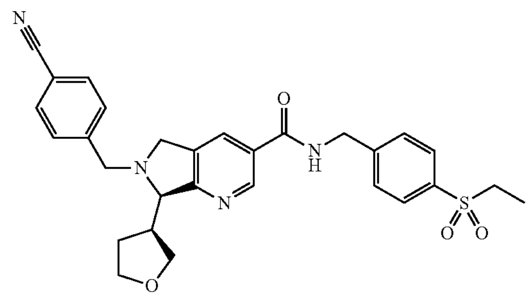 [SMILES: CCS(=O)(=O)c1ccc(CNC(=O)c2cnc3c(c2)CN(Cc2ccc(C#N)cc2)[C@@H]3[C@@H]2CCOC2)cc1] | 531.1 (M + H)+ | (CD₃OD) δ 9.00 (s, 1H), 8.19 (s, 1H), 7.84 (t, J = 8.0 Hz, 4H), 7.78 (d, J = 8.0 Hz, 2H), 7.62 (d, J = 8.0 Hz, 2H), 4.80-4.45 (m, 6H), 4.00-3.65 (m, 5H), 3.18 (q, J = 7.6 Hz, 2H), 3.00-2.88 (m, 1H), 2.27-2.13 (m, 1H), 2.10-1.98 (m, 1H), 1.19 (t, J = 7.6 Hz, 3H). | NC-C₆H₄-CH₂Br | A |
| 52 | 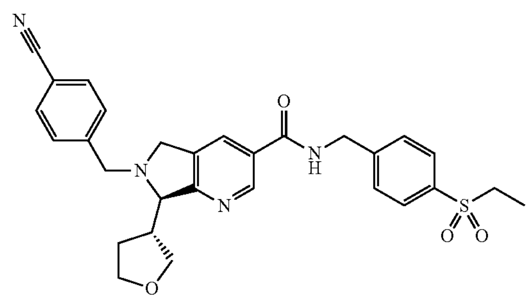 [SMILES: CCS(=O)(=O)c1ccc(CNC(=O)c2cnc3c(c2)CN(Cc2ccc(C#N)cc2)[C@@H]3[C@H]2CCOC2)cc1] | 531.1 (M + H)+ | (CD₃OD) δ 8.99 (s, 1H), 8.19 (s, 1H), 7.85 (dd, J = 8.0, 17.6 Hz, 4H), 7.80-7.70 (m, 2H), 7.62 (d, J = 8.4 Hz, 2H), 4.70-4.35 (m, 6H), 3.95-3.65 (m, 5H), 3.18 (q, J = 7.6 Hz, 2H), 3.00-2.88 (m, 1H), 2.12-2.06 (m, 1H), 2.00-1.87 (m, 1H), 1.19 (t, J = 7.6 Hz, 3H). | NC-C₆H₄-CH₂Br | A |
| 53 | 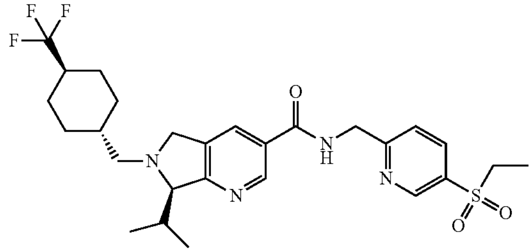 [SMILES: CCS(=O)(=O)c1ccc(CNC(=O)c2cnc3c(c2)CN(C[C@H]2CC[C@H](C(F)(F)F)CC2)[C@@H]3C(C)C)nc1] | 553.1 (M + H)+ | (CD₃OD) δ 9.12 (s, 1H), 9.01 (d, J = 2.0 Hz, 1H), 8.36-8.32 (m, 2H), 7.75 (d, J = 8.0 Hz, 1H), 5.16 (d, J = 15.6 Hz, 1H), 4.89-4.87 (m, 2H), 4.73 (d, J = 15.2 Hz, 1H), 3.42-3.34 (m, 3H), 3.31-3.28 (m, | F₃C-cyclohexyl-CHO | B |

TABLE 1-continued

| Cmpd No. | Structure | LCMS | ¹H-NMR | Starting Material | General Method |
|---|---|---|---|---|---|
| | | | 2H), 2.58-2.51 (m, 1H), 2.20-1.90 (m, 6H) 1.50-1.39 (m, 2H), 1.33 (d, J = 7.2 Hz, 3H), 1.26 (t, J = 7.2 Hz, 3H), 1.24-1.20 (m, 2H), 1.10 (d, J = 6.8 Hz, 3H). | | |
| 54 | 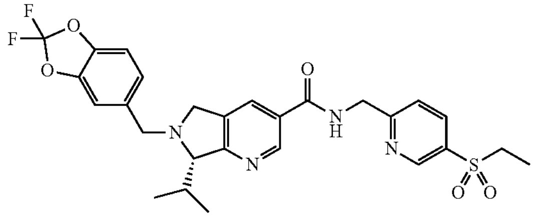 [SMILES: CCS(=O)(=O)c1ccc(CNC(=O)c2cnc3c(c2)CN(Cc2ccc4c(c2)OC(F)(F)O4)[C@H]3C(C)C)nc1] | 559.50 (M + H)+ | (CD₃OD) δ 9.11 (s, 1H), 9.01 (s, 1H), 8.35 (dd, J = 2.0, 8.4 Hz, 1H), 8.31 (s, 1H), 7.75 (d, J = 8.4 Hz, 1H), 7.62 (d, J = 1.2 Hz 1H), 7.50 (dd, J = 1.6, 8.5 Hz, 1H), 7.37 (d, J = 8.0 Hz, 1H), 5.01 (d, J = 15.6 Hz, 1H), 4.84 (s, 2H), 4.68 (dd, J = 12.8, 24.0 Hz, 2H), 3.34 (s, 2H), 3.30 (q, J = 7.6 Hz, 2H), 2.38 (broad s, 1H), 1.25 (t, J = 7.6 Hz, 3H), 1.16 (d, J = 6.0 Hz, 3H), 0.90 (d, J = 6.8 Hz, 3H). | | A |
| 55 | 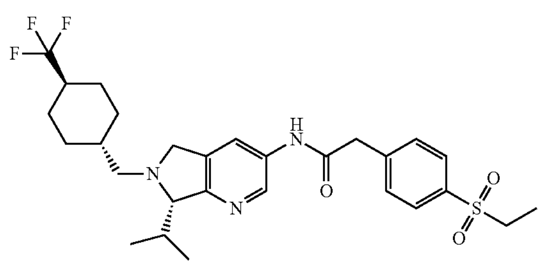 [SMILES: CCS(=O)(=O)c1ccc(CC(=O)Nc2cnc3c(c2)CN(C[C@H]2CC[C@H](C(F)(F)F)CC2)[C@H]3C(C)C)cc1] | 552.7 (M + H)+ | (CD₃OD) δ 8.60 (s, 1H), 8.33 (s, 1H), 7.89 (d, J = 8.4 Hz, 2H), 7.64 (d, J = 8.4 Hz, 2H), 4.95 (m, 1H), 4.62 (m, 4H), 3.89 (s, 2H), 3.21 (q, J = 7.2 Hz, 2H), 2.48-2.38 (m, 1H), 2.24-2.12 (m, 1H), 2.11-1.86 (m, 5H), 1.48-1.38 (m, 2H), 1.37-1.24 (m, 2H), 1.29 (d, J = | | B |

TABLE 1-continued

| Cmpd No. | Structure | LCMS | ¹H-NMR | Starting Material | General Method |
|---|---|---|---|---|---|
| | | | 6.8 Hz, 3H), 1.22 (t, J = 7.6 Hz, 3H), 1.06 (d, J = 6.8 Hz, 3H). | | |
| 56 | 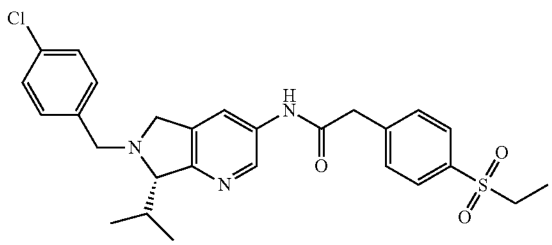 [SMILES: CCS(=O)(=O)c1ccc(CC(=O)Nc2cnc3c(c2)CN(Cc2ccc(Cl)cc2)[C@H]3C(C)C)cc1] | 512.8 (M + H)+ | (CD₃OD) δ 8.69 (s, 1H), 8.31 (s, 1H), 7.89 (d, J = 8.4 Hz, 2H), 7.64 (d, J = 8.8 Hz, 4H), 7.52 (d, J = 8.8 Hz, 2H), 4.95 (d, J = 15.6 Hz, 1H), 4.72 (m, 2H), 4.66 (d, J = 14.4 Hz, 1H), 4.54 (d, J = 12.8 Hz, 1H), 3.90 (s, 2H), 3.21 (q, J = 7.2 Hz, 2H), 2.38-2.23 (m, 1H), 1.22 (t, J = 7.2 Hz, 3H), 1.08 (d, J = 6.0 Hz, 3H), 0.86 (d, J = 6.8 Hz, 3H). | | A |
| 57 | 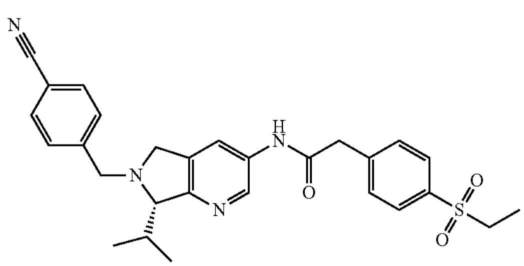 [SMILES: CCS(=O)(=O)c1ccc(CC(=O)Nc2cnc3c(c2)CN(Cc2ccc(C#N)cc2)[C@H]3C(C)C)cc1] | 503.7 (M + H)+ | (CD₃OD) δ 8.66 (s, 1H), 8.30 (s, 1H), 7.90-7.82 (m, 6H), 7.65-7.56 (m, 2H), 4.94 (d, J = 15.6 Hz, 1H), 4.71 (m, 2H), 4.64 (m, 2H), 3.90 (s, 2H), 3.21 (q, J = 7.2 Hz, 2H), 2.39-2.27 (m, 1H), 1.22 (t, J = 7.2 Hz, 3H), 1.04 (d, J = 6.8 Hz, 3H), 0.87 (d, J = 6.8 Hz, 3H). | | A |

TABLE 1-continued

| Cmpd No. | Structure | LCMS | ¹H-NMR | Starting Material | General Method |
|---|---|---|---|---|---|
| 58 | 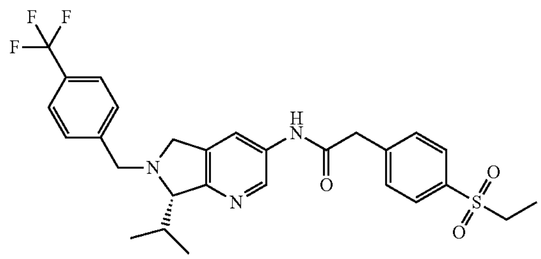 [SMILES: CCS(=O)(=O)c1ccc(CC(=O)Nc2cnc3c(c2)CN(Cc2ccc(C(F)(F)F)cc2)[C@H]3C(C)C)cc1] | 546.5 (M + H)+ | (CD₃OD) δ 8.67 (s, 1H), 8.31 (s, 1H), 7.90-7.81 (m, 6H), 7.67-7.56 (m, 2H), 4.95 (d, J = 15.6 Hz, 1H), 4.73 (m, 3H), 4.65 (m, 1H), 3.90 (s, 2H), 3.21 (q, J = 7.2 Hz, 2H), 2.38-2.25 (m, 1H), 1.22 (t, J = 7.2 Hz, 3H), 1.04 (d, J = 7.2 Hz, 3H), 0.87 (d, J = 6.8 Hz, 3H). | F₃C-C₆H₄-CH₂Br | A |
| 59 | 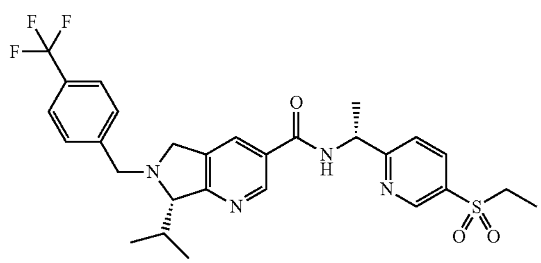 [SMILES: CCS(=O)(=O)c1ccc([C@@H](C)NC(=O)c2cnc3c(c2)CN(Cc2ccc(C(F)(F)F)cc2)[C@H]3C(C)C)nc1] | 561.1 (M + H)+ | (CD3OD) δ 9.11 (d, J = 1.6 Hz, 1H), 9.03 (d, J = 2.0 Hz, 1H), 8.36-8.25 (m, 2H), 7.89 (dd, J = 8.0, 24.0 Hz, 4H), 7.78 (d, J = 8.4 Hz, 1H), 5.38 (q, J = 7.2 Hz, 1H), 5.08-5.03 (m, 1H), 4.85-4.65 (m, 4H), 3.32-3.29 (m, 2H), 2.40-2.35 (m, 1H), 1.68 (d, J = 7.2 Hz, 3H), 1.28 (t, J = 7.2 Hz, 3H), 1.16 (d, J = 6.8 Hz, 3H), 0.90 (d, J = 6.8 Hz, 3H). | F₃C-C₆H₄-CH₂Br | A |
| 60 | 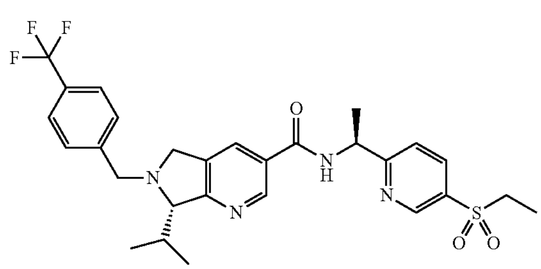 [SMILES: CCS(=O)(=O)c1ccc([C@H](C)NC(=O)c2cnc3c(c2)CN(Cc2ccc(C(F)(F)F)cc2)[C@H]3C(C)C)nc1] | 561.1 (M + H)+ | (CD3OD) δ 9.12 (d, J = 1.6 Hz, 1H), 9.02 (d, J = 1.6 Hz, 1H), 8.35-8.25 (m, 2H), 7.88 (q, J = 8.0 Hz, 4H), 7.75 (d, J = 8.0 Hz, 1H), 5.38 (q, J = 7.2 Hz, 1H), 5.05-4.95 (m, 1H), 4.85-4.71 (m, 4H), 3.31-3.28 | F₃C-C₆H₄-CH₂Br | A |

TABLE 1-continued

| Cmpd No. | Structure | LCMS | ¹H-NMR | Starting Material | General Method |
|---|---|---|---|---|---|
| | | | (m, 2H), 2.45-2.35 (m, 1H), 1.67 (d, J = 6.8 Hz, 3H), 1.28 (t, J = 7.2 Hz, 3H), 1.17 (d, J = 6.8 Hz, 3H), 0.90 (d, J = 6.8 Hz, 3H). | | |
| 61 | 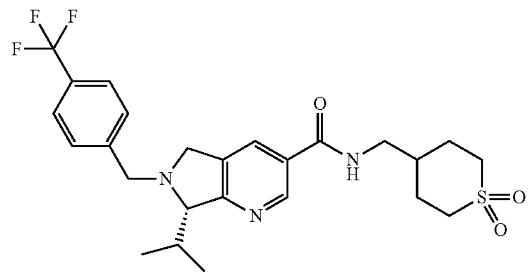 [SMILES: CC(C)[C@H]1c2ncc(C(=O)NCC3CCS(=O)(=O)CC3)cc2CN1Cc1ccc(C(F)(F)F)cc1] | 510.5 (M + H)+ | | | G |
| 62 | 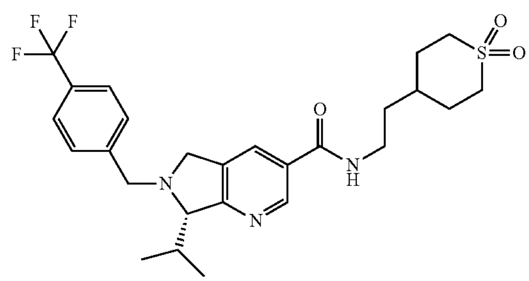 [SMILES: CC(C)[C@H]1c2ncc(C(=O)NCCC3CCS(=O)(=O)CC3)cc2CN1Cc1ccc(C(F)(F)F)cc1] | 524.5 (M + H)+ | | | G |
| 63 | 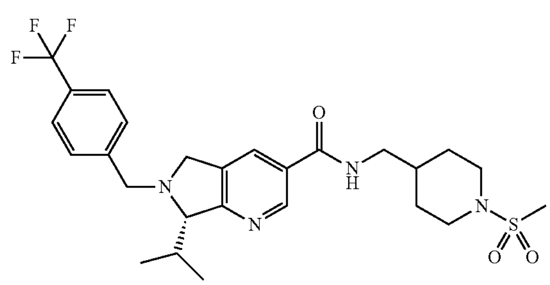 [SMILES: CC(C)[C@H]1c2ncc(C(=O)NCC3CCN(S(C)(=O)=O)CC3)cc2CN1Cc1ccc(C(F)(F)F)cc1] | 539.5 (M + H)+ | | | G |
| 64 | 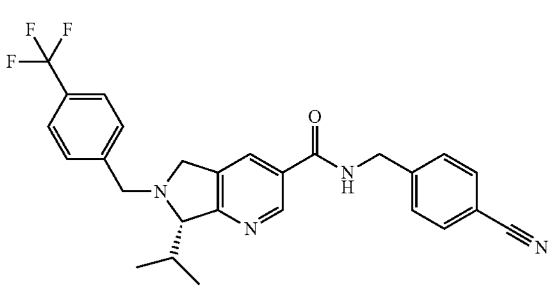 [SMILES: CC(C)[C@H]1c2ncc(C(=O)NCc3ccc(C#N)cc3)cc2CN1Cc1ccc(C(F)(F)F)cc1] | 479.5 (M + H)+ | | | G |

TABLE 1-continued

| Cmpd No. | Structure | LCMS | ¹H-NMR | Starting Material | General Method |
|---|---|---|---|---|---|
| 66 | 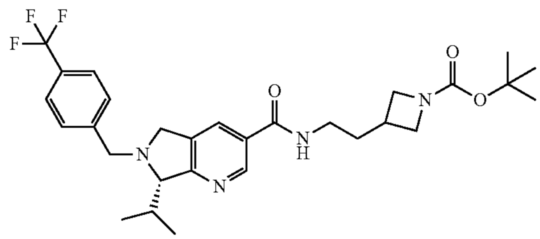 [SMILES: CC(C)[C@H]1c2ncc(C(=O)NCCC3CN(C(=O)OC(C)(C)C)C3)cc2CN1Cc1ccc(C(F)(F)F)cc1] | 547.7 (M + H)+ | | | G |
| 67 | 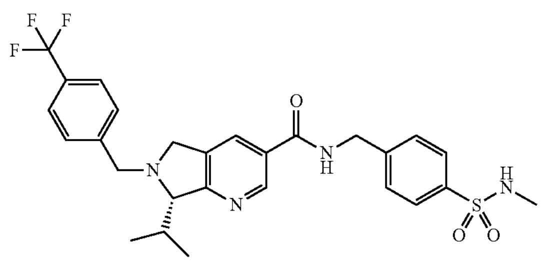 [SMILES: CNS(=O)(=O)c1ccc(CNC(=O)c2cnc3c(c2)CN(Cc2ccc(C(F)(F)F)cc2)[C@H]3C(C)C)cc1] | 547.5 (M + H)+ | | | G |
| 68 | 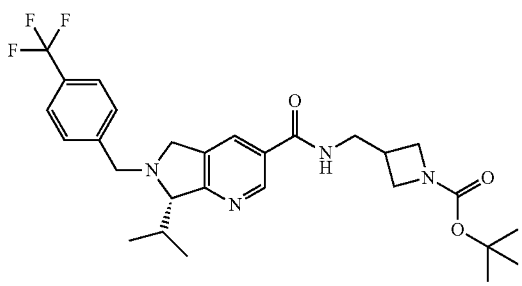 [SMILES: CC(C)[C@H]1c2ncc(C(=O)NCC3CN(C(=O)OC(C)(C)C)C3)cc2CN1Cc1ccc(C(F)(F)F)cc1] | 533.6 (M + H)+ | | | G |
| 69 | 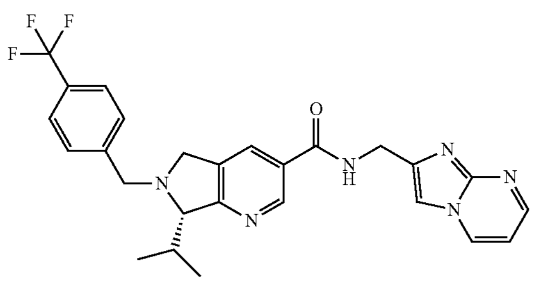 [SMILES: CC(C)[C@H]1c2ncc(C(=O)NCc3cn4cccnc4n3)cc2CN1Cc1ccc(C(F)(F)F)cc1] | 495.6 (M + H)+ | | | G |
| 70 | 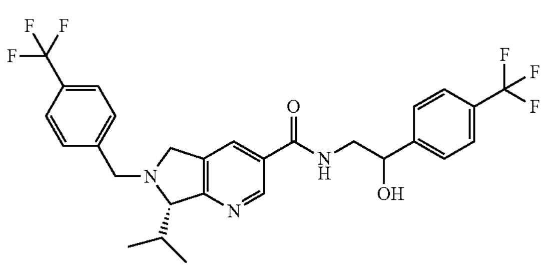 [SMILES: CC(C)[C@H]1c2ncc(C(=O)NCC(O)c3ccc(C(F)(F)F)cc3)cc2CN1Cc1ccc(C(F)(F)F)cc1] | 552.6 (M + H)+ | | | G |

TABLE 1-continued

| Cmpd No. | Structure | LCMS | ¹H-NMR | Starting Material | General Method |
|---|---|---|---|---|---|
| 71 | 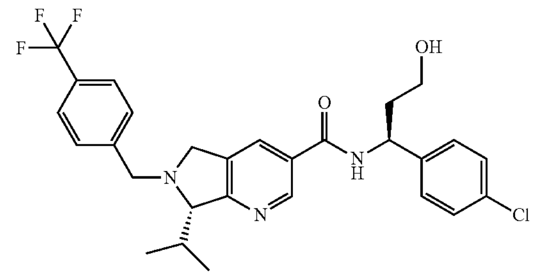 [SMILES: CC(C)[C@H]1c2ncc(C(=O)N[C@@H](CCO)c3ccc(Cl)cc3)cc2CN1Cc1ccc(C(F)(F)F)cc1] | 532.6 (M + H)+ | | | G |
| 72 | 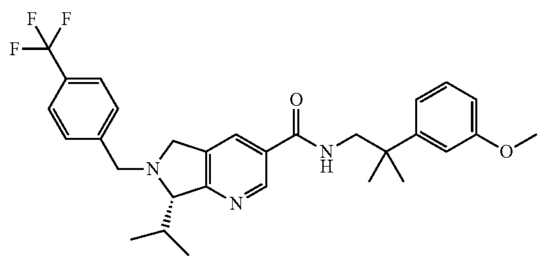 [SMILES: COc1cccc(C(C)(C)CNC(=O)c2cnc3c(c2)CN(Cc2ccc(C(F)(F)F)cc2)[C@H]3C(C)C)c1] | 526.6 (M + H)+ | | | G |
| 73 | 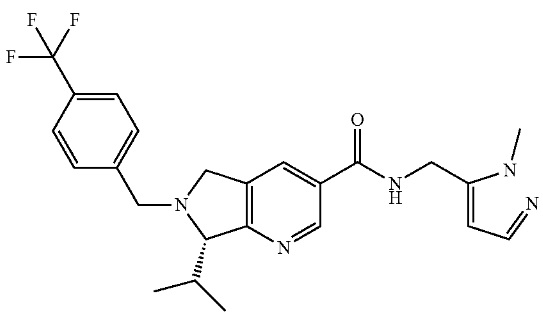 [SMILES: CN/C(=C\C=N)CNC(=O)c1cnc2c(c1)CN(Cc1ccc(C(F)(F)F)cc1)[C@H]2C(C)C] | 458.5 (M + H)+ | | | G |
| 74 | 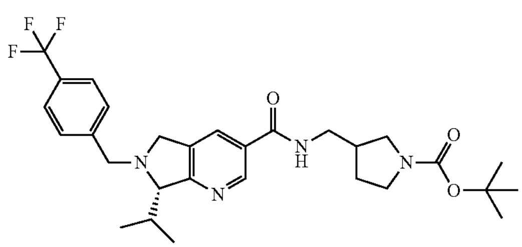 [SMILES: CC(C)[C@H]1c2ncc(C(=O)NCC3CCN(C(=O)OC(C)(C)C)C3)cc2CN1Cc1ccc(C(F)(F)F)cc1] | 547.7 (M + H)+ | | | G |
| 75 | 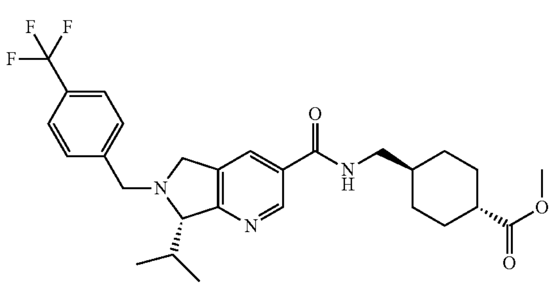 [SMILES: COC(=O)[C@H]1CC[C@H](CNC(=O)c2cnc3c(c2)CN(Cc2ccc(C(F)(F)F)cc2)[C@H]3C(C)C)CC1] | 518.6 (M + H)+ | | | G |

TABLE 1-continued

| Cmpd No. | Structure | LCMS | ¹H-NMR | Starting Material | General Method |
|---|---|---|---|---|---|
| 76 | 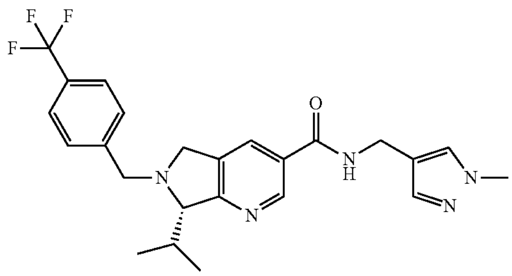 [SMILES: CN/C=C(\C=N)CNC(=O)c1cnc2c(c1)CN(Cc1ccc(C(F)(F)F)cc1)[C@H]2C(C)C] | 458.53 (M + H)+ | | | G |
| 77 | 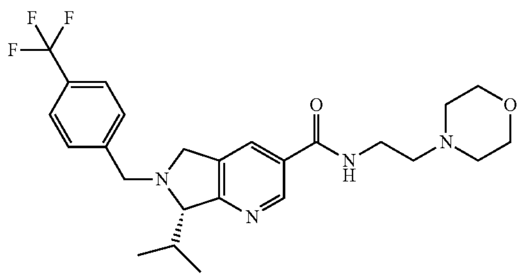 [SMILES: CC(C)[C@H]1c2ncc(C(=O)NCCN3CCOCC3)cc2CN1Cc1ccc(C(F)(F)F)cc1] | 477.55 (M + H)+ | | | G |
| 78 | 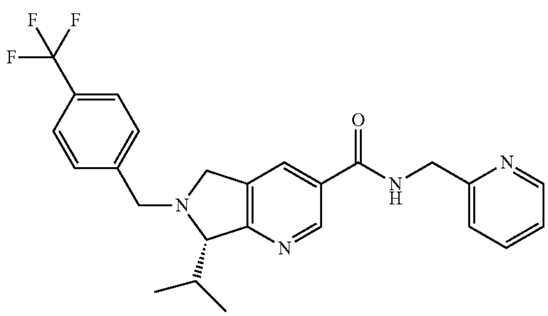 [SMILES: CC(C)[C@H]1c2ncc(C(=O)NCc3ccccn3)cc2CN1Cc1ccc(C(F)(F)F)cc1] | 455.41 (M + H)+ | | | G |
| 79 | 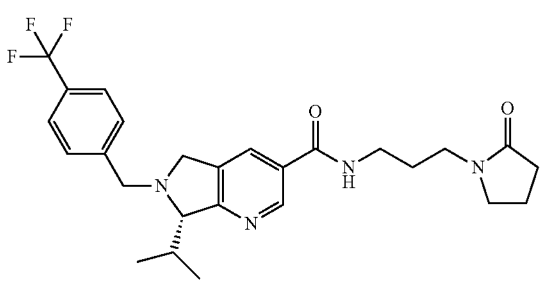 [SMILES: CC(C)[C@H]1c2ncc(C(=O)NCCCN3CCCC3=O)cc2CN1Cc1ccc(C(F)(F)F)cc1] | 489.55 (M + H)+ | | | G |
| 80 | 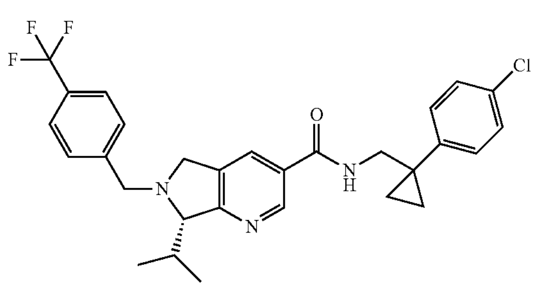 [SMILES: CC(C)[C@H]1c2ncc(C(=O)NCC3(c4ccc(Cl)cc4)CC3)cc2CN1Cc1ccc(C(F)(F)F)cc1] | 528.56 (M + H)+ | | | G |

TABLE 1-continued

| Cmpd No. | Structure | LCMS | ¹H-NMR | Starting Material | General Method |
|---|---|---|---|---|---|
| 81 | 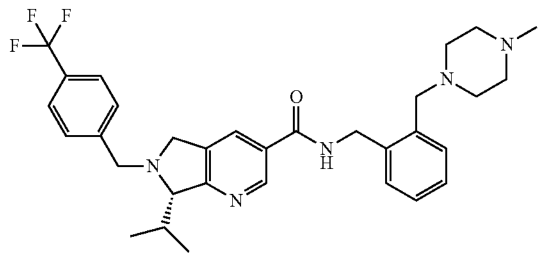 [SMILES: CC(C)[C@H]1c2ncc(C(=O)NCc3ccccc3CN3CCN(C)CC3)cc2CN1Cc1ccc(C(F)(F)F)cc1] | 566.46 (M + H)+ | | | G |
| 82 | 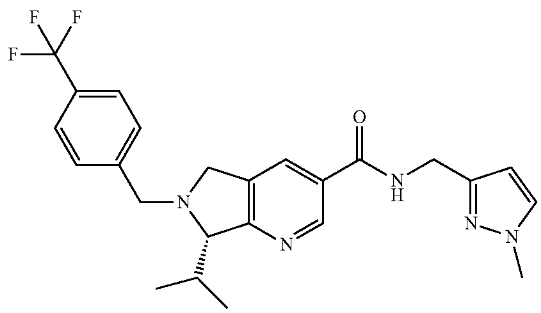 [SMILES: CC(C)[C@H]1c2ncc(C(=O)NCc3ccn(C)n3)cc2CN1Cc1ccc(C(F)(F)F)cc1] | 458.5 (M + H)+ | | | G |
| 83 | 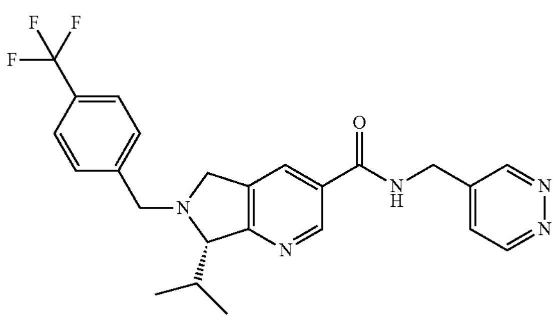 [SMILES: CC(C)[C@H]1c2ncc(C(=O)NCc3ccnnc3)cc2CN1Cc1ccc(C(F)(F)F)cc1] | 456.49 (M + H)+ | | | G |
| 84 | 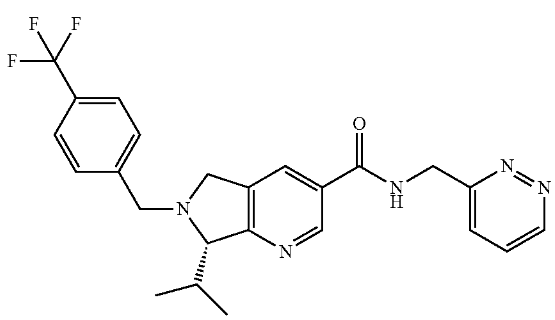 [SMILES: CC(C)[C@H]1c2ncc(C(=O)NCc3cccnn3)cc2CN1Cc1ccc(C(F)(F)F)cc1] | 456.49 (M + H)+ | | | G |
| 85 | 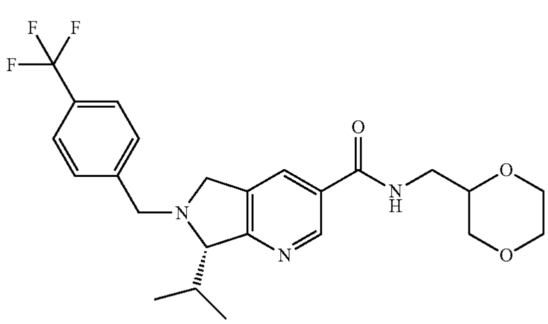 [SMILES: CC(C)[C@H]1c2ncc(C(=O)NCC3COCCO3)cc2CN1Cc1ccc(C(F)(F)F)cc1] | 464.45 (M + H)+ | | | G |

TABLE 1-continued

| Cmpd No. | Structure | LCMS | ¹H-NMR | Starting Material | General Method |
|---|---|---|---|---|---|
| 86 | 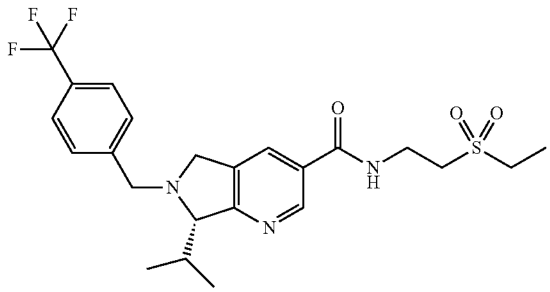 [SMILES: CCS(=O)(=O)CCNC(=O)c1cnc2c(c1)CN(Cc1ccc(C(F)(F)F)cc1)[C@H]2C(C)C] | 484.5 (M + H)+ | | | G |
| 87 | 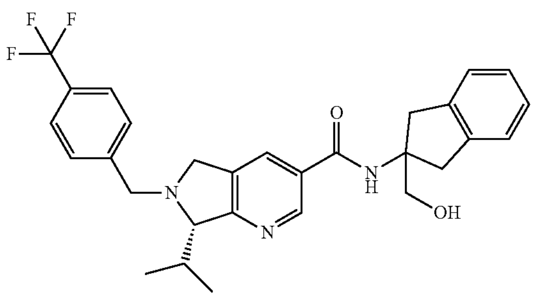 [SMILES: CC(C)[C@H]1c2ncc(C(=O)NC3(CO)Cc4ccccc4C3)cc2CN1Cc1ccc(C(F)(F)F)cc1] | 510.5 (M + H)+ | | | G |
| 88 | 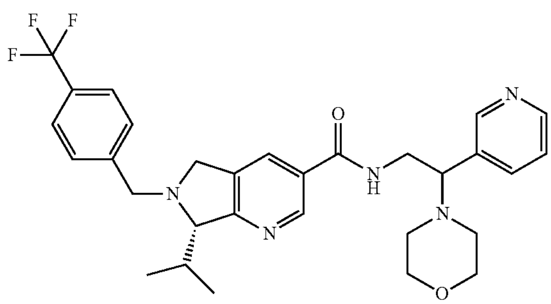 [SMILES: CC(C)[C@H]1c2ncc(C(=O)NCC(c3cccnc3)N3CCOCC3)cc2CN1Cc1ccc(C(F)(F)F)cc1] | 554.7 (M + H)+ | | | G |
| 89 | 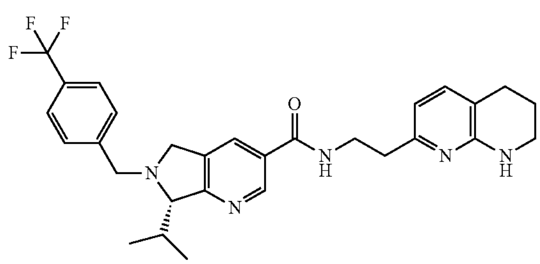 [SMILES: CC(C)[C@H]1c2ncc(C(=O)NCCc3ccc4c(n3)NCCC4)cc2CN1Cc1ccc(C(F)(F)F)cc1] | 524.6 (M + H)+ | | | G |
| 90 | 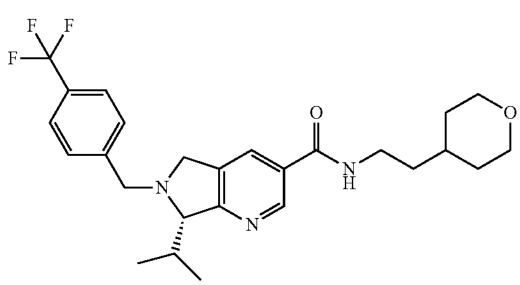 [SMILES: CC(C)[C@H]1c2ncc(C(=O)NCCC3CCOCC3)cc2CN1Cc1ccc(C(F)(F)F)cc1] | 476.6 (M + H)+ | | | G |

TABLE 1-continued

| Cmpd No. | Structure | LCMS | ¹H-NMR | Starting Material | General Method |
|---|---|---|---|---|---|
| 91 | 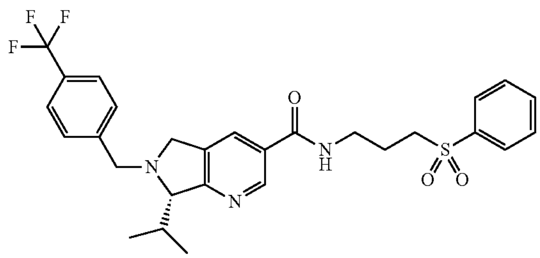 [SMILES: CC(C)[C@H]1c2ncc(C(=O)NCCCS(=O)(=O)c3ccccc3)cc2CN1Cc1ccc(C(F)(F)F)cc1] | 546.6 (M + H)+ | | | G |
| 92 | 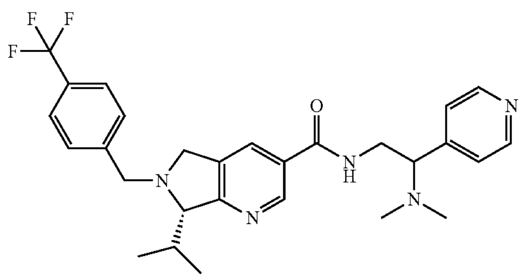 [SMILES: CC(C)[C@H]1c2ncc(C(=O)NCC(c3ccncc3)N(C)C)cc2CN1Cc1ccc(C(F)(F)F)cc1] | 512.6 (M + H)+ | | | G |
| 93 | 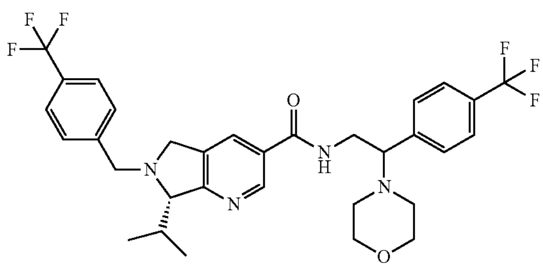 [SMILES: CC(C)[C@H]1c2ncc(C(=O)NCC(c3ccc(C(F)(F)F)cc3)N3CCOCC3)cc2CN1Cc1ccc(C(F)(F)F)cc1] | 621.6 (M + H)+ | | | G |
| 94 | 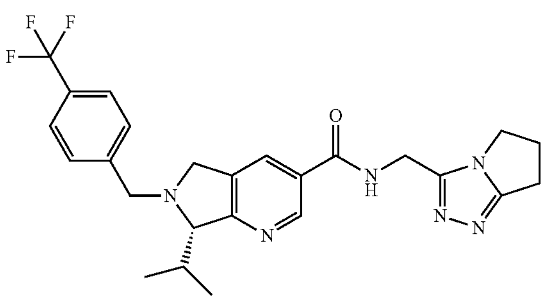 [SMILES: CC(C)[C@H]1c2ncc(C(=O)NCc3nnc4n3CCC4)cc2CN1Cc1ccc(C(F)(F)F)cc1] | 485.5 (M + H)+ | | | G |
| 95 | 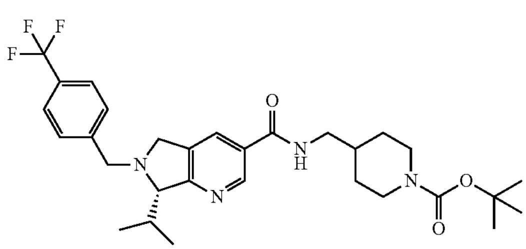 [SMILES: CC(C)[C@H]1c2ncc(C(=O)NCC3CCN(C(=O)OC(C)(C)C)CC3)cc2CN1Cc1ccc(C(F)(F)F)cc1] | 561.6 (M + H)+ | | | G |

TABLE 1-continued

| Cmpd No. | Structure | LCMS | ¹H-NMR | Starting Material | General Method |
|---|---|---|---|---|---|
| 96 | 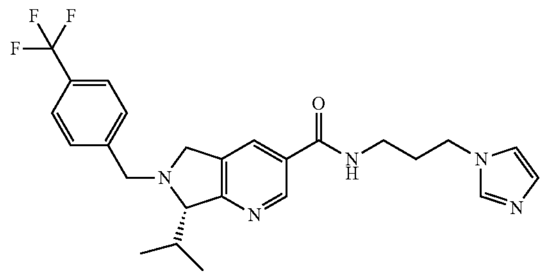 [SMILES: CC(C)[C@H]1c2ncc(C(=O)NCCCn3ccnc3)cc2CN1Cc1ccc(C(F)(F)F)cc1] | 472.51 (M + H)+ | | H₂N-propyl-imidazole | G |
| 97 | 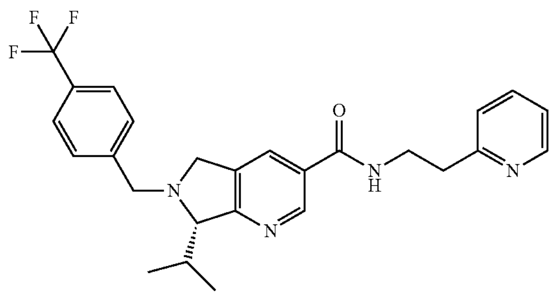 [SMILES: CC(C)[C@H]1c2ncc(C(=O)NCCc3ccccn3)cc2CN1Cc1ccc(C(F)(F)F)cc1] | 469.55 (M + H)+ | | H₂N-ethyl-2-pyridyl | G |
| 98 | 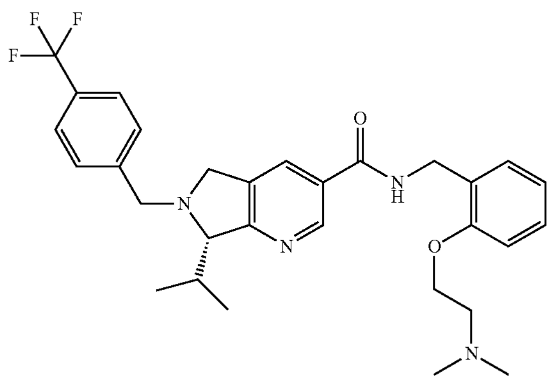 [SMILES: CC(C)[C@H]1c2ncc(C(=O)NCc3ccccc3OCCN(C)C)cc2CN1Cc1ccc(C(F)(F)F)cc1] | 541.66 (M + H)+ | | 2-(2-(dimethylamino)ethoxy)benzylamine | G |
| 99 | 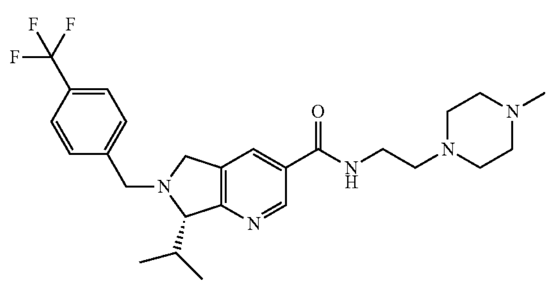 [SMILES: CC(C)[C@H]1c2ncc(C(=O)NCCN3CCN(C)CC3)cc2CN1Cc1ccc(C(F)(F)F)cc1] | 490.59 (M + H)+ | | H₂N-ethyl-(4-methylpiperazine) | G |
| 100 | 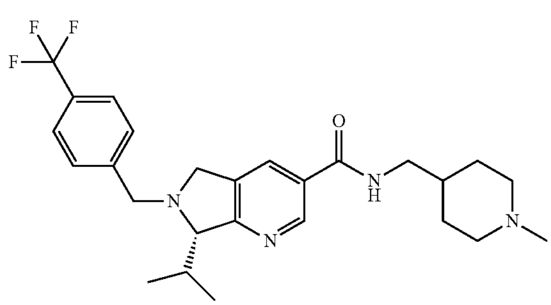 [SMILES: CC(C)[C@H]1c2ncc(C(=O)NCC3CCN(C)CC3)cc2CN1Cc1ccc(C(F)(F)F)cc1] | 475.57 (M + H)+ | | H₂N-CH₂-(1-methylpiperidin-4-yl) | G |

TABLE 1-continued

| Cmpd No. | Structure | LCMS | ¹H-NMR | Starting Material | General Method |
|---|---|---|---|---|---|
| 101 | 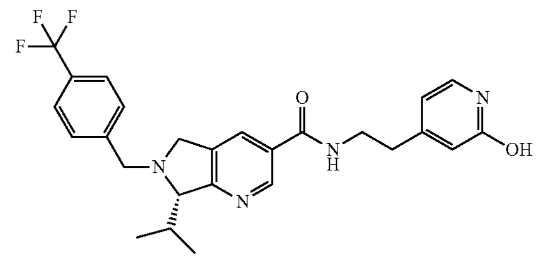 [SMILES: CC(C)[C@H]1c2ncc(C(=O)NCCc3ccnc(O)c3)cc2CN1Cc1ccc(C(F)(F)F)cc1] | 485.45 (M + H)+ | | | G |
| 102 | 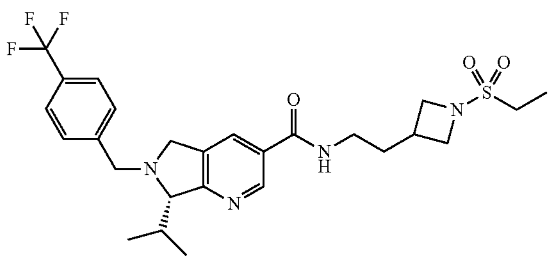 [SMILES: CCS(=O)(=O)N1CC(CCNC(=O)c2cnc3c(c2)CN(Cc2ccc(C(F)(F)F)cc2)[C@H]3C(C)C)C1] | 539.5 (M + H)+ | | | G |
| 103 | 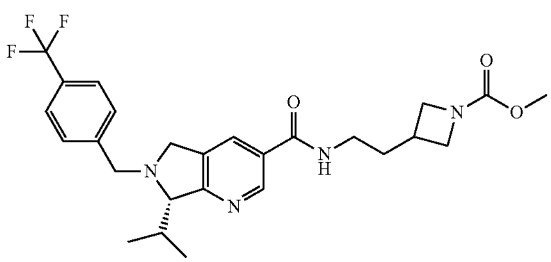 [SMILES: COC(=O)N1CC(CCNC(=O)c2cnc3c(c2)CN(Cc2ccc(C(F)(F)F)cc2)[C@H]3C(C)C)C1] | 539.5 (M + H)+ | | | G |
| 104 | 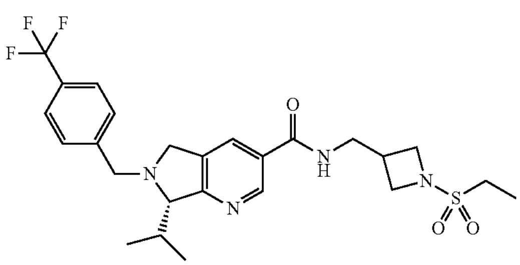 [SMILES: CCS(=O)(=O)N1CC(CNC(=O)c2cnc3c(c2)CN(Cc2ccc(C(F)(F)F)cc2)[C@H]3C(C)C)C1] | 525.5 (M + H)+ | | | G |
| 105 | 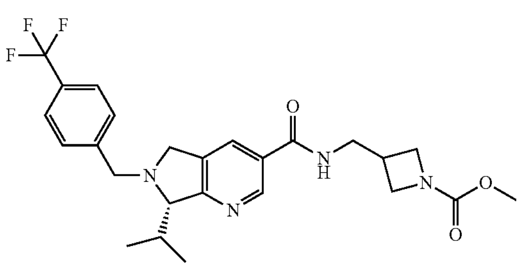 [SMILES: COC(=O)N1CC(CNC(=O)c2cnc3c(c2)CN(Cc2ccc(C(F)(F)F)cc2)[C@H]3C(C)C)C1] | 491.5 (M + H)+ | | | G |

TABLE 1-continued

| Cmpd No. | Structure | LCMS | ¹H-NMR | Starting Material | General Method |
|---|---|---|---|---|---|
| 106 | 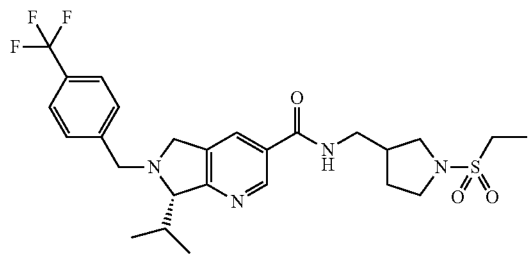 [SMILES: CCS(=O)(=O)N1CCC(CNC(=O)c2cnc3c(c2)CN(Cc2ccc(C(F)(F)F)cc2)[C@H]3C(C)C)C1] | 539.5 (M + H)+ | | | G |
| 107 | 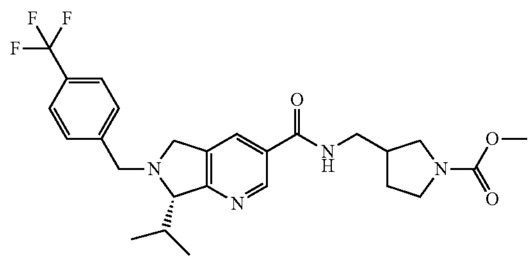 [SMILES: COC(=O)N1CCC(CNC(=O)c2cnc3c(c2)CN(Cc2ccc(C(F)(F)F)cc2)[C@H]3C(C)C)C1] | 505.6 (M + H)+ | | | G |
| 108 | 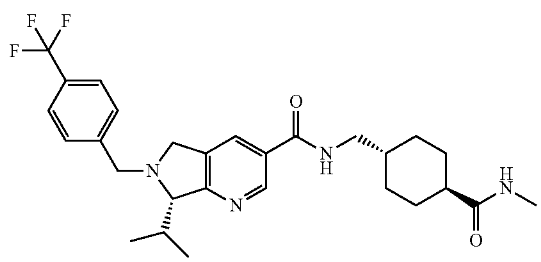 [SMILES: CNC(=O)[C@H]1CC[C@H](CNC(=O)c2cnc3c(c2)CN(Cc2ccc(C(F)(F)F)cc2)[C@H]3C(C)C)CC1] | 517.6 (M + H)+ | | | G |
| 109 | 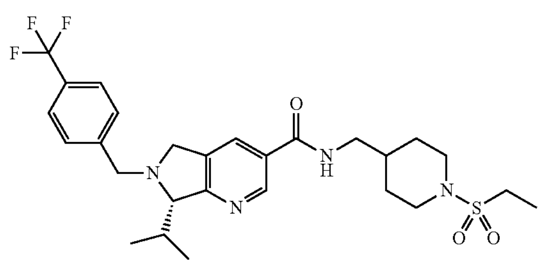 [SMILES: CCS(=O)(=O)N1CCC(CNC(=O)c2cnc3c(c2)CN(Cc2ccc(C(F)(F)F)cc2)[C@H]3C(C)C)CC1] | 553.5 (M + H)+ | | | G |
| 110 | 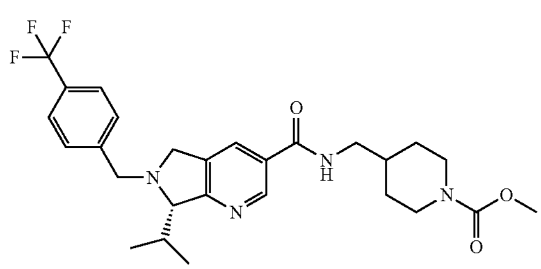 [SMILES: COC(=O)N1CCC(CNC(=O)c2cnc3c(c2)CN(Cc2ccc(C(F)(F)F)cc2)[C@H]3C(C)C)CC1] | 519.6 (M + H)+ | | | G |

TABLE 1-continued

| Cmpd No. | Structure | LCMS | ¹H-NMR | Starting Material | General Method |
|---|---|---|---|---|---|
| 111 | 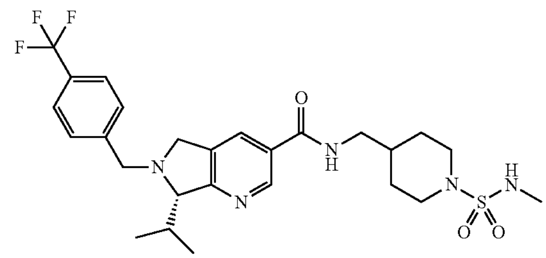 [SMILES: CNS(=O)(=O)N1CCC(CNC(=O)c2cnc3c(c2)CN(Cc2ccc(C(F)(F)F)cc2)[C@H]3C(C)C)CC1] | 554.5 (M + H)+ | | | G |
| 112 | 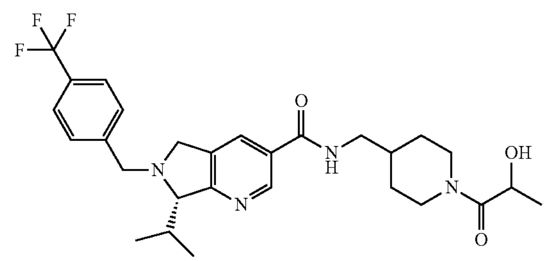 [SMILES: CC(O)C(=O)N1CCC(CNC(=O)c2cnc3c(c2)CN(Cc2ccc(C(F)(F)F)cc2)[C@H]3C(C)C)CC1] | 533.6 (M + H)+ | | | G |
| 113 | 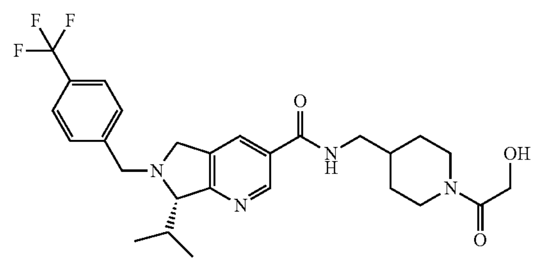 [SMILES: CC(C)[C@H]1c2ncc(C(=O)NCC3CCN(C(=O)CO)CC3)cc2CN1Cc1ccc(C(F)(F)F)cc1] | 519.6 (M + H)+ | | | G |
| 114 | 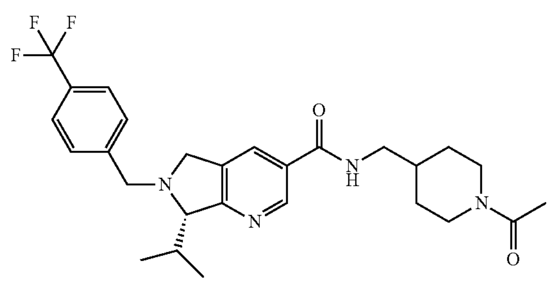 [SMILES: CC(=O)N1CCC(CNC(=O)c2cnc3c(c2)CN(Cc2ccc(C(F)(F)F)cc2)[C@H]3C(C)C)CC1] | 503.6 (M + H)+ | | | G |
| 115 | 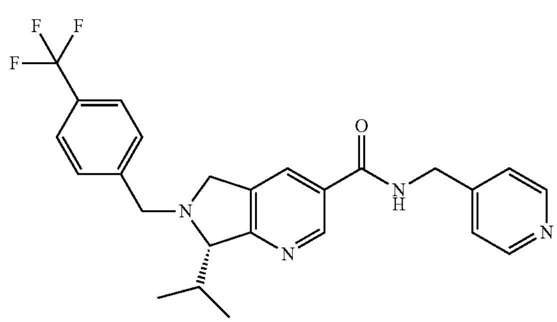 [SMILES: CC(C)[C@H]1c2ncc(C(=O)NCc3ccncc3)cc2CN1Cc1ccc(C(F)(F)F)cc1] | 455.5 (M + H)+ | | | G |

TABLE 1-continued

| Cmpd No. | Structure | LCMS | ¹H-NMR | Starting Material | General Method |
|---|---|---|---|---|---|
| 116 | 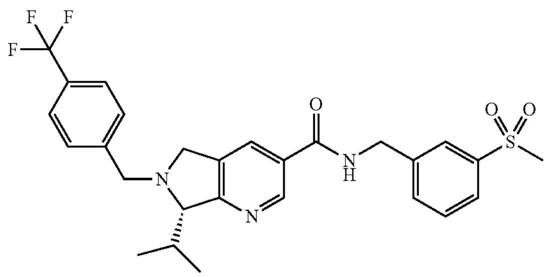 [SMILES: CC(C)[C@H]1c2ncc(C(=O)NCc3cccc(S(C)(=O)=O)c3)cc2CN1Cc1ccc(C(F)(F)F)cc1] | 532.5 (M + H)+ | | | G |
| 117 | 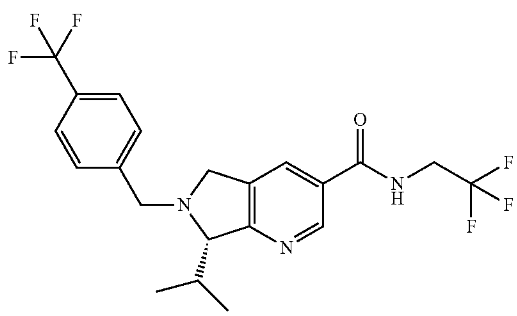 [SMILES: CC(C)[C@H]1c2ncc(C(=O)NCC(F)(F)F)cc2CN1Cc1ccc(C(F)(F)F)cc1] | 446.4 (M + H)+ | | | G |
| 118 | 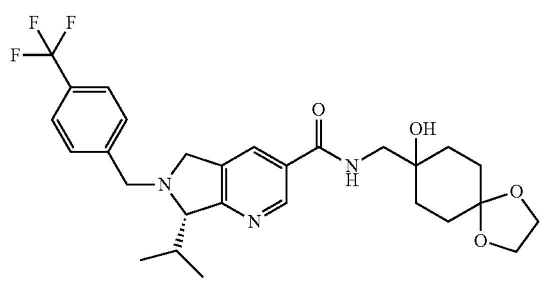 [SMILES: CC(C)[C@H]1c2ncc(C(=O)NCC3(O)CCC4(CC3)OCCO4)cc2CN1Cc1ccc(C(F)(F)F)cc1] | 534.5 (M + H)+ | | | G |
| 119 | 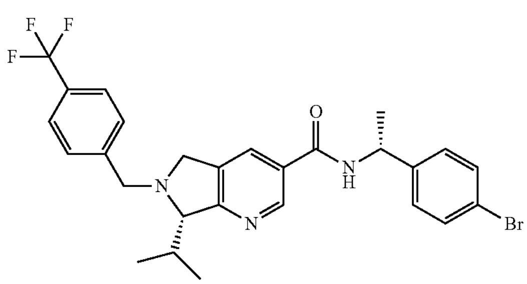 [SMILES: CC(C)[C@H]1c2ncc(C(=O)N[C@H](C)c3ccc(Br)cc3)cc2CN1Cc1ccc(C(F)(F)F)cc1] | 546.5 (M + H)+ | | | G |
| 120 | 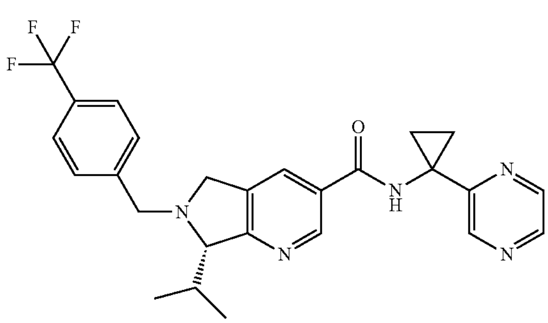 [SMILES: CC(C)[C@H]1c2ncc(C(=O)NC3(c4cnccn4)CC3)cc2CN1Cc1ccc(C(F)(F)F)cc1] | 482.5 (M + H)+ | | | G |

TABLE 1-continued

| Cmpd No. | Structure | LCMS | ¹H-NMR | Starting Material | General Method |
|---|---|---|---|---|---|
| 121 | 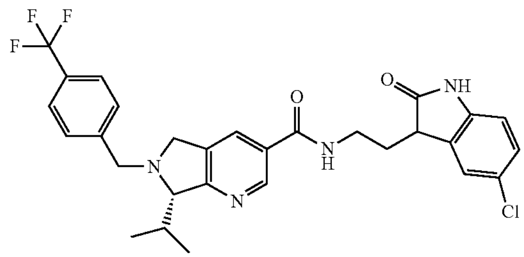 [SMILES: CC(C)[C@H]1c2ncc(C(=O)NCCC3C(=O)Nc4ccc(Cl)cc43)cc2CN1Cc1ccc(C(F)(F)F)cc1] | 557.5 (M + H)+ | | | G |
| 122 | 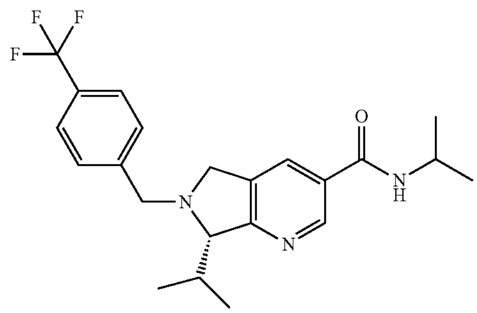 [SMILES: CC(C)NC(=O)c1cnc2c(c1)CN(Cc1ccc(C(F)(F)F)cc1)[C@H]2C(C)C] | 406.4 (M + H)+ | | | G |
| 123 | 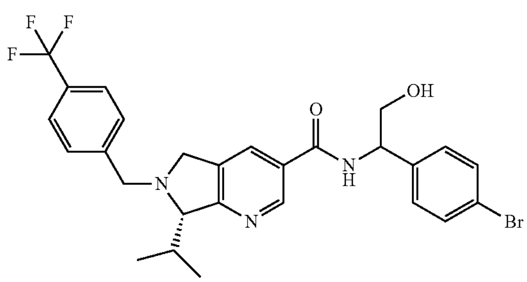 [SMILES: CC(C)[C@H]1c2ncc(C(=O)NC(CO)c3ccc(Br)cc3)cc2CN1Cc1ccc(C(F)(F)F)cc1] | 562.4 (M + H)+ | | | G |
| 124 | 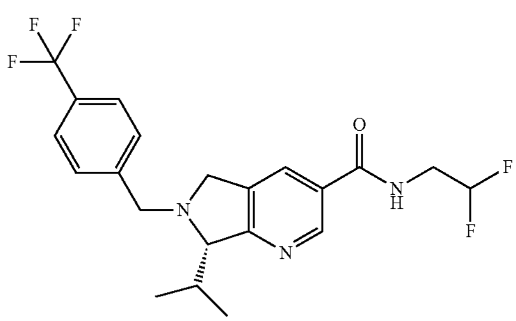 [SMILES: CC(C)[C@H]1c2ncc(C(=O)NCC(F)F)cc2CN1Cc1ccc(C(F)(F)F)cc1] | 428.4 (M + H)+ | | | G |
| 125 | 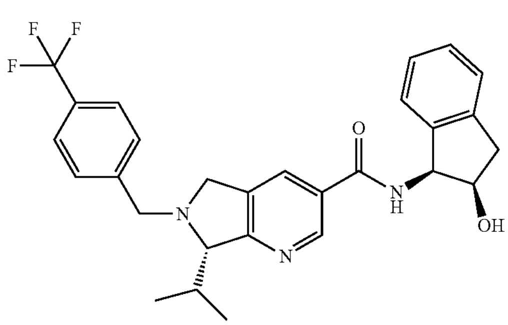 [SMILES: CC(C)[C@H]1c2ncc(C(=O)N[C@H]3c4ccccc4C[C@H]3O)cc2CN1Cc1ccc(C(F)(F)F)cc1] | 496.5 (M + H)+ | | | G |

TABLE 1-continued

| Cmpd No. | Structure | LCMS | ¹H-NMR | Starting Material | General Method |
|---|---|---|---|---|---|
| 126 | 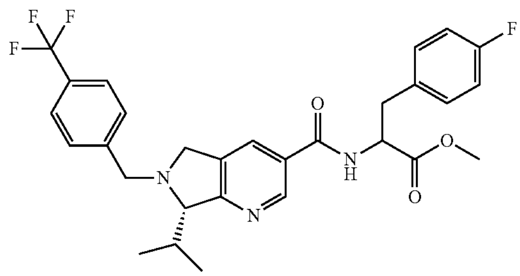 [SMILES: COC(=O)C(Cc1ccc(F)cc1)NC(=O)c1cnc2c(c1)CN(Cc1ccc(C(F)(F)F)cc1)[C@H]2C(C)C] | 544.6 (M + H)+ | | | G |
| 127 | 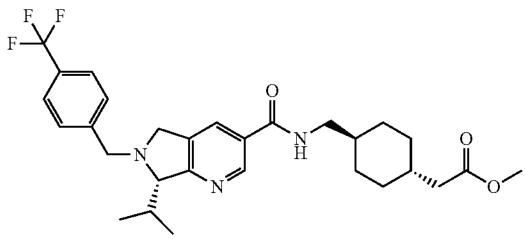 [SMILES: COC(=O)C[C@H]1CC[C@H](CNC(=O)c2cnc3c(c2)CN(Cc2ccc(C(F)(F)F)cc2)[C@H]3C(C)C)CC1] | 532.6 (M + H)+ | | | G |
| 128 | 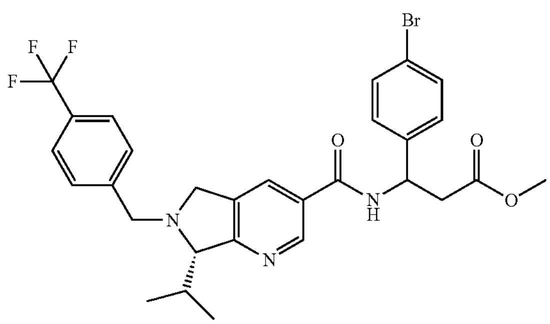 [SMILES: COC(=O)CC(NC(=O)c1cnc2c(c1)CN(Cc1ccc(C(F)(F)F)cc1)[C@H]2C(C)C)c1ccc(Br)cc1] | 604.5 (M + H)+ | | | G |
| 129 | 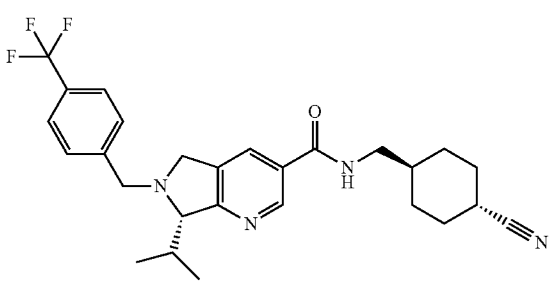 [SMILES: CC(C)[C@H]1c2ncc(C(=O)NC[C@H]3CC[C@H](C#N)CC3)cc2CN1Cc1ccc(C(F)(F)F)cc1] | 485.6 (M + H)+ | | | G |
| 130 | 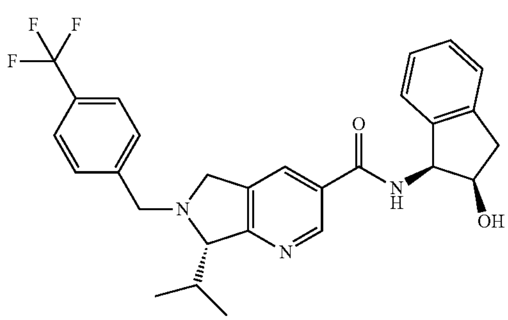 [SMILES: CC(C)[C@H]1c2ncc(C(=O)N[C@H]3c4ccccc4C[C@H]3O)cc2CN1Cc1ccc(C(F)(F)F)cc1] | 496.5 (M + H)+ | | | G |

TABLE 1-continued

| Cmpd No. | Structure | LCMS | ¹H-NMR | Starting Material | General Method |
|---|---|---|---|---|---|
| 131 | 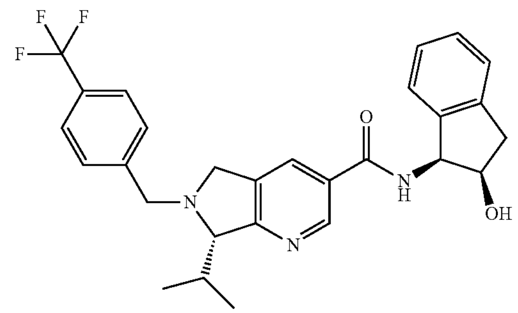 [SMILES: CC(C)[C@H]1c2ncc(C(=O)N[C@H]3c4ccccc4C[C@H]3O)cc2CN1Cc1ccc(C(F)(F)F)cc1] | 496.5 (M + H)+ | | | G |
| 132 | 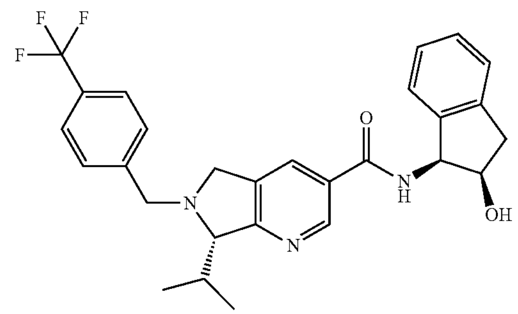 [SMILES: CC(C)[C@H]1c2ncc(C(=O)N[C@H]3c4ccccc4C[C@H]3O)cc2CN1Cc1ccc(C(F)(F)F)cc1] | 496.5 (M + H)+ | | | G |
| 133 | 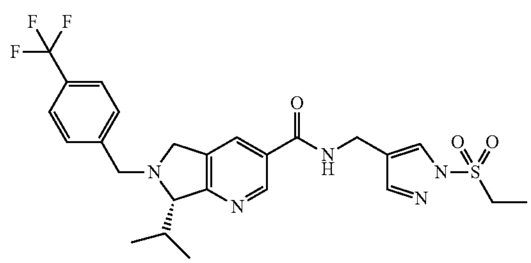 [SMILES: CCS(=O)(=O)N/C=C(\C=N)CNC(=O)c1cnc2c(c1)CN(Cc1ccc(C(F)(F)F)cc1)[C@H]2C(C)C] | 536.46 (M + H)+ | (CD₃OD) δ 9.02 (s, 1H), 8.24 (s, 1H), 8.18 (s, 1H), 7.90 (s, 1H), 7.82 (m, 4H), 4.96 (d, J = 16.0 Hz, 1H), 4.91 (m, 2H), 4.78 (s, 2H), 4.52 (s, 2H), 3.58 (q, J = 7.6 Hz, 2H), 2.38 (m, 1H), 1.21 (t, J = 7.6 Hz, 3H), 1.17 (d, J = 8.0 Hz, 3H), 0.89 (d, J = 6.8 Hz, 3H). | | G |
| 134 | 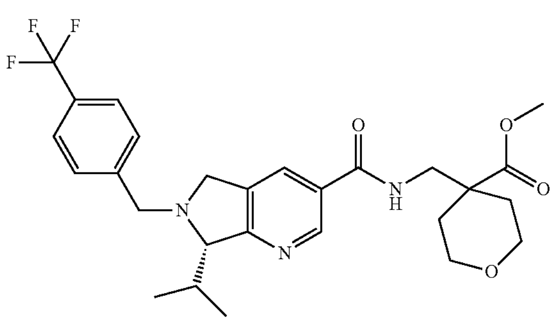 [SMILES: COC(=O)C1(CNC(=O)c2cnc3c(c2)CN(Cc2ccc(C(F)(F)F)cc2)[C@H]3C(C)C)CCOCC1] | 520.56 (M + H)+ | | | G |

TABLE 1-continued

| Cmpd No. | Structure | LCMS | ¹H-NMR | Starting Material | General Method |
|---|---|---|---|---|---|
| 135 | 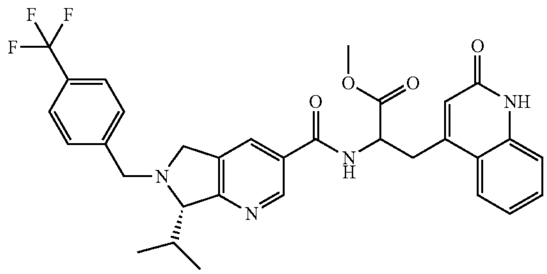 [SMILES: COC(=O)C(Cc1cc(=O)[nH]c2ccccc12)NC(=O)c1cnc2c(c1)CN(Cc1ccc(C(F)(F)F)cc1)[C@H]2C(C)C] | 593.61 (M + H)+ | | | G |
| 136 | 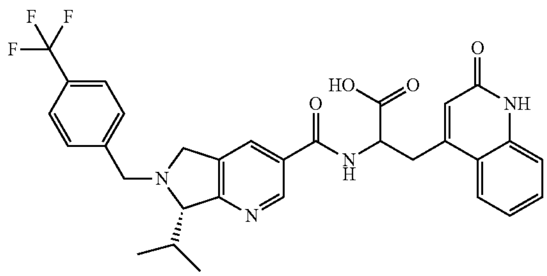 [SMILES: CC(C)[C@H]1c2ncc(C(=O)NC(Cc3cc(=O)[nH]c4ccccc34)C(=O)O)cc2CN1Cc1ccc(C(F)(F)F)cc1] | 579.47 (M + H)+ | | 135 | H |
| 137 | 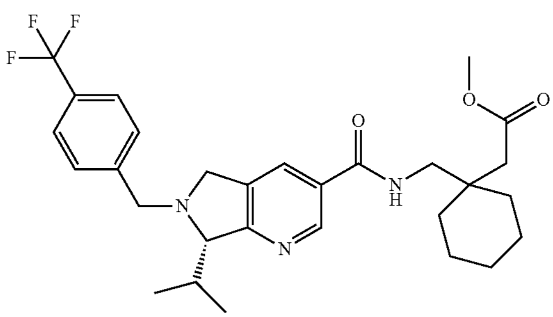 [SMILES: COC(=O)CC1(CNC(=O)c2cnc3c(c2)CN(Cc2ccc(C(F)(F)F)cc2)[C@H]3C(C)C)CCCCC1] | 532.62 (M + H)+ | | | G |
| 138 | 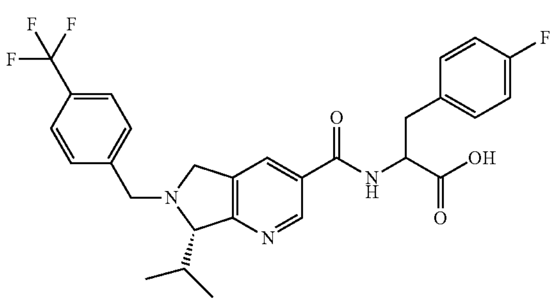 [SMILES: CC(C)[C@H]1c2ncc(C(=O)NC(Cc3ccc(F)cc3)C(=O)O)cc2CN1Cc1ccc(C(F)(F)F)cc1] | 530.5 (M + H)+ | | 126 | H |
| 139 | 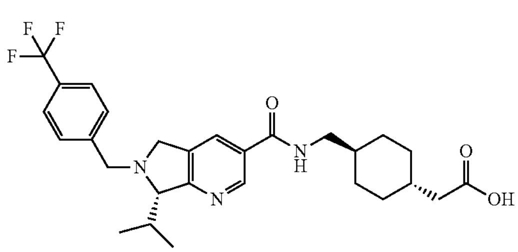 [SMILES: CC(C)[C@H]1c2ncc(C(=O)NC[C@H]3CC[C@H](CC(=O)O)CC3)cc2CN1Cc1ccc(C(F)(F)F)cc1] | 518.5 (M + H)+ | | 127 | H |

TABLE 1-continued

| Cmpd No. | Structure | LCMS | ¹H-NMR | Starting Material | General Method |
|---|---|---|---|---|---|
| 140 | 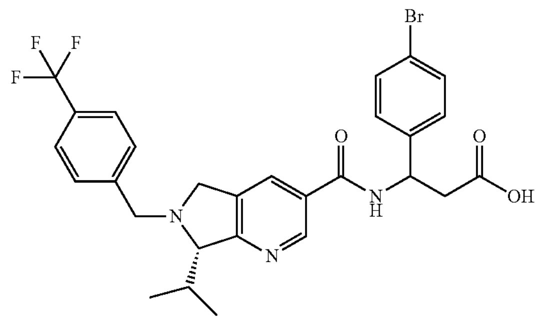 [SMILES: CC(C)[C@H]1c2ncc(C(=O)NC(CC(=O)O)c3ccc(Br)cc3)cc2CN1Cc1ccc(C(F)(F)F)cc1] | 590.5 (M + H)+ | | 128 | H |
| 141 | 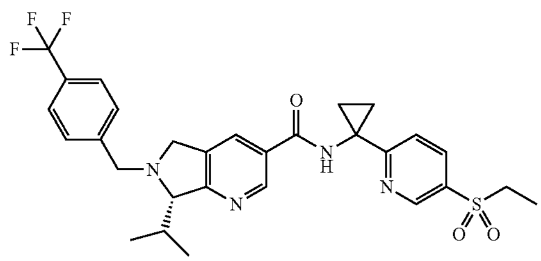 [SMILES: CCS(=O)(=O)c1ccc(C2(NC(=O)c3cnc4c(c3)CN(Cc3ccc(C(F)(F)F)cc3)[C@H]4C(C)C)CC2)nc1] | 574.50 (M + H)+ | (CD₃OD) δ 9.12 (s, 1H), 8.90 (s, 1H), 8.32 (s, 1H), 8.17 (d, J = 8.4 Hz, 1H), 7.90 (d, J = 8.0 Hz, 2H), 7.84 (d, J = 8.0 Hz, 2H), 7.65 (d, J = 8.4 Hz, 1H), 5.05 (d, J = 15.6 Hz, 1H), 4.77 (dd, J = 13.2, 30.0 Hz, 2H), 3.34 (s, 2H), 3.26 (q, J = 7.6 Hz, 2H), 2.37 (broad s, 1H), 1.84 (dd, J = 4.4, 7.6 Hz, 2H), 1.52 (dd, J = 4.4, 7.6 Hz, 2H), 1.23 (t, J = 7.6 Hz, 3H), 1.16 (d, J = 6.0, 3H), 0.89 (d, J = 6.8 Hz, 3H). | | G |
| 142 | 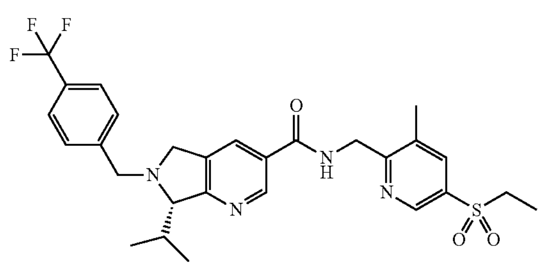 [SMILES: CCS(=O)(=O)c1cnc(CNC(=O)c2cnc3c(c2)CN(Cc2ccc(C(F)(F)F)cc2)[C@H]3C(C)C)c(C)c1] | 561.55 (M + H)+ | (CD₃OD) δ 9.11 (s, 1H), 8.87 (s, 1H), 8.33 (d, J = 8.0 Hz, 2H), 7.90 (d, J = 8.0 Hz, 2H), 7.84 (d, J = 8.0 Hz, 2H), 5.04 (d, J = 15.6 Hz, 1H), 4.89 4.82 (m, 2H), 4.87 (s, 2H), 4.76 (dd, J = 3.2, 28.8 Hz, 2H), 3.33 (q, J = 7.6 Hz, 2H), 2.58 (s, 3H), 2.36 (bs, 1H), 1.26 (t, | | G |

TABLE 1-continued

| Cmpd No. | Structure | LCMS | ¹H-NMR | Starting Material | General Method |
|---|---|---|---|---|---|
| | | | J = 7.6 Hz, 3H), 1.14 (d, J = 6.0 Hz, 3H), 0.88 (d, J = 6.8 Hz, 3H). | | |
| 143 | 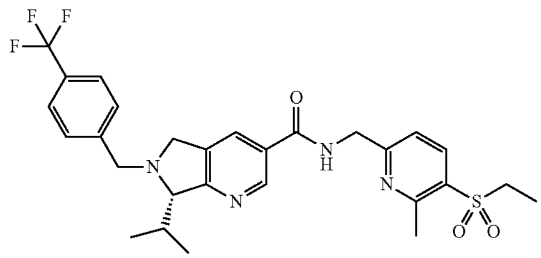 [SMILES: CCS(=O)(=O)c1ccc(CNC(=O)c2cnc3c(c2)CN(Cc2ccc(C(F)(F)F)cc2)[C@H]3C(C)C)nc1C] | 561.52 (M + H)+ | (CD₃OD) δ 9.12 (s, 1H), 8.72 (d, J = 7.6 Hz, 1H), 8.35 (s, 1H), 7.92 (d, J = 7.6 Hz, 1H), 7.92 (d, J = 8.0 Hz, 2H), 7.83 (d, J = 8.0 Hz, 2H), 5.07 (d, J = 15.2 Hz, 1H), 4.91-4.71 (m, 4H), 4.77 (dd, J = 12.4, 35.4 Hz, 2H), 3.41 (q, J = 7.6 Hz, 2H), 3.06 (s, 3H), 2.36 (broad s, 1H), 1.28 (t, J = 7.6 Hz, 3H), 1.14 (d, J = 5.2 Hz, 3H), 0.88 (d, J = 6.8 Hz, 3H). | | G |
| 144 | 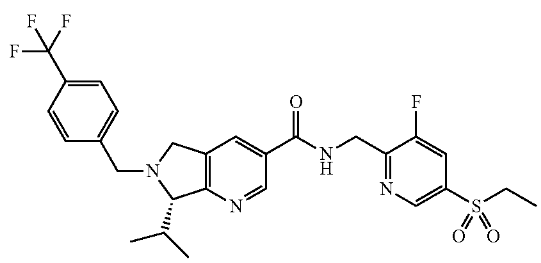 | 565.51 (M + H)+ | (CD₃OD) δ 9.08 (s, 1H), 8.81 (s, 1H), 8.28 (s, 1H), 8.12 (d, J = 8.8 Hz, 1H), 7.91 (d, J = 8.0 Hz, 2H), 7.83 (d, J = 8.0 Hz, 2H), 5.04 (d, J = 14.4 Hz, 1H), 4.91-4.70 (m, 2H), 4.88 (s, 2H), 4.76 (dd, J = 12.4, 33.4 Hz, 2H), 3.33 (q, J = 7.6 Hz, 2H), 2.35 (broad s, 1H), 1.25 (t, J = 7.6 Hz, 3H), 1.13 (d, J = 5.2 Hz, 3H), 0.87 (d, J = 6.8 Hz, 3H). | | G |

TABLE 1-continued

| Cmpd No. | Structure | LCMS | ¹H-NMR | Starting Material | General Method |
|---|---|---|---|---|---|
| 145 | 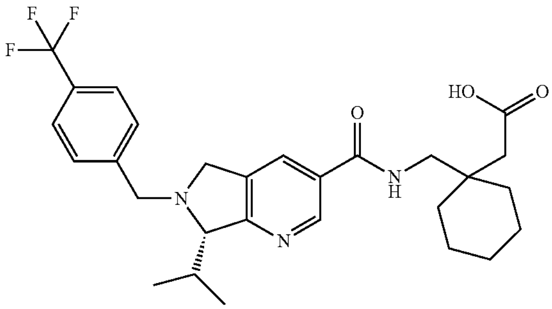 [SMILES: CC(C)[C@H]1c2ncc(C(=O)NCC3(CC(=O)O)CCCCC3)cc2CN1Cc1ccc(C(F)(F)F)cc1] | 518.55 (M + H)+ | | 137 | H |
| 146 | 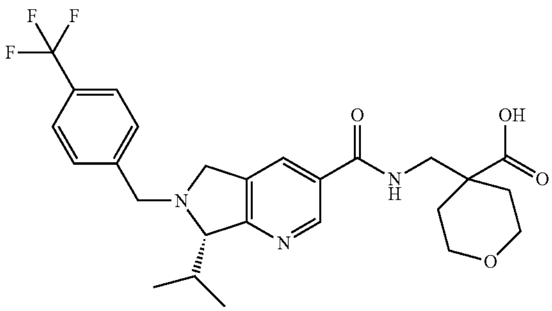 [SMILES: CC(C)[C@H]1c2ncc(C(=O)NCC3(C(=O)O)CCOCC3)cc2CN1Cc1ccc(C(F)(F)F)cc1] | 506.58 (M + H)+ | | 134 | H |
| 148 | 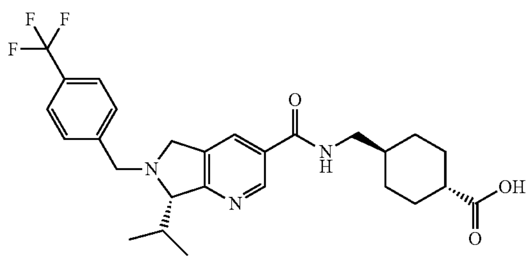 [SMILES: CC(C)[C@H]1c2ncc(C(=O)NC[C@H]3CC[C@H](C(=O)O)CC3)cc2CN1Cc1ccc(C(F)(F)F)cc1] | 504.6 (M + H)+ | | 127 | H |
| 149 | 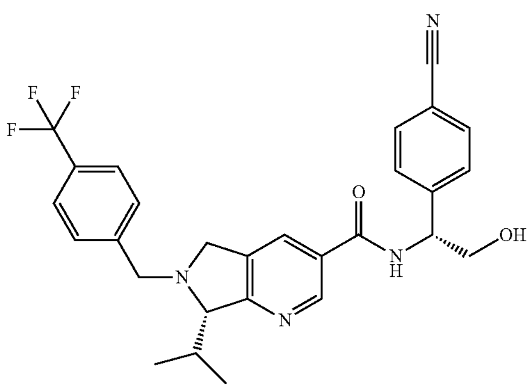 [SMILES: CC(C)[C@H]1c2ncc(C(=O)N[C@@H](CO)c3ccc(C#N)cc3)cc2CN1Cc1ccc(C(F)(F)F)cc1] | 509.5 (M + H)+ | | | G |
| 150 | 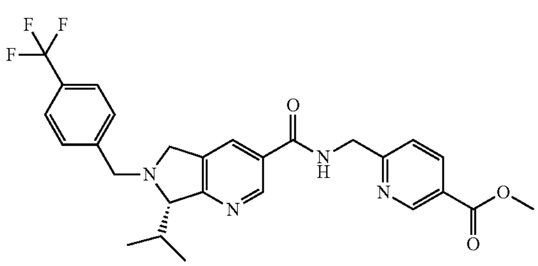 [SMILES: COC(=O)c1ccc(CNC(=O)c2cnc3c(c2)CN(Cc2ccc(C(F)(F)F)cc2)[C@H]3C(C)C)nc1] | 513.6 (M + H)+ | | | G |

TABLE 1-continued

| Cmpd No. | Structure | LCMS | ¹H-NMR | Starting Material | General Method |
|---|---|---|---|---|---|
| 151 | 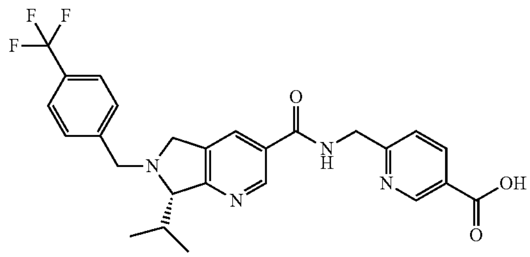 [SMILES: CC(C)[C@H]1c2ncc(C(=O)NCc3ccc(C(=O)O)cn3)cc2CN1Cc1ccc(C(F)(F)F)cc1] | 499.6 (M + H)+ | | 150 | H |
| 152 | 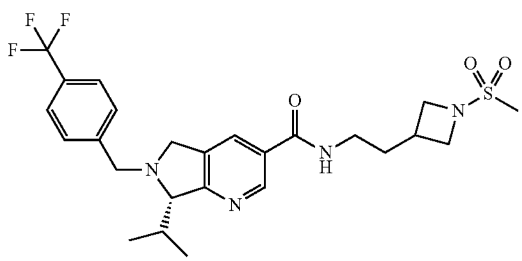 [SMILES: CC(C)[C@H]1c2ncc(C(=O)NCCC3CN(S(C)(=O)=O)C3)cc2CN1Cc1ccc(C(F)(F)F)cc1] | 525.6 (M + H)+ | | | G |
| 153 | 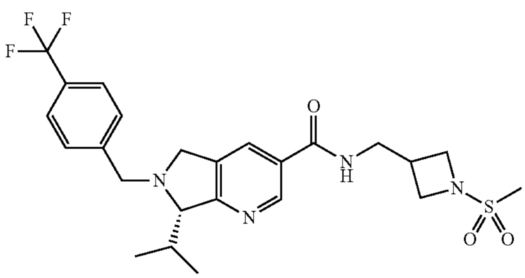 [SMILES: CC(C)[C@H]1c2ncc(C(=O)NCC3CN(S(C)(=O)=O)C3)cc2CN1Cc1ccc(C(F)(F)F)cc1] | 511.5 (M + H)+ | | | G |
| 154 | 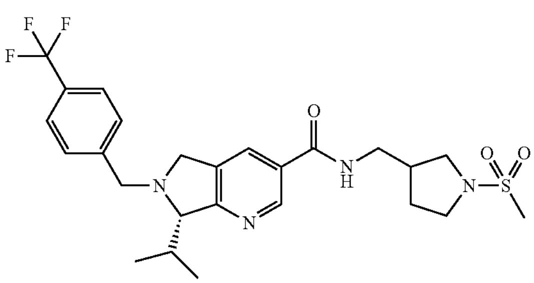 [SMILES: CC(C)[C@H]1c2ncc(C(=O)NCC3CCN(S(C)(=O)=O)C3)cc2CN1Cc1ccc(C(F)(F)F)cc1] | 525.5 (M + H)+ | | | G |
| 155 | 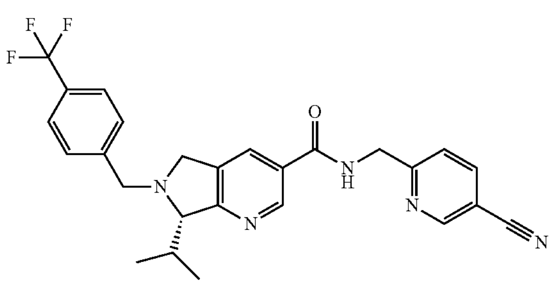 | 480.5 (M + H)+ | | | G |

TABLE 1-continued

| Cmpd No. | Structure | LCMS | ¹H-NMR | Starting Material | General Method |
|---|---|---|---|---|---|
| 156 | 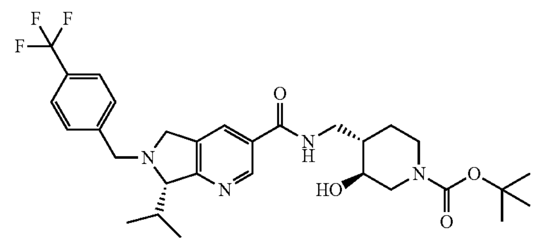 [SMILES: CC(C)[C@H]1c2ncc(C(=O)NC[C@@H]3CCN(C(=O)OC(C)(C)C)C[C@H]3O)cc2CN1Cc1ccc(C(F)(F)F)cc1] | 577.5 (M + H)+ | | | G |
| 157 | 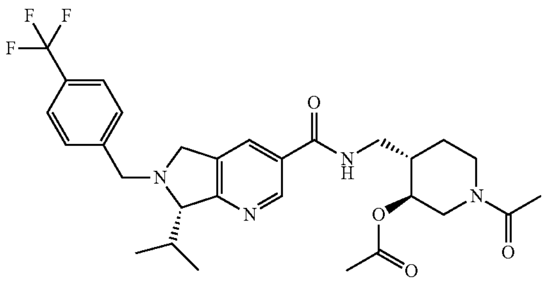 [SMILES: CC(=O)O[C@@H]1CN(C(C)=O)CC[C@H]1CNC(=O)c1cnc2c(c1)CN(Cc1ccc(C(F)(F)F)cc1)[C@H]2C(C)C] | 561.6 (M + H)+ | | | G |
| 158 | 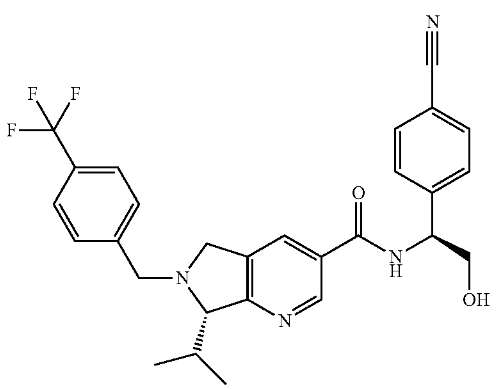 [SMILES: CC(C)[C@H]1c2ncc(C(=O)N[C@H](CO)c3ccc(C#N)cc3)cc2CN1Cc1ccc(C(F)(F)F)cc1] | 509.5 (M + H)+ | | | G |
| 159 | 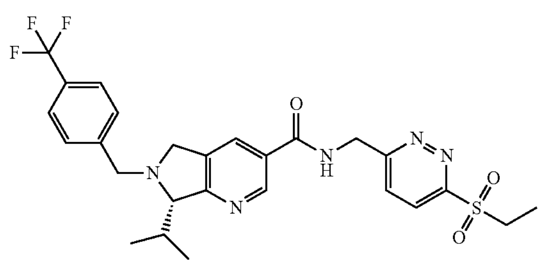 [SMILES: CCS(=O)(=O)c1ccc(CNC(=O)c2cnc3c(c2)CN(Cc2ccc(C(F)(F)F)cc2)[C@H]3C(C)C)nn1] | 548.1 (M + H)+ | (CD$_3$OD) δ 9.13 (d, J = 2.0 Hz, 1H), 8.32 (d, J = 3.2 Hz, 1H), 8.29 (s, 1H), 8.07 (d, J = 8.8 Hz, 1H), 7.92-7.85 (m, 4H), 5.10-5.04 (m, 3H), 4.89-4.85 (m, 1H), 4.80-4.76 (m, 3H), 3.60 (q, J = 7.2 Hz, 2H), 2.42-2.38 (m, 1H), 1.33 (t, J = 7.2 Hz, 3H), 1.17 (d, J = 6.8 Hz, 3H), 0.91 (d, J = 7.2 Hz, 3H). | | G |

Biological Assays

Radio-Ligand RORγ Binding Assay (Assay 1)

Compounds of the present invention were tested for ability to bind to RORγ in a cell-free competition assay with commercially available radio-ligand (RL), 25-hydroxy [26, 27-$^3$H]-cholesterol (PerkinElmer, Cat. #NET674250UC), for a ligand binding site on a recombinant RORγ Ligand Binding Domain (LBD) protein expressed as a 6×His-Glutathione-S-Transferase (GST) fusion. The assay was performed in 96-well SPA plates (PerkinElmer, Cat. #1450-401) in 50 mM HEPES buffer, pH 7.4, containing 150 mM NaCl, 5 mM MgCl$_2$, 10% (v/v) glycerol, 2 mM CHAPS, 0.5 mM β-octylglucopyranoside and 5 mM DTT. Tested compounds were dissolved in DMSO, and semi-log (3.162×) serial dilutions of the compounds were prepared in the same solvent. Two μL of the DMSO solutions were mixed with 28 μL of 8.6 nM 25-hydroxy [26,27-$^3$H]-cholesterol and 50 μL of 24 nM RORγ LBD. The plate was shaken at 700 rpm for 20 min and incubated for 10 min at rt, after which 40 μL of poly-Lys YSi SPA beads (PerkinElmer, Cat. #RPNQ0010) were added to achieve 50 μg of the beads per well. The plate was incubated on an orbital shaker for 20 min and then for 10 min without agitation at rt. SPA signal for tritium beta radiation was registered on PerkinElmer Microbeta plate reader. Percent inhibition values were calculated based on the high signal obtained with DMSO control and the low signal observed with 10 μM standard RORγ inverse agonist T0901317 (SigmaAldrich, Cat. #T2320). The percent inhibition vs. concentration data were fit into a four-parameter model, and IC50 values were calculated from the fit as the concentrations corresponding to the inflection points on the dose-response curves. Inhibitory constants (Ki) were calculated using the following equation, where [RL] is the concentration in the assay and $K_D$ is a dissociation constant of 25-hydroxy [26,27-$^3$H]-cholesterol:

$$K_i = \frac{IC_{50}}{\left(1 + \frac{[RL]}{K_D}\right)}.$$

RORγt 5×RORE Assay in Jurkat Cells (Assay 2)

Compounds of the present invention were tested for RORγ inverse agonist activity in a cell-based, transcriptional activity assay. Secreted Nanoluc® luciferase was used as a reporter for transcriptional activity of the full-length RORγt in Jurkat cells (ATCC, Cat. #TIB-152). A reporter plasmid was constructed by inserting 5 repeats of the ROR Response Element (RORE) AAAGTAGGTCA (SEQ ID NO:1) into a commercially available promoterless plasmid pNL1.3[secNluc] (Promega, Cat. #N1021) using KpnI and HindIII restriction sites. The expression plasmid for RORγt was purchased (Geneocopoeia, Cat. #EX-T6988-M02). Jurkat cells (30 million cells) were transfected with 11 μg of EX-T6988-MO2 and 26 μg of the reporter plasmid in OptiMEM® media using Lipofectamine® LTX and Plus™ reagents (Life Technologies, Cat. #15338-100). After 5-6 hrs of incubation at 37° C./5% CO$_2$, the cells were collected, resuspended in phenol-red free RPMI media containing 10% (v/v) delipidated FBS (Hyclone, Cat. #SH30855.03) and dispensed into 96-well clear bottom tissue culture plates (CoStar, Cat. #3603), at 80,000 cells per well. Tested compounds were added to the cells in the same media (final concentration of DMSO was 0.1% (v/v)), and the plates were incubated at 37° C./5% CO$_2$ for 16-18 hrs. Luciferase activity in the conditioned supernatants was determined with NanoGlo® assay reagents (Promega, Cat. #N1130). Percent inhibition values were calculated based on the fully inhibited and non-inhibited (DMSO) controls, and the values were regressed against concentrations of the tested compounds to derive IC50 values using a four-parameter non-linear fitting model.

The results of assays 1 and 2 are shown in Table 2.

TABLE 2

| Compound # | RORγ Binding Ki Range* (nM) | RORγt5X IC50 Range* (nM) |
|---|---|---|
| 1 | +++ | +++ |
| 2 | +++ | +++ |
| 3 | +++ | +++ |
| 4 | +++ | +++ |
| 5 | +++ | +++ |
| 6 | +++ | + |
| 7 | +++ | ++ |
| 8 | +++ | + |
| 9 | +++ | ++ |
| 10 | +++ | + |
| 11 | ++ | + |
| 12 | ++ | + |
| 13 | + | |
| 14 | ++ | |
| 15 | +++ | + |
| 16 | ++ | |
| 17 | +++ | +++ |
| 18 | + | |
| 19 | + | |
| 20 | +++ | +++ |
| 21 | ++ | ++ |
| 22 | +++ | +++ |
| 23 | ++ | |
| 24 | +++ | + |
| 25 | +++ | + |
| 26 | ++ | |
| 27 | +++ | ++ |
| 28 | +++ | +++ |
| 29 | +++ | +++ |
| 30 | +++ | +++ |
| 31 | +++ | +++ |
| 32 | +++ | ++ |
| 33 | +++ | +++ |
| 34 | +++ | +++ |
| 35 | +++ | ++ |
| 36 | ++ | |
| 37 | + | |
| 38 | +++ | ++ |
| 39 | +++ | +++ |
| 40 | ++ | |
| 41 | +++ | + |
| 42 | +++ | + |
| 43 | +++ | + |
| 44 | +++ | ++ |
| 45 | +++ | +++ |
| 46 | +++ | + |
| 47 | +++ | ++ |
| 48 | + | + |
| 49 | +++ | +++ |
| 50 | + | + |
| 51 | ++ | ++ |
| 52 | ++ | ++ |
| 53 | ++ | |
| 54 | +++ | +++ |
| 55 | +++ | +++ |
| 56 | +++ | ++ |
| 57 | +++ | +++ |
| 58 | +++ | +++ |
| 59 | +++ | +++ |
| 60 | ++ | |
| 61 | + | |
| 62 | + | |
| 63 | +++ | ++ |
| 64 | +++ | ++ |

TABLE 2-continued

| Compound # | RORγ Binding Ki Range* (nM) | RORγt5X IC50 Range* (nM) |
|---|---|---|
| 65 | ++ | |
| 66 | + | |
| 67 | +++ | +++ |
| 68 | + | |
| 69 | + | |
| 70 | + | |
| 71 | ++ | |
| 72 | ++ | |
| 73 | + | |
| 74 | + | |
| 75 | + | |
| 76 | ++ | |
| 77 | + | |
| 78 | ++ | |
| 79 | + | |
| 80 | + | |
| 81 | + | |
| 82 | + | |
| 83 | ++ | |
| 84 | + | |
| 85 | + | |
| 86 | + | |
| 87 | + | |
| 88 | + | |
| 89 | ++ | |
| 90 | ++ | |
| 91 | ++ | |
| 92 | + | |
| 93 | + | |
| 94 | + | |
| 95 | ++ | |
| 96 | + | |
| 97 | + | |
| 98 | + | |
| 99 | + | |
| 100 | + | |
| 101 | + | |
| 102 | ++ | |
| 103 | + | |
| 104 | ++ | |
| 105 | + | |
| 106 | ++ | |
| 107 | ++ | |
| 108 | + | |
| 109 | +++ | + |
| 110 | + | |
| 111 | ++ | |
| 112 | + | |
| 113 | ++ | |
| 114 | + | |
| 115 | ++ | |
| 116 | ++ | |
| 117 | + | |
| 118 | + | |
| 119 | + | |
| 120 | + | |
| 121 | + | |
| 122 | + | |
| 123 | ++ | |
| 124 | + | |
| 125 | + | |
| 126 | + | |
| 127 | ++ | |
| 128 | ++ | |
| 129 | ++ | |
| 130 | + | |
| 131 | ++ | |
| 132 | ++ | |
| 133 | +++ | ++ |
| 134 | + | |
| 135 | + | |
| 136 | + | |
| 137 | + | |
| 138 | + | |
| 139 | +++ | ++ |
| 140 | + | |
| 141 | +++ | +++ |
| 142 | +++ | +++ |
| 143 | +++ | ++ |
| 144 | +++ | +++ |
| 145 | + | |
| 146 | + | |
| 147 | ++ | |
| 148 | + | |
| 149 | +++ | ++ |
| 150 | + | |
| 151 | ++ | |
| 152 | + | |
| 153 | + | |
| 154 | + | |
| 155 | ++ | + |
| 156 | + | |
| 157 | + | |
| 158 | ++ | |
| 159 | +++ | ++ |

*+ means >1000 nM; ++ means 100 nM-1000 nM; +++ means <100 nM.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A compound of Formula (III):

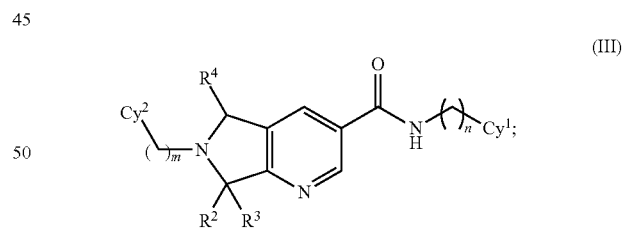

or a pharmaceutically acceptable salt thereof, wherein
$R^2$ and $R^3$ are each independently hydrogen, hydroxy, monocyclic cycloalkyl, monocyclic heterocyclyl, or $(C_1$-$C_6)$alkyl, wherein the $(C_1$-$C_6)$alkyl is optionally substituted with 1 to 2 groups independently selected from hydroxy, halo, and cyano;
$R^4$ is hydrogen, $(C_1$-$C_3)$alkyl, or =O;
X is —C(O)NH— or —NHC(O)—;
m is 0, 1, or 2;
n is 0, 1, 2, or 3;
$Cy^1$ is absent or is selected from $(C_1$-$C_3)$alkyl, halo($C_1$-$C_3$)alkyl, aryl, heteroaryl, heterocyclyl, and cycloalkyl, wherein the aryl, heteroaryl, heterocyclyl, and cycloalkyl are each optionally substituted with 1 to 3 groups independently selected from $R^5$;

$Cy^2$ is absent or is selected from $(C_1-C_6)$alkoxycarbonyl, phenyl$(C_1-C_3)$alkoxycarbonyl, halophenyl$(C_1-C_3)$ alkoxycarbonyl, aryl, heteroaryl, monocyclic cycloalkyl, and monocyclic heterocyclyl, wherein the aryl, heteroaryl, monocyclic cycloalkyl, and moncyclic heterocyclyl are each optionally substituted with 1 to 3 groups independently selected from $R^6$; and $R^5$ and $R^6$ are each independently selected from halo, cyano, nitro, amino, hydroxy, carboxy, $(C_1-C_6)$alkyl, heterocyclyl, hydroxy$(C_1-C_6)$alkyl, $CO_2H$, $(CH_2)_{1-3}$COOH, $(C_1-C_3)$alkylcarbonyloxy, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkylsulfinyl, $(C_3-C_6)$cycloalkylsulfinyl, $(C_4-C_7)$cycloalkylalkylsulfinyl, halo$(C_1-C_6)$alkylsulfonyl, halo$(C_3-C_6)$cycloalkylsulfinyl, halo$(C_4-C_7)$cycloalkylalkylsulfinyl, $(C_1-C_6)$alkylsulfonyl, $(C_3-C_6)$cycloalkylsulfonyl, $(C_4-C_7)$cycloalkylalkylsulfonyl, halo$(C_1-C_6)$alkylsulfonyl, halo$(C_3-C_6)$cycloalkylsulfonyl, halo$(C_4-C_7)$cycloalkylalkylsulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkyl-carbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, aryl, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, hydroxy$(C_1-C_6)$alkylcarbonyl, $(C_1-C_6)$alkylhydroxycarbonyl, $(C_1-C_6)$alkylhydroxy$(C_1-C_6)$alkyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminosulfonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl, [$(C_1-C_6)$alkyl$(C_4-C_6)$heterocyclyl]$(C_1-C_6)$alkyl, and di$(C_3-C_6)$cycloalkylaminocarbonyl$(C_1-C_6)$alkyl.

2. The compound of claim 1, wherein the compound is of Formula (IV):

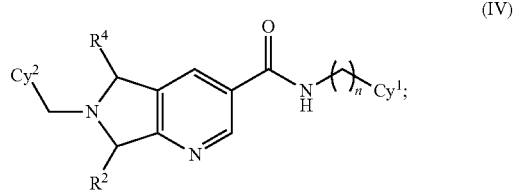

or a pharmaceutically acceptable salt thereof.

3. The compound of claim 2, wherein the compound is of Formula (V) or (VI):

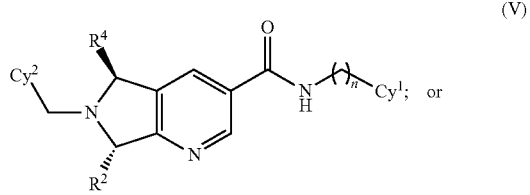

or a pharmaceutically acceptable salt thereof.

4. The compound of claim 3, wherein the compound is of Formula (VII):

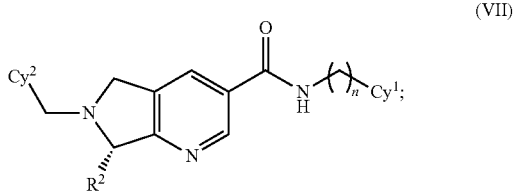

or a pharmaceutically acceptable salt thereof.

5. The compound of claim 4, wherein $R^2$ and $R^3$ are each independently hydrogen, hydroxy, or $(C_1-C_3)$alkyl.

6. The compound of claim 5, wherein $Cy^2$ is present and is selected from aryl, heteroaryl, monocyclic cycloalkyl, and monocyclic heterocyclyl, each of which is optionally substituted with 1 to 2 groups independently selected from $R^6$.

7. The compound of claim 6, wherein $Cy^2$ is phenyl, pyrimidinyl, cyclohexyl, or pyridinyl, each of which are optionally substituted with 1 to 2 groups independently selected from $R^6$.

8. The compound of claim 7, wherein $Cy^1$ is phenyl, piperidinyl, tetrahydro-2H-thiopyranyl 1,1-dioxide, pyridinyl, piperazinyl, azetidinyl, imidazolyl, tetrahydropyranyl, 1,4-dioxanyl, pyridazinyl, pyrazolyl, pyrrolidinyl, cyclohexyl, morpholinyl, 6,7-dihydro-5H-pyrrolo[2,1-c][1,2,4]triazolyl, 1,2,3,4-tetrahydro-1,8-naphthyridinyl, 2,3-dihydro-1H-indenyl, or imidazo[1,2-a]pyrimidinyl, each of which is optionally substituted with 1 to 2 groups independently selected from $R^5$.

9. The compound of claim 8, wherein $Cy^1$ is phenyl, piperidinyl, tetrahydro-2H-thiopyranyl 1,1-dioxide, pyridinyl, piperazinyl, azetidinyl, imidazolyl, tetrahydropyranyl, 1,4-dioxanyl, pyridazinyl, pyrazolyl, pyrrolidinyl, cyclohexyl, morpholinyl, 6,7-dihydro-5H-pyrrolo[2,1-c][1,2,4]triazolyl, 1,2,3,4-tetrahydro-1,8-naphthyridinyl, 2,3-dihydro-1H-indenyl, or imidazo[1,2-a]pyrimidinyl, each of which is optionally substituted with 1 to 2 groups independently selected from $R^5$, wherein at least one $R^5$ is $(C_1-C_3)$alkylsulfonyl or $(C_1-C_3)$alkylaminosulfonyl.

10. The compound of claim 9, wherein
$R^2$ is $(C_1-C_3)$alkyl;
n is 1 or 2; and
$Cy^1$ is phenyl, pyridinyl, or piperidinyl, each of which is optionally substituted with 1 to 2 groups independently selected from $R^5$, wherein at least one $R^5$ is $(C_1-C_3)$alkylsulfonyl or $(C_1-C_3)$alkylaminosulfonyl.

11. The compound of claim 10, wherein $Cy^2$ is cyclohexyl optionally substituted with 1 to 2 groups independently selected from $R^6$.

12. The compound of claim 11, wherein
$R^5$ is selected from halo, $(C_1-C_3)$alkyl, halo$(C_1-C_3)$alkyl, cyano, hydroxy$(C_1-C_3)$alkyl, $(C_1-C_3)$alkoxycarbonyl, $(C_1-C_3)$alkylsulfonyl, $(C_1-C_3)$alkoxy, halo$(C_1-C_3)$alkoxy, oxo, hydroxy, $(C_1-C_3)$alkylcarbonyl, hydroxy$(C_1-C_3)$alkylcarbonyl, $(C_1-C_3)$alkylhydroxycarbonyl, $(C_1-C_3)$alkylaminosulfonyl, $(C_1-C_3)$alkylaminocarbonyl, di$(C_1-C_3)$alkylamino$(C_2-C_6)$alkoxy, $(C_1-C_6)$alkoxycarbonyl, $[(C_1-C_3)$alkyl$(C_4-C_6)$heterocyclyl]$(C_1-C_3)$alkyl, and $(C_1-C_3)$alkylhydroxy$(C_1-C_3)$alkyl; and
$R^6$ is selected from halo, $(C_1-C_3)$alkyl, halo$(C_1-C_3)$alkyl, cyano, hydroxy$(C_1-C_3)$alkyl, $(C_1-C_3)$alkoxycarbonyl, $(C_1-C_3)$alkylsulfonyl, $(C_1-C_3)$alkoxy, halo$(C_1-C_3)$alkoxy, oxo, hydroxy, aryl$(C_1-C_3)$alkoxycarbonyl, $(C_1-C_3)$alkylhydroxy$(C_1-C_3)$alkyl, heteroaryl, and $(C_1-C_3)$alkoxycarbonyl.

13. The compound of claim 12, wherein
$R^5$ is selected from halo, $(C_1-C_3)$alkoxy, hydroxy, $(C_1-C_3)$alkyl, hydroxy$(C_1-C_3)$alkyl, halo$(C_1-C_3)$alkyl, $(C_1-C_6)$alkoxycarbonyl, di$(C_1-C_3)$alkylamino$(C_2-C_6)$alkoxy, $[(C_1-C_3)$alkyl$(C_4-C_6)$heterocyclyl]$(C_1-C_3)$alkyl, oxo, $(C_1-C_3)$alkylcarbonyl, $(C_1-C_3)$alkylaminosulfonyl, $(C_1-C_3)$alkylsulfonyl, and cyano; and
$R^6$ is selected from halo$(C_1-C_3)$alkyl, $(C_1-C_3)$alkoxy, halo, cyano, $(C_1-C_3)$alkoxycarbonyl, $(C_1-C_3)$alkylhydroxy$(C_1-C_3)$alkyl, 2-methyl-2H-tetrazolyl, hydroxy$(C_1-C_3)$alkyl, and halo$(C_1-C_3)$alkoxy.

14. The compound of claim 13, wherein $R^5$ is selected from halo, cyano, $(C_1-C_3)$alkyl, $(C_1-C_3)$alkylaminosulfonyl, and $(C_1-C_3)$alkylsulfonyl; and $R^6$ is selected from halo$(C_1-C_3)$alkyl, $(C_1-C_3)$alkoxy, halo, cyano, $(C_1-C_3)$alkoxycarbonyl, 2-methyl-2H-tetrazolyl, and halo$(C_1-C_3)$alkoxy.

15. The compound of claim 14, wherein
$Cy^1$ is

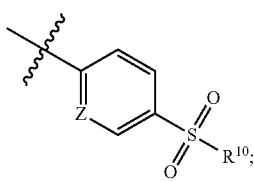

$R^{10}$ is $(C_1-C_3)$alkyl or $(C_1-C_3)$alkylamino; and
Z is CH or N.

16. The compound of claim 15, wherein

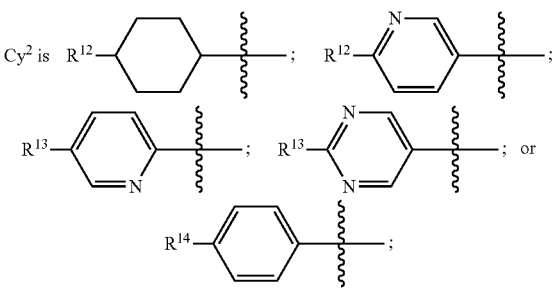

$R^{12}$ is $(C_1-C_3)$alkoxycarbonyl, halo, dihalo, $(C_1-C_3)$alkoxy, or halo$(C_1-C_3)$alkyl;
$R^{13}$ is halo or halo$(C_1-C_3)$alkyl; and
$R^{14}$ is halo, cyano, halo$(C_1-C_3)$alkyl, halo$(C_1-C_3)$alkoxy, or 2-methyl-2H-tetrazolyl.

17. The compound of claim 16, wherein $R^{12}$ to $R^{14}$ are each $CF_3$.

18. The compound of claim 17, wherein $R^2$ is isopropyl.

19. A pharmaceutical composition comprising a compound of claim 1, or a pharmaceutically acceptable salt thereof, and a pharmaceutically acceptable carrier.

20. A method of treating a disease or disorder selected from psoriasis, psoriatic arthritis (PsA), inflammatory bowel disease (IBD), rheumatoid arthritis, juvenile rheumatoid arthritis, systemic lupus erythematosus (SLE), multiple sclerosis, ankylosing spondylitis, and asthma, comprising administering to the subject a therapeutically effective amount of a compound of claim 1, or a pharmaceutically acceptable salt thereof.

21. The method of claim 20, wherein the disease or disorder is selected from ankylosing spondylitis psoriasis, and psoriatic arthritis (PsA).

22. The compound of claim 1, wherein the compound is of the formula:

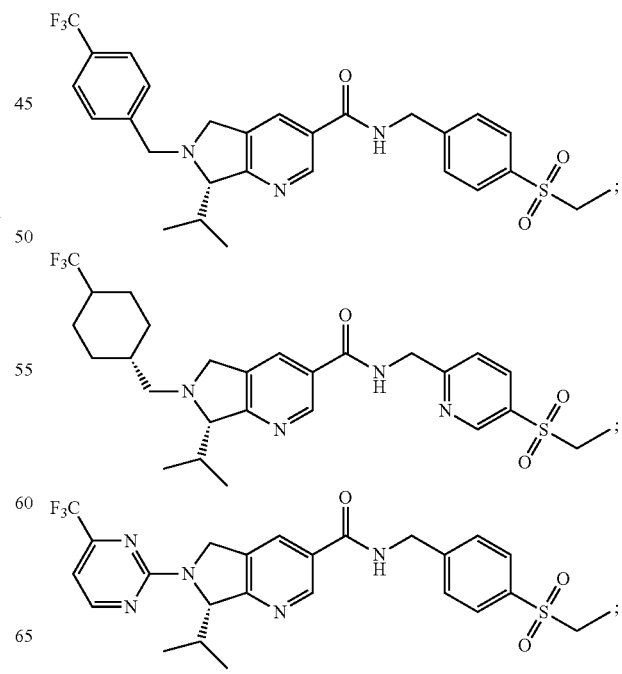

149
-continued
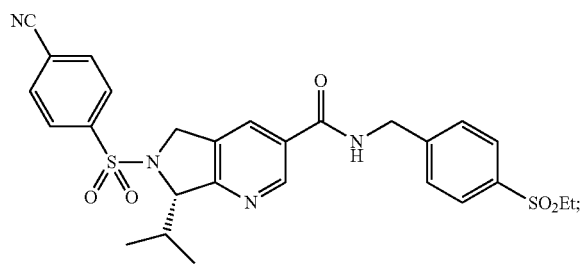
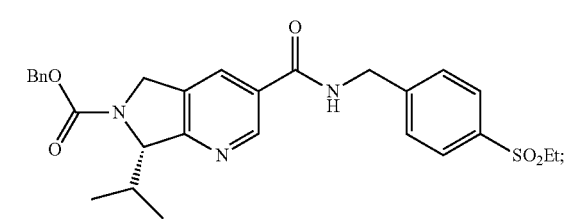
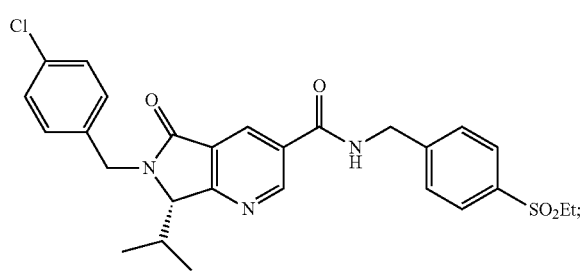
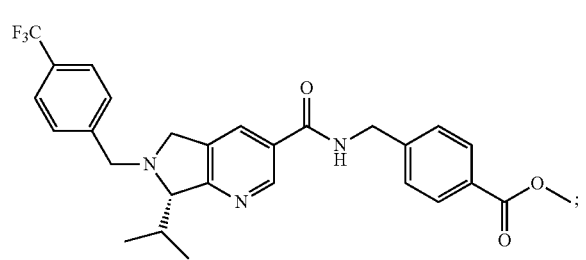
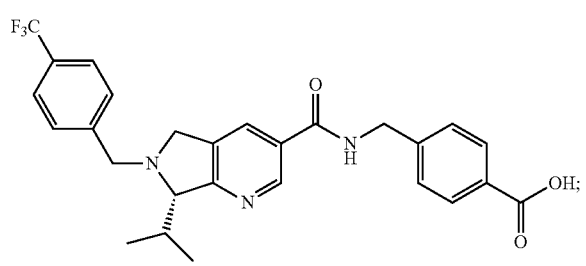
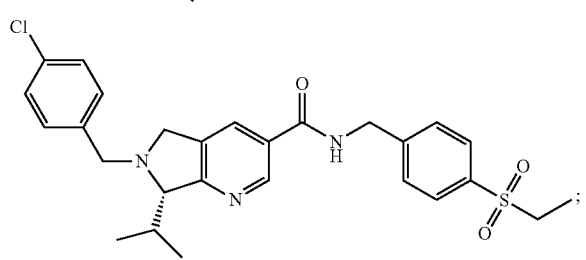
150
-continued
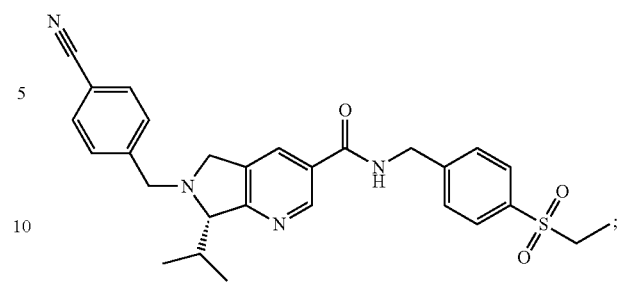
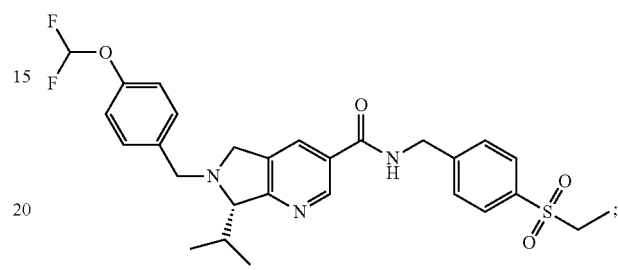
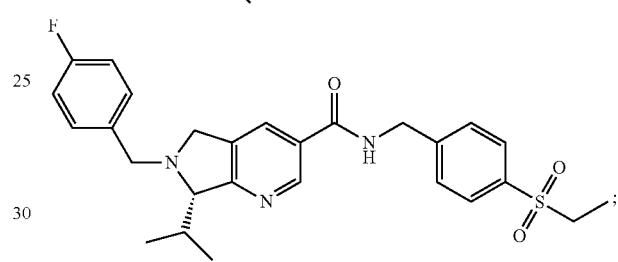
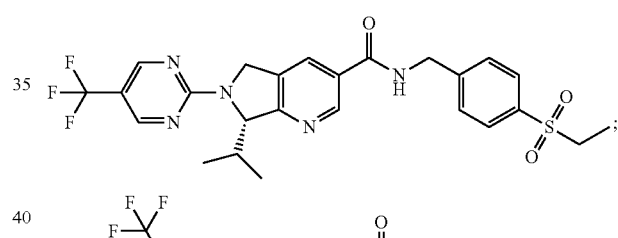
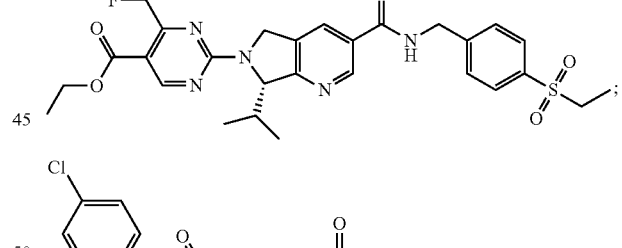
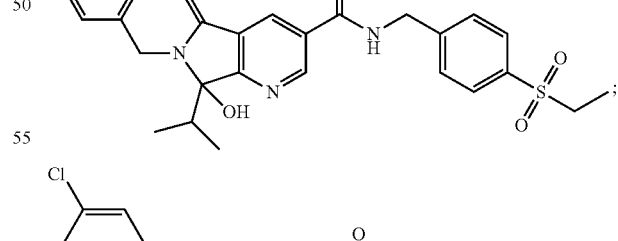
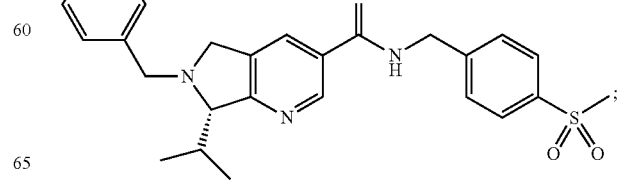

151
-continued
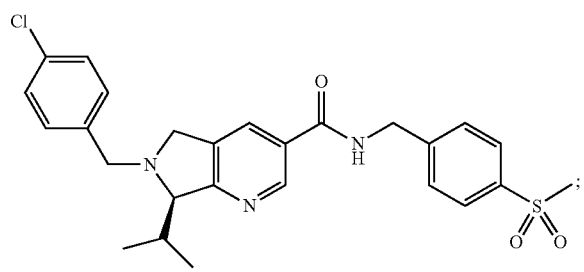
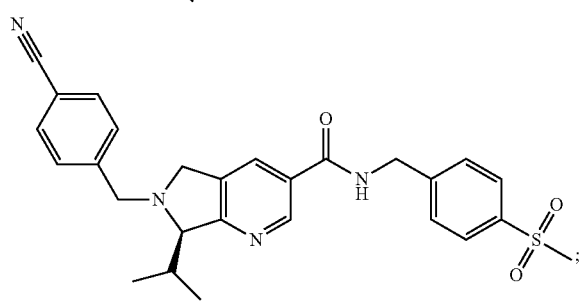
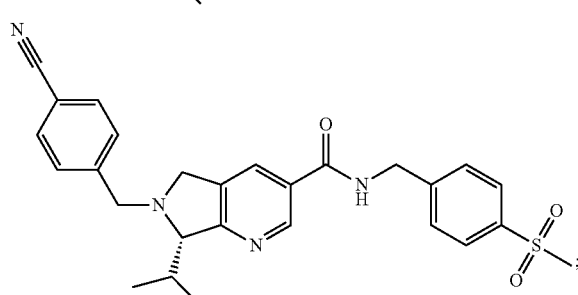
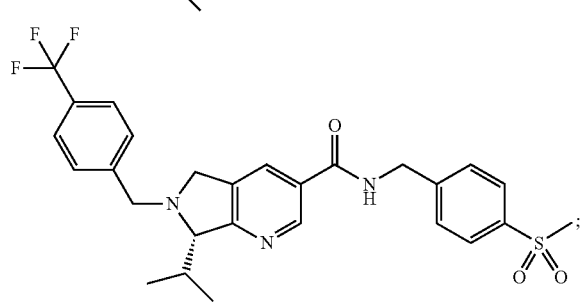
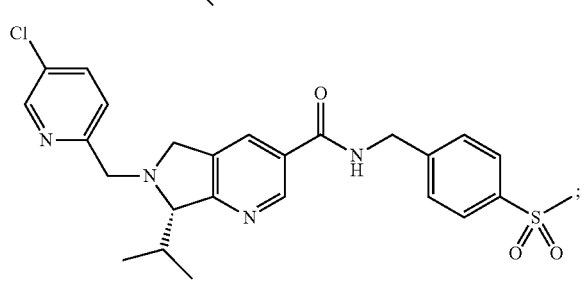
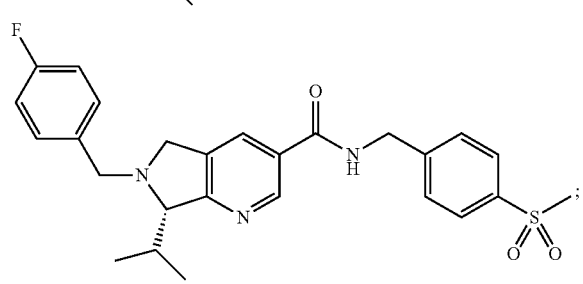
152
-continued
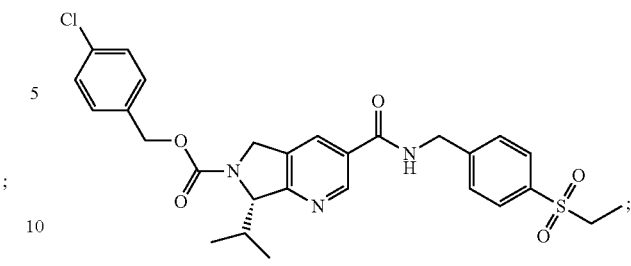
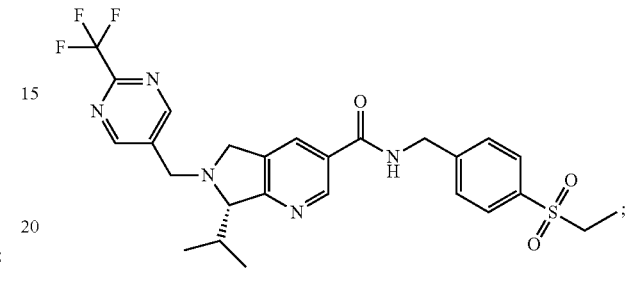
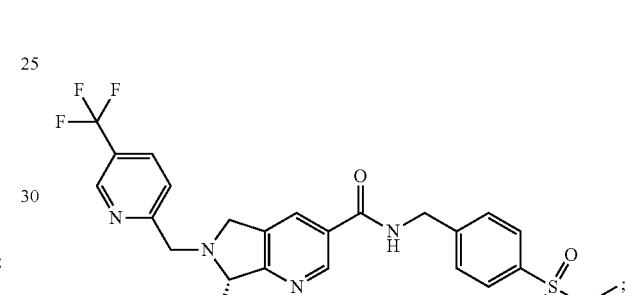
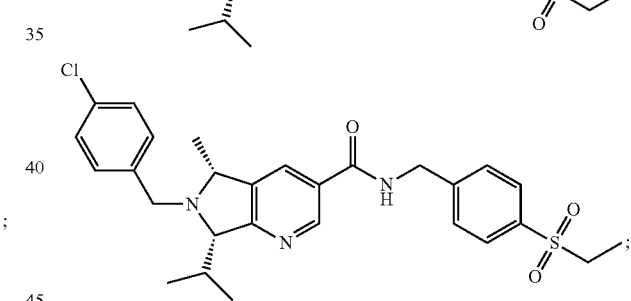
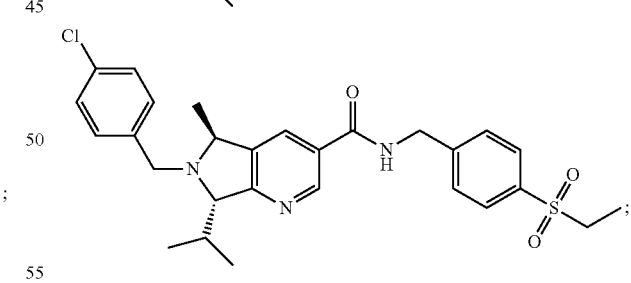
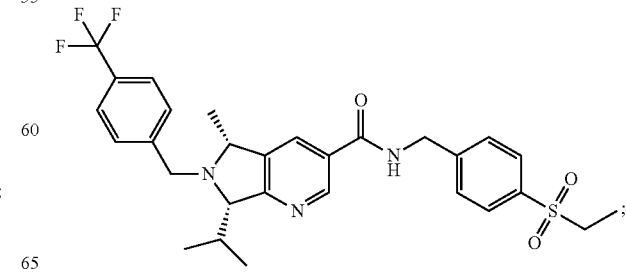

153
-continued
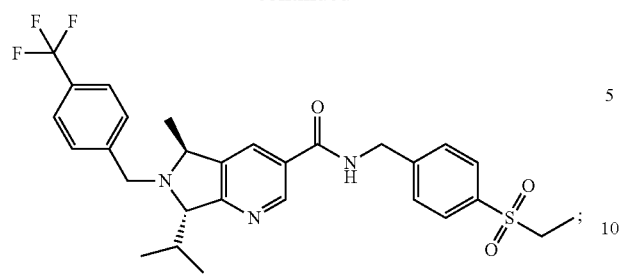
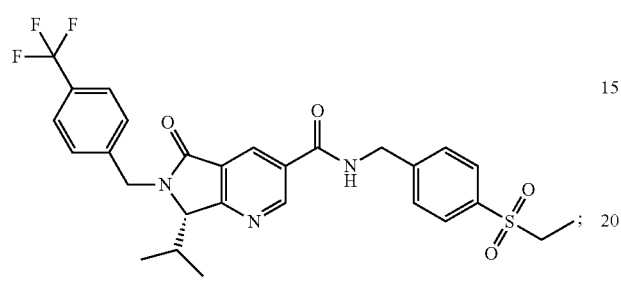
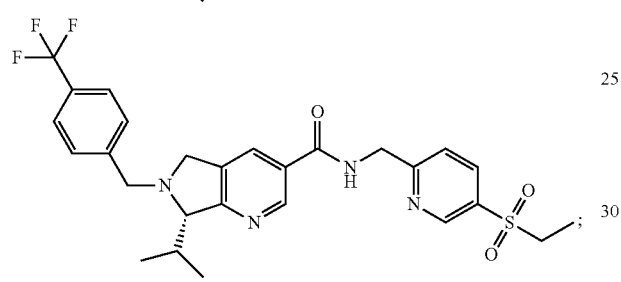
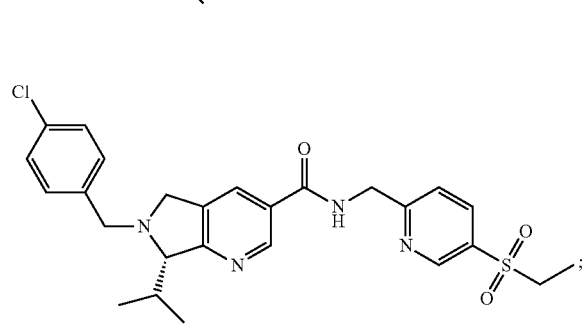
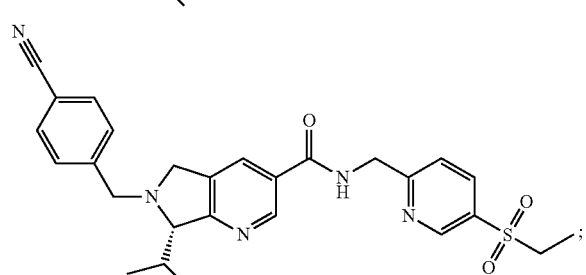
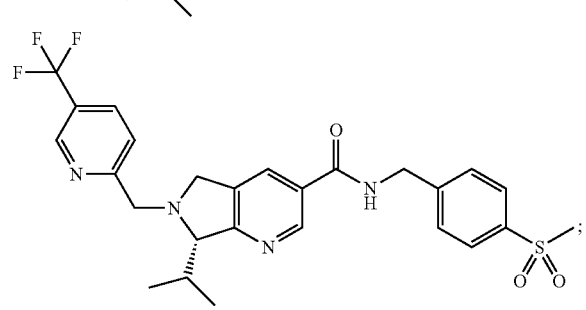
154
-continued
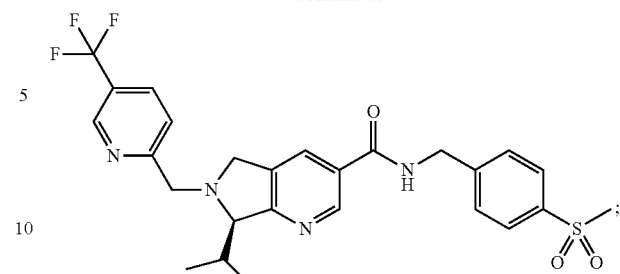
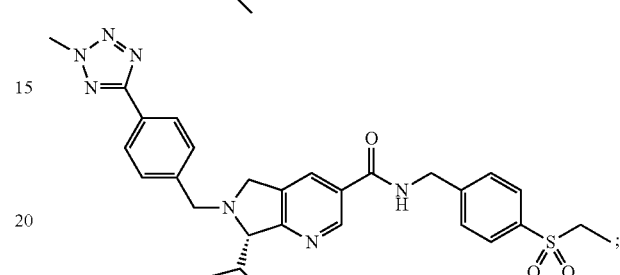
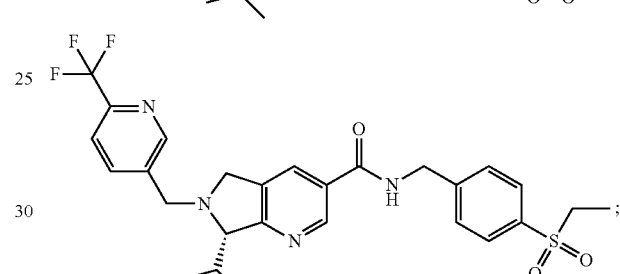
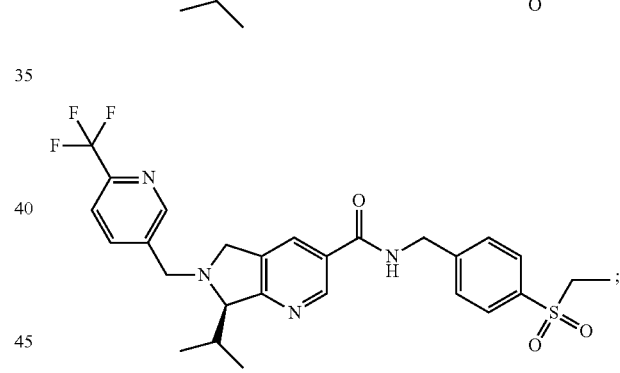
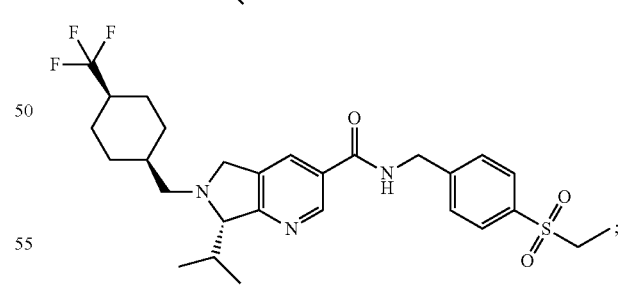
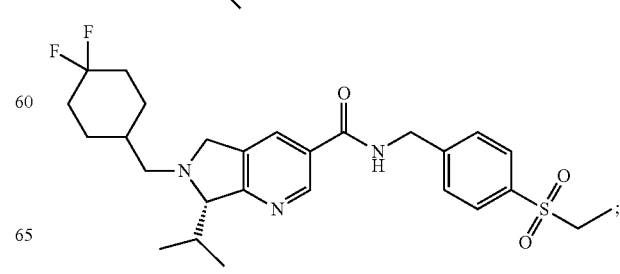

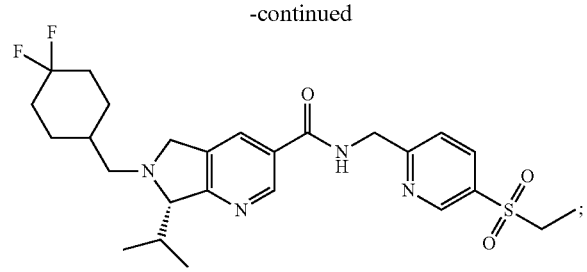
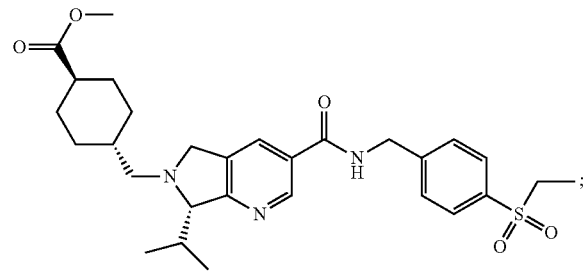
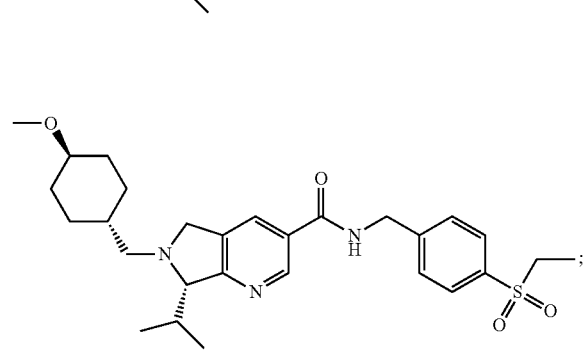
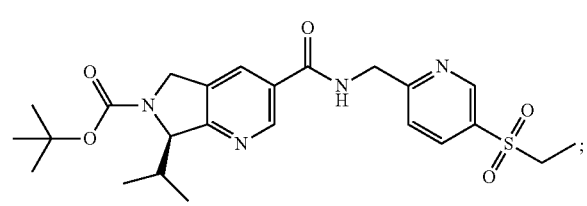
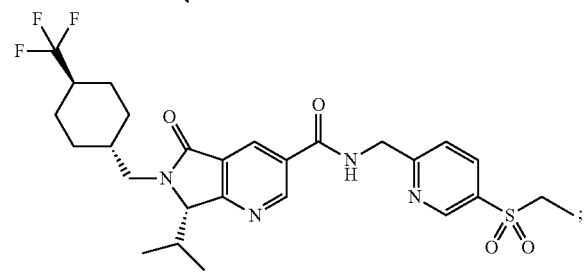
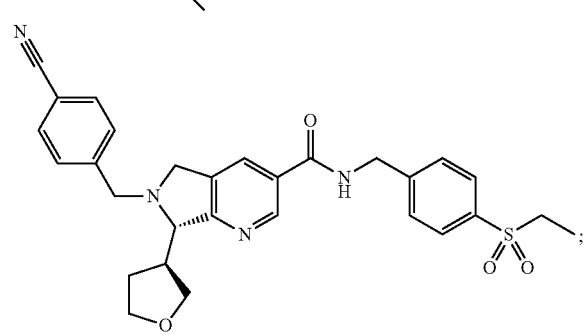
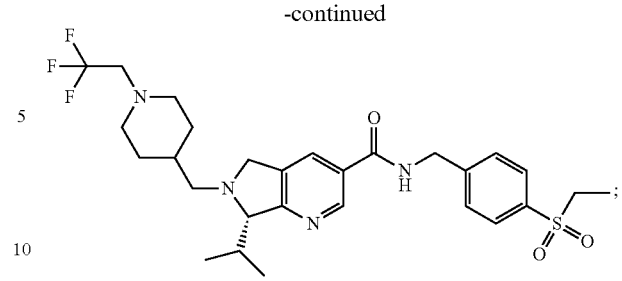
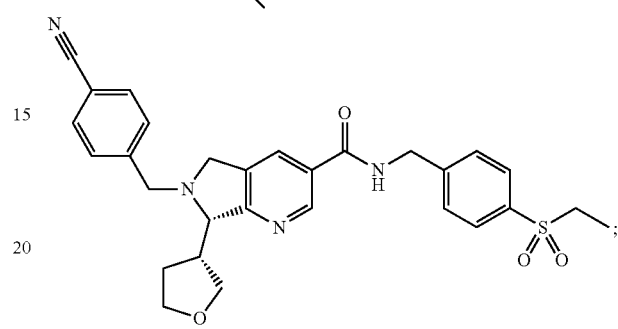
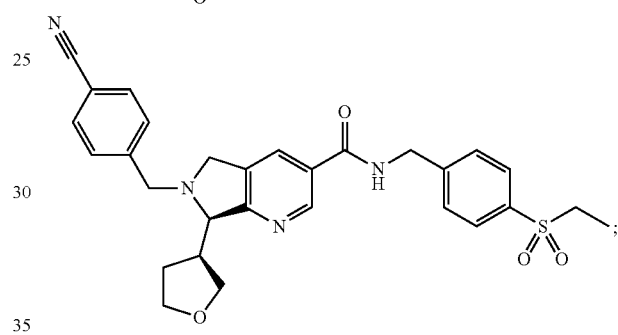
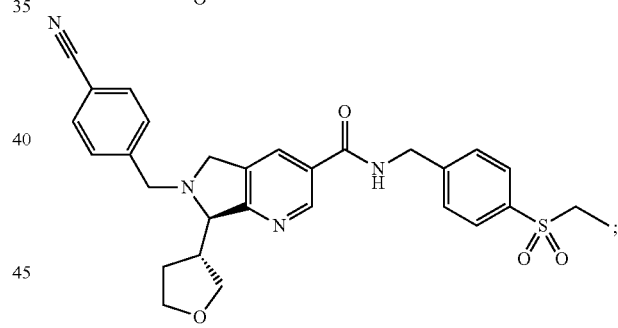
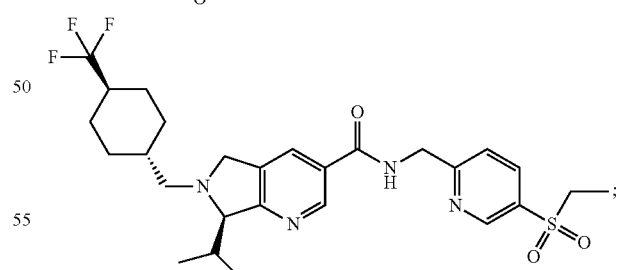
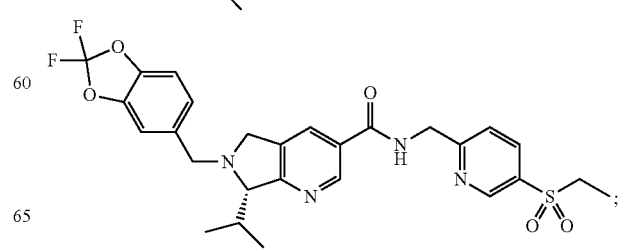

157
-continued
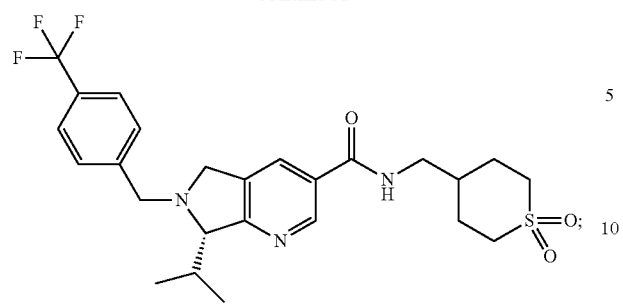
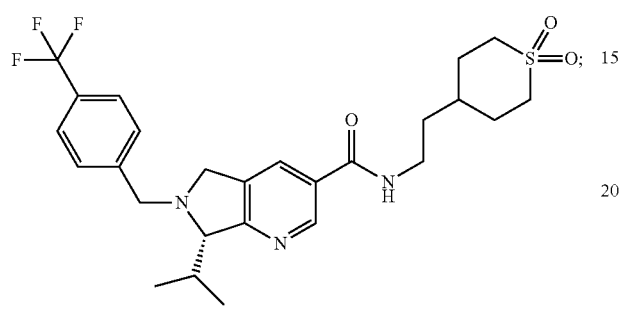
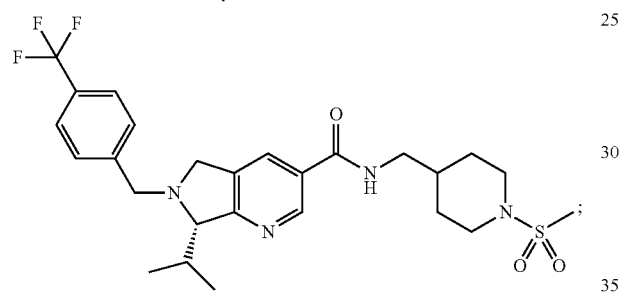
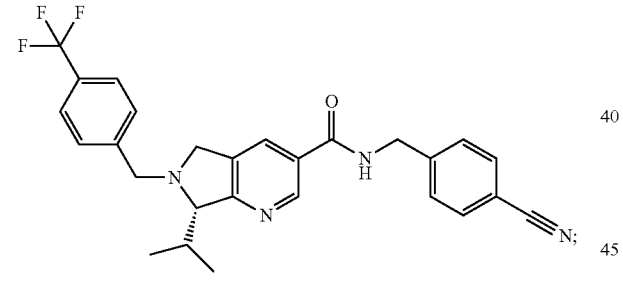
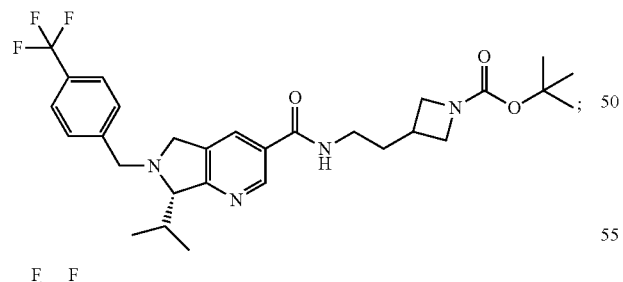
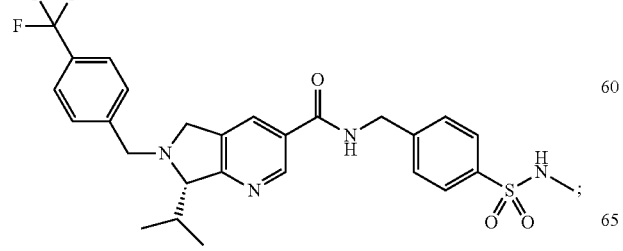
158
-continued
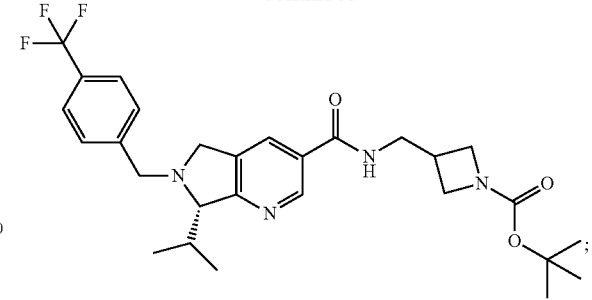
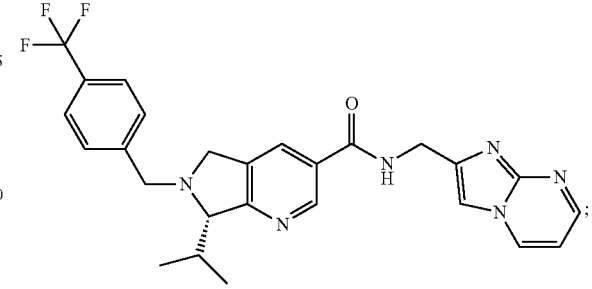
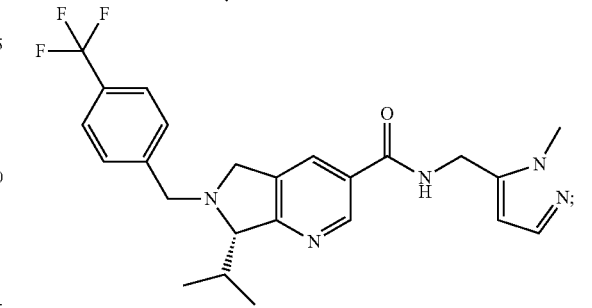
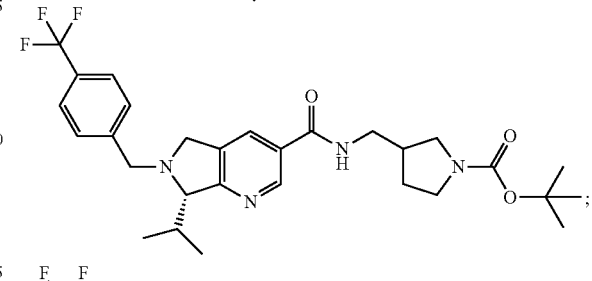
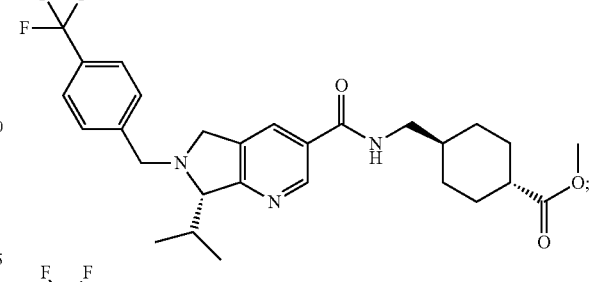
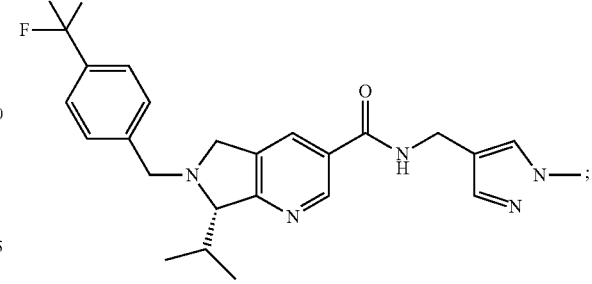

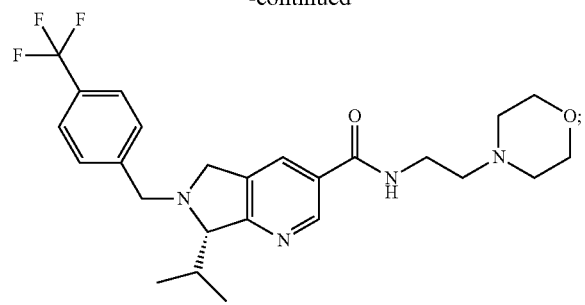
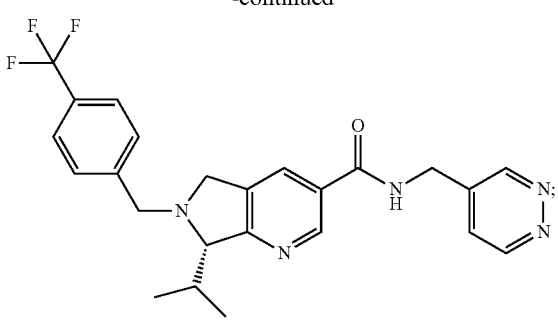
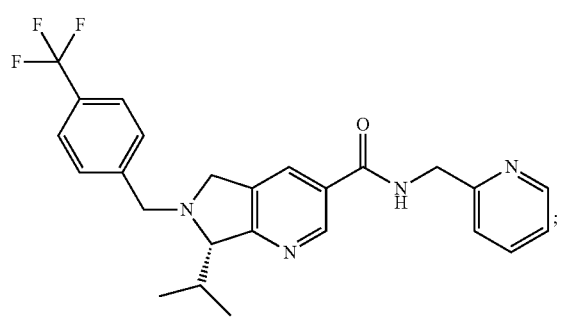
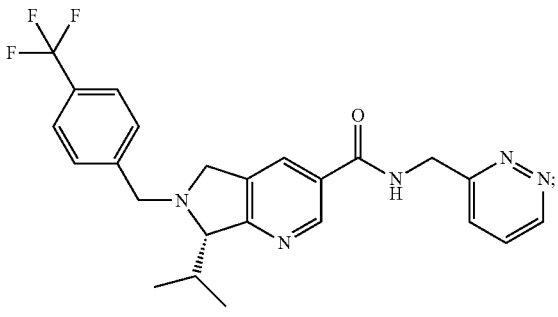
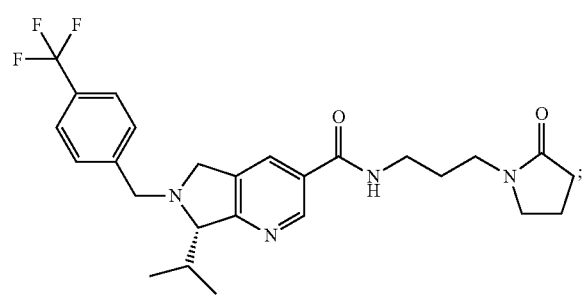
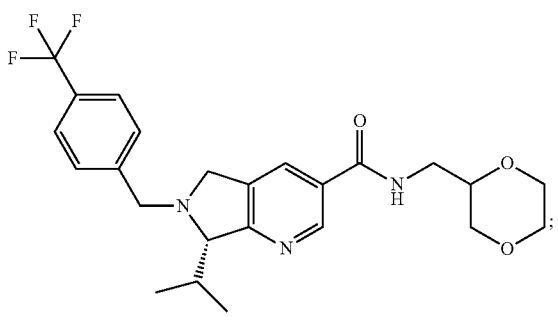
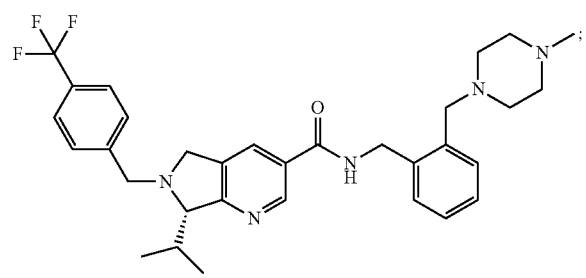
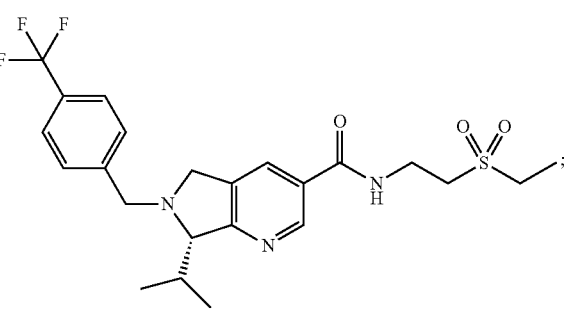
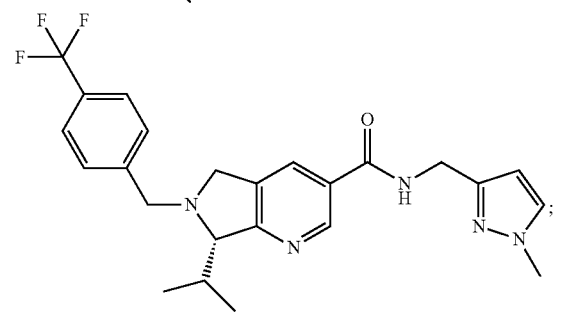
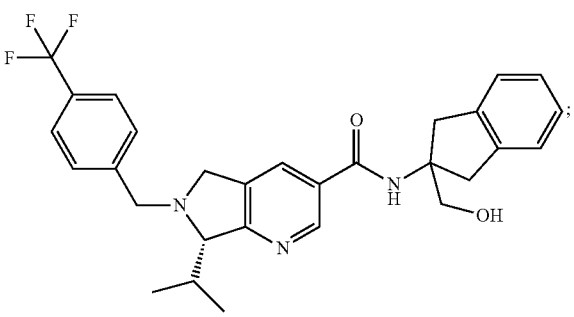

161
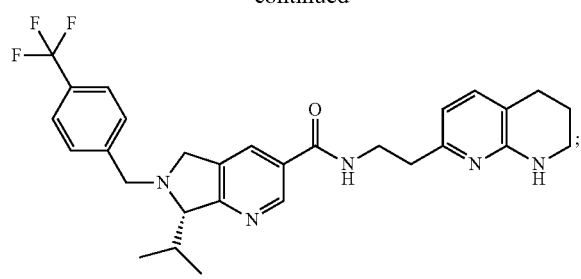
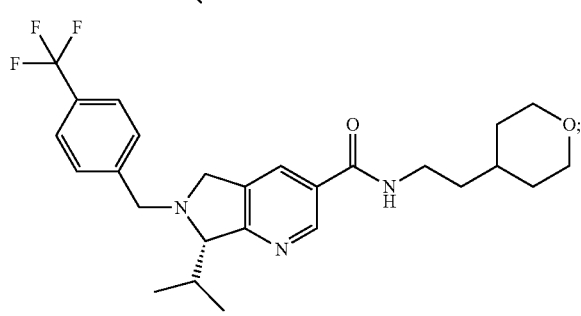
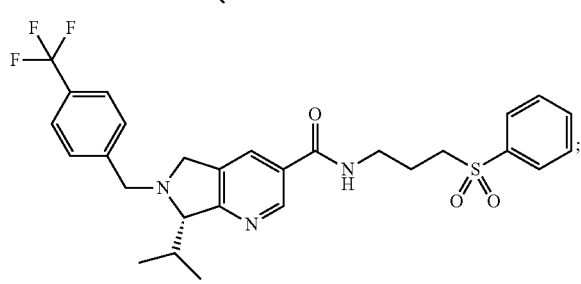
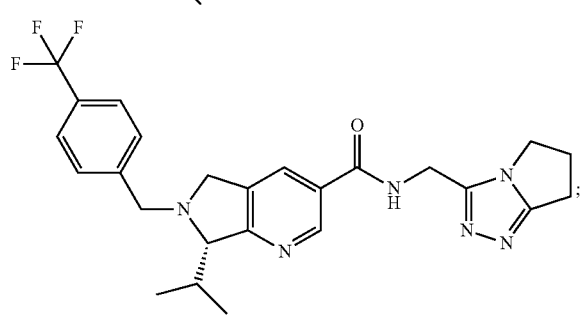
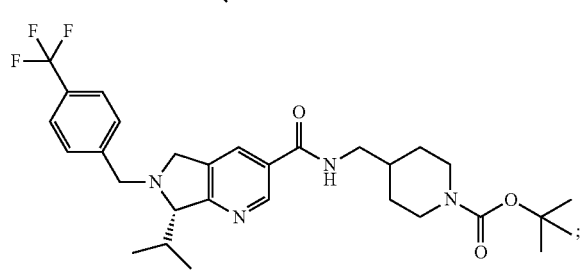
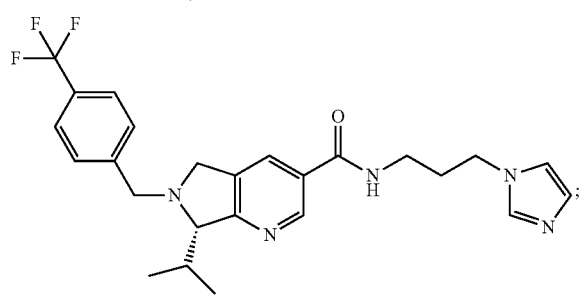
162
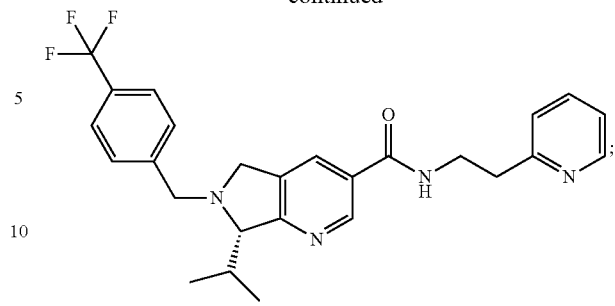
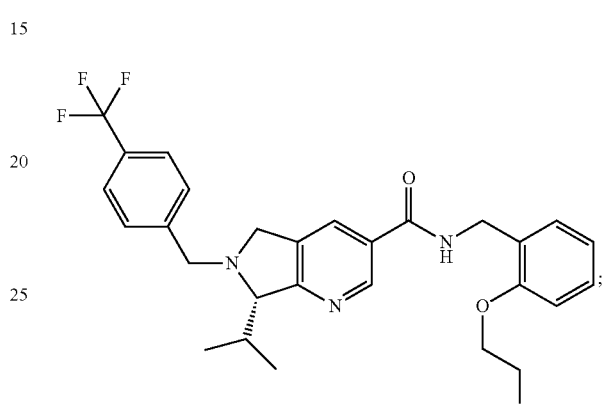
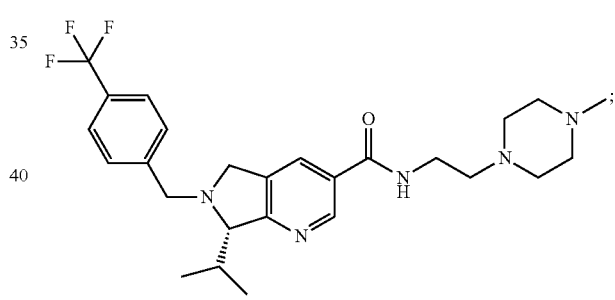
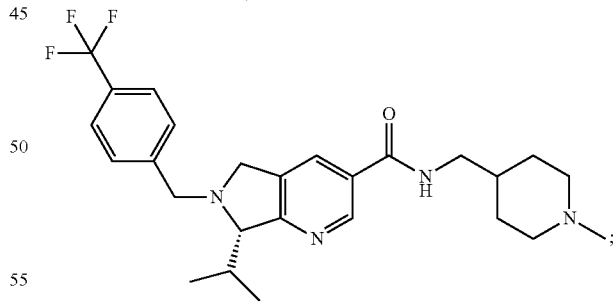
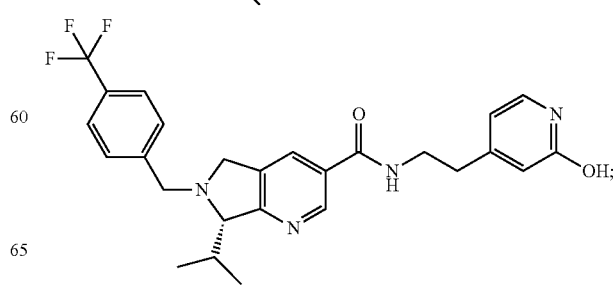

163
-continued
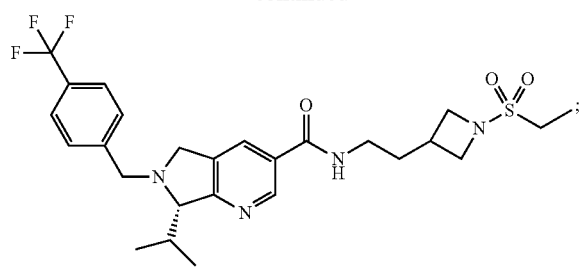
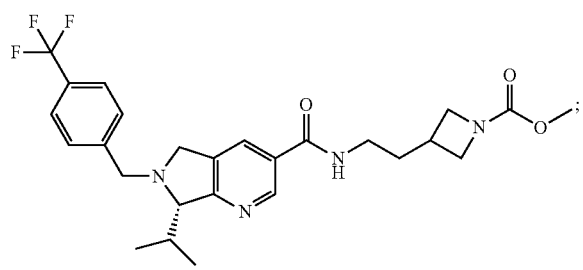
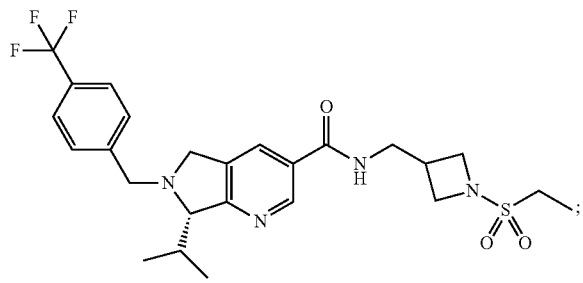
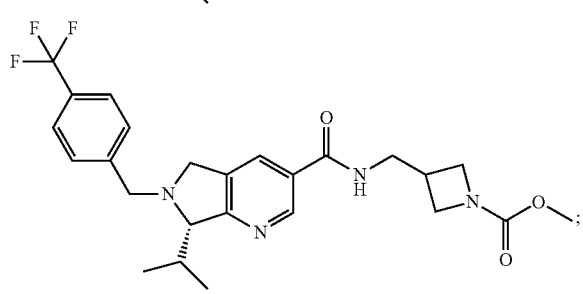
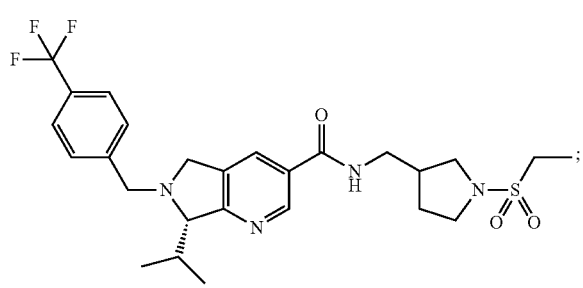
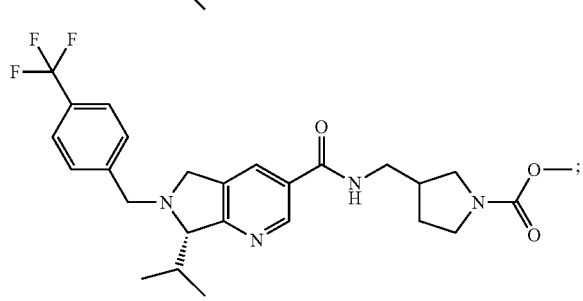
164
-continued
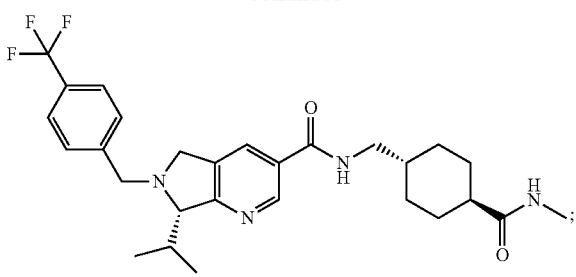
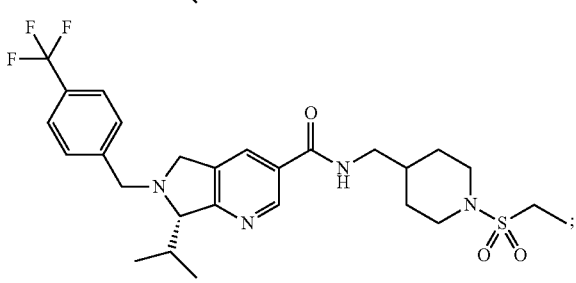
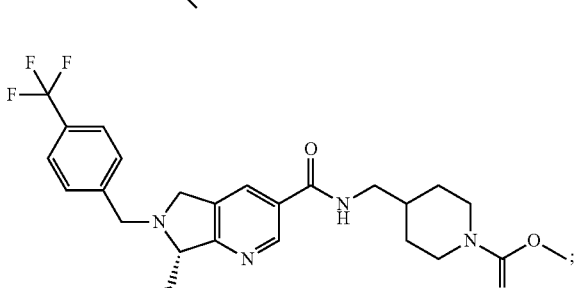
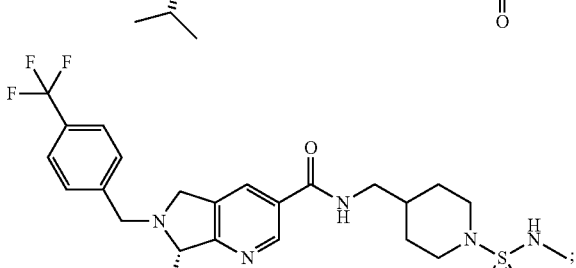
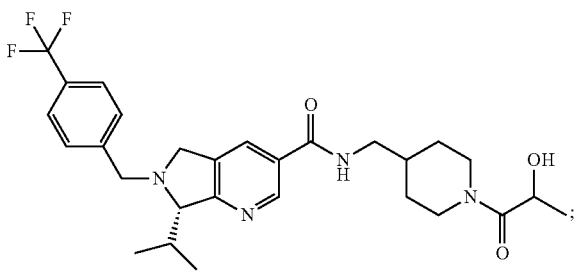
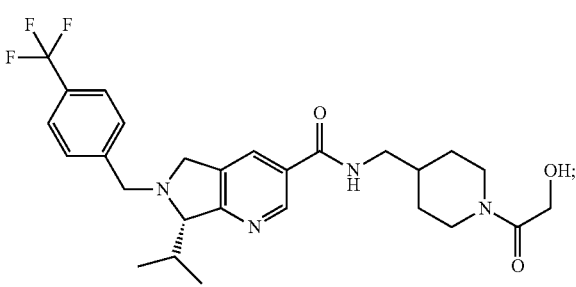

165
-continued
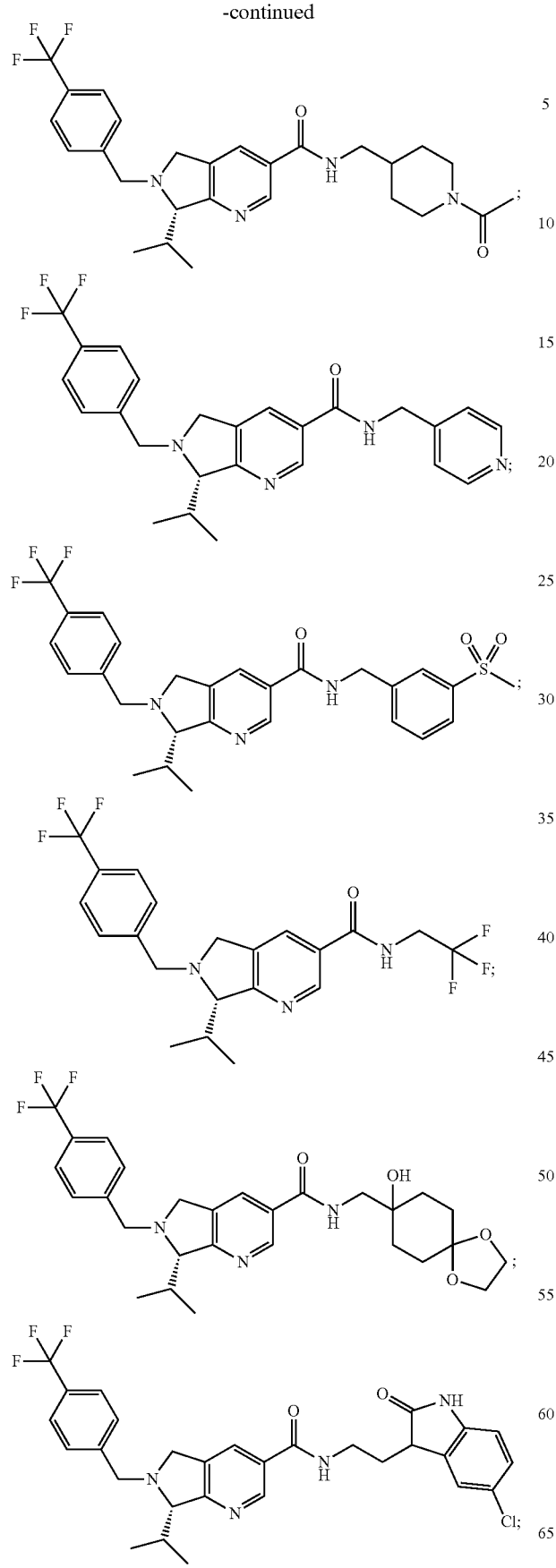
166
-continued
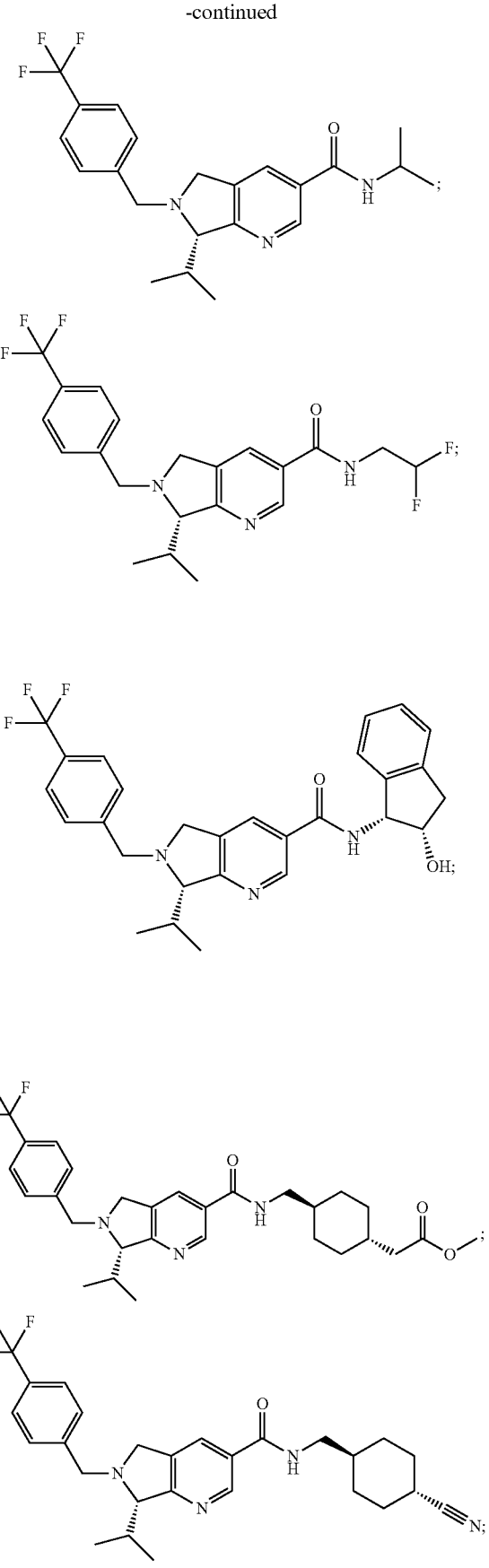

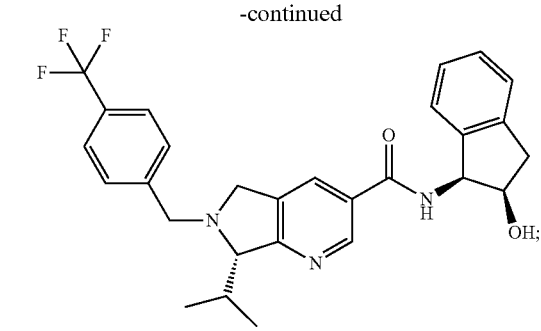
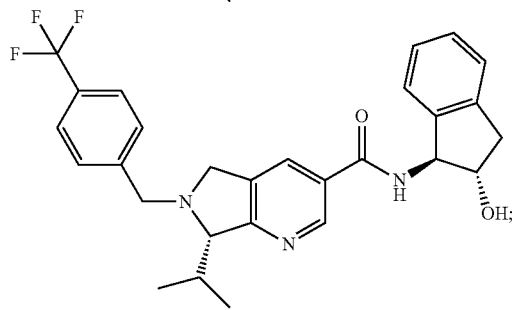
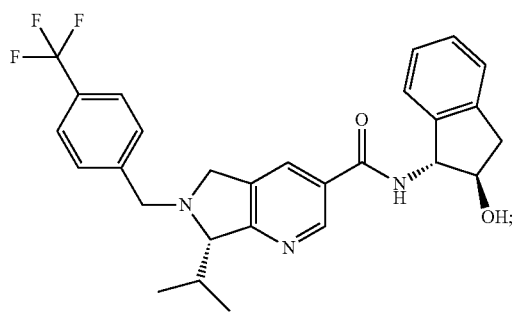
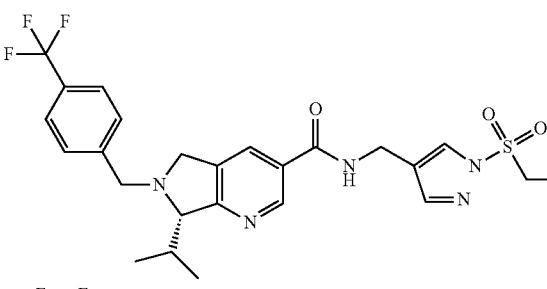
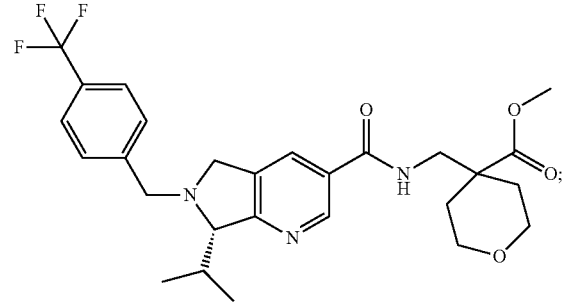
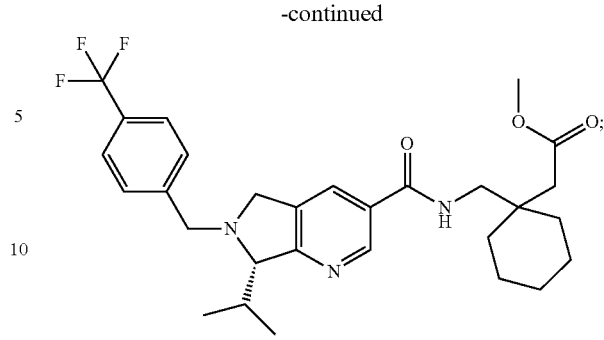
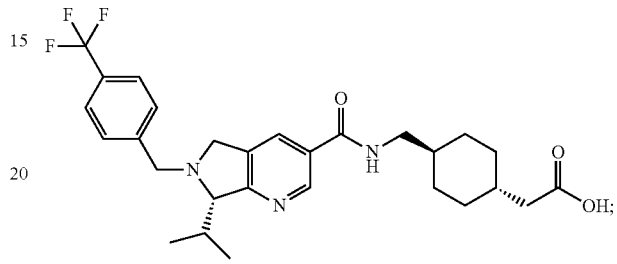
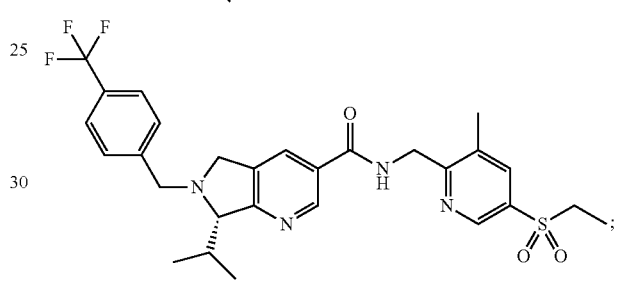
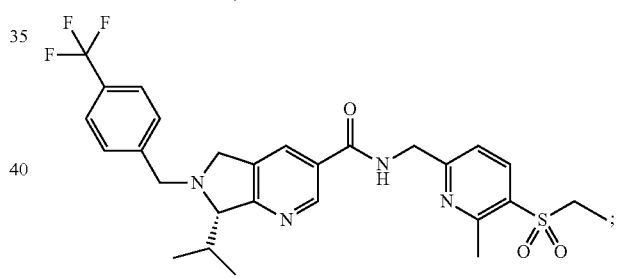
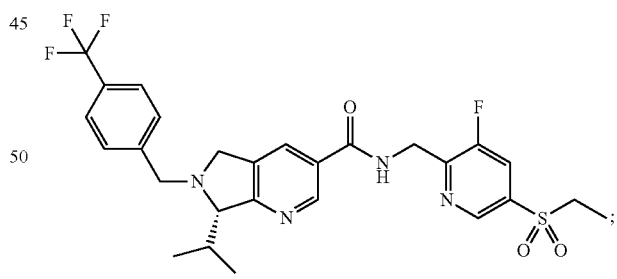
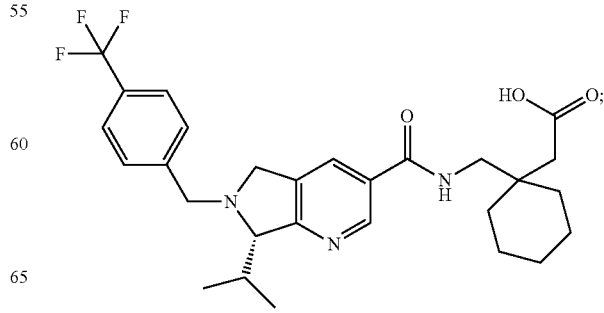

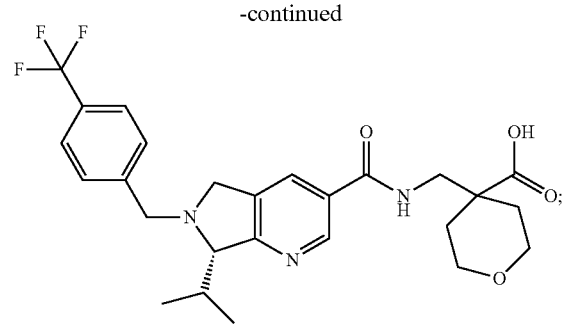
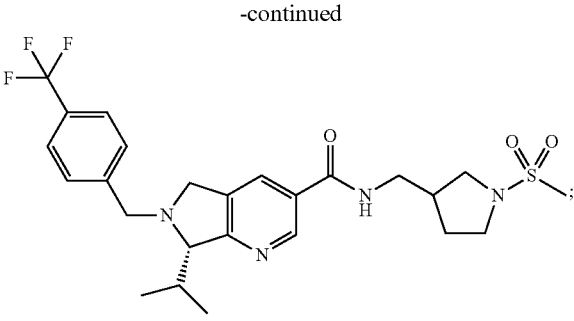
or a pharmaceutically acceptable salt thereof.

UNITED STATES PATENT AND TRADEMARK OFFICE
CERTIFICATE OF CORRECTION

PATENT NO. : 9,624,217 B2  
APPLICATION NO. : 14/990430  
DATED : April 18, 2017  
INVENTOR(S) : David A. Claremon et al.

It is certified that error appears in the above-identified patent and that said Letters Patent is hereby corrected as shown below:

In the Claims

Column 148, Claim 16, Lines 4-7, please replace " 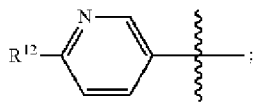 " with -- 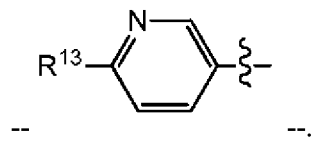 --.

Signed and Sealed this  
Fourteenth Day of November, 2017

Joseph Matal  
*Performing the Functions and Duties of the*  
*Under Secretary of Commerce for Intellectual Property and*  
*Director of the United States Patent and Trademark Office*